US012576135B2

(12) United States Patent
Wang et al.

(10) Patent No.: US 12,576,135 B2
(45) Date of Patent: Mar. 17, 2026

(54) COMPOSITIONS AND METHODS FOR ANTI-TnMUC1 GOLD CAR T-CELLS

(71) Applicant: Chimera Bioengineering, Inc., Pacifica, CA (US)

(72) Inventors: Benjamin Wang, Menlo Park, CA (US); Gusti Zeiner, Pacifica, CA (US); Albert Gacerez, Fremont, CA (US); Eytan Herzig, San Mateo, CA (US)

(73) Assignee: Chimera Bioengineering, Inc.

( * ) Notice: Subject to any disclaimer, the term of this patent is extended or adjusted under 35 U.S.C. 154(b) by 0 days.

(21) Appl. No.: 17/934,091

(22) Filed: Sep. 21, 2022

(65) Prior Publication Data

US 2023/0128385 A1 Apr. 27, 2023

Related U.S. Application Data

(60) Provisional application No. 63/249,730, filed on Sep. 29, 2021, provisional application No. 63/331,804, filed on Apr. 16, 2022.

(51) Int. Cl.

| | |
|---|---|
| *A61K 40/11* | (2025.01) |
| *A61K 38/17* | (2006.01) |
| *A61K 38/20* | (2006.01) |
| *A61K 40/31* | (2025.01) |
| *A61K 40/42* | (2025.01) |
| *A61P 1/18* | (2006.01) |
| *A61P 13/08* | (2006.01) |
| *A61P 35/00* | (2006.01) |
| *C12N 5/0783* | (2010.01) |
| *C12N 15/86* | (2006.01) |

(52) U.S. Cl.

CPC ........ *A61K 38/208* (2013.01); *A61K 38/1774* (2013.01); *A61K 40/11* (2025.01); *A61K 40/31* (2025.01); *A61K 40/4202* (2025.01); *A61K 40/4211* (2025.01); *A61K 40/4257* (2025.01); *A61P 1/18* (2018.01); *A61P 13/08* (2018.01); *A61P 35/00* (2018.01); *C12N 5/0636* (2013.01); *C12N 15/86* (2013.01); *A61K 2239/48* (2023.05); *A61K 2239/54* (2023.05); *C12N 2501/515* (2013.01); *C12N 2501/599* (2013.01); *C12N 2502/30* (2013.01); *C12N 2740/15043* (2013.01)

(58) Field of Classification Search

CPC .... A61K 40/11; A61K 40/31; A61K 40/4257; A61K 38/208; A61P 35/00; A61P 1/18; A61P 13/08

See application file for complete search history.

(56) References Cited

U.S. PATENT DOCUMENTS

| | | | | |
|---|---|---|---|---|
| 8,501,464 | B2 * | 8/2013 | Naldini | C12N 15/85 435/71.1 |
| 11,459,572 | B2 * | 10/2022 | Wang | C12N 15/63 |
| 11,535,853 | B2 * | 12/2022 | Wang | C12N 15/635 |
| 11,572,566 | B2 * | 2/2023 | Wang | A61P 35/02 |
| 11,648,277 | B2 * | 5/2023 | Wang | C07K 14/70578 424/93.71 |
| 2009/0048191 | A1 | 2/2009 | Rakoczy et al. | |
| 2010/0316609 | A1 | 12/2010 | Dewhurst | |
| 2011/0003385 | A1 | 1/2011 | Crabtree | |
| 2013/0245096 | A1 | 9/2013 | Abitbol | |
| 2014/0120622 | A1 | 5/2014 | Gregory et al. | |
| 2014/0242701 | A1 | 8/2014 | Shiku et al. | |
| 2014/0271583 | A1 | 9/2014 | Allen-Hoffmann et al. | |
| 2014/0286987 | A1 | 9/2014 | Spencer et al. | |
| 2014/0349402 | A1 | 11/2014 | Cooper et al. | |
| 2015/0307564 | A1 | 10/2015 | Young et al. | |
| 2016/0040126 | A1 | 2/2016 | Baik et al. | |
| 2016/0130357 | A1 * | 5/2016 | Mukherjee | C07K 14/70578 435/372.3 |
| 2018/0044424 | A1 | 2/2018 | June et al. | |
| 2018/0273618 | A1 | 9/2018 | Murriel et al. | |
| 2019/0270817 | A1 | 9/2019 | Ali et al. | |
| 2019/0290692 | A1 * | 9/2019 | Bamdad | A61K 35/17 |
| 2019/0314411 | A1 * | 10/2019 | Xiao | A61K 39/464412 |
| 2019/0365810 | A1 | 12/2019 | Wang et al. | |
| 2019/0367612 | A1 | 12/2019 | Chaen et al. | |
| 2020/0289565 | A1 | 9/2020 | Green et al. | |
| 2020/0306304 | A1 * | 10/2020 | Posey | A61P 35/00 |

(Continued)

FOREIGN PATENT DOCUMENTS

| | | |
|---|---|---|
| WO | WO 2015092440 | 6/2015 |
| WO | WO 2015123527 | 8/2015 |
| WO | WO 2015123642 | 8/2015 |

(Continued)

OTHER PUBLICATIONS

Zhou et al, CAR T Cells Targeting the Tumor MUC1 Glycoprotein Reduce Triple-Negative Breast Cancer Growth, Frontiers in Immunology 10(Article 1140): 12 pages, doi:10.3389/fimmu.2019.01149; May 24, 2019.*

(Continued)

*Primary Examiner* — Kevin K Hill
(74) *Attorney, Agent, or Firm* — HelixIP LLP

(57) ABSTRACT

Methods and compositions for delivering a payload at TnMUC1 positive cancer cells. Anti-TnMUC1 CARs and transgene payloads can be engineered into immune cells so that the transgene payload is expressed and delivered at desired times from the immune cell. Such anti-TnMUC1 CAR T-cells with transgene payloads can be combined with the administration of other molecules, e.g., other therapeutics such as anticancer therapies.

17 Claims, 24 Drawing Sheets

Specification includes a Sequence Listing.

(56) References Cited

U.S. PATENT DOCUMENTS

| | | | | |
|---|---|---|---|---|
| 2022/0135678 A1* | 5/2022 | Chaudhary | ............ | C07K 16/18 424/136.1 |
| 2022/0204582 A1* | 6/2022 | Chaudhary | ............ | A61P 35/02 |

FOREIGN PATENT DOCUMENTS

| | | |
|---|---|---|
| WO | WO 2015140268 | 9/2015 |
| WO | WO 2015142661 | 9/2015 |
| WO | WO 2015142675 | 9/2015 |
| WO | WO 2015193406 | 12/2015 |
| WO | WO 2016028896 | 2/2016 |
| WO | WO 2016126608 | 8/2016 |
| WO | WO 2016/149254 | 9/2016 |
| WO | WO 2017/149515 | 9/2017 |

OTHER PUBLICATIONS

Koneru et al, IL-12 secreting tumor-targeted chimeric antigen receptor T cells eradicate ovarian tumors in vivo, OncoImmunology 4(3): e994446; 12 pages, doi: 10.4161/2162402X.2014.994446; available online Mar. 16, 2015.*
Lenneke et al, A Bitter Sweet Symphony: Immune Responses to Altered O-glycan Epitopes in Cancer, Biomolecules 6(26): 19 pages, doi:10.3390/biom6020026; May 3, 2016.*
You et al, Phase 1 clinical trial demonstrated that MUC1 positive metastatic seminal vesicle cancer can be effectively eradicated by modified Anti-MUC1 chimeric antigen receptor transduced T cells, Science China, Life Sciences 59(4): 386-397, 2016.*
Lin et al, 37P—Chemokine receptor CCR2b expressing anti-Tn-MUC1 CAR-T cells enhanced anti-breast cancer activity, Annals of Oncology 30(Suppl 11): xi12-xi15, 1 page, doi:10.1093/annonc/mdz448; Dec. 2019.*
Liu et al, Armored Inducible Expression of IL-12 Enhances Antitumor Activity of Glypican-3-Targeted Chimeric Antigen Receptor-Engineered T Cells in Hepatocellular Carcinoma, J. Immunol. 203(1): 198-207, Jul. 1, 2019.*
Iwamoto et al., A general chemical method to regulate protein stability in the mammalian nervous system, 2010, Chem & Biol vol. 17, pp. 981-988.
Rakhit et al., Evaluation of FKBP and DHFR based destabilizing domains in *Saccharomyces cerivisiae*, 2011, Bioorg & Med Chem Lett vol. 21, pp. 4965-4968.
Jena et al., Redirecting T-cell specificity by introducing a tumor-specific chimeric antigen receptor, 2010, Blood vol. 116, pp. 1035-1044.
Nielsen et al., Split-receptors in the tachykinin neurokinin-1 system, 1998, Eur. J. Biochem. vol. 251, pp. 217-226.
Auslander et al, A ligand-dependent hammerhead ribozyme switch for controlling mammalian gene expression, 2010, Molc Biosys vol. 6, pp. 807-814.
Budde et al., Combining a CD20 chimeric antigen receptor and an inducible caspace 9 suicide switch to improve the effriciacy amd safety of . . . , 2013, PLoS ONE vol. 8, pp. 1-10.
Grada et al, TanCAR: a novel bispecific chimeric antigen receptor for cancer immunotherapy, 2013, Molc Therapy—Nucl Acids vol. 2, pp. e105.
Liu et al, Genetically modified adenoviral vector with the protein transduction domain of Tat improves transfer to CAR-deficient cells, 2009, Biosc Rep vol. 29, pp. 103.
Win et al, A modular and extensible RNA-based gene-regulatory platform for engineering cellular function, 2007, Proc Natl Acad Sci vol. 104, pp. 14283-14288.
Peng et al, Ectodomain shedding of Fca receptor is mediated by ADAM10 and ADAM17, 2010, Immunology vol. 130, pp. 83-91.
Zhou et al, Codon usage is an important determinant of gene expression levels largely through effects on transcription, 2016, Proc Natl Acad Sci vol. 113, pp. E6117-E6125.
Feng et al, Theophylline-dependent aptazyme as a novel tool for transgene expression regulation in mammalian cells, 2015, Molc Therap vol. 23, pp. s66.
Jensen et al, Design and implementation of adoptive therapy with chimeric antigen receptor-modified T cells, 2013, Immunol Rev vol. 257, pp. 127-144.
Kenderian et al, CD33-specific chimeric antigen receptor T cells exhibit potent preclinical activity against human acute myeoloid . . . , 2015, Blood Cancer J vol. 29, pp. 1637-1647.
Mardiros et al, T cells expression CD123-specific chimeric antigen receptors edhibit specific cytolytic effector functions and antitumor . . . , 2013, Blood vol. 122, pp. 3138-3148.
Walter et al, Acute myeloid leukemia stem cells and CD33-targeted immunotherapy, 2012, Blood vol. 119, pp. 6198-6208.
White et al., A dimer interface mutation in glyceraldehyde-3-phosphate dehydrigenase regulates its binding to AU-rich RNA, 2015, J. Biol. Chem. vol. 290, pp. 1770-1785.
Adusumilli et al., Regional Delivery of Mesothelin-Targeted CAR T-cell Therapy Generates Potent . . . Tumor Immunity, Nov. 2014, Sci. Transl. Med. 6:261ra151.
Aranda et al., Adoptive Cell Transfer for Anticancer Immunotherapy, Apr. 2015, Oncoimmunol. 3:5, e28344.
Auslander, et al., From Gene Switches to Mammalian Designer Cells: Present and Future Prospects, Mar. 2013, Trends Biotechnol. 31:155-168.
Baker et al., Structural and Dynamic Control of T-cell Receptor Specificity, Cross-Reactivity, and Binding Mechanism, 2012, Immunol. Rev. 250:10-31.
Beilstein, et al., Conditional Control of Mammalian Gene Expression by Tetracycline-Dependent Hammerhead Ribozymes, Sep. 2014, Synth. Biol. 4:526-534.
Berens, et al., RNA Aptamers as Genetic Control Devices: The Potential of Riboswitches as Synthetic Elements for Regulating Gene Expression, 2015, Biotechnol. 10:246-257.
Bonifant, et al., Toxicity and Management in CAR T-cell Therapy, 2016, Oncolytics 3:16011.
Bray, et al., On-Site CAR Parking, 2015, Sci. Transl. Med. 7:275ra22.
Brayer et al., Developing Strategies in the Immunotherapy of Leukemias, Jan. 2013, Cancer Control 20:49-59.
Brentjens, et al., Adoptive Therapy of Cancer with T cells Genetically Targeted to Tumor Associated Antigens Through . . . , May 2011, Am Soc Gene Cell Therap., presentation.
Buckley et al., Update on Antigen-Specific Immunotherapy of Acute Myeloid Leukemia, 2015, Curr. Hematol. Malig. Rep. 10:65-75.
Budde et al., Combining a CD20 Chimeric Antigen Receptor and an Inducible Caspace 9 Suicide Switch to Improve the Efficacy . . . , Dec. 2013, PLoS ONE 8:e82742.
Cantelmo, et al., Inhibition of the Glycolytic Activator PFKFB3 in Endothelium Induces Tumor Vessel Normalization . . . , Dec. 2016, Cancer Cell 30:968-985.
Caruso et al., Tuning Sensitivity of CAR to EGFR Density Limits Recognition of Normal Tissue While Maintaining . . . , 2015, Cancer Res. 75:3505-3518.
Chakravarti et al., Synthetic Biology in Cell-Based Cancer Immunotherapy, 2015, Trends Biotechnol. 33:449-461.
Chang et al., Posttranscriptional Control of T Cell Effector Function by Aerobic Glycolysis, Jun. 2013, Cell 153:1239-1251.
Chang et al., Identification and Selective Expansion of Functionally Superior T cells Expressing Chimeric Antigen Receptors, 2015, J. Transl. Med. 13:161.
Cheadle et al., CAR T cells: Driving the Road from the Laboratory to the Clinic, 2013, Immunol. Rev. 257:91-106.
Chen et al., Genetic Control of Mammalian T-cell Proliferation with Synthetic RNA Regulatory Systems, 2010, Proc. Natl Acad. Sci. 107:8531-8536.
Chen et al., Efficient Gene Editing in Primary Human T cells, Nov. 2015, Trends Immunol. 36:667-669.
Cooper et al., Moving from Tinkering in the Garage to Assembly Line Production: the Manufacture of Genetically Modified T cells . . . , 2015, Cancer Gene Therap. 22:64-66.
Darcy et al., Adoptive Immnotherapy: a New Era for the Treatment of Cancer, 2015, Immunotherap. 7:469-471.

(56) References Cited

OTHER PUBLICATIONS

Davila et al., Efficacy and Toxicity Management of 19-28z CAR T cell Therapy in B cell Acute Lymphoblastic Leukemia, Feb. 2014, Sci Transl Med 6:224ra25.
Di Stasi et al., Inducible Apoptosis as a Safety Switch for Adoptive Cell Therapy, 2011, N. Engl. J. Med. 265:1673-83.
Dotti et al., Design and Development of Therapies Using Chimeric Antigen Receptor-Expressing T cells, Jan. 2014, Immunol. Rev. 257:107-126.
Elert et al., Calling Cells to Arms, Dec. 2013, Nature 504:S2-S3.
Elfakess et al., Unique Translation Initiation of mRNAs-Containing TISU Element, Jun. 2011, Nucl. Acids. Res. 39:7598-7609.
Ellebrecht et al., Reengineering Chimeric Antigen Receptor T cells for Targeted Therapy of Autoimmune Disease, Jul. 2016, Science 353:179-184.
Farajnia et al., Development Trends for Generation of Single-Chain Antibody Fragments, Aug. 2014, Immunopharmacol. Immunotoxicol. 36:297-308.
Federov et al., PD-1 and CTLA-4 Based Inhibitory Chimeric Antigen Receptors (iCARs) Divert Off-Target Immunotherapy . . . , Dec. 2013, Sci. Transl. Med. 5:215ra172.
Festuccia et al., Allogenic Stem Cell Transplantation in Multiple Myeloma: Immunotherapy and New Drugs, Jun. 2015, Expert Opin. Biol. Therapy 15:857-872.
Garber et al., Adoptive T-cell Therapy for Leukemia, 2014, Molc. Cell. Therap. 2:25-.
Garcia-Sanz et al., Translational Control: a General Mechanism for Gene Regulation During T cell Activation, 1998, FASEB J. 12:299-306.
Ghorashian et al., CD19 Chimeric Antigen Receptor T cell Therapy for Haematological Malignancies, Mar. 2015, Brit, J. Haematol. 169:463-478.
Grada et al., TanCAR: A Novel Bispecific Chimeric Antigen Receptor for Cancer Immunotherapy, 2013, Molc. Therap. Nucl. Acids 2:e105.
Hamilton et al., Delineation of a Novel Pathway that Regulates CD154 (CD40 Ligand) Expression, 2003, Molc. Cell. Biol. 23:510-525.
Hjelm et al., Mifepristone-Inducible Transgene Expression in Neural Progenitor Cells in vitro and in vivo, 2016, Gene Therap. 23:424-437.
Horton et al., Recent Advances in Acute Myeloid Leukemia Stem Cell Biology, 2012, Haematolog. 97:966-974.
Huang et al., Driving an Improved CAR for Cancer Immunotherpy, 2016, J. Clin. Invest. 126:2795-2798.
Hudecek et al., The Nonsignaling Extracellular Spacer Domain of Chimeric Antigen Receptors is Decisive for In Vivo . . . , Sep. 2014, Cancer Immunol. Res. 3:125-135.
Hurton et al., Tethered IL-15 Augments Antitumor Activity and Promotes a Stem-Cell Memory Subset in Tumor-Specific T cells, Nov. 2016, Proc. Natl Acad Sci 113:E7788-E7797.
Hussaini et al., Targeting CD123 in AML Using a T-cell Directed Dual-Affinity Re-Targeting (DART) Platform, Nov. 2015, Blood 127:122-131.
Iwamoto et al., A General Chemical Method to Regulate Protein Stability in the Mammalian Central Nervous System, 2010, Chem Biol 17:981-988.
Jensen et al., Enhancing the IQ of CAR Modified T Cells, 2015, Powerpoint Slides.
Jensen et al., Mathematical Modeling of Chimeric TCR Triggering Predicts the Magnitude of target Lysis and its Impairment by TCR . . . , 2010, J. Immunol. 184:4284-4294.
Jensen et al., Design and Implementation of Adoptive Therapy with Chimeric Antigen Receptor-Modified T cells, 2014, Immunol. Rev. 257:127-144.
Jensen, Synthetic Immunobiology Boosts the IQ of T cells, Oct. 2015, Science 350:514-515.
Jensen et al., Designing Chimeric Antigen Receptors to Effectively and Safely Target Tumors, 2015, Curr. Opin. Immunol. 33:9-15.
Johnson et al., Rational Development and Characterization of Humanized Anti-EGFR Variant III Chimeric Antigen Receptor . . . , Feb. 2015, Sci. Transl. Med. 7:275ra22.
Juillerat et al., Design of Chimeric Antigen Receptors with Intergrated Controllable Transient Functions, 2016, Sci. Rep. 6:18950.
June, Drugging the Undruggable Ras—Immunotherapy to the Rescue? 2016, N. Eng. J. Med. 375:2286-2289.
Kakarla et al., CAR T cells for Solid Tumors: Armed and Ready to Go? Mar.-Apr. 2014, Cancer J. 20:151-155.
Kalos et al., Adoptive T cell Transfer for Cancer Immunotherapy in the Era of Synthetic Biology, Jul. 2013, Immunity 39:49-60.
Kawalekar et al., Distinct Signaling of Coreceptors Regulates Specific Metabolism Pathways and Impacts Memory Development . . . , 2016, Immunity 44:380-390.
Kebriaei et al., Future of Therapy in Acute Lymphoblastic Leukemia (ALL)—Potential Role of Immune-Based Therapies, 2015, Curr. Hematol. Malig. Rep. 10:76-85.
Kebriaei et al., Phase I Trials Using Sleeping Beuaty to Generate CD19-Specific CAR T cells, 2016, J. Clin. Invest. 126:3363-3376.
Kershaw et al., Clinical Application of Genetically Modified T cells in Cancer Therapy, May 2014, Clin. Transl. Immunol. 3:e16.
Kim et al., Highly Efficient RNA-Guided Genome Editing in Human Cells via Delivery of Purified Cas9 Ribonucleoproteins, Jun. 2014, Gen. Res. 24:1012-1019.
Kis et al., Mammalian Synthetic Biology: Emerging Medical Applications, Mar. 2015, J. R. Soc. Interface 12:20141000.
Kochenderfer et al., Chemotherapy-Refractory Diffuse Large B-cell Lymphoma and Indolent B-cell Malignancies can be Effectively . . . , Aug. 2014, J. CLin. Oncol. 33:540-549.
Ledford, T-cell Therapy Extends Cancer Survival to Years, Dec. 2015, Nature 516:156.
Liang et al., Engineering Biological Systems with Synthetic RNA Molecules, 2011, Molc. Cell 43:915-926.
Lynn et al., Targeting of Folate Receptor-beta on Acute Myeloid Leukemia Blasts with Chimeric Antigen Receptor-Expressing T cells, May 2015, Blood 125:3466-3476.
Lindsten et al., Regulation of Lymphokine Messenger RNA Stability by a Surface-Mediated T Cell Activation Pathway, 1989, Science 244:339-343.
Liu et al., Affinity Tuned ErbB2 or EGFR Chimeric Antigen Receptor T Cells Exhibit an Increased Therapeutic Index Against Tumors in Mice, Sep. 2015, Cancer Res. 75:3596-3607.
Long et al., 4-1BB Cotimulation Ameliorates T cell Exhaustion Induced by Tonic Signaling of Chimeric Antigen Receptors, Jun. 2015, Nat Med 21:581-590.
Marcus et al., Allogenic Chimeric Antigen Receptor-Modified Cells for Adoptive Cell Therapy of Cancer, Mar. 2014, Expert Opin Biol Therap 14:947-954.
Mardiros et al., T cells Expressing CD123-Specific Chimeric Antigen Receptors Exhibit Specific Cytolytic Effector Functions . . . , Sep. 2013, Blood 122:3138-3148.
Maude et al., Chimeric Antigen Receptor T cells for Sustained Remissions in Leukemia, Mar. 2014, N. Eng. J. Med. 371:1507-1517.
Maus et al., Antibody-Modified T cells: CARs Take the Front Seat for Hematologic Malignancies, Apr. 2014, Blood 123:2625-2635.
Morgan et al., Case Report of a Serious Adverse Event Following the Administration of T cells Transduced with a Chimeric Antigen Receptor . . . , 2010, Molc Therap 18:843-851.
Nagy et al., Glyceraldehyde-3-phosphate Dehydrogenase Selectively Binds AU-Rich RNA in the NAD+-Binding Region, 1995, J Biol Chem 270:2755-2763.
Nelson et al., Novel Immunotherapies for Hematologic Malignancies, Jan. 2015, Immunol. Rev. 263:90-105.
Newick et al., CAR T cell Therapy for Solid Tumors, Jul. 2016, Ann. Rev. Med. 68:3.1-3.14.
Norelli et al., Clinical Pharmacology of CAR-T cells: Linking Cellular Pharmacodynamics to Pharmacokinetics and Antitumor Effects, 2016, Biochim Biophys Acta 1865:90-100.
Okoye et al., The Protein LEM Promotes CD8+ T cell Immunity Through Effects on Mitochondrial Respiration, May 2015, Science 348:995-1001.

(56) References Cited

OTHER PUBLICATIONS

Paszkiewicz et al., Targeted Antibody-Mediated Depletion of Murine CD19 CAR T cells Permanently Reverses B cell Aplasia, 2016, J Clin Ivest 126:4262-4272.
Pizzitola et al., Chimeric Antigen Receptors Against CD33/CD123 Antigens Efficiently Target Primary Acute Myeloid Leukemia Cells in vivo, Aug. 2014, Leukemia 28:1596-1605.
Poirot et al., Multiplex Genome-Edited T-cell Manufacturing Platform for "Off-the-Shelf" Adoptive T-cell Immunotherapies, 2015, Cancer Res 75:3853-3864.
Posey et al., Engineered CAR T cells Targeting the Cancer-Associated Tn-Glycoform of the Membrane Mucin MUC1 Control Adenocarcinoma, 2016, Immunity 44:1444-1454.
Qin et al., Systematic Comparison of Constitutive Promoters and the Doxycycline-Inducible Promoter, 2010, PLoS ONE 5:e10611.
Rakhit et al., Chemical Biology Strategies for Posttranslational Control of Protein Function, Sep. 2014, Chem Biol 21:1238-1252.
Reddy, Changing Landscape of Immuno-Oncology: CAR-T Therapy and PD1/PDL1 Blockade, 2016, Boston University Theses.
Rodgers et al., Switch-Mediated Activation and Retargeting of CAR-T cells for B-cell Malignancies, 2016, Proc Natl Acad Sci 113:E459-E468.
Rosenberg, Cell Transfer Immunotherapy for Metastataic Solid Cancer—What Clinicians Need to Know, 2011, Nat Rev Clin Oncol 8:577-585.
Rosenberg et al., Adoptive Cell Transfer as Personalized Immunotherapy for Human Cancer, Apr. 2015, Science 348:62-68.
Roybal et al., Precision Tumor Recognition by T cells with Combinatorial Antigen-Sensing Circuits, 2016, Cell 164:770-779.
Roybal et al., Engineering T cells with Customized Therapeutic Response Programs Using Synthetic Notch Receptors, 2016, Cell 167:1-14.
Sadelain et al., Sage Harbours for the Integration of New DNA in the Human Genome, 2012, Nat. Rev. 12:51-58.
Shi et al., Chimeric Antigen Receptor for Adoptive Immunotherapy of Cancer: Latest Research and Future Prospects, Sep. 2014, Molc Cancer 13:219.
Sommermeyer et al., Chimeric Antigen Receptor-Modified T cells Derived from Defined CD8+ and CD4+ Subsets Confer Superior Antitumor . . . , Feb. 2016 Leukemia 30:492-500.
Srivastava et al., Engineering CAR-T cells: Design Concepts, Aug. 2015, Trends Immunol 36:494-502.
Sun et al., The Quest for Spatio-Temporal Control of CAR T cells, Dec. 2015, Cell Res. 25:1281-1282.
Tettamanti et al., CD123 AML Targeting by Chimeric Antigen Receptors: A Novel Magic Bullet for AML Therapeutics? May 2014, Oncolimmunol 3:e28835.
Till et al., Adoptive Immunotherapy for Idolent Non-Hodgkin Lymphoma and Mantle Cell Lymphoma Using Genetically Modified . . . , 2008, Blood 112:2261-2271.
Turatti et al., Redirected Activity of Human Antitumor Chimeric Immune Receptors is Governed by Antigen and Receptor Expression Levels . . . , 2007, J Immunotherap 30:684-693.
Turtle et al., CD19 CAR-T cells of Defined CD4+:CD8+ Composition in Adult B cell ALL Patients, 2016, J Clin Ivest 126:2123-2138.
Turtle et al., Immunotherapy of Non-Hodgkin's Lymphoma with a Defined Ratio of CD8+ and CD4+ CD19-Specific Chimeric Antigen Receptor . . . , 2016, Sci Transl Med 8:355ra116.
Vanderlugt et al., Epitope Spreading in Immune-Mediated Diseases: Implications for Immunotherapy, 2002, Nat Rev 2:85-95.
Vigano et al., Functional Avidity: a Measure to Predict the Efficacy of Effector T cells? 2012, Clin Develop Immunol 2012:153863.
Wang et al., ZAP-70: An Essential Kinase in T-cell Signaling, 2010, Cold Spring Barb Perspect Biol 2:a002279.
Wang et al., One-Step Generation of Mice Carrying Mutations in Multiple Genes by CRISPR/Cas-Mediated Genome Engineering, 2013, Cell 153:910-918.
Wang et al., Manufacture of tumor- and virus-specific T lymphocytes for adoptive cell therapies, Feb. 2015, Cancer Gene Therapy 22:85-94.
Watanabe et al., Target Antigen Density Governs the Efficacy of Anti-CD20-CD28-CD3 Zeta Chimeric Antigen Receptor-Modified . . . , Dec. 2014, J Immunol 194:911-920.
Weigand et al., Tetracycline Aptamer-Controlled Regulation of Pre-mRNA Splicing in Yeast, 2007, Nucl Acids Res 35:4179-4185.
Win et al., A Modular and Extensible RNA-Based Gene-Regulatory Platform for Engineering Cellular Function, 2007, Proc Natl Acad Sci 104:14283-14288.
Win et al., Frameworks for Programming Biological Function Through RNA Parts and Devices, 2009, Chem Biol 16:298-310.
Wu et al., Remote Control of Therapeutic T cells Through a Small Molecule-Gated Chimeric Receptor, Sep. 2015, Science 350:aab4077.
Xie et al., Mammalian Designer Cells: Engineering Principles and Biomedical Applications, Jul. 2015, Biotechnol J 10:1005-1018.
Xie et al., Synthetic Biology—Application-Oriented Cell Engineering, 2016, Curr. Opin. Biotechnol. 40:139-148.
Ye et al., Synthetic Mammalian Gene Circuits for Biomedical Applications, 2013, Curr. Opin. Chem Biol 17:910-917.
Zhao et al., Structural Design of Engineered Costimulation Determines Tumor Rejection Kinetics and Persistence of CAR T cells, Oct. 2015, Cancer Cell 28:415-428.
Zheng et al., Protein L: A Novel Reagent for the Detection of Chimeric Antigen Receptor (CAR) Expression by Flow Cytometry, 2012, J Transl Med 10:29.
Zhong et al., Rational Design of Aptazyme Riboswitches for Efficient Control of Gene Expression in Mammalian Cells, Nov. 2016, eLife 5:e18858.
Auslander et al., A ligand-dependent hammerhead ribozyme switch for controlling mammalian gene expression, Molc. Biosys. vol. 6, pp. 807-814 (2010).
Chen et al, Selective degradation of early-response gene mRNAs: functional analysis of sequence features of the AU-rich elements, 1994, Mol Cell Biol vol. 14, pp. 8471-8482.
Drury et al, FasL expression in activated T-lymphocytes involves HuR mediated stabilization, 2010, J. Biol. Chem. vol. 285, pp. 31130-31138.
Larsen et al, Sensitivity to restimulation-induced cell death is linked to glycolytic metabolism in human T-cells, 2016, J. Immunol. vol. 198, pp. 147-155.
Christopherson et al., Classfication of AML using a monoclonal antibody microarray, 2006, Meth in Mocl Med vol. 125, pp. 241-251.
Kloss et al, Combinatorial antigen recognition with balanced signalling promotes selective tumor eradication . . . , 2013, Nat Biotechnol vol. 31, pp. 71-75.
Kondo et al., Binding of glyceraldehyde-3-phosphate dehydrogenase to the cis-acting element of structure-anchored . . . , 2011, Blochem Biophys Res Comm vol. 405, pp. 382-387.
Palmer et al, Glucose metabolism regulates T cell activation, differentiation, and functions, 2015, Frontiers Immunol vol. 5, pp. 1-6.
Aldape et al., Glioblastoma: pathology, molecular mechanisms and markers, Acta Neuropathol., 2015, vol. 129, pp. 829-848.
Chester et al., 4-1BB agonism: adding the accelerator to cancer immunotherapy, 2016, Cancer Immunol Immunother vol. 65, pp. 1243-1248.
Garrett, Using patient-derived gliomaspheres to moleculary charaterize and dissect distinctive . . . , 2016, UCLA Electronic Theses and Dissertations.
Kovarik et al, Posttranscriptional regulation of cytokine expression, 2017, Cytokine vol. 89, pp. 21-26.
Mardiana et al., A multifunctional role for adjuvant anti-4-1BB therapy in augmenting antitumor responses by CAR T cells, 2018, AACR Ann Mtg Abst 1530.
Rodriguez et al., Chimeric antigen receptor T-cell therpy for glioblastoma, 2017, Translational Res Sep. 2017, pp. 93-102.
Wang et al, Metabolic checkpoints in activated T cells, 2012, Nature Immunol. vol. 13, pp. 907-915.

(56) References Cited

OTHER PUBLICATIONS

Wieten et al, A novel heat shock protein coinducer boosts stress protein Hsp70 to activate T cell regulation of inflammation . . . , 2010, Arth Rheum vol. 62, pp. 1026-1035.

* cited by examiner

SEQUENCE LISTING

```
Sequence total quantity: 42
SEQ ID NO: 1            moltype = DNA  length = 1401
FEATURE                 Location/Qualifiers
misc_feature            1..1401
                        note = Chimeric Antigen Receptor
source                  1..1401
                        mol_type = other DNA
```

-continued

```
                        organism = synthetic construct
SEQUENCE: 1
gacatcgtga tgacccagag ccccgacagc ctggccgtga gcctgggcga gagggccacc  60
atcaactgca agagcagcca gagcctgctg aacagcggcg accagaagaa ctacctgacc  120
tggtaccagc agaagcccgg ccagcccccc aagctgctga tctactgggc cagcaccagg  180
gagagcggcg tgcccgacag gttcagcggc agcggcagcg gcaccgactt caccctgacc  240
atcagcagcc tgcaggccga ggacgtggcc gtgtactact gccagaacga ctacagctac  300
cccctgacct tcggccaggg caccaaggtg gagatcaagg gcggcggcgg cagcggcggc  360
ggcggcagcg gcggcggcgg cagccaggtg cagctggtgc agagcggcgc cgaggtgaag  420
aagaccggca gcagcgtgaa ggtgagctgc aaggccagcg gctacacctt caccgaccac  480
gccatccact gggtgaggca ggcccccggc caggccctgg agtggatggg ccacttcagc  540
cccggcaaca ccgacatcaa gtacaacgac aagttcaagg gcagggtgac cctgaccgtg  600
gacaggagca tgagcaccgc ctacatggag ctgagcagcc tgaggagcga ggacaccgcc  660
atgtactact gcaagaccag caccttcttc ttcgactact ggggccaggg caccatggtg  720
accgtgagca gcaccacgac gccagcgccg cgaccaccaa caccggcgcc caccatcgcg  780
tcgcagcccc tgtccctgcg cccagaggcg tgccggccag cggcgggggg cgcagtgcac  840
acgagggggc tggacttcgc ctgtgatatc tacatctggg cgcccttggc cgggacttgt  900
ggggtccttc tcctgtcact ggttatcacc ctttactgca aacggggcag aaagaaactc  960
ctgtatatat tcaaacaacc atttatgaga ccagtacaaa ctactcaaga ggaagatggc  1020
tgtagctgcc gatttccaga agaagaagaa ggaggatgtg aactgagagt gaagttcagc  1080
aggagcgcag acgcccccgc gtacaagcag ggccagaacc agctctataa cgagctcaat  1140
ctaggacgaa gagaggagta cgatgttttg gacaagagac gtggccggga ccctgagatg  1200
gggggaaagc cgagaaggaa gaaccctcag gaaggcctgt acaatgaact gcagaaagat  1260
aagatggcgg aggcctacag tgagattggg atgaaaggcg agcgccggag gggcaagggg  1320
cacgatggcc tttaccaggg tctcagtaca gccaccaagg acacctacga cgcccttcac  1380
atgcaggccc tgccccctcg c                                            1401

SEQ ID NO: 2            moltype = AA  length = 488
FEATURE                 Location/Qualifiers
REGION                  1..488
                        note = Chimeric Antigen Receptor
source                  1..488
                        mol_type = protein
                        organism = synthetic construct
SEQUENCE: 2
MALPVTALLL PLALLLHAAR PDIVMTQSPD SLAVSLGERA TINCKSSQSL LNSGDQKNYL  60
TWYQQKPGQP PKLLIYWAST RESGVPDRFS GSGSGTDFTL TISSLQAEDV AVYYCQNDYS  120
YPLTFGQGTK VEIKGGGGSG GGGSGGGGSQ VQLVQSGAEV KKTGSSVKVS CKASGYTFTD  180
HAIHWVRQAP GQALEWMGHF SPGNTDIKYN DKFKGRVTLT VDRSMSTAYM ELSSLRSEDT  240
AMYYCKTSTF FFDYWGQGTM VTVSSTTTPA PRPPTPAPTI ASQPLSLRPE ACRPAAGGAV  300
HTRGLDFACD IYIWAPLAGT CGVLLLSLVI TLYCKRGRKK LLYIFKQPFM RPVQTTQEED  360
GCSCRFPEEE EGGCELRVKF SRSADAPAYK QGQNQLYNEL NLGRREEYDV LDKRRGRDPE  420
MGGKPRRKNP QEGLYNELQK DKMAEAYSEI GMKGERRRGK GHDGLYQGLS TATKDTYDAL  480
HMQALPPR                                                          488

SEQ ID NO: 3            moltype = DNA  length = 60
FEATURE                 Location/Qualifiers
misc_feature            1..60
                        note = Signal sequence
source                  1..60
                        mol_type = other DNA
                        organism = synthetic construct
SEQUENCE: 3
gccttaccag tgaccgcctt gctcctgccg ctggccttgc tgctccacgc cgccaggccg  60

SEQ ID NO: 4            moltype = DNA  length = 5402
FEATURE                 Location/Qualifiers
misc_feature            1..5402
                        note = Gold CAR construct
source                  1..5402
                        mol_type = other DNA
                        organism = synthetic construct
SEQUENCE: 4
tctggttaga ccagatctga gcctgggagc tctctggcta actagggaac ccactgctta  60
agcctcaata aagcttgcct tgagtgcttc aagtagtgtg tgcccgtctg ttgtgtgact  120
ctggtaacta gagatccctc agaccctttt agtcagtgtg gaaaatctct agcagtggcg  180
cccgaacagg gacctgaaag cgaaagggaa accagagctc tctcgacgca ggactcggct  240
tgctgaagcg cgcacggcaa gaggcgaggg gcggcgactg gtgagtacgc caaaaatttt  300
gactagcgga ggctagaagg agagagatgg gtgcgagagc gtcagtatta agcgggggag  360
aattagatcg cgatgggaaa aaattcggtt aaggccaggg ggaaagaaaa aatataaatt  420
aaaacatata gtatgggcaa gcagggagct agaacgattc gcagttaatc ctggcctgtt  480
agaaacatca gaaggctgta gacaaatact gggacagcta caaccatccc ttcagacagg  540
atcagaagaa cttagatcat tatataatac agtagcaacc ctctattgtg tgcatcaaag  600
gatagagata aaagacacca aggaagcttt agacaagata gaggaagagc aaaacaaaag  660
taagaccacc gcacagcaag cggccactga tcttcagacc tggaggagga gatatgaggg  720
acaattggag aagtgaatta tataaatata aagtagtaaa aattgaacca ttaggagtag  780
cacccaccaa ggcaaagaga agagtggtgc agagagaaaa aagagcagtg ggaataggag  840
ctttgttcct tgggttcttg ggagcagcag gaagcactat gggcgcagcc tcaatgacgc  900
tgacggtaca ggccagacaa ttattgtctg gtatagtgca gcagcagaac aatttgctga  960
```

```
gggctattga ggcgcaacag catctgttgc aactcacagt ctggggcatc aagcagctcc  1020
aggcaagaat cctggctgtg gaaagatacc taaaggatca acagctcctg gggatttggg  1080
gttgctctgg aaaactcatt tgcaccactg ctgtgccttg gaatgctagt tggagtaata  1140
aatctctgga acagattgga atcacacgac ctggatggag tgggacagag aaattaacaa  1200
ttacacaagc ttaatacact ccttaattga agaatcgcaa aaccagcaag aaaagaatga  1260
acaagaatta ttggaattag ataaatgggc aagtttgtgg aattggttta acataacaaa  1320
ttggctgtgg tatataaaat tattcataat gatagtagga ggcttggtag gtttaagaat  1380
agtttttgct gtactttcta tagtgaatag agttaggcag ggatattcac cattatcgtt  1440
tcagacccac ctcccaaccc cgaggggacc cgacaggccc gaaggaatag aagaagaagg  1500
tggagagaga gacagagaca gatccattcg attagtgaac ggatctcgac ggtatcggtt  1560
aacttttaaa agaaaagggg ggattggggg gtacagtgca ggggaaagaa tagtagacat  1620
aatagcaaca gacatacaaa ctaaagaatt acaaaaacaa attacaaaaa ttcaaaattt  1680
tatctcgagg tttaaacggg gttggggttg cgccttttcc aaggcagccc tgggtttgcg  1740
cagggacgcg gctgctctgg gcgtggttcc gggaaacgca gcggcgccga ccctgggtct  1800
cgcacattct tcacgtccgt tcgcagcgtc acccggatct tcgccgctac ccttgtgggc  1860
cccccggcga cgcttcctgc tccgccccta agtcgggaag gttccttgcg gttcgcggcg  1920
tgccggacgt gacaaacgga agccgcacgt ctcactagta ccctcgcaga cggacagcgc  1980
cagggagcaa tggcagcgcg ccgaccgcga tgggctgtgg ccaatagcgg ctgctcagca  2040
gggcgcgccg agagcagcgg ccgggaaggg gcggtgcggg aggcggggtg tggggcggta  2100
gtgtgggccc tgttcctgcc cgcgcggtgt tccgcattct gcaagcctcc ggagcgcacg  2160
tcggcagtcg gctccctcgt tgaccgaatc accgacctct ctccccagcg ctagcgctac  2220
cggtcgccaa gatggcggcg gtgagcaagg gcgaggagga taacatggcc atcatcaagg  2280
agttcatgcg cttcaaggtg cacatggagg gctccgtgaa cggccacgag ttcgagatcg  2340
agggcgaggg cgagggccgc ccctacgagg gcacccagac cgccaagctg aaggtgacca  2400
agggtggccc cctgcccttc gcctgggaca tcctgtcccc tcagttcatg tacggctcca  2460
aggcctacgt gaagcacccc gccgacatcc ccgactactt gaagctgtcc ttccccgagg  2520
gcttcaagtg ggagcgcgtg atgaacttcg aggacggcgg cgtggtgacc gtgacccagg  2580
actcctccct gcaggacggc gagttcatct acaaggtgaa gctgcgcggc accaacttcc  2640
cctccgacgg ccccgtaatg cagaagaaga ccatgggctg ggaggcctcc tccgagcgga  2700
tgtaccccga ggacggcgcc ctgaagggcg agatcaagca gaggctgaag ctgaaggacg  2760
gcggccacta cgacgctgag gtcaagacca cctacaaggc caagaagccc gtgcagctgc  2820
ccggcgccta caacgtcaac atcaagttgg acatcacctc ccacaacgag gactacacca  2880
tcgtggaaca gtacgaacgc gccgagggcc gccactccac cggcggcatg gacgagctgt  2940
acaagggcag cggagagggt aggggtagtc ttttgacgtg tggggacgtc gaggaaaatc  3000
ctgggcctgc cttaccagtg accgccttgc tcctgccgct ggccttgctg ctccacgccg  3060
ccaggccgga catcgtgatg acccagagcc ccgacagcct ggccgtgagc ctgggcgaga  3120
gggccaccat caactgcaag agcagccaga gcctgctgaa cagcggcgac cagaagaact  3180
acctgacctg gtaccagcag aagcccggcc agccccccaa gctgctgatc tactgggcca  3240
gcaccaggga gagcggcgtg cccgacaggt tcagcggcag cggcagcggc accgacttca  3300
ccctgaccat cagcagcctg caggccgagg acgtggccgt gtactactgc cagaacgact  3360
acagctaccc cctgaccttc ggccagggca ccaaggtgga gatcaagggc ggcggcggca  3420
gcggcggcgg cggcagcggc ggcggcggca gccaggtgca gctggtgcag agcggcgccg  3480
aggtgaagaa gaccggcagc agcgtgaagg tgagctgcaa ggccagcggc tacaccttca  3540
ccgaccacgc catccactgg gtgaggcagg cccccggcca ggccctggag tggatgggcc  3600
acttcagccc cggcaacacc gacatcaagt acaacgacaa gttcaagggc agggtgaccc  3660
tgaccgtgga caggagcatg agcaccgcct acatggagct gagcagcctg aggagcgagg  3720
acaccgccat gtactactgc aagaccagca ccttcttctt cgactactgg ggccagggca  3780
ccatggtgac cgtgagcagc accacgacgc cagcgccgcg accaccaaca ccggcgccca  3840
ccatcgcgtc gcagcccctg tccctgcgcc cagaggcgtg ccggccagcg gcgggggggcg  3900
cagtgcacac gagggggctg gacttcgcct gtgatatcta catctgggcg cccttggccg  3960
ggacttgtgg ggtccttctc ctgtcactgg ttatcaccct ttactgcaaa cggggcagaa  4020
agaaactcct gtatatattc aaacaaccat ttatgagacc agtacaaact actcaagagg  4080
aagatggctg tagctgccga tttccagaag aagaagaagg aggatgtgaa ctgagagtga  4140
agttcagcag gagcgcagac gcccccgcgt acaagcaggg ccagaaccag ctctataacg  4200
agctcaatct aggacgaaga gaggagtacg atgttttgga caagagacgt ggccgggacc  4260
ctgagatggg gggaaagccg agaaggaaga accctcagga aggcctgtac aatgaactgc  4320
agaaagataa gatggcggag gcctacagtg agattgggat gaaaggcgag cgccggaggg  4380
gcaaggggca cgatggcctt taccagggtc tcagtacagc caccaaggac acctacgacg  4440
cccttcacat gcaggccctg ccccctcgct gaagagacgt cataatcagc cagcggccgc  4500
gtcgacaatc aacctctgga ttacaaaatt tgtgaaagat tgactggtat tcttaactat  4560
gttgctcctt ttacgctatg tggatacgct gctttaatgc ctttgtatca tgctattgct  4620
tcccgtatgg ctttcatttt ctcctccttg tataaatcct ggttgctgtc tctttatgag  4680
gagttgtggc ccgttgtcag gcaacgtggc gtggtgtgca ctgtgtttgc tgacgcaacc  4740
cccactggtt ggggcattgc caccacctgt cagctccttt ccgggacttt cgctttcccc  4800
ctccctattg ccacggcgga actcatcgcc gcctgccttg cccgctgctg gacaggggct  4860
cggctgttgg gcactgacaa ttccgtggtg ttgtcgggga aatcatcgtc ctttccttgg  4920
ctgctcgcct gtgttgccac ctggattctg cgcgggacgt ccttctgcta cgtcccttcg  4980
gccctcaatc cagcggacct tccttcccgc ggcctgctgc cggctctgcg gcctcttccg  5040
cgtcttcgcc ttcgccctca gacgagtcgg atctcccttt gggccgcctc cccgcctggt  5100
acctttaaga ccaatgactt acaaggcagc tgtagatctt agccactttt taaaagaaaa  5160
ggggggactg gaagggctaa ttcactccca acgaaaataa gatctgcttt ttgcttgtac  5220
tgggtctctc tggttagacc agatctgagc ctgggagctc tctggctaac tagggaaccc  5280
actgcttaag cctcaataaa gcttgccttg agtgcttcaa gtagtgtgtg cccgtctgtt  5340
gtgtgactct ggtaactaga gatccctcag accctttag tcagtgtgga aaatctctag  5400
ca                                                                5402
```

```
SEQ ID NO: 5            moltype = DNA  length = 7758
FEATURE                 Location/Qualifiers
misc_feature            1..7758
```

-continued

```
                         note = Gold CAR construct
source                   1..7758
                         mol_type = other DNA
                         organism = synthetic construct
SEQUENCE: 5
tctggttaga ccagatctga gcctgggagc tctctggcta actagggaac ccactgctta  60
agcctcaata aagcttgcct tgagtgcttc aagtagtgtg tgcccgtctg ttgtgtgact  120
ctggtaacta gagatccctc agaccctttt agtcagtgtg gaaaatctct agcagtggcg  180
cccgaacagg gacctgaaag cgaaagggaa accagagctc tctcgacgca ggactcggct  240
tgctgaagcg cgcacggcaa gaggcgaggg gcggcgactg gtgagtacgc caaaaatttt  300
gactagcgga ggctagaagg agagagatgg gtgcgagagc gtcagtatta agcgggggag  360
aattagatcg cgatgggaaa aaattcggtt aaggccaggg ggaaagaaaa aatataaatt  420
aaaacatata gtatgggcaa gcagggagct agaacgattc gcagttaatc ctggcctgtt  480
agaaacatca gaaggctgta gacaaatact gggacagcta caaccatccc ttcagacagg  540
atcagaagaa cttagatcat tatataatac agtagcaacc ctctattgtg tgcatcaaag  600
gatagagata aaagacacca aggaagcttt agacaagata gaggaagagc aaaacaaaag  660
taagaccacc gcacagcaag cggccactga tcttcagacc tggaggagga gatatgaggg  720
acaattggag aagtgaatta tataaatata aagtagtaaa aattgaacca ttaggagtag  780
cacccaccaa ggcaaagaga agagtggtgc agagagaaaa aagagcagtg ggaataggag  840
ctttgttcct tgggttcttg ggagcagcag gaagcactat gggcgcagcc tcaatgacgc  900
tgacggtaca ggccagacaa ttattgtctg gtatagtgca gcagcagaac aatttgctga  960
gggctattga ggcgcaacag catctgttgc aactcacagt ctggggcatc aagcagctcc  1020
aggcaagaat cctggctgtg gaaagatacc taaaggatca acagctcctg gggatttggg  1080
gttgctctgg aaaactcatt tgcaccactg ctgtgccttg gaatgctagt tggagtaata  1140
aatctctgga acagattgga atcacacgac ctggatggag tgggacagag aaattaacaa  1200
ttacacaagc ttaatacact ccttaattga agaatcgcaa aaccagcaag aaaagaatga  1260
acaagaatta ttggaattag ataaatgggc aagtttgtgg aattggttta acataacaaa  1320
ttggctgtgg tatataaaat tattcataat gatagtagga ggcttggtag gtttaagaat  1380
agtttttgct gtactttcta tagtgaatag agttaggcag ggatattcac cattatcgtt  1440
tcagacccac ctcccaaccc cgaggggacc cgacaggccc gaaggaatag aagaagaagg  1500
tggagagaga gacagagaca gatccattcg attagtgaac ggatctcgac ggtatcggtt  1560
aacttttaaa agaaaagggg ggattggggg gtacagtgca ggggaaagaa tagtagacat  1620
aatagcaaca gacatacaaa ctaaagaatt acaaaaacaa attacaaaaa ttcaaaattt  1680
tatctcgagt agttgtgaac ttacacttta ttcatatata ttagatattg ataattttaa  1740
caaatgagtt actttccatt tgggtacagt cacagttgtc aacaatattt ggaagcacca  1800
ggcatgaaat ctcctgagat gctatgtttt catcagggtc acctgacaca ttcaagttct  1860
gtctgacatg ccattaaagc actggctcag attgcaggca tattttcaaa ccggcagtaa  1920
ctggatagta tcacttcact tataagtgtt cattgtatca tcaagtgaaa taaacacaca  1980
acccatggga tcttgcttag gttggctgcc tagttggccc ctgagataaa gccttgtaat  2040
cacatagcct tgcctaatta gtcagaaaac aaaggattaa gtgagacagt cacaggatat  2100
aggaattata aataatacat atattaatag atattcattt tcattacaca aaagttgcta  2160
ttataaatac ttatttgatt gatgagtcta aaaatatatt ccccatataa ataatgttaa  2220
atattaataa atagatttag atttaaaatt caaatattgc aggcaggaca accacccggg  2280
ttaacttgca ttcaaatatg acattaccct atcaattgta acggccctga ttctaaaagc  2340
atgcaaaagt atacacagct ttatttttgt cttgtaaaaa tcaggttctt caagagagct  2400
tttttgagga accgtttcag aattaaaatt aagagcttgc atcagctcat caataacggc  2460
aagcatattc tgatcaagga atatctgtcg cttggggtcc atcaaaagtt ttgcgttcat  2520
tgtcttgaac tcaacctggt acatcttaag atcttcatat atagaagaca agcacagggc  2580
catcataaag cttgttttgc ggctggccaa acaagatcca ttggtaatga aagaagtctc  2640
tctggaattg agacaagatt cgtttttagt gagttccagt ggcaggcatg cctccacggt  2700
ggatgttttg tccttagtaa tatcttcgtg gtctatttcc tcacttgtgc aagggtaaaa  2760
ttcaagtgtt tgtcgggcct tctggagcat gttggagaca gccctaagca agttttgaga  2820
gtggtgaaga catgggaaca tgcctgggtc tggggttgca acaggcaagt tccgagaacc  2880
gcccccacca ccacctgagc atgggacaga tgcccattcg ctccagctag atgagtagta  2940
tctgtcttgg gctctgacac ttatgcttgc gttctttctg caaatgactg ttgcagacgt  3000
tttatcagtg aaaacccgat ctttcttttc cctttttgat ttccttgcaa cctggacaca  3060
aaatgtcaaa ctaaagtaag agtgcggagt tgaccaggtg tcggggtact cccaagaaac  3120
ttcaacctgg cgtgagttct tcaaaggctt aagctgcaga ttcttcggag gatcgggctt  3180
gataatgtcc cggataaaaa agctgctcgt gtaattttca tacttcaact tgtgtacggc  3240
gtcaaccatc acctctattg gcaggctctc ctctgctgcg gggcaagcgg agtcttcctg  3300
gcattccacg ctatattcgt attctttgtt gtcccccgt accctctccg cagaaagcgt  3360
agcagcaccg cacgttacac cttgtgggtc actggaaccc ctactagact taacagaaaa  3420
cgtaagatcc gtagagattg ttgtcaacca ccagcaagta aagcgtccgg agtaattttt  3480
tgcttcacag cgcagaaacg ttttgttttt gggttctttc tgatccttaa ggatatctgt  3540
actccaaatg ccatcctctt ttttgtgcag gagcagcagg ctgtgagaaa ggacctcgcc  3600
tcccttatgg cacgtatact gcccggcatc tccaaactct tttacctgga tagtaagtgt  3660
tttgccgctg ccaagcacct ctgagctttg gtccagggtc caggttatcc catcttcttc  3720
aggtgtatcg caggtgagga ccaccatctc gcccggtgcg tcgggatacc aatccaattc  3780
aacaacatat acgtctttct taagttccca aatagcgacc aatggtgacg ccagaaaaac  3840
aagtgagaac caagagatta ccagttgttg atggcacatg gtgggaattc ctggaattcg  3900
agcttccatt atataccctc tagagtctag atctacgcct tctgtatgaa acagtttttc  3960
ctccacgcct tctgtatgaa acagtttttc ctccacgcct tctgtatgaa acagtttttc  4020
ctccgtttaa acgtaagtca ttggtcttaa aggtagcttt atttagtctc cagaaaaagg  4080
ggggaatgaa agaccccacc tgtaggtttg gcaagctagg atcaaggtta ggaacagaga  4140
gacagcagaa tatgggccaa acaggatatc tgtggtaagc agttcctgcc ccggctcagg  4200
gccaagaaca gttggaacag cagaatatgg gccaaacagg atatctgtgg taagcagttc  4260
ctgccccggc tcagggccaa gaacagatgg tccccagatg cggtcccgcc ctcagcagtt  4320
tctagagaac catcagatgt ttccagggtg ccccaaggac ctgaaatgac cctgtgcctt  4380
atttgaacta accaatcagt tcgcttctcg cttctgttcg cgcgcttctg ctccccgagc  4440
```

-continued

```
tcaataaaag agcccacgct agcgctaccg gtcgccaaga tgggggcagg tgccaccggc  4500
cgcgcaatgg atggtccgcg tctactgctg ttactacttc tgggtgtgtc ccttggaggt  4560
gccaaagagg catgccccac aggtctatac acacatagcg gtgaatgctg caaagcatgc  4620
aacctgggcg aaggtgtggc ccaaccttgt ggagccaatc aaaccgtttg tgagccatgt  4680
ctggacagcg tgacgttctc cgatgttgtt agcgcgaccg agccatgcaa accgtgtacc  4740
gagtgtgttg gtctccaaag tatgtcggcg ccgtgcgtgg aggccgacga cgccgtgtgt  4800
cgctgtgcct acggttatta ccaggatgaa actactggtc gctgtgaagc gtgccgcgtg  4860
tgtgaggcgg gctcaggcct cgtgttctcc tgtcaggaca aacagaacac tgtgtgtgaa  4920
gaatgccccg acggtactta ttccgacgag gccaaccatg tggacccgtg tctgccctgc  4980
accgtttgcg aggataccga gcgccagcta cgtgagtgca cacgttgggc cgacgccgag  5040
tgcgaggaaa tccctggccg ttggattaca cggtccacac caccagaagg ctcggacagc  5100
acagcaccca gcactcagga acctgaggca cctccagaac aagacctaat agccagcact  5160
gtggcaggtg ttgtgactac agtgatgggt agctcacaac ccgttgttac tcgaggcacc  5220
accgacaatc taattcctgt ctattgttcc atcctggctg ctgtggttgt gggtcttgtt  5280
gcatatatag ccttcaagag gggcagcgga gagggtaggg gtagtctttt gacgtgtggg  5340
gacgtcgagg aaaatcctgg gcctgcctta ccagtgaccg ccttgctcct gccgctggcc  5400
ttgctgctcc acgccgccag gccggacatc gtgatgaccc agagccccga cagcctggcc  5460
gtgagcctgg gcgagagggc caccatcaac tgcaagagca gccagagcct gctgaacagc  5520
ggcgaccaga agaactacct gacctggtac cagcagaagc ccggccagcc ccccaagctg  5580
ctgatctact gggccagcac cagggagagc ggcgtgcccg acaggttcag cggcagcggc  5640
agcggcaccg acttcaccct gaccatcagc agcctgcagg ccgaggacgt ggccgtgtac  5700
tactgccaga acgactacag ctacccctg accttcggcc agggcaccaa ggtggagatc  5760
aagggcggcg gcggcagcgg cggcggcggc agcggcggcg gcggcagcca ggtgcagctg  5820
gtgcagagcg gcgccgaggt gaagaagacc ggcagcagcg tgaaggtgag ctgcaaggcc  5880
agcggctaca ccttcaccga ccacgccatc cactgggtga ggcaggcccc cggccaggcc  5940
ctggagtgga tgggccactt cagccccggc aacaccgaca tcaagtacaa cgacaagttc  6000
aagggcaggg tgaccctgac cgtggacagg agcatgagca ccgcctacat ggagctgagc  6060
agcctgagga gcgaggacac cgccatgtac tactgcaaga ccagcacctt cttcttcgac  6120
tactggggcc agggcaccat ggtgaccgtg agcagcacca cgacgccagc gccgcgacca  6180
ccaacaccgg cgcccaccat cgcgtcgcag cccctgtccc tgcgcccaga ggcgtgccgg  6240
ccagcggcgg ggggcgcagt gcacacgagg gggctggact tcgcctgtga tatctacatc  6300
tgggcgccct tggccgggac ttgtggggtc cttctcctgt cactggttat caccctttac  6360
tgcaaacggg gcagaaagaa actcctgtat atattcaaac aaccatttat gagaccagta  6420
caaactactc aagaggaaga tggctgtagc tgccgatttc cagaagaaga agaaggagga  6480
tgtgaactga gagtgaagtt cagcaggagc gcagacgccc ccgcgtacaa gcagggccag  6540
aaccagctct ataacgagct caatctagga cgaagagagg agtacgatgt tttggacaag  6600
agacgtggcc gggaccctga gatgggggga aagccgagaa ggaagaaccc tcaggaaggc  6660
ctgtacaatg aactgcagaa agataagatg gcggaggcct acagtgagat tgggatgaaa  6720
ggcgagcgcc ggaggggcaa ggggcacgat ggcctttacc agggtctcag tacagccacc  6780
aaggacacct acgacgccct tcacatgcag gccctgcccc ctcgctgaag agacgtcata  6840
atcagccagc ggccgcgtcg acaatcaacc tctggattac aaaatttgtg aaagattgac  6900
tggtattctt aactatgttg ctccttttac gctatgtgga tacgctgctt taatgccttt  6960
gtatcatgct attgcttccc gtatggcttt cattttctcc tccttgtata aatcctggtt  7020
gctgtctctt tatgaggagt tgtggcccgt tgtcaggcaa cgtggcgtgg tgtgcactgt  7080
gtttgctgac gcaaccccca ctggttgggg cattgccacc acctgtcagc tcctttccgg  7140
gactttcgct ttccccctcc ctattgccac ggcggaactc atcgccgcct gccttgcccg  7200
ctgctggaca ggggctcggc tgttgggcac tgacaattcc gtggtgttgt cggggaaatc  7260
atcgtccttt ccttggctgc tcgcctgtgt tgccacctgg attctgcgcg ggacgtcctt  7320
ctgctacgtc ccttcggccc tcaatccagc ggaccttcct tcccgcggcc tgctgccggc  7380
tctgcggcct cttccgcgtc ttcgccttcg ccctcagacg agtcggatct ccctttgggc  7440
cgcctccccg cctggtacct ttaagaccaa tgacttacaa ggcagctgta gatcttagcc  7500
actttttaaa agaaaagggg ggactggaag ggctaattca ctcccaacga aaataagatc  7560
tgctttttgc ttgtactggg tctctctggt tagaccagat ctgagcctgg gagctctctg  7620
gctaactagg gaacccactg cttaagcctc aataaagctt gccttgagtg cttcaagtag  7680
tgtgtgcccg tctgttgtgt gactctggta actagagatc cctcagaccc ttttagtcag  7740
tgtggaaaat ctctagca                                                7758

SEQ ID NO: 6            moltype = DNA  length = 6735
FEATURE                 Location/Qualifiers
misc_feature            1..6735
                        note = Gold CAR construct
source                  1..6735
                        mol_type = other DNA
                        organism = synthetic construct
SEQUENCE: 6
tctggttaga ccagatctga gcctgggagc tctctggcta actagggaac ccactgctta  60
agcctcaata aagcttgcct tgagtgcttc aagtagtgtg tgcccgtctg ttgtgtgact  120
ctggtaacta gagatccctc agaccctttt agtcagtgtg gaaaatctct agcagtggcg  180
cccgaacagg gacctgaaag cgaaagggaa accagagctc tctcgacgca ggactcggct  240
tgctgaagcg cgcacggcaa gaggcgaggg gcggcgactg gtgagtacgc caaaaatttt  300
gactagcgga ggctagaagg agagagatgg gtgcgagagc gtcagtatta agcgggggag  360
aattagatcg cgatgggaaa aaattcggtt aaggccaggg ggaaagaaaa aatataaatt  420
aaaacatata gtatgggcaa gcagggagct agaacgattc gcagttaatc ctggcctgtt  480
agaaacatca gaaggctgta gacaaatact gggacagcta caaccatccc ttcagacagg  540
atcagaagaa cttagatcat tatataatac agtagcaacc ctctattgtg tgcatcaaag  600
gatagagata aaagacacca aggaagcttt agacaagata gaggaagagc aaaacaaaag  660
taagaccacc gcacagcaag cggccactga tcttcagacc tggaggagga gatatgaggg  720
acaattggag aagtgaatta tataaatata aagtagtaaa aattgaacca ttaggagtag  780
cacccaccaa ggcaaagaga agagtggtgc agagagaaaa aagagcagtg ggaataggag  840
```

-continued

```
ctttgttcct tgggttcttg ggagcagcag gaagcactat gggcgcagcc tcaatgacgc  900
tgacggtaca ggccagacaa ttattgtctg gtatagtgca gcagcagaac aatttgctga  960
gggctattga ggcgcaacag catctgttgc aactcacagt ctggggcatc aagcagctcc  1020
aggcaagaat cctggctgtg gaaagatacc taaaggatca acagctcctg gggatttggg  1080
gttgctctgg aaaactcatt tgcaccactg ctgtgccttg gaatgctagt tggagtaata  1140
aatctctgga acagattgga atcacacgac ctggatggag tgggacagag aaattaacaa  1200
ttacacaagc ttaatacact ccttaattga agaatcgcaa aaccagcaag aaaagaatga  1260
acaagaatta ttggaattag ataaatgggc aagtttgtgg aattggttta acataacaaa  1320
ttggctgtgg tatataaaat tattcataat gatagtagga ggcttggtag gtttaagaat  1380
agtttttgct gtactttcta tagtgaatag agttaggcag ggatattcac cattatcgtt  1440
tcagacccac ctcccaaccc cgaggggacc cgacaggccc gaaggaatag aagaagaagg  1500
tggagagaga gacagagaca gatccattcg attagtgaac ggatctcgac ggtatcggtt  1560
aacttttaaa agaaaagggg ggattggggg gtacagtgca ggggaaagaa tagtagacat  1620
aatagcaaca gacatacaaa ctaaagaatt acaaaaacaa attacaaaaa ttcaaaattt  1680
tatctcgagt agttgtgaac ttacacttta ttcatatata ttagatattg ataattttaa  1740
caaatgagtt actttccatt tgggtacagt cacagttgtc aacaatattt ggaagcacca  1800
ggcatgaaat ctcctgagat gctatgtttt catcagggtc acctgacaca ttcaagttct  1860
gtctgacatg ccattaaagc actggctcag attgcaggca tattttcaaa ccggcagtaa  1920
ctggatagta tcacttcact tataagtgtt cattgtatca tcaagtgaaa taaacacaca  1980
acccatggga tcttgcttag gttggctgcc tagttggccc ctgagataaa gccttgtaat  2040
cacatagcct tgcctaatta gtcagaaaac aaaggattaa gtgagacagt cacaggatat  2100
aggaattata aataatacat atattaatag atattcattt tcattacaca aaagttgcta  2160
ttataaatac ttatttgatt gatgagtcta aaaatatatt ccccatataa ataatgttaa  2220
atattaataa atagatttag atttaaaatt caaatattgc aggcaggaca accacccggg  2280
tcacacgcgg tagcagtaga agatgatgat gacggagatg gccacgccca gggggggcag  2340
gaggctgatg ccggtcacct ggaagatgac cagcaacaag tcggggttgc tggtgttgta  2400
ctcctcggag aagatgatgt tgtcgttgca ctcgtcggag ctgcaggagc acatgaagaa  2460
ggtctcgccg ggcttcttct tctccttcat gatgcacttg ggggaggcgg cgtcctccag  2520
gatgaagtcg tggtagggga gcttggggtc gtggcacacg gtctccaggg tgatgttctc  2580
gtcgttcttc ctccacacgg ccacgcagac ctcctggggc ttctcgcaga tggaggtgat  2640
gctgcagttg ctcatgcagg acttctggtt gtcgcaggtg gagaacctca cgtcgcagaa  2700
cttgcacagc tgggggaact tgacggcgcc gttgttgtcg gtgacgatca tgtcgttgtt  2760
caccgacttc tgcacgtgcg gggggatcgt gctggcgatc cgcgtccaca ggacgatgtg  2820
cagcggccac aggcccctga gcagcccccg gcccatggtg ggaattcctg gaattcgagc  2880
ttccattata taccctctag agtctagatc tacgccttct gtatgaaaca gtttttcctc  2940
cacgccttct gtatgaaaca gtttttcctc cacgccttct gtatgaaaca gtttttcctc  3000
cgtttaaacg taagtcattg gtcttaaagg tagctttatt tagtctccag aaaaaggggg  3060
gaatgaaaga ccccacctgt aggtttggca agctaggatc aaggttagga acagagagac  3120
agcagaatat gggccaaaca ggatatctgt ggtaagcagt tcctgccccg gctcagggcc  3180
aagaacagtt ggaacagcag aatatgggcc aaacaggata tctgtggtaa gcagttcctg  3240
ccccggctca gggccaagaa cagatggtcc ccagatgcgg tcccgccctc agcagtttct  3300
agagaaccat cagatgtttc cagggtgccc caaggacctg aaatgaccct gtgccttatt  3360
tgaactaacc aatcagttcg cttctcgctt ctgttcgcgc gcttctgctc cccgagctca  3420
ataaaagagc ccacgctagc gctaccggtc gccaagatgg gggcaggtgc caccggccgc  3480
gcaatggatg gtccgcgtct actgctgtta ctacttctgg gtgtgtccct tggaggtgcc  3540
aaagaggcat gccccacagg tctatacaca catagcggtg aatgctgcaa agcatgcaac  3600
ctgggcgaag gtgtggccca accttgtgga gccaatcaaa ccgtttgtga gccatgtctg  3660
gacagcgtga cgttctccga tgttgttagc gcgaccgagc catgcaaacc gtgtaccgag  3720
tgtgttggtc tccaaagtat gtcggcgccg tgcgtggagg ccgacgacgc cgtgtgtcgc  3780
tgtgcctacg gttattacca ggatgaaact actggtcgct gtgaagcgtg ccgcgtgtgt  3840
gaggcgggct caggcctcgt gttctcctgt caggacaaac agaacactgt gtgtgaagaa  3900
tgccccgacg gtacttattc cgacgaggcc aaccatgtgg acccgtgtct gccctgcacc  3960
gtttgcgagg ataccgagcg ccagctacgt gagtgcacac gttgggccga cgccgagtgc  4020
gaggaaatcc ctggccgttg gattacacgg tccacaccac cagaaggctc ggacagcaca  4080
gcacccagca ctcaggaacc tgaggcacct ccagaacaag acctaatagc cagcactgtg  4140
gcaggtgttg tgactacagt gatgggtagc tcacaacccg ttgttactcg aggcaccacc  4200
gacaatctaa ttcctgtcta ttgttccatc ctggctgctg tggttgtggg tcttgttgca  4260
tatatagcct tcaagagggg cagcggagag ggtaggggta gtcttttgac gtgtggggac  4320
gtcgaggaaa atcctgggcc tgccttacca gtgaccgcct tgctcctgcc gctggccttg  4380
ctgctccacg ccgccaggcc ggacatcgtg atgacccaga gccccgacag cctggccgtg  4440
agcctgggcg agagggccac catcaactgc aagagcagcc agagcctgct gaacagcggc  4500
gaccagaaga actacctgac ctggtaccag cagaagcccg gccagccccc caagctgctg  4560
atctactggg ccagcaccag ggagagcggc gtgcccgaca ggttcagcgg cagcggcagc  4620
ggcaccgact tcaccctgac catcagcagc ctgcaggccg aggacgtggc cgtgtactac  4680
tgccagaacg actacagcta ccccctgacc ttcggccagg gcaccaaggt ggagatcaag  4740
ggcggcggcg gcagcggcgg cggcggcagc ggcggcggcg gcagccaggt gcagctggtg  4800
cagagcggcg ccgaggtgaa gaagaccggc agcagcgtga aggtgagctg caaggccagc  4860
ggctacacct tcaccgacca cgccatccac tgggtgaggc aggcccccgg ccaggccctg  4920
gagtggatgg gccacttcag ccccggcaac accgacatca agtacaacga caagttcaag  4980
ggcagggtga ccctgaccgt ggacaggagc atgagcaccg cctacatgga gctgagcagc  5040
ctgaggagcg aggacaccgc catgtactac tgcaagacca gcaccttctt cttcgactac  5100
tggggccagg gcaccatggt gaccgtgagc agcaccacga cgccagcgcc gcgaccacca  5160
acaccggcgc ccaccatcgc gtcgcagccc ctgtccctgc gcccagaggc gtgccggcca  5220
gcggcggggg gcgcagtgca cacgaggggg ctggacttcg cctgtgatat ctacatctgg  5280
gcgcccttgg ccgggacttg tggggtcctt ctcctgtcac tggttatcac cctttactgc  5340
aaacggggca gaaagaaact cctgtatata ttcaaacaac catttatgag accagtacaa  5400
actactcaag aggaagatgg ctgtagctgc cgatttccag aagaagaaga aggaggatgt  5460
gaactgagag tgaagttcag caggagcgca gacgcccccg cgtacaagca gggccagaac  5520
cagctctata acgagctcaa tctaggacga agagaggagt acgatgtttt ggacaagaga  5580
```

```
cgtggccggg accctgagat gggggaaag ccgagaagga agaaccctca ggaaggcctg  5640
tacaatgaac tgcagaaaga taagatggcg gaggcctaca gtgagattgg gatgaaaggc  5700
gagcgccgga ggggcaaggg gcacgatggc ctttaccagg gtctcagtac agccaccaag  5760
gacacctacg acgcccttca catgcaggcc ctgccccctc gctgaagaga cgtcataatc  5820
agccagcggc cgcgtcgaca atcaacctct ggattacaaa atttgtgaaa gattgactgg  5880
tattcttaac tatgttgctc cttttacgct atgtggatac gctgctttaa tgcctttgta  5940
tcatgctatt gcttcccgta tggctttcat tttctcctcc ttgtataaat cctggttgct  6000
gtctctttat gaggagttgt ggcccgttgt caggcaacgt ggcgtggtgt gcactgtgtt  6060
tgctgacgca acccccactg gttggggcat tgccaccacc tgtcagctcc tttccgggac  6120
tttcgctttc cccctcccta ttgccacggc ggaactcatc gccgcctgcc ttgcccgctg  6180
ctggacaggg gctcggctgt tgggcactga caattccgtg gtgttgtcgg ggaaatcatc  6240
gtcctttcct tggctgctcg cctgtgttgc cacctggatt ctgcgcggga cgtccttctg  6300
ctacgtccct tcggccctca atccagcgga ccttccttcc cgcggcctgc tgccggctct  6360
gcggcctctt ccgcgtcttc gccttcgccc tcagacgagt cggatctccc tttgggccgc  6420
ctccccgcct ggtaccttta agaccaatga cttacaaggc agctgtagat cttagccact  6480
ttttaaaaga aaaggggga ctggaagggc taattcactc ccaacgaaaa taagatctgc  6540
tttttgcttg tactgggtct ctctggttag accagatctg agcctgggag ctctctggct  6600
aactagggaa cccactgctt aagcctcaat aaagcttgcc ttgagtgctt caagtagtgt  6660
gtgcccgtct gttgtgtgac tctggtaact agagatccct cagacccttt tagtcagtgt  6720
ggaaaatctc tagca                                                  6735

SEQ ID NO: 7            moltype = DNA  length = 6741
FEATURE                 Location/Qualifiers
misc_feature            1..6741
                        note = Gold CAR construct
source                  1..6741
                        mol_type = other DNA
                        organism = synthetic construct
SEQUENCE: 7
tctggttaga ccagatctga gcctgggagc tctctggcta actagggaac ccactgctta  60
agcctcaata aagcttgcct tgagtgcttc aagtagtgtg tgcccgtctg ttgtgtgact  120
ctggtaacta gagatccctc agaccctttt agtcagtgtg gaaaatctct agcagtggcg  180
cccgaacagg gacctgaaag cgaaagggaa accagagctc tctcgacgca ggactcggct  240
tgctgaagcg cgcacggcaa gaggcgaggg gcggcgactg gtgagtacgc caaaaatttt  300
gactagcgga ggctagaagg agagagatgg gtgcgagagc gtcagtatta agcgggggag  360
aattagatcg cgatgggaaa aaattcggtt aaggccaggg ggaaagaaaa aatataaatt  420
aaaacatata gtatgggcaa gcagggagct agaacgattc gcagttaatc ctggcctgtt  480
agaaacatca gaaggctgta gacaaatact gggacagcta caaccatccc ttcagacagg  540
atcagaagaa cttagatcat tatataatac agtagcaacc ctctattgtg tgcatcaaag  600
gatagagata aaagacacca aggaagcttt agacaagata gaggaagagc aaaacaaaag  660
taagaccacc gcacagcaag cggccactga tcttcagacc tggaggagga gatatgaggg  720
acaattggag aagtgaatta tataaatata aagtagtaaa aattgaacca ttaggagtag  780
cacccaccaa ggcaaagaga agagtggtgc agagagaaaa aagagcagtg ggaataggag  840
ctttgttcct tgggttcttg ggagcagcag gaagcactat gggcgcagcc tcaatgacgc  900
tgacggtaca ggccagacaa ttattgtctg gtatagtgca gcagcagaac aatttgctga  960
gggctattga ggcgcaacag catctgttgc aactcacagt ctggggcatc aagcagctcc  1020
aggcaagaat cctggctgtg gaaagatacc taaaggatca acagctcctg gggatttggg  1080
gttgctctgg aaaactcatt tgcaccactg ctgtgccttg gaatgctagt tggagtaata  1140
aatctctgga acagatttgga atcacacgac ctggatggag tgggacagag aaattaacaa  1200
ttacacaagc ttaatacact ccttaattga agaatcgcaa aaccagcaag aaaagaatga  1260
acaagaatta ttggaattag ataaatgggc aagtttgtgg aattggttta acataacaaa  1320
ttggctgtgg tatataaaat tattcataat gatagtagga ggcttggtag gtttaagaat  1380
agtttttgct gtactttcta tagtgaatag agttaggcag ggatattcac cattatcgtt  1440
tcagacccac ctcccaaccc cgaggggacc cgacaggccc gaaggaatag aagaagaagg  1500
tggagagaga gacagagaca gatccattcg attagtgaac ggatctcgac ggtatcggtt  1560
aacttttaaa agaaaagggg ggattggggg gtacagtgca ggggaaagaa tagtagacat  1620
aatagcaaca gacatacaaa ctaaagaatt acaaaaacaa attacaaaaa ttcaaaattt  1680
tatctcgagt agttgtgaac ttacacttta ttcatatata ttagatattg ataattttaa  1740
caaatgagtt actttccatt tgggtacagt cacagttgtc aacaatattt ggaagcacca  1800
ggcatgaaat ctcctgagat gctatgtttt catcagggtc acctgacaca ttcaagttct  1860
gtctgacatg ccattaaagc actggctcag attgcaggca tattttcaaa ccggcagtaa  1920
ctggatagta tcacttcact tataagtgtt cattgtatca tcaagtgaaa taaacacaca  1980
acccatggga tcttgcttag gttggctgcc tagttggccc ctgagataaa gccttgtaat  2040
cacatagcct tgcctaatta gtcagaaaac aaaggattaa gtgagacagt cacaggatat  2100
aggaattata aataatacat atattaatag atattcattt tcattacaca aaagttgcta  2160
ttataaatac ttatttgatt gatgagtcta aaaatatatt ccccatataa ataatgttaa  2220
atattaataa atagatttag atttaaaatt caaatattgc aggcaggaca accacccggg  2280
ctagtcctcg ttctgcacgg tgaacatgat ggacctgtcc cccaactcgt cctccttctt  2340
caagatgagc ttgaacaggt ccctctcctt ctcgcaggcc aggaagtagc cctcgtagga  2400
ggaggactcg aactgcatct tgttgtcgtg gccggggacg ctcctctgga agaagatgat  2460
gtcgctcttg gtgtccttga tgttgtcggg ggggttcatc tccttgaagg agatgatctt  2520
gttctcgcag gagagggtgg agatcttctc gcacttcacg gagatggtca cggccttgcc  2580
cctggccctg ctgtcgccgt aggcgctgat gatgaagatg gtccgggggg cgttgtccct  2640
gcagtcggag tcggtcatgt cctcgaacag gggccggttg ccctggtcga tgaagagcac  2700
ctggtcgttc aagttcctga tgacggacaa cttggactcc agcttgccga agtagtcgga  2760
ctccaggttc tcgtcgtcct cggcgatgaa gtacagcgtg ttgtcgatga acttcatggc  2820
cacgaagttg atgcagttgt cctccacggg ctcggcggcc atggtgggaa ttcctggaat  2880
tcgagcttcc attatatacc ctctagagtc tagatctacg ccttctgtat gaaacagttt  2940
ttcctccacg ccttctgtat gaaacagttt ttcctccacg ccttctgtat gaaacagttt  3000
```

-continued

```
ttcctccgtt taaacgtaag tcattggtct taaaggtagc tttatttagt ctccagaaaa  3060
agggggggaat gaaagacccc acctgtaggt ttggcaagct aggatcaagg ttaggaacag  3120
agagacagca gaatatgggc caaacaggat atctgtggta agcagttcct gccccggctc  3180
agggccaaga acagttggaa cagcagaata tgggccaaac aggatatctg tggtaagcag  3240
ttcctgcccc ggctcagggc caagaacaga tggtccccag atgcggtccc gccctcagca  3300
gtttctagag aaccatcaga tgtttccagg gtgccccaag gacctgaaat gaccctgtgc  3360
cttatttgaa ctaaccaatc agttcgcttc tcgcttctgt tcgcgcgctt ctgctccccg  3420
agctcaataa aagagcccac gctagcgcta ccggtcgcca agatgggggc aggtgccacc  3480
ggccgcgcaa tggatggtcc gcgtctactg ctgttactac ttctgggtgt gtcccttgga  3540
ggtgccaaag aggcatgccc cacaggtcta tacacacata gcggtgaatg ctgcaaagca  3600
tgcaacctgg gcgaaggtgt ggcccaacct tgtggagcca atcaaaccgt ttgtgagcca  3660
tgtctggaca gcgtgacgtt ctccgatgtt gttagcgcga ccgagccatg caaaccgtgt  3720
accgagtgtg ttggtctcca aagtatgtcg gcgccgtgcg tggaggccga cgacgccgtg  3780
tgtcgctgtg cctacggtta ttaccaggat gaaactactg gtcgctgtga agcgtgccgc  3840
gtgtgtgagg cgggctcagg cctcgtgttc tcctgtcagg acaaacagaa cactgtgtgt  3900
gaagaatgcc ccgacggtac ttattccgac gaggccaacc atgtggaccc gtgtctgccc  3960
tgcaccgttt gcgaggatac cgagcgccag ctacgtgagt gcacacgttg ggccgacgcc  4020
gagtgcgagg aaatccctgg ccgttggatt acacggtcca caccaccaga aggctcggac  4080
agcacagcac ccagcactca ggaacctgag gcacctccag aacaagacct aatagccagc  4140
actgtggcag gtgttgtgac tacagtgatg ggtagctcac aacccgttgt tactcgaggc  4200
accaccgaca atctaattcc tgtctattgt tccatcctgg ctgctgtggt tgtgggtctt  4260
gttgcatata tagccttcaa gaggggcagc ggagagggta ggggtagtct tttgacgtgt  4320
ggggacgtcg aggaaaatcc tggcctgcc ttaccagtga ccgccttgct cctgccgctg  4380
gccttgctgc tccacgccgc caggccggac atcgtgatga cccagagccc cgacagcctg  4440
gccgtgagcc tgggcgagag ggccaccatc aactgcaaga gcagccagag cctgctgaac  4500
agcggcgacc agaagaacta cctgacctgg taccagcaga agcccggcca gcccccccaag  4560
ctgctgatct actgggccag caccagggag agcggcgtgc ccgacaggtt cagcggcagc  4620
ggcagcggca ccgacttcac cctgaccatc agcagcctgc aggccgagga cgtggccgtg  4680
tactactgcc agaacgacta cagctacccc ctgaccttcg gccagggcac caaggtggag  4740
atcaagggcg gcggcggcag cggcggcggc ggcagcggcg gcggcggcag ccaggtgcag  4800
ctggtgcaga gcggcgccga ggtgaagaag accggcagca gcgtgaaggt gagctgcaag  4860
gccagcggct acaccttcac cgaccacgcc atccactggg tgaggcaggc ccccggccag  4920
gccctggagt ggatgggcca cttcagcccc ggcaacaccg acatcaagta caacgacaag  4980
ttcaagggca gggtgaccct gaccgtggac aggagcatga gcaccgccta catggagctg  5040
agcagcctga ggagcgagga caccgccatg tactactgca agaccagcac cttcttcttc  5100
gactactggg gccagggcac catggtgacc gtgagcagca ccacgacgcc agcgccgcga  5160
ccaccaacac cggcgcccac catcgcgtcg cagcccctgt ccctgcgccc agaggcgtgc  5220
cggccagcgg cggggggcgc agtgcacacg agggggctgg acttcgcctg tgatatctac  5280
atctgggcgc ccttggccgg gacttgtggg gtccttctcc tgtcactggt tatcaccctt  5340
tactgcaaac ggggcagaaa gaaactcctg tatatattca aacaaccatt tatgagacca  5400
gtacaaacta ctcaagagga agatggctgt agctgccgat ttccagaaga agaagaagga  5460
ggatgtgaac tgagagtgaa gttcagcagg agcgcagacg cccccgcgta caagcagggc  5520
cagaaccagc tctataacga gctcaatcta ggacgaagag aggagtacga tgttttggac  5580
aagagacgtg gccgggaccc tgagatgggg ggaaagccga gaaggaagaa ccctcaggaa  5640
ggcctgtaca atgaactgca gaaagataag atggcggagg cctacagtga gattgggatg  5700
aaaggcgagc gccggagggg caaggggcac gatggccttt accagggtct cagtacagcc  5760
accaaggaca cctacgacgc ccttcacatg caggccctgc cccctcgctg aagagacgtc  5820
ataatcagcc agcggccgcg tcgacaatca acctctggat tacaaaattt gtgaaagatt  5880
gactggtatt cttaactatg ttgctccttt tacgctatgt ggatacgctg ctttaatgcc  5940
tttgtatcat gctattgctt cccgtatggc tttcattttc tcctccttgt ataaatcctg  6000
gttgctgtct ctttatgagg agttgtggcc cgttgtcagg caacgtggcg tggtgtgcac  6060
tgtgtttgct gacgcaaccc ccactggttg gggcattgcc accacctgtc agctcctttc  6120
cgggactttc gctttccccc tccctattgc cacggcggaa ctcatcgccg cctgccttgc  6180
ccgctgctgg acaggggctc ggctgttggg cactgacaat tccgtggtgt tgtcggggaa  6240
atcatcgtcc tttccttggc tgctcgcctg tgttgccacc tggattctgc gcgggacgtc  6300
cttctgctac gtcccttcgg ccctcaatcc agcggacctt ccttcccgcg gcctgctgcc  6360
ggctctgcgg cctcttccgc gtcttcgcct tcgccctcag acgagtcgga tctccctttg  6420
ggccgcctcc ccgcctggta cctttaagac caatgactta caaggcagct gtagatctta  6480
gccacttttt aaaagaaaag gggggactgg aagggctaat tcactcccaa cgaaaataag  6540
atctgctttt tgcttgtact gggtctctct ggttagacca gatctgagcc tgggagctct  6600
ctggctaact agggaaccca ctgcttaagc ctcaataaag cttgccttga gtgcttcaag  6660
tagtgtgtgc ccgtctgttg tgtgactctg gtaactagag atccctcaga cccttttagt  6720
cagtgtggaa aatctctagc a                                            6741

SEQ ID NO: 8            moltype = DNA  length = 6621
FEATURE                 Location/Qualifiers
misc_feature            1..6621
                        note = Gold CAR construct
source                  1..6621
                        mol_type = other DNA
                        organism = synthetic construct
SEQUENCE: 8
tctggttaga ccagatctga gcctgggagc tctctggcta actagggaac ccactgctta  60
agcctcaata aagcttgcct tgagtgcttc aagtagtgtg tgcccgtctg ttgtgtgact  120
ctggtaacta gagatccctc agaccctttt agtcagtgtg gaaaatctct agcagtggcg  180
cccgaacagg gacctgaaag cgaaagggaa accagagctc tctcgacgca ggactcggct  240
tgctgaagcg cgcacggcaa gaggcgaggg gcggcgactg gtgagtacgc caaaaatttt  300
gactagcgga ggctagaagg agagagatgg gtgcgagagc gtcagtatta agcgggggag  360
aattagatcg cgatgggaaa aaattcggtt aaggccaggg ggaaagaaaa aatataaatt  420
```

-continued

```
aaaacatata gtatgggcaa gcagggagct agaacgattc gcagttaatc ctggcctgtt  480
agaaacatca gaaggctgta gacaaatact gggacagcta caaccatccc ttcagacagg  540
atcagaagaa cttagatcat tatataatac agtagcaacc ctctattgtg tgcatcaaag  600
gatagagata aaagacacca aggaagcttt agacaagata gaggaagagc aaaacaaaag  660
taagaccacc gcacagcaag cggccactga tcttcagacc tggaggagga gatatgaggg  720
acaattggag aagtgaatta tataaatata aagtagtaaa aattgaacca ttaggagtag  780
cacccaccaa ggcaaagaga agagtggtgc agagagaaaa aagagcagtg ggaataggag  840
ctttgttcct tgggttcttg ggagcagcag gaagcactat gggcgcagcc tcaatgacgc  900
tgacggtaca ggccagacaa ttattgtctg gtatagtgca gcagcagaac aatttgctga  960
gggctattga ggcgcaacag catctgttgc aactcacagt ctggggcatc aagcagctcc  1020
aggcaagaat cctggctgtg gaaagatacc taaaggatca acagctcctg gggatttggg  1080
gttgctctgg aaaactcatt tgcaccactg ctgtgccttg gaatgctagt tggagtaata  1140
aatctctgga acagattgga atcacacgac ctggatggag tgggacagag aaattaacaa  1200
ttacacaagc ttaatacact ccttaattga agaatcgcaa aaccagcaag aaaagaatga  1260
acaagaatta ttggaattag ataaatgggc aagtttgtgg aattggttta acataacaaa  1320
ttggctgtgg tatataaaat tattcataat gatagtagga ggcttggtag gtttaagaat  1380
agtttttgct gtactttcta tagtgaatag agttaggcag ggatattcac cattatcgtt  1440
tcagacccac ctcccaaccc cgaggggacc cgacaggccc gaaggaatag aagaagaagg  1500
tggagagaga gacagagaca gatccattcg attagtgaac ggatctcgac ggtatcggtt  1560
aacttttaaa agaaaagggg ggattggggg gtacagtgca ggggaaagaa tagtagacat  1620
aatagcaaca gacatacaaa ctaaagaatt acaaaaacaa attacaaaaa ttcaaaattt  1680
tatctcgagt agttgtgaac ttacacttta ttcatatata ttagatattg ataattttaa  1740
caaatgagtt actttccatt tgggtacagt cacagttgtc aacaatattt ggaagcacca  1800
ggcatgaaat ctcctgagat gctatgtttt catcagggtc acctgacaca ttcaagttct  1860
gtctgacatg ccattaaagc actggctcag attgcaggca tattttcaaa ccggcagtaa  1920
ctggatagta tcacttcact tataagtgtt cattgtatca tcaagtgaaa taaacacaca  1980
acccatggga tcttgcttag gttggctgcc tagttggccc ctgagataaa gccttgtaat  2040
cacatagcct tgcctaatta gtcagaaaac aaaggattaa gtgagacagt cacaggatat  2100
aggaattata aataatacat atattaatag atattcattt tcattacaca aaagttgcta  2160
ttataaatac ttatttgatt gatgagtcta aaaatatatt ccccatataa ataatgttaa  2220
atattaataa atagatttag atttaaaatt caaatattgc aggcaggaca accacccggg  2280
tcaggtcagg gtggagatga tgctctggca gaaggtgatc cacctgttca ggaactccac  2340
gatggtggcg gtctcgtcgg cgtactcgca catgaaggtg gtctcggagc ccttcagctc  2400
cagcacgatc acgttgatgt tgctgatcag gtccctgggc ctcaggtgga agttcttgct  2460
ctgggccagg ttcagcacct cctccagggg cttcagctcc tcctccaggc actgcaggtg  2520
cttcagctcg gtggccttct tgggcatgta gaacttgaag gtcagcatcc tggtcagctt  2580
ggggttcttg tagttgttga tgccgttcag gatcatctgc aggtccagca gcaggtgctc  2640
cagctgcagc tgggtcttct tggtggagct ggaggtgggg gcgctgttgg tcaccagggc  2700
caggctcagg gcgatgcagg acagcagctg catccggtac atggtgggaa ttcctggaat  2760
tcgagcttcc attatatacc ctctagagtc tagatctacg ccttctgtat gaaacagttt  2820
ttcctccacg ccttctgtat gaaacagttt ttcctccacg ccttctgtat gaaacagttt  2880
ttcctccgtt taaacgtaag tcattggtct taaaggtagc tttatttagt ctccagaaaa  2940
agggggggaat gaaagacccc acctgtaggt ttggcaagct aggatcaagg ttaggaacag  3000
agagacagca gaatatgggc caaacaggat atctgtggta agcagttcct gccccggctc  3060
agggccaaga acagttggaa cagcagaata tgggccaaac aggatatctg tggtaagcag  3120
ttcctgcccc ggctcagggc caagaacaga tggtccccag atgcggtccc gccctcagca  3180
gtttctagag aaccatcaga tgtttccagg gtgccccaag gacctgaaat gaccctgtgc  3240
cttatttgaa ctaaccaatc agttcgcttc tcgcttctgt tcgcgcgctt ctgctccccg  3300
agctcaataa aagagcccac gctagcgcta ccggtcgcca agatgggggc aggtgccacc  3360
ggccgcgcaa tggatggtcc gcgtctactg ctgttactac ttctgggtgt gtcccttgga  3420
ggtgccaaag aggcatgccc cacaggtcta tacacacata gcggtgaatg ctgcaaagca  3480
tgcaacctgg gcgaaggtgt ggcccaacct tgtggagcca atcaaaccgt ttgtgagcca  3540
tgtctggaca gcgtgacgtt ctccgatgtt gttagcgcga ccgagccatg caaaccgtgt  3600
accgagtgtg ttggtctcca aagtatgtcg gcgccgtgcg tggaggccga cgacgccgtg  3660
tgtcgctgtg cctacggtta ttaccaggat gaaactactg gtcgctgtga agcgtgccgc  3720
gtgtgtgagg cgggctcagg cctcgtgttc tcctgtcagg acaaacagaa cactgtgtgt  3780
gaagaatgcc ccgacggtac ttattccgac gaggccaacc atgtggaccc gtgtctgccc  3840
tgcaccgttt gcgaggatac cgagcgccag ctacgtgagt gcacacgttg ggccgacgcc  3900
gagtgcgagg aaatccctgg ccgttggatt acacggtcca caccaccaga aggctcggac  3960
agcacagcac ccagcactca ggaacctgag gcacctccag aacaagacct aatagccagc  4020
actgtggcag gtgttgtgac tacagtgatg ggtagctcac aacccgttgt tactcgaggc  4080
accaccgaca atctaattcc tgtctattgt tccatcctgg ctgctgtggt tgtgggtctt  4140
gttgcatata tagccttcaa gaggggcagc ggagagggta ggggtagtct tttgacgtgt  4200
ggggacgtcg aggaaaatcc tgggcctgcc ttaccagtga ccgccttgct cctgccgctg  4260
gccttgctgc tccacgccgc caggccggac atcgtgatga cccagagccc cgacagcctg  4320
gccgtgagcc tgggcgagag ggccaccatc aactgcaaga gcagccagag cctgctgaac  4380
agcggcgacc agaagaacta cctgacctgg taccagcaga agcccggcca gcccccccaag  4440
ctgctgatct actgggccag caccagggag agcggcgtgc ccgacaggtt cagcggcagc  4500
ggcagcggca ccgacttcac cctgaccatc agcagcctgc aggccgagga cgtggccgtg  4560
tactactgcc agaacgacta cagctacccc ctgaccttcg gccagggcac caaggtggag  4620
atcaagggcg gcggcggcag cggcggcggc ggcagcggcg gcggcggcag ccaggtgcag  4680
ctggtgcaga gcggcgccga ggtgaagaag accggcagca gcgtgaaggt gagctgcaag  4740
gccagcggct acaccttcac cgaccacgcc atccactggg tgaggcaggc cccccggccag  4800
gccctggagt ggatgggcca cttcagcccc ggcaacaccg acatcaagta caacgacaag  4860
ttcaagggca gggtgaccct gaccgtggac aggagcatga gcaccgccta catggagctg  4920
agcagcctga ggagcgagga caccgccatg tactactgca agaccagcac cttcttcttc  4980
gactactggg gccagggcac catggtgacc gtgagcagca ccacgacgcc agcgccgcga  5040
ccaccaacac cggcgcccac catcgcgtcg cagcccctgt ccctgcgccc agaggcgtgc  5100
cggccagcgg cgggggggcgc agtgcacacg aggggggctgg acttcgcctg tgatatctac  5160
```

```
atctgggcgc ccttggccgg gacttgtggg gtccttctcc tgtcactggt tatcaccctt  5220
tactgcaaac ggggcagaaa gaaactcctg tatatattca aacaaccatt tatgagacca  5280
gtacaaacta ctcaagagga agatggctgt agctgccgat ttccagaaga agaagaagga  5340
ggatgtgaac tgagagtgaa gttcagcagg agcgcagacg cccccgcgta caagcagggc  5400
cagaaccagc tctataacga gctcaatcta ggacgaagag aggagtacga tgttttggac  5460
aagagacgtg gccgggaccc tgagatgggg ggaaagccga gaaggaagaa ccctcaggaa  5520
ggcctgtaca atgaactgca gaaagataag atggcggagg cctacagtga gattgggatg  5580
aaaggcgagc gccggagggg caaggggcac gatggccttt accagggtct cagtacagcc  5640
accaaggaca cctacgacgc ccttcacatg caggccctgc cccctcgctg aagagacgtc  5700
ataatcagcc agcggccgcg tcgacaatca acctctggat tacaaaattt gtgaaagatt  5760
gactggtatt cttaactatg ttgctccttt tacgctatgt ggatacgctg ctttaatgcc  5820
tttgtatcat gctattgctt cccgtatggc tttcattttc tcctccttgt ataaatcctg  5880
gttgctgtct ctttatgagg agttgtggcc cgttgtcagg caacgtggcg tggtgtgcac  5940
tgtgtttgct gacgcaaccc ccactggttg gggcattgcc accacctgtc agctcctttc  6000
cgggactttc gctttccccc tccctattgc cacggcggaa ctcatcgccg cctgccttgc  6060
ccgctgctgg acaggggctc ggctgttggg cactgacaat tccgtggtgt tgtcggggaa  6120
atcatcgtcc tttccttggc tgctcgcctg tgttgccacc tggattctgc gcgggacgtc  6180
cttctgctac gtcccttcgg ccctcaatcc agcggacctt ccttcccgcg gcctgctgcc  6240
ggctctgcgg cctcttccgc gtcttcgcct tcgccctcag acgagtcgga tctccctttg  6300
ggccgcctcc ccgcctggta cctttaagac caatgactta caaggcagct gtagatctta  6360
gccacttttt aaaagaaaag gggggactgg aagggctaat tcactcccaa cgaaaataag  6420
atctgctttt tgcttgtact gggtctctct ggttagacca gatctgagcc tgggagctct  6480
ctggctaact agggaaccca ctgcttaagc ctcaataaag cttgccttga gtgcttcaag  6540
tagtgtgtgc ccgtctgttg tgtgactctg gtaactagag atccctcaga cccttttagt  6600
cagtgtggaa aatctctagc a                                           6621

SEQ ID NO: 9            moltype = DNA  length = 6759
FEATURE                 Location/Qualifiers
misc_feature            1..6759
                        note = Gold CAR construct
source                  1..6759
                        mol_type = other DNA
                        organism = synthetic construct
SEQUENCE: 9
tctggttaga ccagatctga gcctgggagc tctctggcta actagggaac ccactgctta  60
agcctcaata aagcttgcct tgagtgcttc aagtagtgtg tgcccgtctg ttgtgtgact  120
ctggtaacta gagatccctc agaccctttt agtcagtgtg gaaaatctct agcagtggcg  180
cccgaacagg gacctgaaag cgaaagggaa accagagctc tctcgacgca ggactcggct  240
tgctgaagcg cgcacggcaa gaggcgaggg gcggcgactg gtgagtacgc caaaaatttt  300
gactagcgga ggctagaagg agagagatgg gtgcgagagc gtcagtatta agcgggggag  360
aattagatcg cgatgggaaa aaattcggtt aaggccaggg ggaaagaaaa aatataaatt  420
aaaacatata gtatgggcaa gcagggagct agaacgattc gcagttaatc ctggcctgtt  480
agaaacatca gaaggctgta gacaaatact gggacagcta caaccatccc ttcagacagg  540
atcagaagaa cttagatcat tatataatac agtagcaacc ctctattgtg tgcatcaaag  600
gatagagata aaagacacca aggaagcttt agacaagata gaggaagagc aaaacaaaag  660
taagaccacc gcacagcaag cggccactga tcttcagacc tggaggagga gatatgaggg  720
acaattggag aagtgaatta tataaatata aagtagtaaa aattgaacca ttaggagtag  780
cacccaccaa ggcaaagaga agagtggtgc agagagaaaa aagagcagtg ggaataggag  840
ctttgttcct tgggttcttg ggagcagcag gaagcactat gggcgcagcc tcaatgacgc  900
tgacggtaca ggccagacaa ttattgtctg gtatagtgca gcagcagaac aatttgctga  960
gggctattga ggcgcaacag catctgttgc aactcacagt ctggggcatc aagcagctcc  1020
aggcaagaat cctggctgtg gaaagatacc taaaggatca acagctcctg gggatttggg  1080
gttgctctgg aaaactcatt tgcaccactg ctgtgccttg gaatgctagt tggagtaata  1140
aatctctgga acagattgga atcacacgac ctggatggag tgggacagag aaattaacaa  1200
ttacacaagc ttaatacact ccttaattga agaatcgcaa aaccagcaag aaaagaatga  1260
acaagaatta ttggaattag ataaatgggc aagtttgtgg aattggttta acataacaaa  1320
ttggctgtgg tatataaaat tattcataat gatagtagga ggcttggtag gtttaagaat  1380
agtttttgct gtactttcta tagtgaatag agttaggcag ggatattcac cattatcgtt  1440
tcagacccac ctcccaaccc cgaggggacc cgacaggccc gaaggaatag aagaagaagg  1500
tggagagaga gacagagaca gatccattcg attagtgaac ggatctcgac ggtatcggtt  1560
aacttttaaa agaaaagggg ggattggggg gtacagtgca ggggaaagaa tagtagacat  1620
aatagcaaca gacatacaaa ctaaagaatt acaaaaacaa attacaaaaa ttcaaaattt  1680
tatctcgagt agttgtgaac ttacacttta ttcatatata ttagatattg ataattttaa  1740
caaatgagtt actttccatt tgggtacagt cacagttgtc aacaatattt ggaagcacca  1800
ggcatgaaat ctcctgagat gctatgtttt catcagggtc acctgacaca ttcaagttct  1860
gtctgacatg ccattaaagc actggctcag attgcaggca tattttcaaa ccggcagtaa  1920
ctggatagta tcacttcact tataagtgtt cattgtatca tcaagtgaaa taaacacaca  1980
acccatggga tcttgcttag gttggctgcc tagttggccc ctgagataaa gccttgtaat  2040
cacatagcct tgcctaatta gtcagaaaac aaaggattaa gtgagacagt cacaggatat  2100
aggaattata aataatacat atattaatag atattcattt tcattacaca aaagttgcta  2160
ttataaatac ttatttgatt gatgagtcta aaaatatatt ccccatataa ataatgttaa  2220
atattaataa atagatttag atttaaaatt caaatattgc aggcaggaca accacccggg  2280
tcacgccaga atgcgttcgc acagccgcca gccggtcact ccgttgatgg ttactcggaa  2340
cagcagggag ccgtcggggt tgatcaggcg ctcgtcgata attttgttgc cgttccacag  2400
ggtccctgtt acagtgatct ttttgccgtc gaacacggcg atgccttcat acggccgtcc  2460
gaaatagtcg atcatgttcg gcgtaacccc gtcgattacc agtgtgccat agtgcaggat  2520
caccttaaag tgatgatcat ccacagggta caccacctta aaaatttttt cgatctggcc  2580
catttggtcg ccgctcagac cttcatacgg gatgatgaca tggatgtcga tcttcagccc  2640
attttcaccg ctcaggacaa tcctttggat cggagttacg gacaccccga gattctgaaa  2700
```

```
caaactggac acacctccct gttcaaggac ttggtccagg ttgtagccgg ctgtctgtcg  2760
ccagtcccca acgaaatctt cgagtgtgaa gactggggca gggaaggcag caggcaacac  2820
caggagcagg cccagggaga aggcaactgg accgaaggcg cttgtggaga aggagttcat  2880
ggtgggaatt cctggaattc gagcttccat tatataccct ctagagtcta gatctacgcc  2940
ttctgtatga aacagttttt cctccacgcc ttctgtatga aacagttttt cctccacgcc  3000
ttctgtatga aacagttttt cctccgttta aacgtaagtc attggtctta aaggtagctt  3060
tatttagtct ccagaaaaag gggggaatga aagaccccac ctgtaggttt ggcaagctag  3120
gatcaaggtt aggaacagag agacagcaga atatgggcca aacaggatat ctgtggtaag  3180
cagttcctgc cccggctcag ggccaagaac agttggaaca gcagaatatg ggccaaacag  3240
gatatctgtg gtaagcagtt cctgccccgg ctcagggcca agaacagatg gtccccagat  3300
gcggtcccgc cctcagcagt ttctagagaa ccatcagatg tttccagggt gccccaagga  3360
cctgaaatga ccctgtgcct tatttgaact aaccaatcag ttcgcttctc gcttctgttc  3420
gcgcgcttct gctccccgag ctcaataaaa gagcccacgc tagcgctacc ggtcgccaag  3480
atgggggcag gtgccaccgg ccgcgccatg gacgggccgc gcctgctgct gttgctgctt  3540
ctgggggtgt cccttggagg tgccaaggag gcatgcccca caggcctgta cacacacagc  3600
ggtgagtgct gcaaagcctg caacctgggc gagggtgtgg cccagccttg tggagccaac  3660
cagaccgtgt gtgagccctg cctggacagc gtgacgttct ccgacgtggt gagcgcgacc  3720
gagccgtgca agccgtgcac cgagtgcgtg gggctccaga gcatgtcggc gccgtgcgtg  3780
gaggccgacg acgccgtgtg ccgctgcgcc tacggctact accaggatga gacgactggg  3840
cgctgcgagg cgtgccgcgt gtgcgaggcg ggctcgggcc tcgtgttctc ctgccaggac  3900
aagcagaaca ccgtgtgcga ggagtgcccc gacggcacgt attccgacga ggccaaccac  3960
gtggacccgt gcctgccctg caccgtgtgc gaggacaccg agcgccagct ccgcgagtgc  4020
acacgctggg ccgacgccga gtgcgaggag atccctggcc gttggattac acggtccaca  4080
cccccagagg gctcggacag cacagccccc agcacccagg agcctgaggc acctccagaa  4140
caagacctca tagccagcac ggtggcaggt gtggtgacca cagtgatggg cagctcccag  4200
cccgtggtga cccgaggcac caccgacaac ctcatccctg tctattgctc catcctggct  4260
gctgtggttg tgggtcttgt ggcctacata gccttcaaga ggggcagcgg agagggtagg  4320
ggtagtcttt tgacgtgtgg ggacgtcgag gaaaatcctg ggcctgcctt accagtgacc  4380
gccttgctcc tgccgctggc cttgctgctc cacgccgcca ggccggacat cgtgatgacc  4440
cagagccccg acagcctggc cgtgagcctg ggcgagaggg ccaccatcaa ctgcaagagc  4500
agccagagcc tgctgaacag cggcgaccag aagaactacc tgacctggta ccagcagaag  4560
cccggccagc cccccaagct gctgatctac tgggccagca ccagggagag cggcgtgccc  4620
gacaggttca gcggcagcgg cagcggcacc gacttcaccc tgaccatcag cagcctgcag  4680
gccgaggacg tggccgtgta ctactgccag aacgactaca gctacccccct gaccttcggc  4740
cagggcacca aggtggagat caagggcggc ggcggcagcg gcggcggcgg cagcggcggc  4800
ggcggcagcc aggtgcagct ggtgcagagc ggcgccgagg tgaagaagac cggcagcagc  4860
gtgaaggtga gctgcaaggc cagcggctac accttcaccg accacgccat ccactgggtg  4920
aggcaggccc ccggccaggc cctggagtgg atgggccact tcagccccgg caacaccgac  4980
atcaagtaca acgacaagtt caagggcagg gtgaccctga ccgtggacag gagcatgagc  5040
accgcctaca tggagctgag cagcctgagg agcgaggaca ccgccatgta ctactgcaag  5100
accagcacct tcttcttcga ctactggggc cagggcacca tggtgaccgt gagcagcacc  5160
acgacgccag cgccgcgacc accaacaccg gcgcccacca tcgcgtcgca gcccctgtcc  5220
ctgcgcccag aggcgtgccg gccagcggcg gggggcgcag tgcacacgag ggggctggac  5280
ttcgcctgtg atatctacat ctgggcgccc ttggccggga cttgtggggt ccttctcctg  5340
tcactggtta tcacccttta ctgcaaacgg ggcagaaaga aactcctgta tatattcaaa  5400
caaccattta tgagaccagt acaaactact caagaggaag atggctgtag ctgccgattt  5460
ccagaagaag aagaaggagg atgtgaactg agagtgaagt tcagcaggag cgcagacgcc  5520
cccgcgtaca agcagggcca gaaccagctc tataacgagc tcaatctagg acgaagagag  5580
gagtacgatg ttttggacaa gagacgtggc cgggaccctg agatgggggg aaagccgaga  5640
aggaagaacc ctcaggaagg cctgtacaat gaactgcaga aagataagat ggcggaggcc  5700
tacagtgaga ttgggatgaa aggcgagcgc cggaggggca aggggcacga tggcctttac  5760
cagggtctca gtacagccac caaggacacc tacgacgccc ttcacatgca ggccctgccc  5820
cctcgctgaa gagacgtcat aatcagccag cggccgcgtc gacaatcaac ctctggatta  5880
caaaatttgt gaaagattga ctggtattct taactatgtt gctcctttta cgctatgtgg  5940
atacgctgct ttaatgcctt tgtatcatgc tattgcttcc cgtatggctt tcattttctc  6000
ctccttgtat aaatcctggt tgctgtctct ttatgaggag ttgtggcccg ttgtcaggca  6060
acgtggcgtg gtgtgcactg tgtttgctga cgcaacccccc actggttggg gcattgccac  6120
cacctgtcag ctcctttccg ggactttcgc tttccccctc cctattgcca cggcggaact  6180
catcgccgcc tgccttgccc gctgctggac aggggctcgg ctgttgggca ctgacaattc  6240
cgtggtgttg tcggggaaat catcgtcctt tccttggctg ctcgcctgtg ttgccacctg  6300
gattctgcgc gggacgtcct tctgctacgt cccttcggcc ctcaatccag cggaccttcc  6360
ttcccgcggc ctgctgccgg ctctgcggcc tcttccgcgt cttcgccttc gccctcagac  6420
gagtcggatc tccctttggg ccgcctcccc gcctggtacc tttaagacca atgacttaca  6480
aggcagctgt agatcttagc cactttttaa aagaaaaggg gggactggaa gggctaattc  6540
actcccaacg aaaataagat ctgctttttg cttgtactgg gtctctctgg ttagaccaga  6600
tctgagcctg ggagctctct ggctaactag ggaacccact gcttaagcct caataaagct  6660
tgccttgagt gcttcaagta gtgtgtgccc gtctgttgtg tgactctggt aactagagat  6720
ccctcagacc cttttagtca gtgtggaaaa tctctagca                         6759
```

```
SEQ ID NO: 10          moltype = DNA  length = 7758
FEATURE                Location/Qualifiers
misc_feature           1..7758
                       note = Gold CAR construct
source                 1..7758
                       mol_type = other DNA
                       organism = synthetic construct
SEQUENCE: 10
tctggttaga ccagatctga gcctgggagc tctctggcta actagggaac ccactgctta  60
agcctcaata aagcttgcct tgagtgcttc aagtagtgtg tgcccgtctg ttgtgtgact  120
```

-continued

```
ctggtaacta gagatccctc agaccctttt agtcagtgtg gaaaatctct agcagtggcg  180
cccgaacagg gacctgaaag cgaaagggaa accagagctc tctcgacgca ggactcggct  240
tgctgaagcg cgcacggcaa gaggcgaggg gcggcgactg gtgagtacgc caaaaatttt  300
gactagcgga ggctagaagg agagagatgg gtgcgagagc gtcagtatta agcgggggag  360
aattagatcg cgatgggaaa aaattcggtt aaggccaggg ggaaagaaaa aatataaatt  420
aaaacatata gtatgggcaa gcagggagct agaacgattc gcagttaatc ctggcctgtt  480
agaaacatca gaaggctgta gacaaatact gggacagcta caaccatccc ttcagacagg  540
atcagaagaa cttagatcat tatataatac agtagcaacc ctctattgtg tgcatcaaag  600
gatagagata aaagacacca aggaagcttt agacaagata gaggaagagc aaaacaaaag  660
taagaccacc gcacagcaag cggccactga tcttcagacc tggaggagga gatatgaggg  720
acaattggag aagtgaatta tataaatata aagtagtaaa aattgaacca ttaggagtag  780
cacccaccaa ggcaaagaga agagtggtgc agagagaaaa aagagcagtg ggaataggag  840
ctttgttcct tgggttcttg ggagcagcag gaagcactat gggcgcagcc tcaatgacgc  900
tgacggtaca ggccagacaa ttattgtctg gtatagtgca gcagcagaac aatttgctga  960
gggctattga ggcgcaacag catctgttgc aactcacagt ctggggcatc aagcagctcc  1020
aggcaagaat cctggctgtg gaaagatacc taaaggatca acagctcctg gggatttggg  1080
gttgctctgg aaaactcatt tgcaccactg ctgtgccttg gaatgctagt tggagtaata  1140
aatctctgga acagattgga atcacacgac ctggatggag tgggacagag aaattaacaa  1200
ttacacaagc ttaatacact ccttaattga agaatcgcaa aaccagcaag aaaagaatga  1260
acaagaatta ttggaattag ataaatgggc aagtttgtgg aattggttta acataacaaa  1320
ttggctgtgg tatataaaat tattcataat gatagtagga ggcttggtag gtttaagaat  1380
agtttttgct gtactttcta tagtgaatag agttaggcag ggatattcac cattatcgtt  1440
tcagacccac ctcccaaccc cgaggggacc cgacaggccc gaaggaatag aagaagaagg  1500
tggagagaga gacagagaca gatccattcg attagtgaac ggatctcgac ggtatcggtt  1560
aacttttaaa agaaaagggg ggattggggg gtacagtgca ggggaaagaa tagtagacat  1620
aatagcaaca gacatacaaa ctaaagaatt acaaaaacaa attacaaaaa ttcaaaattt  1680
tatctcgagt agttgtgaac ttacacttta ttcatatata ttagatattg ataattttaa  1740
caaatgagtt actttccatt tggtacagt cacagttgtc aacaatattt ggaagcacca  1800
ggcatgaaat ctcctgagat gctatgtttt catcagggtc acctgacaca ttcaagttct  1860
gtctgacatg ccattaaagc actggctcag attgcaggca tattttcaaa ccggcagtaa  1920
ctggatagta tcacttcact tataagtgtt cattgtatca tcaagtgaaa taaacacaca  1980
acccatggga tcttgcttag gttggctgcc tagttggccc ctgagataaa gccttgtaat  2040
cacatagcct tgcctaatta gtcagaaaac aaaggattaa gtgagacagt cacaggatat  2100
aggaattata aataatacat atattaatag atattcattt tcattacaca aaagttgcta  2160
ttataaatac ttatttgatt gatgagtcta aaaatatatt ccccatataa ataatgttaa  2220
atattaataa atagatttag atttaaaatt caaatattgc aggcaggaca accacccggg  2280
ttaacttgca ttcaaatatg acattaccct atcaattgta acggccctga ttctaaaagc  2340
atgcaaaagt atacacagct ttatttttgt cttgtaaaaa tcaggttctt caagagagct  2400
tttttgagga accgtttcag aattaaaatt aagagcttgc atcagctcat caataacggc  2460
aagcatattc tgatcaagga atatctgtcg cttggggtcc atcaaaagtt ttgcgttcat  2520
tgtcttgaac tcaacctggt acatcttaag atcttcatat atagaagaca agcacagggc  2580
catcataaag cttgttttgc ggctggccaa acaagatcca ttggtaatga aagaagtctc  2640
tctggaattg agacaagatt cgtttttagt gagttccagt ggcaggcatg cctccacggt  2700
ggatgttttg tccttagtaa tatcttcgtg gtctatttcc tcacttgtgc aagggtaaaa  2760
ttcaagtgtt tgtcgggcct tctggagcat gttggagaca gccctaagca agttttgaga  2820
gtggtgaaga catgggaaca tgcctgggtc tggggttgca acaggcaagt tccgagaacc  2880
gcccccacca ccacctgagc atgggacaga tgcccattcg ctccagctag atgagtagta  2940
tctgtcttgg gctctgacac ttatgcttgc gttctttctg caaatgactg ttgcagacgt  3000
tttatcagtg aaaacccgat ctttcttttc cctttttgat tttccttgca cctggacaca  3060
aaatgtcaaa ctaaagtaag agtgcggagt tgaccaggtg tcggggtact cccaagaaac  3120
ttcaacctgg cgtgagttct tcaaaggctt aagctgcaga ttcttcggag gatcgggctt  3180
gataatgtcc cggataaaaa agctgctcgt gtaattttca tacttcaact tgtgtacggc  3240
gtcaaccatc acctctattg gcaggctctc ctctgctgcg ggcaagcgg agtcttcctg  3300
gcattccacg ctatattcgt attctttgtt gtccccccgt accctctccg cagaaagcgt  3360
agcagcaccg cacgttacac cttgtgggtc actggaaccc ctactagact taacagaaaa  3420
cgtaagatcc gtagagattg ttgtcaacca ccagcaagta aagcgtccgg agtaattttt  3480
tgcttcacag cgcagaaacg ttttgttttt gggttctttc tgatccttaa ggatatctgt  3540
actccaaatg ccatcctctt ttttgtgcag gagcagcagg ctgtgagaaa ggacctcgcc  3600
tcccttatgg cacgtatact gcccggcatc tccaaactct tttacctgga tagtaagtgt  3660
tttgccgctg ccaagcacct ctgagctttg gtccagggtc caggttatcc catcttcttc  3720
aggtgtatcg caggtgagga ccaccatctc gcccggtgcg tcgggatacc aatccaattc  3780
aacaacatat acgtctttct taagttccca aatagcgacc aatggtgacg ccagaaaaac  3840
aagtgagaac caagagatta ccagttgttg atggcacatg gtgggaattc ctggaattcg  3900
agcttccatt atataccctc tagagtctag atctacgcct tctgtatgaa acagtttttc  3960
ctccacgcct tctgtatgaa acagtttttc ctccacgcct tctgtatgaa acagtttttc  4020
ctccgtttaa acgtaagtca ttggtcttaa aggtagcttt atttagtctc cagaaaaagg  4080
ggggaatgaa agaccccacc tgtaggtttg gcaagctagg atcaaggtta ggaacagaga  4140
gacagcagaa tatgggccaa acaggatatc tgtggtaagc agttcctgcc ccggctcagg  4200
gccaagaaca gttggaacag cagaatatgg gccaaacagg atatctgtgg taagcagttc  4260
ctgccccggc tcagggccaa gaacagatgg tccccagatg cggtcccgcc ctcagcagtt  4320
tctagagaac catcagatgt ttccagggtg ccccaaggac ctgaaatgac cctgtgcctt  4380
atttgaacta accaatcagt tcgcttctcg cttctgttcg cgcgcttctg ctccccgagc  4440
tcaataaaag agcccacgct agcgctaccg gtcgccaaga tgggggcagg tgccaccggc  4500
cgcgccatgg acgggccgcg cctgctgctg ttgctgcttc tgggggtgtc ccttggaggt  4560
gccaaggagg catgccccac aggcctgtac acacacagcg gtgagtgctg caaagcctgc  4620
aacctgggcg agggtgtggc ccagccttgt ggagccaacc agaccgtgtg tgagccctgc  4680
ctggacagcg tgacgttctc cgacgtggtg agcgcgaccg agccgtgcaa gccgtgcacc  4740
gagtgcgtgg ggctccagag catgtcggcg ccgtgcgtgg aggccgacga cgccgtgtgc  4800
cgctgcgcct acggctacta ccaggatgag acgactgggc gctgcgaggc gtgccgcgtg  4860
```

-continued

```
tgcgaggcgg gctcgggcct cgtgttctcc tgccaggaca agcagaacac cgtgtgcgag  4920
gagtgccccg acggcacgta ttccgacgag gccaaccacg tggacccgtg cctgccctgc  4980
accgtgtgcg aggacaccga gcgccagctc cgcgagtgca cacgctgggc cgacgccgag  5040
tgcgaggaga tccctggccg ttggattaca cggtccacac ccccagaggg ctcggacagc  5100
acagccccca gcacccagga gcctgaggca cctccagaac aagacctcat agccagcacg  5160
gtggcaggtg tggtgaccac agtgatgggc agctcccagc ccgtggtgac ccgaggcacc  5220
accgacaacc tcatccctgt ctattgctcc atcctggctg ctgtggttgt gggtcttgtg  5280
gcctacatag ccttcaagag gggcagcgga gagggtaggg gtagtctttt gacgtgtggg  5340
gacgtcgagg aaaatcctgg gcctgcctta ccagtgaccg ccttgctcct gccgctggcc  5400
ttgctgctcc acgccgccag gccggacatc gtgatgaccc agagccccga cagcctggcc  5460
gtgagcctgg gcgagagggc caccatcaac tgcaagagca gccagagcct gctgaacagc  5520
ggcgaccaga agaactacct gacctggtac cagcagaagc ccggccagcc ccccaagctg  5580
ctgatctact gggccagcac cagggagagc ggcgtgcccg acaggttcag cggcagcggc  5640
agcggcaccg acttcaccct gaccatcagc agcctgcagg ccgaggacgt ggccgtgtac  5700
tactgccaga acgactacag ctacccccctg accttcggcc agggcaccaa ggtggagatc  5760
aagggcggcg gcggcagcgg cggcggcggc agcggcggcg gcggcagcca ggtgcagctg  5820
gtgcagagcg gcgccgaggt gaagaagacc ggcagcagcg tgaaggtgag ctgcaaggcc  5880
agcggctaca ccttcaccga ccacgccatc cactgggtga ggcaggcccc cggccaggcc  5940
ctggagtgga tgggccactt cagccccggc aacaccgaca tcaagtacaa cgacaagttc  6000
aagggcaggg tgaccctgac cgtggacagg agcatgagca ccgcctacat ggagctgagc  6060
agcctgagga gcgaggacac cgccatgtac tactgcaaga ccagcacctt cttcttcgac  6120
tactggggcc agggcaccat ggtgaccgtg agcagcacca cgacgccagc gccgcgacca  6180
ccaacaccgg cgcccaccat cgcgtcgcag cccctgtccc tgcgcccaga ggcgtgccgg  6240
ccagcggcgg ggggcgcagt gcacacgagg gggctggact tcgcctgtga tatctacatc  6300
tgggcgccct tggccgggac ttgtggggtc cttctcctgt cactggttat caccctttac  6360
tgcaaacggg gcagaaagaa actcctgtat atattcaaac aaccatttat gagaccagta  6420
caaactactc aagaggaaga tggctgtagc tgccgatttc cagaagaaga agaaggagga  6480
tgtgaactga gagtgaagtt cagcaggagc gcagacgccc ccgcgtacaa gcagggccag  6540
aaccagctct ataacgagct caatctagga cgaagagagg agtacgatgt tttggacaag  6600
agacgtggcc gggaccctga gatgggggga aagccgagaa ggaagaaccc tcaggaaggc  6660
ctgtacaatg aactgcagaa agataagatg gcggaggcct acagtgagat tgggatgaaa  6720
ggcgagcgcc ggaggggcaa ggggcacgat ggcctttacc agggtctcag tacagccacc  6780
aaggacacct acgacgccct tcacatgcag gccctgcccc ctcgctgaag agacgtcata  6840
atcagccagc ggccgcgtcg acaatcaacc tctggattac aaaatttgtg aaagattgac  6900
tggtattctt aactatgttg ctccttttac gctatgtgga tacgctgctt taatgccttt  6960
gtatcatgct attgcttccc gtatggcttt cattttctcc tccttgtata aatcctggtt  7020
gctgtctctt tatgaggagt tgtggcccgt tgtcaggcaa cgtggcgtgg tgtgcactgt  7080
gtttgctgac gcaaccccca ctggttgggg cattgccacc acctgtcagc tcctttccgg  7140
gactttcgct ttccccctcc ctattgccac ggcggaactc atcgccgcct gccttgcccg  7200
ctgctggaca ggggctcggc tgttgggcac tgacaattcc gtggtgttgt cggggaaatc  7260
atcgtccttt ccttggctgc tcgcctgtgt tgccacctgg attctgcgcg ggacgtcctt  7320
ctgctacgtc ccttcggccc tcaatccagc ggaccttcct tcccgcggcc tgctgccggc  7380
tctgcggcct cttccgcgtc ttcgccttcg ccctcagacg agtcggatct ccctttgggc  7440
cgcctccccg cctggtacct ttaagaccaa tgacttacaa ggcagctgta gatcttagcc  7500
actttttaaa agaaaagggg ggactggaag ggctaattca ctcccaacga aaataagatc  7560
tgctttttgc ttgtactggg tctctctggt tagaccagat ctgagcctgg gagctctctg  7620
gctaactagg gaacccactg cttaagcctc aataaagctt gccttgagtg cttcaagtag  7680
tgtgtgcccg tctgttgtgt gactctggta actagagatc cctcagaccc ttttagtcag  7740
tgtggaaaat ctctagca                                                 7758

SEQ ID NO: 11          moltype = DNA  length = 10009
FEATURE                Location/Qualifiers
misc_feature           1..10009
                       note = Gold CAR construct
source                 1..10009
                       mol_type = other DNA
                       organism = synthetic construct
SEQUENCE: 11
acgcgtgtag tcttatgcaa tactcttgta gtcttgcaac atggtaacga tgagttagca  60
acatgcctta caaggagaga aaaagcaccg tgcatgccga ttggtggaag taaggtggta  120
cgatcgtgcc ttattaggaa ggcaacagac gggtctgaca tggattggac gaaccactga  180
attgccgcat tgcagagata ttgtatttaa gtgcctagct cgatacaata aacgggtctc  240
tctggttaga ccagatctga gcctgggagc tctctggcta actagggaac ccactgctta  300
agcctcaata aagcttgcct tgagtgcttc aagtagtgtg tgcccgtctg ttgtgtgact  360
ctggtaacta gagatccctc agaccctttt agtcagtgtg gaaaatctct agcagtggcg  420
cccgaacagg gacctgaaag cgaaagggaa accagagctc tctcgacgca ggactcggct  480
tgctgaagcg cgcacggcaa gaggcgaggg gcggcgactg gtgagtacgc caaaaatttt  540
gactagcgga ggctagaagg agagagatgg gtgcgagagc gtcagtatta agcgggggag  600
aattagatcg cgatgggaaa aaattcggtt aaggccaggg ggaaagaaaa aatataaatt  660
aaaacatata gtatgggcaa gcagggagct agaacgattc gcagttaatc ctggcctgtt  720
agaaacatca gaaggctgta gacaaatact gggacagcta caaccatccc ttcagacagg  780
atcagaagaa cttagatcat tatataatac agtagcaacc ctctattgtg tgcatcaaag  840
gatagagata aaagacacca aggaagcttt agacaagata gaggaagagc aaaacaaaag  900
taagaccacc gcacagcaag cggccactga tcttcagacc tggaggagga gatatgaggg  960
acaattggag aagtgaatta tataaatata aagtagtaaa aattgaacca ttaggagtag  1020
cacccaccaa ggcaaagaga agagtggtgc agagagaaaa aagagcagtg ggaataggag  1080
ctttgttcct tgggttcttg ggagcagcag gaagcactat gggcgcagcc tcaatgacgc  1140
tgacggtaca ggccagacaa ttattgtctg gtatagtgca gcagcagaac aatttgctga  1200
gggctattga ggcgcaacag catctgttgc aactcacagt ctggggcatc aagcagctcc  1260
```

-continued

```
aggcaagaat cctggctgtg gaaagatacc taaaggatca acagctcctg gggatttggg  1320
gttgctctgg aaaactcatt tgcaccactg ctgtgccttg gaatgctagt tggagtaata  1380
aatctctgga acagattgga atcacacgac ctggatggag tgggacagag aaattaacaa  1440
ttacacaagc ttaatacact ccttaattga agaatcgcaa aaccagcaag aaaagaatga  1500
acaagaatta ttggaattag ataaatgggc aagtttgtgg aattggttta acataacaaa  1560
ttggctgtgg tatataaaat tattcataat gatagtagga ggcttggtag gtttaagaat  1620
agtttttgct gtactttcta tagtgaatag agttaggcag ggatattcac cattatcgtt  1680
tcagacccac ctcccaaccc cgaggggacc cgacaggccc gaaggaatag aagaagaagg  1740
tggagagaga gacagagaca gatccattcg attagtgaac ggatctcgac ggtatcggtt  1800
aacttttaaa agaaaagggg ggattggggg gtacagtgca ggggaaagaa tagtagacat  1860
aatagcaaca gacatacaaa ctaaagaatt acaaaaacaa attacaaaaa ttcaaaattt  1920
tatctcgagt agttgtgaac ttacacttta ttcatatata ttagatattg ataattttaa  1980
caaatgagtt actttccatt tgggtacagt cacagttgtc aacaatattt ggaagcacca  2040
ggcatgaaat ctcctgagat gctatgtttt catcagggtc acctgacaca ttcaagttct  2100
gtctgacatg ccattaaagc actggctcag attgcaggca tattttcaaa ccggcagtaa  2160
ctggatagta tcacttcact tataagtgtt cattgtatca tcaagtgaaa taaacacaca  2220
acccatggga tcttgcttag gttggctgcc tagttggccc ctgagataaa gccttgtaat  2280
cacatagcct tgcctaatta gtcagaaaac aaaggattaa gtgagacagt cacaggatat  2340
aggaattata aataatacat atattaatag atattcattt tcattacaca aaagttgcta  2400
ttataaatac ttatttgatt gatgagtcta aaaatatatt ccccatataa ataatgttaa  2460
atattaataa atagatttag atttaaaatt caaatattgc aggcaggaca accacccggg  2520
tcacgccaga atgcgttcgc acagccgcca gccggtcact ccgttgatgg ttactcggaa  2580
cagcagggag ccgtcggggt tgatcaggcg ctcgtcgata attttgttgc cgttccacag  2640
ggtccctgtt acagtgatct tttgccgtc gaacacggcg atgccttcat acggccgtcc  2700
gaaatagtcg atcatgttcg gcgtaacccc gtcgattacc agtgtgccat agtgcaggat  2760
caccttaaag tgatgatcat ccacagggta caccacctta aaaatttttt cgatctggcc  2820
catttggtcg ccgctcagac cttcatacgg gatgatgaca tggatgtcga tcttcagccc  2880
attttcaccg ctcaggacaa tcctttggat cggagttacg gacaccccga gattctgaaa  2940
caaactggac acacctccct gttcaaggac ttggtccagg ttgtagccgg ctgtctgtcg  3000
ccagtcccca acgaaatctt cgagtgtgaa gactggggca gggaaggcag caggcaacac  3060
caggagcagg cccagggaga aggcaactgg accgaaggcg cttgtggaga aggagttcat  3120
ggtgggaatt cctggaattc gagcttccat tatataccct ctagagtcta gatctacgcc  3180
ttctgtatga aacagttttt cctccacgcc ttctgtatga aacagttttt cctccacgcc  3240
ttctgtatga aacagttttt cctccgttta aacgtaagtc attggtctta aaggtagctt  3300
tatttagtct ccagaaaaag gggggaatga aagaccccac ctgtaggttt ggcaagctag  3360
gatcaaggtt aggaacagag agacagcaga atatgggcca aacaggatat ctgtggtaag  3420
cagttcctgc cccggctcag ggccaagaac agttggaaca gcagaatatg ggccaaacag  3480
gatatctgtg gtaagcagtt cctgccccgg ctcagggcca agaacagatg gtccccagat  3540
gcggtcccgc cctcagcagt ttctagagaa ccatcagatg tttccagggt gccccaagga  3600
cctgaaatga ccctgtgcct tatttgaact aaccaatcag ttcgcttctc gcttctgttc  3660
gcgcgcttct gctccccgag ctcaataaaa gagcccacgc tagcgctacc ggtcgccaag  3720
atgggggcag gtgccaccgg ccgcgcaatg gatggtccgc gtctactgct gttactactt  3780
ctgggtgtgt cccttggagg tgccaaagag gcatgcccca caggtctata cacacatagc  3840
ggtgaatgct gcaaagcatg caacctgggc gaaggtgtgg cccaaccttg tggagccaat  3900
caaaccgttt gtgagccatg tctggacagc gtgacgttct ccgatgttgt tagcgcgacc  3960
gagccatgca aaccgtgtac cgagtgtgtt ggtctccaaa gtatgtcggc gccgtgcgtg  4020
gaggccgacg acgccgtgtg tcgctgtgcc tacggttatt accaggatga aactactggt  4080
cgctgtgaag cgtgccgcgt gtgtgaggcg ggctcaggcc tcgtgttctc ctgtcaggac  4140
aaacagaaca ctgtgtgtga agaatgcccc gacggtactt attccgacga ggccaaccat  4200
gtggacccgt gtctgccctg caccgtttgc gaggataccg agcgccagct acgtgagtgc  4260
acacgttggg ccgacgccga gtgcgaggaa atccctggcc gttggattac acggtccaca  4320
ccaccagaag gctcggacag cacagcaccc agcactcagg aacctgaggc acctccagaa  4380
caagacctaa tagccagcac tgtggcaggt gttgtgacta cagtgatggg tagctcacaa  4440
cccgttgtta ctcgaggcac caccgacaat ctaattcctg tctattgttc catcctggct  4500
gctgtggttg tgggtcttgt tgcatatata gccttcaaga ggggcagcgg agagggtagg  4560
ggtagtcttt tgacgtgtgg ggacgtcgag gaaaatcctg ggcctgcctt accagtgacc  4620
gccttgctcc tgccgctggc cttgctgctc cacgccgcca ggccggacat cgtgatgacc  4680
cagagccccg acagcctggc cgtgagcctg ggcgagaggg ccaccatcaa ctgcaagagc  4740
agccagagcc tgctgaacag cggcgaccag aagaactacc tgacctggta ccagcagaag  4800
cccggccagc cccccaagct gctgatctac tgggccagca ccagggagag cggcgtgccc  4860
gacaggttca gcggcagcgg cagcggcacc gacttcaccc tgaccatcag cagcctgcag  4920
gccgaggacg tggccgtgta ctactgccag aacgactaca gctacccccct gaccttcggc  4980
cagggcacca aggtggagat caagggcggc ggcggcagcg gcggcggcgg cagcggcggc  5040
ggcggcagcc aggtgcagct ggtgcagagc ggcgccgagg tgaagaagac cggcagcagc  5100
gtgaaggtga gctgcaaggc cagcggctac accttcaccg accacgccat ccactgggtg  5160
aggcaggccc ccggccaggc cctggagtgg atgggccact tcagccccgg caacaccgac  5220
atcaagtaca acgacaagtt caagggcagg gtgaccctga ccgtggacag gagcatgagc  5280
accgcctaca tggagctgag cagcctgagg agcgaggaca ccgccatgta ctactgcaag  5340
accagcacct tcttcttcga ctactggggc cagggcacca tggtgaccgt gagcagcacc  5400
acgacgccag cgccgcgacc accaacaccg gcgcccacca tcgcgtcgca gcccctgtcc  5460
ctgcgcccag aggcgtgccg gccagcggcg gggggcgcag tgcacacgag ggggctggac  5520
ttcgcctgtg atatctacat ctgggcgccc ttggccggga cttgtggggt ccttctcctg  5580
tcactggtta tcaccettta ctgcaaacgg ggcagaaaga aactcctgta tatattcaaa  5640
caaccattta tgagaccagt acaaactact caagaggaag atggctgtag ctgccgattt  5700
ccagaagaag aagaaggagg atgtgaactg agagtgaagt tcagcaggag cgcagacgcc  5760
cccgcgtaca agcagggcca gaaccagctc tataacgagc tcaatctagg acgaagagag  5820
gagtacgatg ttttggacaa gagacgtggc cgggaccctg agatgggggg aaagccgaga  5880
aggaagaacc ctcaggaagg cctgtacaat gaactgcaga aagataagat ggcggaggcc  5940
tacagtgaga ttgggatgaa aggcgagcgc cggaggggca aggggcacga tggcctttac  6000
```

```
cagggtctca gtacagccac caaggacacc tacgacgccc ttcacatgca ggccctgccc  6060
cctcgctgaa gagacgtcat aatcagccag cggccgcgtc gacaatcaac ctctggatta  6120
caaaatttgt gaaagattga ctggtattct taactatgtt gctcctttta cgctatgtgg  6180
atacgctgct ttaatgcctt tgtatcatgc tattgcttcc cgtatggctt tcattttctc  6240
ctccttgtat aaatcctggt tgctgtctct ttatgaggag ttgtggcccg ttgtcaggca  6300
acgtggcgtg gtgtgcactg tgtttgctga cgcaaccccc actggttggg gcattgccac  6360
cacctgtcag ctcctttccg ggactttcgc tttccccctc cctattgcca cggcggaact  6420
catcgccgcc tgccttgccc gctgctggac aggggctcgg ctgttgggca ctgacaattc  6480
cgtggtgttg tcggggaaat catcgtcctt tccttggctg ctcgcctgtg ttgccacctg  6540
gattctgcgc gggacgtcct tctgctacgt cccttcggcc ctcaatccag cggaccttcc  6600
ttcccgcggc ctgctgccgg ctctgcggcc tcttccgcgt cttcgccttc gccctcagac  6660
gagtcggatc tccctttggg ccgcctcccc gcctggtacc tttaagacca atgacttaca  6720
aggcagctgt agatcttagc cactttttaa aagaaaaggg gggactggaa gggctaattc  6780
actcccaacg aaaataagat ctgctttttg cttgtactgg gtctctctgg ttagaccaga  6840
tctgagcctg ggagctctct ggctaactag ggaacccact gcttaagcct caataaagct  6900
tgccttgagt gcttcaagta gtgtgtgccc gtctgttgtg tgactctggt aactagagat  6960
ccctcagacc cttttagtca gtgtggaaaa tctctagcag tagtagttca tgtcatctta  7020
ttattcagta tttataactt gcaaagaaat gaatatcaga gagtgagagg aacttgttta  7080
ttgcagctta taatggttac aaataaagca atagcatcac aaatttcaca aataaagcat  7140
tttttcact gcattctagt tgtggtttgt ccaaactcat caatgtatct tatcatgtct  7200
ggctctagct atcccgcccc taactccgcc cagttccgcc cattctccgc cccatggctg  7260
actaattttt tttatttatg cagaggccga ggccgcctcg gcctctgagc tattccagaa  7320
gtagtgagga ggcttttttg gaggcctaga cttttgcaga gacggcccaa attcgtaatc  7380
atggtcatag ctgtttcctg tgtgaaattg ttatccgctc acaattccac acaacatacg  7440
agccggaagc ataaagtgta aagcctgggg tgcctaatga gtgagctaac tcacattaat  7500
tgcgttgcgc tcactgcccg ctttccagtc gggaaacctg tcgtgccagc tgcattaatg  7560
aatcggccaa cgcgcgggga gaggcggttt gcgtattggg cgctcttccg cttcctcgct  7620
cactgactcg ctgcgctcgg tcgttcggct gcggcgagcg gtatcagctc actcaaaggc  7680
ggtaatacgg ttatccacag aatcagggga taacgcagga aagaacatgt gagcaaaagg  7740
ccagcaaaag gccaggaacc gtaaaaaggc cgcgttgctg gcgtttttcc ataggctccg  7800
cccccctgac gagcatcaca aaaatcgacg ctcaagtcag aggtggcgaa acccgacagg  7860
actataaaga taccaggcgt ttccccctgg aagctccctc gtgcgctctc ctgttccgac  7920
cctgccgctt accggatacc tgtccgcctt tctcccttcg ggaagcgtgg cgctttctca  7980
tagctcacgc tgtaggtatc tcagttcggt gtaggtcgtt cgctccaagc tgggctgtgt  8040
gcacgaaccc cccgttcagc ccgaccgctg cgccttatcc ggtaactatc gtcttgagtc  8100
caacccggta agacacgact tatcgccact ggcagcagcc actggtaaca ggattagcag  8160
agcgaggtat gtaggcggtg ctacagagtt cttgaagtgg tggcctaact acggctacac  8220
tagaaggaca gtatttggta tctgcgctct gctgaagcca gttaccttcg gaaaaagagt  8280
tggtagctct tgatccggca aacaaaccac cgctggtagc ggtggttttt ttgtttgcaa  8340
gcagcagatt acgcgcagaa aaaaaggatc tcaagaagat cctttgatct tttctacggg  8400
gtctgacgct cagtggaacg aaaactcacg ttaagggatt ttggtcatga gattatcaaa  8460
aaggatcttc acctagatcc ttttaaatta aaaatgaagt tttaaatcaa tctaaagtat  8520
atatgagtaa acttggtctg acagttacca atgcttaatc agtgaggcac ctatctcagc  8580
gatctgtcta tttcgttcat ccatagttgc ctgactcccc gtcgtgtaga taactacgat  8640
acgggagggc ttaccatctg gccccagtgc tgcaatgata ccgcgagacc cacgctcacc  8700
ggctccagat ttatcagcaa taaaccagcc agccggaagg gccgagcgca gaagtggtcc  8760
tgcaacttta tccgcctcca tccagtctat taattgttgc cgggaagcta gagtaagtag  8820
ttcgccagtt aatagtttgc gcaacgttgt tgccattgct acaggcatcg tggtgtcacg  8880
ctcgtcgttt ggtatggctt cattcagctc cggttcccaa cgatcaaggc gagttacatg  8940
atcccccatg ttgtgcaaaa aagcggttag ctccttcggt cctccgatcg ttgtcagaag  9000
taagttggcc gcagtgttat cactcatggt tatggcagca ctgcataatt ctcttactgt  9060
catgccatcc gtaagatgct tttctgtgac tggtgagtac tcaaccaagt cattctgaga  9120
atagtgtatg cggcgaccga gttgctcttg cccggcgtca atacgggata ataccgcgcc  9180
acatagcaga actttaaaag tgctcatcat tggaaaacgt tcttcggggc gaaaactctc  9240
aaggatctta ccgctgttga gatccagttc gatgtaaccc actcgtgcac ccaactgatc  9300
ttcagcatct tttactttca ccagcgtttc tgggtgagca aaaacaggaa ggcaaaatgc  9360
cgcaaaaaag ggaataaggg cgacacggaa atgttgaata ctcatactct tcctttttca  9420
atattattga agcatttatc agggttattg tctcatgagc ggatacatat ttgaatgtat  9480
ttagaaaaat aaacaaatag gggttccgcg cacatttccc cgaaaagtgc cacctgacgt  9540
ctaagaaacc attattatca tgacattaac ctataaaaat aggcgtatca cgaggccctt  9600
tcgtctcgcg cgtttcggtg atgacggtga aaacctctga cacatgcagc tcccggagac  9660
ggtcacagct tgtctgtaag cggatgccgg gagcagacaa gcccgtcagg gcgcgtcagc  9720
gggtgttggc gggtgtcggg gctggcttaa ctatgcggca tcagagcaga ttgtactgag  9780
agtgcaccat atgcggtgtg aaataccgca cagatgcgta aggagaaaat accgcatcag  9840
gcgccattcg ccattcaggc tgcgcaactg ttgggaaggg cgatcggtgc gggcctcttc  9900
gctattacgc cagctggcga aagggggatg tgctgcaagg cgattaagtt gggtaacgcc  9960
agggttttcc cagtcacgac gttgtaaaac gacggccagt gccaagctg             10009
```

```
SEQ ID NO: 12           moltype = DNA  length = 10743
FEATURE                 Location/Qualifiers
misc_feature            1..10743
                        note = Gold CAR construct
source                  1..10743
                        mol_type = other DNA
                        organism = synthetic construct
SEQUENCE: 12
acgcgtgtag tcttatgcaa tactcttgta gtcttgcaac atggtaacga tgagttagca  60
acatgcctta caaggagaga aaaagcaccg tgcatgccga ttggtggaag taaggtggta  120
cgatcgtgcc ttattaggaa ggcaacagac gggtctgaca tggattggac gaaccactga  180
```

-continued

```
attgccgcat tgcagagata ttgtatttaa gtgcctagct cgatacaata aacgggtctc  240
tctggttaga ccagatctga gcctgggagc tctctggcta actagggaac ccactgctta  300
agcctcaata aagcttgcct tgagtgcttc aagtagtgtg tgcccgtctg ttgtgtgact  360
ctggtaacta gagatccctc agaccctttt agtcagtgtg gaaaatctct agcagtggcg  420
cccgaacagg gacctgaaag cgaaagggaa accagagctc tctcgacgca ggactcggct  480
tgctgaagcg cgcacggcaa gaggcgaggg gcggcgactg gtgagtacgc caaaaatttt  540
gactagcgga ggctagaagg agagagatgg gtgcgagagc gtcagtatta agcgggggag  600
aattagatcg cgatgggaaa aaattcggtt aaggccaggg ggaaagaaaa aatataaatt  660
aaaacatata gtatgggcaa gcagggagct agaacgattc gcagttaatc ctggcctgtt  720
agaaacatca gaaggctgta gacaaatact gggacagcta caaccatccc ttcagacagg  780
atcagaagaa cttagatcat tatataatac agtagcaacc ctctattgtg tgcatcaaag  840
gatagagata aaagacacca aggaagcttt agacaagata gaggaagagc aaaacaaaag  900
taagaccacc gcacagcaag cggccactga tcttcagacc tggaggagga gatatgaggg  960
acaattggag aagtgaatta tataaatata aagtagtaaa aattgaacca ttaggagtag  1020
cacccaccaa ggcaaagaga agagtggtgc agagagaaaa aagagcagtg ggaataggag  1080
ctttgttcct tgggttcttg ggagcagcag gaagcactat gggcgcagcc tcaatgacgc  1140
tgacggtaca ggccagacaa ttattgtctg gtatagtgca gcagcagaac aatttgctga  1200
gggctattga ggcgcaacag catctgttgc aactcacagt ctggggcatc aagcagctcc  1260
aggcaagaat cctggctgtg gaaagatacc taaaggatca acagctcctg gggatttggg  1320
gttgctctgg aaaactcatt tgcaccactg ctgtgccttg gaatgctagt tggagtaata  1380
aatctctgga acagattgga atcacacgac ctggatggag tgggacagag aaattaacaa  1440
ttacacaagc ttaatacact ccttaattga agaatcgcaa aaccagcaag aaaagaatga  1500
acaagaatta ttggaattag ataaatgggc aagtttgtgg aattggttta acataacaaa  1560
ttggctgtgg tatataaaat tattcataat gatagtagga ggcttggtag gtttaagaat  1620
agtttttgct gtactttcta tagtgaatag agttaggcag ggatattcac cattatcgtt  1680
tcagacccac ctcccaaccc cgaggggacc cgacaggccc gaaggaatag aagaagaagg  1740
tggagagaga gacagagaca gatccattcg attagtgaac ggatctcgac ggtatcggtt  1800
aacttttaaa agaaaagggg ggattggggg gtacagtgca ggggaaagaa tagtagacat  1860
aatagcaaca gacatacaaa ctaaagaatt acaaaaacaa attacaaaaa ttcaaaattt  1920
tatctcgagt agttgtgaac ttacacttta ttcatatata ttagatattg ataattttaa  1980
caaatgagtt actttccatt tgggtacagt cacagttgtc aacaatattt ggaagcacca  2040
ggcatgaaat ctcctgagat gctatgtttt catcagggtc acctgacaca ttcaagttct  2100
gtctgacatg ccattaaagc actggctcag attgcaggca tattttcaaa ccggcagtaa  2160
ctggatagta tcacttcact tataagtgtt cattgtatca tcaagtgaaa taaacacaca  2220
acccatggga tcttgcttag gttggctgcc tagttggccc ctgagataaa gccttgtaat  2280
cacatagcct tgcctaatta gtcagaaaac aaaggattaa gtgagacagt cacaggatat  2340
aggaattata aataatacat atattaatag atattcattt tcattacaca aaagttgcta  2400
ttataaatac ttatttgatt gatgagtcta aaaatatatt ccccatataa ataatgttaa  2460
atattaataa atagatttag atttaaaatt caaatattgc aggcaggaca accacccggg  2520
ttaacttgca ttcaaatatg acattaccct atcaattgta acggccctga ttctaaaagc  2580
atgcaaaagt atacacagct ttattttgt cttgtaaaaa tcaggttctt caagagagct  2640
tttttgagga accgtttcag aattaaaatt aagagcttgc atcagctcat caataacggc  2700
aagcatattc tgatcaagga atatctgtcg cttggggtcc atcaaaagtt ttgcgttcat  2760
tgtcttgaac tcaacctggt acatcttaag atcttcatat atagaagaca agcacagggc  2820
catcataaag cttgttttgc ggctggccaa acaagatcca ttggtaatga aagaagtctc  2880
tctggaattg agacaagatt cgtttttagt gagttccagt ggcaggcatg cctccacggt  2940
ggatgttttg tccttagtaa tatcttcgtg gtctatttcc tcacttgtgc aagggtaaaa  3000
ttcaagtgtt tgtcgggcct tctggagcat gttggagaca gccctaagca agttttgaga  3060
gtggtgaaga catgggaaca tgcctgggtc tggggttgca acaggcaagt tccgagaacc  3120
gcccccacca ccacctgagc atgggacaga tgcccattcg ctccagctag atgagtagta  3180
tctgtcttgg gctctgacac ttatgcttgc gttctttctg caaatgactg ttgcagacgt  3240
tttatcagtg aaaacccgat ctttcttttc ccttttttgat tttccttgca cctggacaca  3300
aaatgtcaaa ctaaagtaag agtgcggagt tgaccaggtg tcggggtact cccaagaaac  3360
ttcaacctgg cgtgagttct tcaaaggctt aagctgcaga ttcttcggag gatcgggctt  3420
gataatgtcc cggataaaaa agctgctcgt gtaattttca tacttcaact tgtgtacggc  3480
gtcaaccatc acctctattg gcaggctctc ctctgctgcg gggcaagcgg agtcttcctg  3540
gcattccacg ctatattcgt attctttgtt gtccccccgt accctctccg cagaaagcgt  3600
agcagcaccg cacgttacac cttgtgggtc actggaaccc ctactagact taacagaaaa  3660
cgtaagatcc gtagagattg ttgtcaacca ccagcaagta aagcgtccgg agtaattttt  3720
tgcttcacag cgcagaaacg ttttgttttt gggttctttc tgatccttaa ggatatctgt  3780
actccaaatg ccatcctctt ttttgtgcag gagcagcagg ctgtgagaaa ggacctcgcc  3840
tcccttatgg cacgtatact gcccggcatc tccaaactct tttacctgga tagtaagtgt  3900
tttgccgctg ccaagcacct ctgagctttg gtccagggtc caggttatcc catcttcttc  3960
aggtgtatcg caggtgagga ccaccatctc gcccggtgcg tcgggatacc aatccaattc  4020
aacaacatat acgtctttct taagttccca aatagcgacc aatggtgacg ccagaaaaac  4080
aagtgagaac caagagatta ccagttgttg atggcacatg gtgggaattc ggctgtccca  4140
gcacctcagc gcagagcaag tggtggtcag gggagcgtct caaatcctgc gcagcccaac  4200
gtccggcgcc gccaagtgac gcacgaggtg ctgtgactcg tgccagcccc ctaatctgcg  4260
gaagtggagt gcggggagtg cgccggaaga ggggtacgga agtgcgccgg aagtggggtg  4320
cggaggtgtg cagcgcgctg tcagactggc tcgcaggcgg cgcggccggc ggacccgttc  4380
gagacagcgc gggcggctcg ggtcccctgg ggctccgcag caggaggacg ccgctagcgc  4440
taccggtcgc caagatgggg gcaggtgcca ccggccgcgc catggacggg ccgcgcctgc  4500
tgctgttgct gcttctgggg gtgtcccttg gaggtgccaa ggaggcatgc ccccacaggcc  4560
tgtacacaca cagcggtgag tgctgcaaag cctgcaacct gggcgagggt gtggcccagc  4620
cttgtggagc caaccagacc gtgtgtgagc cctgcctgga cagcgtgacg ttctccgacg  4680
tggtgagcgc gaccgagccg tgcaagccgt gcaccgagtg cgtggggctc cagagcatgt  4740
cggcgccgtg cgtggaggcc gacgacgccg tgtgccgctg cgcctacggc tactaccagg  4800
atgagacgac tgggcgctgc gaggcgtgcc gcgtgtgcga ggcgggctcg ggcctcgtgt  4860
tctcctgcca ggacaagcag aacaccgtgt gcgaggagtg ccccgacggc acgtattccg  4920
```

-continued

```
acgaggccaa ccacgtggac ccgtgcctgc cctgcaccgt gtgcgaggac accgagcgcc  4980
agctccgcga gtgcacacgc tgggccgacg ccgagtgcga ggagatccct ggccgttgga  5040
ttacacggtc cacaccccca gagggctcgg acagcacagc ccccagcacc caggagcctg  5100
aggcacctcc agaacaagac ctcatagcca gcacggtggc aggtgtggtg accacagtga  5160
tgggcagctc ccagcccgtg gtgacccgag gcaccaccga caacctcatc cctgtctatt  5220
gctccatcct ggctgctgtg gttgtgggtc ttgtggccta catagccttc aagaggggca  5280
gcggagaggg taggggtagt cttttgacgt gtggggacgt cgaggaaaat cctgggcctg  5340
ccttaccagt gaccgccttg ctcctgccgc tggccttgct gctccacgcc gccaggccgg  5400
acatcgtgat gacccagagc cccgacagcc tggccgtgag cctgggcgag agggccacca  5460
tcaactgcaa gagcagccag agcctgctga acagcggcga ccagaagaac tacctgacct  5520
ggtaccagca gaagcccggc cagcccccca agctgctgat ctactgggcc agcaccaggg  5580
agagcggcgt gcccgacagg ttcagcggca gcggcagcgg caccgacttc accctgacca  5640
tcagcagcct gcaggccgag gacgtggccg tgtactactg ccagaacgac tacagctacc  5700
ccctgacctt cggccagggc accaaggtgg agatcaaggg cggcggcggc agcggcggcg  5760
gcggcagcgg cggcggcggc agccaggtgc agctggtgca gagcggcgcc gaggtgaaga  5820
agaccggcag cagcgtgaag gtgagctgca aggccagcgg ctacaccttc accgaccacg  5880
ccatccactg ggtgaggcag gcccccggcc aggccctgga gtggatgggc cacttcagcc  5940
ccggcaacac cgacatcaag tacaacgaca agttcaaggg cagggtgacc ctgaccgtgg  6000
acaggagcat gagcaccgcc tacatggagc tgagcagcct gaggagcgag gacaccgcca  6060
tgtactactg caagaccagc accttcttct tcgactactg gggccagggc accatggtga  6120
ccgtgagcag caccacgacg ccagcgccgc gaccaccaac accggcgccc accatcgcgt  6180
cgcagcccct gtccctgcgc ccagaggcgt gccggccagc ggcggggggc gcagtgcaca  6240
cgagggggct ggacttcgcc tgtgatatct acatctgggc gcccttggcc gggacttgtg  6300
gggtccttct cctgtcactg gttatcaccc tttactgcaa acggggcaga aagaaactcc  6360
tgtatatatt caaacaacca tttatgagac cagtacaaac tactcaagag gaagatggct  6420
gtagctgccg atttccagaa gaagaagaag gaggatgtga actgagagtg aagttcagca  6480
ggagcgcaga cgcccccgcg tacaagcagg gccagaacca gctctataac gagctcaatc  6540
taggacgaag agaggagtac gatgttttgg acaagagacg tggccgggac cctgagatgg  6600
ggggaaagcc gagaaggaag aaccctcagg aaggcctgta caatgaactg cagaaagata  6660
agatggcgga ggcctacagt gagattggga tgaaaggcga gcgccggagg ggcaaggggc  6720
acgatggcct ttaccagggt ctcagtacag ccaccaagga cacctacgac gcccttcaca  6780
tgcaggccct gccccctcgc tgaagagacg tcataatcag ccagcggccg cgtcgacaat  6840
caacctctgg attacaaaat ttgtgaaaga ttgactggta ttcttaacta tgttgctcct  6900
tttacgctat gtggatacgc tgctttaatg cctttgtatc atgctattgc ttcccgtatg  6960
gctttcattt tctcctcctt gtataaatcc tggttgctgt ctctttatga ggagttgtgg  7020
cccgttgtca ggcaacgtgg cgtggtgtgc actgtgtttg ctgacgcaac ccccactggt  7080
tggggcattg ccaccacctg tcagctcctt tccgggactt tcgctttccc cctccctatt  7140
gccacggcgg aactcatcgc cgcctgcctt gcccgctgct ggacaggggc tcggctgttg  7200
ggcactgaca attccgtggt gttgtcgggg aaatcatcgt cctttccttg gctgctcgcc  7260
tgtgttgcca cctggattct gcgcgggacg tccttctgct acgtcccttc ggccctcaat  7320
ccagcggacc ttccttcccg cggcctgctg ccggctctgc ggcctcttcc gcgtcttcgc  7380
cttcgccctc agacgagtcg gatctccctt tgggccgcct ccccgcctgg tacctttaag  7440
accaatgact tacaaggcag ctgtagatct tagccacttt ttaaaagaaa aggggggact  7500
ggaagggcta attcactccc aacgaaaata agatctgctt tttgcttgta ctgggtctct  7560
ctggttagac cagatctgag cctgggagct ctctggctaa ctagggaacc cactgcttaa  7620
gcctcaataa agcttgcctt gagtgcttca agtagtgtgt gcccgtctgt tgtgtgactc  7680
tggtaactag agatccctca gaccctttta gtcagtgtgg aaaatctcta gcagtagtag  7740
ttcatgtcat cttattattc agtatttata acttgcaaag aaatgaatat cagagagtga  7800
gaggaacttg tttattgcag cttataatgg ttacaaataa agcaatagca tcacaaattt  7860
cacaaataaa gcattttttt cactgcattc tagttgtggt ttgtccaaac tcatcaatgt  7920
atcttatcat gtctggctct agctatcccg cccctaactc cgcccagttc cgcccattct  7980
ccgccccatg gctgactaat tttttttatt tatgcagagg ccgaggccgc ctcggcctct  8040
gagctattcc agaagtagtg aggaggcttt tttggaggcc tagacttttg cagagacggc  8100
ccaaattcgt aatcatggtc atagctgttt cctgtgtgaa attgttatcc gctcacaatt  8160
ccacacaaca tacgagccgg aagcataaag tgtaaagcct ggggtgccta atgagtgagc  8220
taactcacat taattgcgtt gcgctcactg cccgctttcc agtcgggaaa cctgtcgtgc  8280
cagctgcatt aatgaatcgg ccaacgcgcg gggagaggcg gtttgcgtat tgggcgctct  8340
tccgcttcct cgctcactga ctcgctgcgc tcggtcgttc ggctgcggcg agcggtatca  8400
gctcactcaa aggcggtaat acggttatcc acagaatcag gggataacgc aggaaagaac  8460
atgtgagcaa aaggccagca aaaggccagg aaccgtaaaa aggccgcgtt gctggcgttt  8520
ttccataggc tccgcccccc tgacgagcat cacaaaaatc gacgctcaag tcagaggtgg  8580
cgaaacccga caggactata aagataccag gcgtttcccc ctggaagctc cctcgtgcgc  8640
tctcctgttc cgaccctgcc gcttaccgga tacctgtccg cctttctccc ttcgggaagc  8700
gtggcgcttt ctcatagctc acgctgtagg tatctcagtt cggtgtaggt cgttcgctcc  8760
aagctgggct gtgtgcacga accccccgtt cagcccgacc gctgcgcctt atccggtaac  8820
tatcgtcttg agtccaaccc ggtaagacac gacttatcgc cactggcagc agccactggt  8880
aacaggatta gcagagcgag gtatgtaggc ggtgctacag agttcttgaa gtggtggcct  8940
aactacggct acactagaag gacagtattt ggtatctgcg ctctgctgaa gccagttacc  9000
ttcggaaaaa gagttggtag ctcttgatcc ggcaaacaaa ccaccgctgg tagcggtggt  9060
ttttttgttt gcaagcagca gattacgcgc agaaaaaaag gatctcaaga agatcctttg  9120
atcttttcta cggggtctga cgctcagtgg aacgaaaact cacgttaagg gattttggtc  9180
atgagattat caaaaaggat cttcacctag atccttttaa attaaaaatg aagttttaaa  9240
tcaatctaaa gtatatatga gtaaacttgg tctgacagtt accaatgctt aatcagtgag  9300
gcacctatct cagcgatctg tctatttcgt tcatccatag ttgcctgact ccccgtcgtg  9360
tagataacta cgatacggga gggcttacca tctggcccca gtgctgcaat gataccgcga  9420
gacccacgct caccggctcc agatttatca gcaataaacc agccagccgg aagggccgag  9480
cgcagaagtg gtcctgcaac tttatccgcc tccatccagt ctattaattg ttgccgggaa  9540
gctagagtaa gtagttcgcc agttaatagt ttgcgcaacg ttgttgccat tgctacaggc  9600
atcgtggtgt cacgctcgtc gtttggtatg gcttcattca gctccggttc ccaacgatca  9660
```

-continued

```
aggcgagtta catgatcccc catgttgtgc aaaaaagcgg ttagctcctt cggtcctccg  9720
atcgttgtca gaagtaagtt ggccgcagtg ttatcactca tggttatggc agcactgcat  9780
aattctctta ctgtcatgcc atccgtaaga tgcttttctg tgactggtga gtactcaacc  9840
aagtcattct gagaatagtg tatgcggcga ccgagttgct cttgcccggc gtcaatacgg  9900
gataataccg cgccacatag cagaacttta aaagtgctca tcattggaaa acgttcttcg  9960
gggcgaaaac tctcaaggat cttaccgctg ttgagatcca gttcgatgta acccactcgt  10020
gcacccaact gatcttcagc atcttttact ttcaccagcg tttctgggtg agcaaaaaca  10080
ggaaggcaaa atgccgcaaa aaagggaata agggcgacac ggaaatgttg aatactcata  10140
ctcttccttt ttcaatatta ttgaagcatt tatcagggtt attgtctcat gagcggatac  10200
atatttgaat gtatttagaa aaataaacaa ataggggttc cgcgcacatt tccccgaaaa  10260
gtgccacctg acgtctaaga aaccattatt atcatgacat taacctataa aaataggcgt  10320
atcacgaggc cctttcgtct cgcgcgtttc ggtgatgacg gtgaaaacct ctgacacatg  10380
cagctcccgg agacggtcac agcttgtctg taagcggatg ccgggagcag acaagcccgt  10440
cagggcgcgt cagcgggtgt tggcgggtgt cggggctggc ttaactatgc ggcatcagag  10500
cagattgtac tgagagtgca ccatatgcgg tgtgaaatac cgcacagatg cgtaaggaga  10560
aaataccgca tcaggcgcca ttcgccattc aggctgcgca actgttggga agggcgatcg  10620
gtgcgggcct cttcgctatt acgccagctg gcgaaagggg gatgtgctgc aaggcgatta  10680
agttgggtaa cgccagggtt ttcccagtca cgacgttgta aaacgacggc cagtgccaag  10740
ctg                                                               10743

SEQ ID NO: 13          moltype = DNA  length = 10832
FEATURE                Location/Qualifiers
misc_feature           1..10832
                       note = Gold CAR construct
source                 1..10832
                       mol_type = other DNA
                       organism = synthetic construct
SEQUENCE: 13
gcgatcgcag taatcaatta cggggtcatt agttcatagc ccatatatgg agttccgcgt  60
tacataactt acggtaaatg gcccgcctgg ctgaccgccc aacgaccccc gcccattgac  120
gtcaataatg acgtatgttc ccatagtaac gccaataggg actttccatt gacgtcaatg  180
ggtggagtat ttacggtaaa ctgcccactt ggcagtacat caagtgtatc atatgccaag  240
tacgccccct attgacgtca atgacggtaa atggcccgcc tggcattatg cccagtacat  300
gaccttatgg gactttccta cttggcagta catctacgta ttagtcatcg ctattaccat  360
ggtgatgcgg ttttggcagt acatcaatgg gcgtggatag cggtttgact cacggggatt  420
tccaagtctc caccccattg acgtcaatgg gagtttgttt tggcaccaaa atcaacggga  480
ctttccaaaa tgtcgtaaca actccgcccc attgacgcaa atgggcggta ggcgtgtacg  540
gtgggaggtc tatataagca gagctcgttt agtgaaccgg ggtctctctg gttagaccag  600
atctgagcct gggagctctc tggctaacta gggaacccac tgcttaagcc tcaataaagc  660
ttgccttgag tgcttcaagt agtgtgtgcc cgtctgttgt gtgactctgg taactagaga  720
tccctcagac ccttttagtc agtgtggaaa atctctagca gtggcgcccg aacagggacc  780
tgaaagcgaa agggaaacca gagctctctc gacgcaggac tcggcttgct gaagcgcgca  840
cggcaagagg cgaggggcgg cgactggtga gtacgccaaa aattttgact agcggaggct  900
agaaggagag agatgggtgc gagagcgtca gtattaagcg ggggagaatt agatcgcgat  960
gggaaaaaat tcggttaagg ccagggggaa agaaaaaata taaattaaaa catatagtat  1020
gggcaagcag ggagctagaa cgattcgcag ttaatcctgg cctgttagaa acatcagaag  1080
gctgtagaca aatactggga cagctacaac catcccttca gacaggatca gaagaactta  1140
gatcattata taatacagta gcaaccctct attgtgtgca tcaaaggata gagataaaag  1200
acaccaagga agctttagac aagatagagg aagagcaaaa caaaagtaag accaccgcac  1260
agcaagcggc cgctgatctt cagacctgga ggaggagata tgagggacaa ttggagaagt  1320
gaattatata aatataaagt agtaaaaatt gaaccattag gagtagcacc caccaaggca  1380
aagagaagag tggtgcagag agaaaaaaga gcagtgggaa taggagcttt gttccttggg  1440
ttcttgggag cagcaggaag cactatgggc gcagcctcaa tgacgctgac ggtacaggcc  1500
agacaattat tgtctggtat agtgcagcag cagaacaatt tgctgagggc tattgaggcg  1560
caacagcatc tgttgcaact cacagtctgg ggcatcaagc agctccaggc aagaatcctg  1620
gctgtggaaa gatacctaaa ggatcaacag ctcctgggga tttggggttg ctctggaaaa  1680
ctcatttgca ccactgctgt gccttggaat gctagttgga gtaataaatc tctggaacag  1740
atttggaatc acacgacctg gatggagtgg gacagagaaa ttaacaatta cacaagctta  1800
atacactcct taattgaaga atcgcaaaac cagcaagaaa agaatgaaca agaattattg  1860
gaattagata aatgggcaag tttgtggaat tggtttaaca taacaaattg gctgtggtat  1920
ataaaattat tcataatgat agtaggaggc ttggtaggtt taagaatagt ttttgctgta  1980
ctttctatag tgaatagagt taggcaggga tattcaccat tatcgtttca gacccacctc  2040
ccaaccccga ggggacccga caggcccgaa ggaatagaag aagaaggtgg agagagagac  2100
agagacagat ccattcgatt agtgaacgga tctcgacggt atcggttaac ttttaaaaga  2160
aaagggggga ttggggggta cagtgcaggg gaaagaatag tagacataat agcaacagac  2220
atacaaacta aagaattaca aaaacaaatt acaaaaattc aaaattttgg ctcccgatcg  2280
ttgcgttaca cacacaatta ctgctgatcg agtgtagcct tcgaactcga gtagttgtga  2340
acttacactt tattcatata tattagatat tgataatttt aacaaatgag ttactttcca  2400
tttgggtaca gtcacagttg tcaacaatat ttggaagcac caggcatgaa atctcctgag  2460
atgctatgtt ttcatcaggg tcacctgaca cattcaagtt ctgtctgaca tgccattaaa  2520
gcactggctc agattgcagg catattttca aaccggcagt aactggatag tatcacttca  2580
cttataagtg ttcattgtat catcaagtga aataaacaca caacccatgg gatcttgctt  2640
aggttggctg cctagttggc ccctgagata aagccttgta atcacatagc cttgcctaat  2700
tagtcagaaa acaaaggatt aagtgagaca gtcacaggat ataggaatta taaataatac  2760
atatattaat agatattcat tttcattaca caaaagttgc tattataaat acttatttga  2820
ttgatgagtc taaaaatata ttccccatat aaataatgtt aaatattaat aaatagattt  2880
agatttaaaa ttcaaatatt gcaggcagga caaccacccg ggttaacttg cattcaaata  2940
tgacattacc ctatcaattg taacggccct gattctaaaa gcatgcaaaa gtatacacag  3000
ctttattttt gtcttgtaaa aatcaggttc ttcaagagag ctttttgag gaaccgtttc  3060
```

-continued

```
agaattaaaa ttaagagctt gcatcagctc atcaataacg gcaagcatat tctgatcaag  3120
gaatatctgt cgcttggggt ccatcaaaag ttttgcgttc attgtcttga actcaacctg  3180
gtacatctta agatcttcat atatagaaga caagcacagg gccatcataa agcttgtttt  3240
gcggctggcc aaacaagatc cattggtaat gaaagaagtc tctctggaat tgagacaaga  3300
ttcgttttta gtgagttcca gtggcaggca tgcctccacg gtggatgttt tgtccttagt  3360
aatatcttcg tggtctattt cctcacttgt gcaagggtaa aattcaagtg tttgtcgggc  3420
cttctggagc atgttggaga cagccctaag caagttttga gagtggtgaa gacatgggaa  3480
catgcctggg tctggggttg caacaggcaa gttccgagaa ccgcccccac caccacctga  3540
gcatgggaca gatgcccatt cgctccagct agatgagtag tatctgtctt gggctctgac  3600
acttatgctt gcgttctttc tgcaaatgac tgttgcagac gttttatcag tgaaaacccg  3660
atctttcttt tcccttttg atttccttg cacctggaca caaaatgtca aactaaagta  3720
agagtgcgga gttgaccagg tgtcggggta ctcccaagaa acttcaacct ggcgtgagtt  3780
cttcaaaggc ttaagctgca gattcttcgg aggatcgggc ttgataatgt cccggataaa  3840
aaagctgctc gtgtaatttt catacttcaa cttgtgtacg gcgtcaacca tcacctctat  3900
tggcaggctc tcctctgctg cggggcaagc ggagtcttcc tggcattcca cgctatattc  3960
gtattctttg ttgtcccccc gtaccctctc cgcagaaagc gtagcagcac cgcacgttac  4020
accttgtggg tcactggaac ccctactaga cttaacagaa aacgtaagat ccgtagagat  4080
tgttgtcaac caccagcaag taaagcgtcc ggagtaattt tttgcttcac agcgcagaaa  4140
cgttttgttt ttgggttctt tctgatcctt aaggatatct gtactccaaa tgccatcctc  4200
tttttgtgc aggagcagca ggctgtgaga aaggacctcg cctcccttat ggcacgtata  4260
ctgcccggca tctccaaact cttttacctg gatagtaagt gttttgccgc tgccaagcac  4320
ctctgagctt tggtccaggg tccaggttat cccatcttct tcaggtgtat cgcaggtgag  4380
gaccaccatc tcgcccggtg cgtcgggata ccaatccaat tcaacaacat atacgtcttt  4440
cttaagttcc caaatagcga ccaatggtga cgccagaaaa acaagtgaga accaagagat  4500
taccagttgt tgatggcaca tggtgggaat tcctggaatt cgagcttcca ttatataccc  4560
tctagagtct agatctacgc cttctgtatg aaacagtttt tcctccacgc cttctgtatg  4620
aaacagtttt tcctccacgc cttctgtatg aaacagtttt tcctccgttt aaacgtaagt  4680
cattggtctt aaaggtagct ttatttagtc tccagaaaaa ggggggaatg aaagacccca  4740
cctgtaggtt tggcaagcta ggatcaaggt taggaacaga gagacagcag aatatgggcc  4800
aaacaggata tctgtggtaa gcagttcctg ccccggctca gggccaagaa cagttggaac  4860
agcagaatat gggccaaaca ggatatctgt ggtaagcagt tcctgccccg gctcagggcc  4920
aagaacagat ggtccccaga tgcggtcccg ccctcagcag tttctagaga accatcagat  4980
gtttccaggg tgccccaagg acctgaaatg accctgtgcc ttatttgaac taaccaatca  5040
gttcgcttct cgcttctgtt cgcgcgcttc tgctccccga gctcaataaa agagcccacg  5100
ctagcgctac cggtcgccaa gatgggggca ggtgccaccg gccgcgcaat ggatggtccg  5160
cgtctactgc tgttactact tctgggtgtg tcccttggag gtgccaaaga ggcatgcccc  5220
acaggtctat acacacatag cggtgaatgc tgcaaagcat gcaacctggg cgaaggtgtg  5280
gcccaacctt gtggagccaa tcaaaccgtt tgtgagccat gtctggacag cgtgacgttc  5340
tccgatgttg ttagcgcgac cgagccatgc aaaccgtgta ccgagtgtgt tggtctccaa  5400
agtatgtcgg cgccgtgcgt ggaggccgac gacgccgtgt gtcgctgtgc ctacggttat  5460
taccaggatg aaactactgg tcgctgtgaa gcgtgccgcg tgtgtgaggc gggctcaggc  5520
ctcgtgttct cctgtcagga caaacagaac actgtgtgtg aagaatgccc cgacggtact  5580
tattccgacg aggccaacca tgtggacccg tgtctgccct gcaccgtttg cgaggatacc  5640
gagcgccagc tacgtgagtg cacacgttgg gccgacgccg agtgcgagga aatccctggc  5700
cgttggatta cacggtccac accaccagaa ggctcggaca gcacagcacc cagcactcag  5760
gaacctgagg cacctccaga acaagaccta atagccagca ctgtggcagg tgttgtgact  5820
acagtgatgg gtagctcaca acccgttgtt actcgaggca ccaccgacaa tctaattcct  5880
gtctattgtt ccatcctggc tgctgtggtt gtgggtcttg ttgcatatat agccttcaag  5940
aggggcagcg gagagggtag gggtagtctt ttgacgtgtg gggacgtcga ggaaaatcct  6000
gggcctgcct taccagtgac cgccttgctc ctgccgctgg ccttgctgct ccacgccgcc  6060
aggccggaca tcgtgatgac ccagagcccc gacagcctgg ccgtgagcct gggcgagagg  6120
gccaccatca actgcaagag cagccagagc ctgctgaaca gcggcgacca gaagaactac  6180
ctgacctggt accagcagaa gcccggccag ccccccaagc tgctgatcta ctgggccagc  6240
accagggaga gcggcgtgcc cgacaggttc agcggcagcg gcagcggcac cgacttcacc  6300
ctgaccatca gcagcctgca ggccgaggac gtggccgtgt actactgcca gaacgactac  6360
agctaccccc tgaccttcgg ccagggcacc aaggtggaga tcaagggcgg cggcggcagc  6420
ggcggcggcg gcagcggcgg cggcggcagc caggtgcagc tggtgcagag cggcgccgag  6480
gtgaagaaga ccggcagcag cgtgaaggtg agctgcaagg ccagcggcta caccttcacc  6540
gaccacgcca tccactgggt gaggcaggcc cccggccagg ccctggagtg gatgggccac  6600
ttcagccccg gcaacaccga catcaagtac aacgacaagt tcaagggcag ggtgaccctg  6660
accgtggaca ggagcatgag caccgcctac atggagctga gcagcctgag gagcgaggac  6720
accgccatgt actactgcaa gaccagcacc ttcttcttcg actactgggg ccagggcacc  6780
atggtgaccg tgagcagcac cacgacgcca gcgccgcgac caccaacacc ggcgcccacc  6840
atcgcgtcgc agcccctgtc cctgcgccca gaggcgtgcc ggccagcggc ggggggcgca  6900
gtgcacacga gggggctgga cttcgcctgt gatatctaca tctgggcgcc cttggccggg  6960
acttgtgggg tccttctcct gtcactggtt atcacccttt actgcaaacg gggcagaaag  7020
aaactcctgt atatattcaa acaaccattt atgagaccag tacaaactac tcaagaggaa  7080
gatggctgta gctgccgatt tccagaagaa gaagaaggag gatgtgaact gagagtgaag  7140
ttcagcagga gcgcagacgc ccccgcgtac aagcagggcc agaaccagct ctataacgag  7200
ctcaatctag gacgaagaga ggagtacgat gttttggaca agagacgtgg ccgggaccct  7260
gagatggggg gaaagccgag aaggaagaac cctcaggaag gcctgtacaa tgaactgcag  7320
aaagataaga tggcggaggc ctacagtgag attgggatga aaggcgagcg ccggaggggc  7380
aaggggcacg atggccttta ccagggtctc agtacagcca ccaaggacac ctacgacgcc  7440
cttcacatgc aggccctgcc ccctcgctga agagacgtca taatcagcca gcggccgcgt  7500
cgacaatcaa cctctggatt acaaaatttg tgaaagattg actggtattc ttaactatgt  7560
tgctcctttt acgctatgtg gatacgctgc tttaatgcct ttgtatcatg ctattgcttc  7620
ccgtatggct ttcattttct cctccttgta taaatcctgg ttgctgtctc tttatgagga  7680
gttgtggccc gttgtcaggc aacgtggcgt ggtgtgcact gtgtttgctg acgcaacccc  7740
cactggttgg ggcattgcca ccacctgtca gctcctttcc gggactttcg ctttccccct  7800
```

```
ccctattgcc acggcggaac tcatcgccgc ctgccttgcc cgctgctgga caggggctcg  7860
gctgttgggc actgacaatt ccgtggtgtt gtcggggaag ctgacgtcct ttccatggct  7920
gctcgcctgt gttgccacct ggattctgcg cgggacgtcc ttctgctacg tcccttcggc  7980
cctcaatcca gcggaccttc cttcccgcgg cctgctgccg gctctgcggc ctcttccgcg  8040
tcttcgcctt cgccctcaga cgagtcggat ctccctttgg gccgcctccc cgcctggaat  8100
tcgagctcgg tacctttaag accaatgact tacaaggcag ctgtagatct tagccacttt  8160
ttaaaagaaa aggggggact ggaagggcta attcactccc aacgaagaca agatctgctt  8220
tttgcttgta ctgggtctct ctggttagac cagatctgag cctgggagct ctctggctaa  8280
ctagggaacc cactgcttaa gcctcaataa agcttgcctt gagtgcttca agtagtgtgt  8340
gcccgtctgt tgtgtgactc tggtaactag agatccctca gaccctttta gtcagtgtgg  8400
aaaatctcta gcagtcctgg ccaacgtgag caccgtgctg acctccaaat atcgttaagc  8460
tggagcctgg gagccggcct ggccctccgc cccccccacc cccgcagccc acccctggtc  8520
tttgaataaa gtctgagtga gtggccgaca gtgcccgtgg agttctcgtg acctgaggtg  8580
cagggccggc gctagggaca cgtccgtgca cgtgccgagg ccccctgtgc agctgcaagg  8640
gacaggccta gccctgcagg cctaactccg cccatcccgc ccctaactcc gcccagttcc  8700
gcccattctc cgcctcatgg ctgactaatt ttttttattt atgcagaggc cgaggccgcc  8760
tcggcctctg agctattcca gaagtagtga ggacgctttt ttggaggccg aggcttttgc  8820
aaagatcgaa caagagacag gacctgcagg ttaattaaat ttaaatcatg tgagcaaaag  8880
gccagcaaaa ggccaggaac cgtaaaaagg ccgcgttgct ggcgtttttc cataggctcc  8940
gcccccctga cgagcatcac aaaaatcgac gctcaagtca gaggtggcga aacccgacag  9000
gactataaag ataccaggcg tttccccctg gaagctccct cgtgcgctct cctgttccga  9060
ccctgccgct taccggatac ctgtccgcct ttctcccttc gggaagcgtg gcgctttctc  9120
atagctcacg ctgtaggtat ctcagttcgg tgtaggtcgt tcgctccaag ctgggctgtg  9180
tgcacgaacc ccccgttcag cccgaccgct gcgccttatc cggtaactat cgtcttgagt  9240
ccaacccggt aagacacgac ttatcgccac tggcagcagc cactggtaac aggattagca  9300
gagcgaggta tgtaggcggt gctacagagt tcttgaagtg gtggcctaac tacggctaca  9360
ctagaagaac agtatttggt atctgcgctc tgctgaagcc agttaccttc ggaaaaagag  9420
ttggtagctc ttgatccggc aaacaaacca ccgctggtag cggtggtttt tttgtttgca  9480
agcagcagat tacgcgcaga aaaaaaggat ctcaagaaga tcctttgatc ttttctacgg  9540
ggtctgacgc tcagtggaac gaaaactcac gttaagggat tttggtcatg agattatcaa  9600
aaaggatctt cacctagatc cttttaaatt aaaaatgaag ttttaaatca atctaaagta  9660
tatatgagta aacttggtct gacagttacc aatgcttaat cagtgaggca cctatctcag  9720
cgatctgtct atttcgttca tccatagttg catttaaatg gccggcctgg cgcgccgttt  9780
aaacctagat attgatagtc tgatcggtca acgtataatc gagtcctagc ttttgcaaac  9840
atctatcaag agacaggatc agcaggaggc tttcgcatga ttgaacaaga tggattgcac  9900
gcaggttctc cggcggcttg ggtggagagg ctattcggct atgactgggc acaacagaca  9960
atcggctgct ctgatgccgc cgtgttccgg ctgtcagcgc aggggcgtcc ggttcttttt  10020
gtcaagaccg acctgtccgg tgccctgaat gaactgcaag acgaggcagc gcggctatcg  10080
tggctggcga cgacgggcgt tccttgcgcg gctgtgctcg acgttgtcac tgaagcggga  10140
agggactggc tgctattggg cgaagtgccg gggcaggatc tcctgtcatc tcaccttgct  10200
cctgccgaga aagtatccat catggctgat gcaatgcggc ggctgcatac gcttgatccg  10260
gctacctgcc cattcgacca ccaagcgaaa catcgcatcg agcgagcacg tactcggatg  10320
gaagccggtc ttgtcgatca ggatgatctg gacgaagagc atcaggggct cgcgccagcc  10380
gaactgttcg ccaggctcaa ggcgtctatg cccgacggcg aggatctcgt cgtgacccac  10440
ggcgatgcct gcttgccgaa tatcatggtg gaaaatggcc gcttttctgg attcatcgac  10500
tgtggccgtc tgggtgtggc ggaccgctat caggacatag cgttggctac ccgtgatatt  10560
gctgaagagc ttggcggcga atgggctgac cgcttccttg tgctttacgg tatcgccgcg  10620
cccgattcgc agcgcatcgc cttctatcgc cttcttgacg agttcttctg accgattcta  10680
ggtgcattgg cgcagaaaaa aatgcctgat gcgacgctgc gcgtcttata ctcccacata  10740
tgccagattc agcaacggat acggcttccc caacttgccc acttccatac gtgtcctcct  10800
taccagaaat ttatccttaa ggtcgtttaa ac                               10832

SEQ ID NO: 14           moltype = DNA  length = 10567
FEATURE                 Location/Qualifiers
misc_feature            1..10567
                        note = Gold CAR construct
source                  1..10567
                        mol_type = other DNA
                        organism = synthetic construct
SEQUENCE: 14
gcgatcgcag taatcaatta cggggtcatt agttcatagc ccatatatgg agttccgcgt  60
tacataactt acggtaaatg gcccgcctgg ctgaccgccc aacgaccccc gcccattgac  120
gtcaataatg acgtatgttc ccatagtaac gccaataggg actttccatt gacgtcaatg  180
ggtggagtat ttacggtaaa ctgcccactt ggcagtacat caagtgtatc atatgccaag  240
tacgccccct attgacgtca atgacggtaa atggcccgcc tggcattatg cccagtacat  300
gaccttatgg gactttccta cttggcagta catctacgta ttagtcatcg ctattaccat  360
ggtgatgcgg ttttggcagt acatcaatgg gcgtggatag cggtttgact cacggggatt  420
tccaagtctc caccccattg acgtcaatgg gagtttgttt tggcaccaaa atcaacggga  480
ctttccaaaa tgtcgtaaca actccgcccc attgacgcaa atgggcggta ggcgtgtacg  540
gtgggaggtc tatataagca gagctcgttt agtgaaccgg ggtctctctg gttagaccag  600
atctgagcct gggagctctc tggctaacta gggaacccac tgcttaagcc tcaataaagc  660
ttgccttgag tgcttcaagt agtgtgtgcc cgtctgttgt gtgactctgg taactagaga  720
tccctcagac ccttttagtc agtgtggaaa atctctagca gtggcgcccg aacagggacc  780
tgaaagcgaa agggaaacca gagctctctc gacgcaggac tcggcttgct gaagcgcgca  840
cggcaagagg cgaggggcgg cgactggtga gtacgccaaa aattttgact agcggaggct  900
agaaggagag agatgggtgc gagagcgtca gtattaagcg ggggagaatt agatcgcgat  960
gggaaaaaat tcggttaagg ccagggggaa agaaaaaata taaattaaaa catatagtat  1020
gggcaagcag ggagctagaa cgattcgcag ttaatcctgg cctgttagaa acatcagaag  1080
gctgtagaca aatactggga cagctacaac catcccttca gacaggatca gaagaactta  1140
```

-continued

```
gatcattata taatacagta gcaaccctct attgtgtgca tcaaaggata gagataaaag  1200
acaccaagga agctttagac aagatagagg aagagcaaaa caaaagtaag accaccgcac  1260
agcaagcggc cgctgatctt cagacctgga ggaggagata tgagggacaa ttggagaagt  1320
gaattatata aatataaagt agtaaaaatt gaaccattag gagtagcacc caccaaggca  1380
aagagaagag tggtgcagag agaaaaaaga gcagtgggaa taggagcttt gttccttggg  1440
ttcttgggag cagcaggaag cactatgggc gcagcctcaa tgacgctgac ggtacaggcc  1500
agacaattat tgtctggtat agtgcagcag cagaacaatt tgctgagggc tattgaggcg  1560
caacagcatc tgttgcaact cacagtctgg ggcatcaagc agctccaggc aagaatcctg  1620
gctgtggaaa gatacctaaa ggatcaacag ctcctgggga tttggggttg ctctggaaaa  1680
ctcatttgca ccactgctgt gccttggaat gctagttgga gtaataaatc tctggaacag  1740
atttggaatc acacgacctg gatggagtgg gacagagaaa ttaacaatta cacaagctta  1800
atacactcct taattgaaga atcgcaaaac cagcaagaaa agaatgaaca agaattattg  1860
gaattagata aatgggcaag tttgtggaat tggtttaaca taacaaattg gctgtggtat  1920
ataaaattat tcataatgat agtaggaggc ttggtaggtt taagaatagt ttttgctgta  1980
ctttctatag tgaatagagt taggcaggga tattcaccat tatcgtttca gacccacctc  2040
ccaaccccga ggggacccga caggcccgaa ggaatagaag aagaaggtgg agagagagac  2100
agagacagat ccattcgatt agtgaacgga tctcgacggt atcggttaac ttttaaaaga  2160
aaagggggga ttggggggta cagtgcaggg gaaagaatag tagacataat agcaacagac  2220
atacaaacta aagaattaca aaaacaaatt acaaaaattc aaaattttgg ctcccgatcg  2280
ttgcgttaca cacacaatta ctgctgatcg agtgtagcct tcgaactcga gtagttgtga  2340
acttacactt tattcatata tattagatat tgataatttt aacaaatgag ttactttcca  2400
tttgggtaca gtcacagttg tcaacaatat ttggaagcac caggcatgaa atctcctgag  2460
atgctatgtt ttcatcaggg tcacctgaca cattcaagtt ctgtctgaca tgccattaaa  2520
gcactggctc agattgcagg catattttca aaccggcagt aactggatag tatcacttca  2580
cttataagtg ttcattgtat catcaagtga aataaacaca caacccatgg gatcttgctt  2640
aggttggctg cctagttggc ccctgagata aagccttgta atcacatagc cttgcctaat  2700
tagtcagaaa acaaaggatt aagtgagaca gtcacaggat ataggaatta taaataatac  2760
atatattaat agatattcat tttcattaca caaaagttgc tattataaat acttatttga  2820
ttgatgagtc taaaaatata ttccccatat aaataatgtt aaatattaat aaatagattt  2880
agatttaaaa ttcaaatatt gcaggcagga caaccacccg ggttaacttg cattcaaata  2940
tgacattacc ctatcaattg taacggccct gattctaaaa gcatgcaaaa gtatacacag  3000
ctttattttt gtcttgtaaa aatcaggttc ttcaagagag ctttttttgag gaaccgtttc  3060
agaattaaaa ttaagagctt gcatcagctc atcaataacg gcaagcatat tctgatcaag  3120
gaatatctgt cgcttggggt ccatcaaaag ttttgcgttc attgtcttga actcaacctg  3180
gtacatctta agatcttcat atatagaaga caagcacagg gccatcataa agcttgtttt  3240
gcggctggcc aaacaagatc cattggtaat gaaagaagtc tctctggaat tgagacaaga  3300
ttcgttttta gtgagttcca gtggcaggca tgcctccacg gtggatgttt tgtccttagt  3360
aatatcttcg tggtctattt cctcacttgt gcaagggtaa aattcaagtg tttgtcgggc  3420
cttctggagc atgttggaga cagccctaag caagttttga gagtggtgaa gacatgggaa  3480
catgcctggg tctggggttg caacaggcaa gttccgagaa ccgcccccac caccacctga  3540
gcatgggaca gatgcccatt cgctccagct agatgagtag tatctgtctt gggctctgac  3600
acttatgctt gcgttctttc tgcaaatgac tgttgcagac gttttatcag tgaaaacccg  3660
atctttcttt tcccttttttg attttccttg cacctggaca caaaatgtca aactaaagta  3720
agagtgcgga gttgaccagg tgtcggggta ctcccaagaa acttcaacct ggcgtgagtt  3780
cttcaaaggc ttaagctgca gattcttcgg aggatcgggc ttgataatgt cccggataaa  3840
aaagctgctc gtgtaatttt catacttcaa cttgtgtacg gcgtcaacca tcacctctat  3900
tggcaggctc tcctctgctg cggggcaagc ggagtcttcc tggcattcca cgctatattc  3960
gtattctttg ttgtcccccc gtaccctctc cgcagaaagc gtagcagcac cgcacgttac  4020
accttgtggg tcactggaac ccctactaga cttaacagaa aacgtaagat ccgtagagat  4080
tgttgtcaac caccagcaag taaagcgtcc ggagtaattt tttgcttcac agcgcagaaa  4140
cgttttgttt ttgggttctt tctgatcctt aaggatatct gtactccaaa tgccatcctc  4200
tttttgtgc aggagcagca ggctgtgaga aaggacctcg cctcccttat ggcacgtata  4260
ctgcccggca tctccaaact cttttacctg gatagtaagt gttttgccgc tgccaagcac  4320
ctctgagctt tggtccaggg tccaggttat cccatcttct tcaggtgtat cgcaggtgag  4380
gaccaccatc tcgcccggtg cgtcgggata ccaatccaat tcaacaacat atacgtcttt  4440
cttaagttcc caaatagcga ccaatggtga cgccagaaaa acaagtgaga accaagagat  4500
taccagttgt tgatggcaca tggtgggaat tcggctgtcc cagcacctca gcgcagagca  4560
agtggtggtc aggggagcgt ctcaaatcct gcgcagccca acgtccggcg ccgccaagtg  4620
acgcacgagg tgctgtgact cgtgccagcc ccctaatctg cggaagtgga gtgcggggag  4680
tgcgccggaa gaggggtacg gaagtgcgcc ggaagtgggg tgcggaggtg tgcagcgcgc  4740
tgtcagactg gctcgcaggc ggcgcggccg gcggacccgt tcgagacagc gcgggcggct  4800
cgggtcccct ggggctccgc agcaggagga cgccgctagc gctaccggtc gccaagatgg  4860
gggcaggtgc caccggccgc gccatggacg ggccgcgcct gctgctgttg ctgcttctgg  4920
gggtgtccct tggaggtgcc aaggaggcat gccccacagg cctgtacaca cacagcggtg  4980
agtgctgcaa agcctgcaac ctgggcgagg gtgtggccca gccttgtgga gccaaccaga  5040
ccgtgtgtga gccctgcctg gacagcgtga cgttctccga cgtggtgagc gcgaccgagc  5100
cgtgcaagcc gtgcaccgag tgcgtggggc tccagagcat gtcggcgccg tgcgtggagg  5160
ccgacgacgc cgtgtgccgc tgcgcctacg gctactacca ggatgagacg actgggcgct  5220
gcgaggcgtg ccgcgtgtgc gaggcgggct cgggcctcgt gttctcctgc caggacaagc  5280
agaacaccgt gtgcgaggag tgccccgacg gcacgtattc cgacgaggcc aaccacgtgg  5340
acccgtgcct gccctgcacc gtgtgcgagg acaccgagcg ccagctccgc gagtgcacac  5400
gctgggccga cgccgagtgc gaggagatcc ctggccgttg gattacacgg tccacacccc  5460
cagagggctc ggacagcaca gcccccagca cccaggagcc tgaggcacct ccagaacaag  5520
acctcatagc cagcacggtg gcaggtgtgg tgaccacagt gatgggcagc tcccagcccg  5580
tggtgacccg aggcaccacc gacaacctca tccctgtcta ttgctccatc ctggctgctg  5640
tggttgtggg tcttgtggcc tacatagcct tcaagagggg cagcggagag ggtaggggta  5700
gtcttttgac gtgtggggac gtcgaggaaa atcctgggcc tgccttacca gtgaccgcct  5760
tgctcctgcc gctggccttg ctgctccacg ccgccaggcc ggacatcgtg atgacccaga  5820
gccccgacag cctggccgtg agcctgggcg agagggccac catcaactgc aagagcagcc  5880
```

-continued

```
agagcctgct gaacagcggc gaccagaaga actacctgac ctggtaccag cagaagcccg  5940
gccagccccc caagctgctg atctactggg ccagcaccag ggagagcggc gtgcccgaca  6000
ggttcagcgg cagcggcagc ggcaccgact tcaccctgac catcagcagc ctgcaggccg  6060
aggacgtggc cgtgtactac tgccagaacg actacagcta ccccctgacc ttcggccagg  6120
gcaccaaggt ggagatcaag ggcggcggcg gcagcggcgg cggcggcagc ggcggcggcg  6180
gcagccaggt gcagctggtg cagagcggcg ccgaggtgaa gaagaccggc agcagcgtga  6240
aggtgagctg caaggccagc ggctacacct tcaccgacca cgccatccac tgggtgaggc  6300
aggcccccgg ccaggccctg gagtggatgg gccacttcag ccccggcaac accgacatca  6360
agtacaacga caagttcaag ggcagggtga ccctgaccgt ggacaggagc atgagcaccg  6420
cctacatgga gctgagcagc ctgaggagcg aggacaccgc catgtactac tgcaagacca  6480
gcaccttctt cttcgactac tggggccagg gcaccatggt gaccgtgagc agcaccacga  6540
cgccagcgcc gcgaccacca acaccggcgc ccaccatcgc gtcgcagccc ctgtccctgc  6600
gcccagaggc gtgccggcca gcggcggggg gcgcagtgca cacgaggggg ctggacttcg  6660
cctgtgatat ctacatctgg gcgcccttgg ccgggacttg tggggtcctt ctcctgtcac  6720
tggttatcac cctttactgc aaacggggca gaaagaaact cctgtatata ttcaaacaac  6780
catttatgag accagtacaa actactcaag aggaagatgg ctgtagctgc cgatttccag  6840
aagaagaaga aggaggatgt gaactgagag tgaagttcag caggagcgca gacgcccccg  6900
cgtacaagca gggccagaac cagctctata acgagctcaa tctaggacga agagaggagt  6960
acgatgtttt ggacaagaga cgtggccggg accctgagat gggggggaaag ccgagaagga  7020
agaaccctca ggaaggcctg tacaatgaac tgcagaaaga taagatggcg gaggcctaca  7080
gtgagattgg gatgaaaggc gagcgccgga ggggcaaggg gcacgatggc ctttaccagg  7140
gtctcagtac agccaccaag gacacctacg acgcccttca catgcaggcc ctgccccctc  7200
gctgaagaga cgtcataatc agccagcggc cgcgtcgaca atcaacctct ggattacaaa  7260
atttgtgaaa gattgactgg tattcttaac tatgttgctc cttttacgct atgtggatac  7320
gctgctttaa tgcctttgta tcatgctatt gcttcccgta tggctttcat tttctcctcc  7380
ttgtataaat cctggttgct gtctctttat gaggagttgt ggcccgttgt caggcaacgt  7440
ggcgtggtgt gcactgtgtt tgctgacgca acccccactg gttggggcat tgccaccacc  7500
tgtcagctcc tttccgggac tttcgctttc cccctcccta ttgccacggc ggaactcatc  7560
gccgcctgcc ttgcccgctg ctggacaggg gctcggctgt tgggcactga caattccgtg  7620
gtgttgtcgg ggaagctgac gtcctttcca tggctgctcg cctgtgttgc cacctggatt  7680
ctgcgcggga cgtccttctg ctacgtccct tcggccctca atccagcgga ccttccttcc  7740
cgcggcctgc tgccggctct gcggcctctt ccgcgtcttc gccttcgccc tcagacgagt  7800
cggatctccc tttgggccgc ctccccgcct ggaattcgag ctcggtacct ttaagaccaa  7860
tgacttacaa ggcagctgta gatcttagcc actttttaaa agaaaagggg ggactggaag  7920
ggctaattca ctcccaacga agacaagatc tgctttttgc ttgtactggg tctctctggt  7980
tagaccagat ctgagcctgg gagctctctg gctaactagg gaacccactg cttaagcctc  8040
aataaagctt gccttgagtg cttcaagtag tgtgtgcccg tctgttgtgt gactctggta  8100
actagagatc cctcagaccc ttttagtcag tgtggaaaat ctctagcagt cctggccaac  8160
gtgagcaccg tgctgacctc caaatatcgt taagctggag cctgggagcc ggcctggccc  8220
tccgcccccc ccacccccgc agcccacccc tggtctttga ataaagtctg agtgagtggc  8280
cgacagtgcc cgtggagttc tcgtgacctg aggtgcaggg ccggcgctag ggacacgtcc  8340
gtgcacgtgc cgaggccccc tgtgcagctg caagggacag gcctagccct gcaggcctaa  8400
ctccgcccat cccgccccta actccgccca gttccgccca ttctccgcct catggctgac  8460
taattttttt tatttatgca gaggccgagg ccgcctcggc ctctgagcta ttccagaagt  8520
agtgaggacg ctttttttgga ggccgaggct tttgcaaaga tcgaacaaga gacaggacct  8580
gcaggttaat taaatttaaa tcatgtgagc aaaaggccag caaaaggcca ggaaccgtaa  8640
aaaggccgcg ttgctggcgt ttttccatag gctccgcccc cctgacgagc atcacaaaaa  8700
tcgacgctca agtcagaggt ggcgaaaccc gacaggacta taaagatacc aggcgtttcc  8760
ccctggaagc tccctcgtgc gctctcctgt tccgaccctg ccgcttaccg gatacctgtc  8820
cgcctttctc ccttcgggaa gcgtggcgct ttctcatagc tcacgctgta ggtatctcag  8880
ttcggtgtag gtcgttcgct ccaagctggg ctgtgtgcac gaaccccccg ttcagcccga  8940
ccgctgcgcc ttatccggta actatcgtct tgagtccaac ccggtaagac acgacttatc  9000
gccactggca gcagccactg gtaacaggat tagcagagcg aggtatgtag gcggtgctac  9060
agagttcttg aagtggtggc ctaactacgg ctacactaga agaacagtat ttggtatctg  9120
cgctctgctg aagccagtta ccttcggaaa aagagttggt agctcttgat ccggcaaaca  9180
aaccaccgct ggtagcggtg gtttttttgt ttgcaagcag cagattacgc gcagaaaaaa  9240
aggatctcaa gaagatcctt tgatcttttc tacggggtct gacgctcagt ggaacgaaaa  9300
ctcacgttaa gggattttgg tcatgagatt atcaaaaagg atcttcacct agatcctttt  9360
aaattaaaaa tgaagtttta aatcaatcta aagtatatat gagtaaactt ggtctgacag  9420
ttaccaatgc ttaatcagtg aggcacctat ctcagcgatc tgtctatttc gttcatccat  9480
agttgcattt aaatggccgg cctggcgcgc cgtttaaacc tagatattga tagtctgatc  9540
ggtcaacgta taatcgagtc ctagcttttg caaacatcta tcaagagaca ggatcagcag  9600
gaggctttcg catgattgaa caagatggat tgcacgcagg ttctccggcg gcttgggtgg  9660
agaggctatt cggctatgac tgggcacaac agacaatcgg ctgctctgat gccgccgtgt  9720
tccggctgtc agcgcagggg cgtccggttc tttttgtcaa gaccgacctg tccggtgccc  9780
tgaatgaact gcaagacgag gcagcgcggc tatcgtggct ggcgacgacg ggcgttcctt  9840
gcgcggctgt gctcgacgtt gtcactgaag cgggaaggga ctggctgcta ttgggcgaag  9900
tgccggggca ggatctcctg tcatctcacc ttgctcctgc cgagaaagta tccatcatgg  9960
ctgatgcaat gcggcggctg catacgcttg atccggctac ctgcccattc gaccaccaag  10020
cgaaacatcg catcgagcga gcacgtactc ggatggaagc cggtcttgtc gatcaggatg  10080
atctggacga agagcatcag gggctcgcgc cagccgaact gttcgccagg ctcaaggcgt  10140
ctatgcccga cggcgaggat ctcgtcgtga cccacggcga tgcctgcttg ccgaatatca  10200
tggtggaaaa tggccgcttt tctggattca tcgactgtgg ccgtctgggt gtggcggacc  10260
gctatcagga catagcgttg gctacccgtg atattgctga agagcttggc ggcgaatggg  10320
ctgaccgctt ccttgtgctt tacggtatcg ccgcgcccga ttcgcagcgc atcgccttct  10380
atcgccttct tgacgagttc ttctgaccga ttctaggtgc attggcgcag aaaaaaatgc  10440
ctgatgcgac gctgcgcgtc ttatactccc acatatgcca gattcagcaa cggatacggc  10500
ttccccaact tgcccacttc catacgtgtc ctccttacca gaaatttatc cttaaggtcg  10560
tttaaac                                                           10567
```

```
SEQ ID NO: 15          moltype = AA  length = 157
FEATURE                Location/Qualifiers
REGION                 1..157
                       note = Membrane bound IL18
source                 1..157
                       mol_type = protein
                       organism = synthetic construct
SEQUENCE: 15
YFGKLESKLS VIRNLNDQVL FIDQGNRPLF EDMTDSDCRD NAPRTIFIIS MYKDSQPRGM  60
AVTISVKCEK ISTLSCENKI ISFKEMNPPD NIKDTKSDII FFQRSVPGHD NKMQFESSSY  120
EGYFLACEKE RDLFKLILKK EDELGDRSIM FTVQNED                           157

SEQ ID NO: 16          moltype = AA  length = 193
FEATURE                Location/Qualifiers
REGION                 1..193
                       note = Membrane bound IL18
source                 1..193
                       mol_type = protein
                       organism = synthetic construct
SEQUENCE: 16
MAAEPVEDNC INFVAMKFID NTLYFIAEDD ENLESDYFGK LESKLSVIRN LNDQVLFIDQ  60
GNRPLFEDMT DSDCRDNAPR TIFIISMYKD SQPRGMAVTI SVKCEKISTL SCENKIISFK  120
EMNPPDNIKD TKSDIIFFQR SVPGHDNKMQ FESSSYEGYF LACEKERDLF KLILKKEDEL  180
GDRSIMFTVQ NED                                                     193

SEQ ID NO: 17          moltype = RNA  length = 13
FEATURE                Location/Qualifiers
misc_feature           1..13
                       note = RDE element
source                 1..13
                       mol_type = other RNA
                       organism = synthetic construct
SEQUENCE: 17
atttatttat tta                                                     13

SEQ ID NO: 18          moltype = DNA  length = 302
FEATURE                Location/Qualifiers
misc_feature           1..302
                       note = Promoters
source                 1..302
                       mol_type = other DNA
                       organism = synthetic construct
SEQUENCE: 18
ggctgtccca gcacctcagc gcagagcaag tggtggtcag gggagcgtct caaatcctgc  60
gcagcccaac gtccggcgcc gccaagtgac gcacgaggtg ctgtgactcg tgccagcccc  120
ctaatctgcg gaagtggagt gcggggagtg cgccggaaga ggggtacgga agtgcgccgg  180
aagtggggtg cggaggtgtg cagcgcgctg tcagactggc tcgcaggcgg cgcggccggc  240
ggacccgttc gagacagcgc gggcggctcg ggtcccctgg ggctccgcag caggaggacg  300
cc                                                                 302

SEQ ID NO: 19          moltype = DNA  length = 361
FEATURE                Location/Qualifiers
misc_feature           1..361
                       note = Promoters
source                 1..361
                       mol_type = other DNA
                       organism = synthetic construct
SEQUENCE: 19
cgcctcttct ctgcctagag gaaaagaaaa cgagctccca tgaacacgag gggcaaacga  60
ggaagagcga cgcgtaagtg gcagcggcag ccaatcgcgc accgaacggc tgggccggca  120
ttgtgacgtc tctggcagca ctgacgtggc ccctccctga gccaggggcc cagctggtcg  180
cggtcccccc ctcaacatgg cggcagcggt gctctaggcg ccggaagggg gcgtgaatcg  240
gtgcgaccgc gcgcgtgcgc agtaccgggt ccgcgcctgt ccccgaaact tcgcaccccg  300
tcgaactctc gcgagagcgg tatctgcgtg tcgggacgtg cggaggctct cactttccgt  360
c                                                                  361

SEQ ID NO: 20          moltype = DNA  length = 298
FEATURE                Location/Qualifiers
misc_feature           1..298
                       note = Promoters
source                 1..298
                       mol_type = other DNA
                       organism = synthetic construct
SEQUENCE: 20
catgttgctt gtctgggcaa attccacttc gcgagtgacg cacccggccg cgatgcgcta  60
gaacgccggc cccgccccga ggcggtgcgc ttggccacgc cccttcgttg gaggcctagt  120
cacgccccta aaggaagctc caccccatac ccgtggccac taaaaaactg cgggaagcag  180
gaaagagcac aacaggtttc tctctatttc cggtgtattg tatcctcacg tttccggaga  240
```

-continued

```
ttgacgttgc tcttgtgttc tcgcgagagg cgggaaaggg cgcagggttt gaaacatg    298

SEQ ID NO: 21          moltype = DNA  length = 324
FEATURE                Location/Qualifiers
misc_feature           1..324
                       note = Promoters
source                 1..324
                       mol_type = other DNA
                       organism = synthetic construct
SEQUENCE: 21
catgcctagc gccacgcgcc gagagcgcac accactgcag tcccgggacc acgaggcacg  60
acagctccct cggcgagacc acccgttggt accgggccgc ggcgggcggc gggggtggga  120
agctggagga ggagcgttag cagcaactcg cgctgggaag aagccggcgc tgcgcacgcg  180
cccggcccgc cactgcgcac gcgcccgcgg aagtggcggc tcccgtgtgc aggttgagcc  240
taggtgggcg gggcgggagg cggaagggcc gcggtgcgca gccgcgtcaa cggcccttcg  300
cagcgggcgc gctgtcagac ctca                                          324

SEQ ID NO: 22          moltype = DNA  length = 439
FEATURE                Location/Qualifiers
misc_feature           1..439
                       note = Promoters
source                 1..439
                       mol_type = other DNA
                       organism = synthetic construct
SEQUENCE: 22
cattgggacc cgtggcgacg gcggccacga cggccctcgg gcacccggca gcggcttgga  60
ccttcccgta cccgacggga gtgcgaagcg gagggagagg gggggaccga gcccgggccc  120
gggctgaggg gtgggggaga ggccgccctg cgctgctcgc gcccccacac ccgctaccgg  180
caacgactac tgtgaggtga cagagagggg acagggaggg cccacacgga agagggggcg  240
ggggcaggga tgcacttttg cgcatgtgct tacagtcctg acgtaggaag gggcggggct  300
ttgccgaagg gggcggggct ctcgctgatg ggttggcttt cgtcagggac ataggtagaa  360
gctggttggg gagtgtgcgt gccagcctga cgcgatatag tgcgcacatg cgtgatgacg  420
tagagggcgt tgattggga                                                439

SEQ ID NO: 23          moltype = DNA  length = 305
FEATURE                Location/Qualifiers
misc_feature           1..305
                       note = Promoters
source                 1..305
                       mol_type = other DNA
                       organism = synthetic construct
SEQUENCE: 23
catagcgagg ccggcgatgc cgcagccaca tcacccttcc ggggctcagg cggaagaggc  60
tgcatgtccc gtctgccctt ctcgccctct ccagccgtcc ggttgggctt gtcacggcac  120
cgcctaccaa gacgggcggt taagacacta ggataggctc ctctccaccg gaaaaggcgg  180
gatttagatc acgtcccgca ggccggcgga agtagctgat actctcattg gttgcaaaac  240
cttgatctgt gaaagcgggc gttttggaag ataccggaag tagagtcacg gagaggtagg  300
atccg                                                               305

SEQ ID NO: 24          moltype = DNA  length = 503
FEATURE                Location/Qualifiers
misc_feature           1..503
                       note = Promoters
source                 1..503
                       mol_type = other DNA
                       organism = synthetic construct
SEQUENCE: 24
catcgagcag ggtccggctg cagcaacgag cccagcgccg caacgcccag ggtgtggggc  60
ggagtaagat gtgaaacctc ttcagctcac ggcaccgggc tgcaaccgag gtctgaatgt  120
tgcgaaagcg ccccagacgc cgccgctgct ttccggccgc cccctcggct acagccgcca  180
tttccacgct ccaccaatca aatccattct cgaggaagac gcaccgcccc cacacgcccc  240
gaccaatcgc tcgcgctctg gttgcgctgg cgccttaggg gctccagtgc caccattgct  300
tttgctgctt ttctggcttt ccctttcgga catgcgcgct cggagcaagg cgccctcgca  360
ctcagcttac cgcgcatgta cgttgccagg ggtaacgcag gtagccaaag tggcttgtgg  420
agtggcgacc gttagtgagg cggttgctga gacagacgct gaggcgggta ggaggagccc  480
gagccgtaag ggaagccgtg atg                                           503

SEQ ID NO: 25          moltype = DNA  length = 553
FEATURE                Location/Qualifiers
misc_feature           1..553
                       note = Promoters
source                 1..553
                       mol_type = other DNA
                       organism = synthetic construct
SEQUENCE: 25
caggctagag cctccgggtg gcgcttctcg ccctcagtaa ccggttacct ccagaaccag  60
ggcgccagct ccggccatcc gcggttaagc gggagctccc attggctaat cgcacactga  120
aacgcacgcc ttttcccgcc cctgacgctg ccgtccaatg cgcgcctctc gactctgctc  180
cgccccgccc cgcccccgtc gccctgcctc cctggcgtat ttgcgccatt ggtggatatt  240
```

```
ccggaccgtg atggtggcgc tgcgcgtgcg cactcgctcc gagccctgct cccgggagag  300
ggagctctcg ggtcggggct agggaaggct gaccccgctc ggcccgggtg aaagggcggt  360
gacggcactg ggtggggccg agctccaggg ctggctgctg ggctgctaag ggaactgtga  420
gccgctcaga gccgcgcgcc tcccgggcgg ggcggggccg gccgtgggag tccgcgcgtg  480
cccgcgccga gctgcctgct ccggcggctt cgctgctagc tcgcggcgac gtcgggccga  540
ttttcccagg atg                                                     553

SEQ ID NO: 26          moltype = DNA  length = 326
FEATURE                Location/Qualifiers
misc_feature           1..326
                       note = Promoters
source                 1..326
                       mol_type = other DNA
                       organism = synthetic construct
SEQUENCE: 26
catagccaaa ggagtccgct gccggttgtt aggcaaccga cgtgtacact gactcggcgc  60
cgttcccacc gccccgcgcg cgcagccccg ctccccattg gccgtccgct cgtcgccgcc  120
tctccctatt ggtgcagggc cgaagagggt gggactaacc tggcaaagcc ccggcccagc  180
gcggggaggg gcacgctggc gacagagccc cgtctttatt gggcaagatc acgccgtgag  240
cgccaattgg ctgagtcgtc gccgagctgg gccaatcctc ttggtggagg aagctcggct  300
gattctcggc tcacgcggga ggggag                                      326

SEQ ID NO: 27          moltype = DNA  length = 105
FEATURE                Location/Qualifiers
misc_feature           1..105
                       note = Promoters
source                 1..105
                       mol_type = other DNA
                       organism = synthetic construct
SEQUENCE: 27
gtgggtcacg tgggccgcgc ctcggccaat gcggcggctg cgtagcgccc gggcccgccc  60
ctgagccgcg cgcacgtcgg gggcgggagc ggtgcgcgca acttc                  105

SEQ ID NO: 28          moltype = DNA  length = 350
FEATURE                Location/Qualifiers
misc_feature           1..350
                       note = Promoters
source                 1..350
                       mol_type = other DNA
                       organism = synthetic construct
SEQUENCE: 28
catggatgca acacccgatc cgcctcgggg actgggaaag ttccctccag ggctcccaca  60
ggcgctccgc ctcctgaact cccattggct gctttcgacg ttgtgctcca ccctttccgg  120
gcggggcggc aaaaatactt cccgtctctc cttttcgcct attggctctg tcaaaggtcg  180
acttcgtgac gtcaaagagc ctgggccaat cagagcacac cggactgcgt tttcccgaac  240
gcccgcagca gggtcagaag ggaggtggcc ggtctccgtc gtgacctctg acggtttctg  300
agcgttggcc tttggcacgc gctaccccct tttgctttgg ttctgccatg              350

SEQ ID NO: 29          moltype = DNA  length = 426
FEATURE                Location/Qualifiers
misc_feature           1..426
                       note = Promoters
source                 1..426
                       mol_type = other DNA
                       organism = synthetic construct
SEQUENCE: 29
catcgctgcc gagggccgtg cggccgcgct tggcgggctc agaggtcttg ctcctgggga  60
agctgagaat ctccgcgcgg tggactgtgg ccggccaacc gaaattggcg cgaaacgtcg  120
ccccccacgt gaccggcgcc actgcgtgcg ggccaatcgg acaaggcggc cttcttcacc  180
tcccgctagc cgcaagccaa tcaccgtgcg ggcctagaat gagtgacggg gaggcggtgc  240
gggcgtcgga agggaatctc cgggcggggt agtgcaggcg ccgggtttcc cgcggtccga  300
gctggcgcgg gcggaggaga atcgctctta aagggccagc gcacacgcgt tcttttgttc  360
cggggccgca gggcggggca ggcccgactt tcgccgtctt cttgtctact ctccagaacg  420
gccatg                                                             426

SEQ ID NO: 30          moltype = DNA  length = 240
FEATURE                Location/Qualifiers
misc_feature           1..240
                       note = Promoters
source                 1..240
                       mol_type = other DNA
                       organism = synthetic construct
SEQUENCE: 30
gcacgcgcac agcgccgggc cgcacacctc cgggctctgg gcggagcgcc tcgggcgttg  60
taggcgggac cggaccctct ggcccgcccc tccgtgtccc ttctggtcgc cagtggacgc  120
cgacgtcatg acgtcgcgtt ccgtagggct cttcccgggc tttggtgggt cacgtgaacc  180
acttttcgcg cgaaacctgg ttgttgctgt agtggcggag aggatcgtgg tactgctatg  240

SEQ ID NO: 31          moltype = DNA  length = 190
```

```
FEATURE                Location/Qualifiers
misc_feature           1..190
                       note = Promoters
source                 1..190
                       mol_type = other DNA
                       organism = synthetic construct
SEQUENCE: 31
cattgttcgc ctcaggctcg ccaccttccg acagctgtgt ttgcgcatgc gcgacgggtg  60
tgcaccgcct ctcgacttcc ggttcaccca gcatttcctc ttccctgttt tctttcgtcg  120
tcgtgggtgg gaattgtcgc ctaagtggtt ccgggttggt ggatgacctt gagccctcag  180
gaacgagatg                                                         190

SEQ ID NO: 32          moltype = DNA  length = 316
FEATURE                Location/Qualifiers
misc_feature           1..316
                       note = Promoters
source                 1..316
                       mol_type = other DNA
                       organism = synthetic construct
SEQUENCE: 32
accacaccgc cttgttaaat gccgtcgccg ccgccgccgt cttcgtcacc gtcacagtcg  60
ccgccgccat ctttgttgtg tctccgactc ccttcccgcc cccctgcctt gctcaagtct  120
cgcgtgagca ggatggaggg cgaaagcgag gaggggcctg tttgtctctc ttggggttcc  180
gtaggcagca gggggcaggg attaaggggg ggtgtgtgcg gggcgggtac tgagtgggcg  240
gggccttgct cgggtaactc ccaggggctg gctagagacc cagaggcgca gagcggagag  300
gcctgcggcg aggatg                                                  316

SEQ ID NO: 33          moltype = DNA  length = 316
FEATURE                Location/Qualifiers
misc_feature           1..316
                       note = Promoters
source                 1..316
                       mol_type = other DNA
                       organism = synthetic construct
SEQUENCE: 33
accacaccgc cttgttaaat gccgtcgccg ccgccgccgt cttcgtcacc gtcacagtcg  60
ccgccgccat ctttgttgtg tctccgactc ccttcccgcc cccctgcctt gctcaagtct  120
cgcgtgagca ggatggaggg cgaaagcgag gaggggcctg tttgtctctc ttggggttcc  180
gtaggcagca gggggcaggg attaaggggg ggtgtgtgcg gggcgggtac tgagtgggcg  240
gggccttgct cgggtaactc ccaggggctg gctagagacc cagaggcgca gagcggagag  300
gcctgcggcg aggatg                                                  316

SEQ ID NO: 34          moltype = AA  length = 18
FEATURE                Location/Qualifiers
REGION                 1..18
                       note = 2A element
source                 1..18
                       mol_type = protein
                       organism = synthetic construct
SEQUENCE: 34
EGRGSLLTCG DVEENPGP                                                18

SEQ ID NO: 35          moltype = AA  length = 19
FEATURE                Location/Qualifiers
REGION                 1..19
                       note = 2A element
source                 1..19
                       mol_type = protein
                       organism = synthetic construct
SEQUENCE: 35
ATNFSLLKQA GDVEENPGP                                               19

SEQ ID NO: 36          moltype = AA  length = 20
FEATURE                Location/Qualifiers
REGION                 1..20
                       note = 2A element
source                 1..20
                       mol_type = protein
                       organism = synthetic construct
SEQUENCE: 36
QCTNYALLKL AGDVESNPGP                                              20

SEQ ID NO: 37          moltype = AA  length = 22
FEATURE                Location/Qualifiers
REGION                 1..22
                       note = 2A element
source                 1..22
                       mol_type = protein
                       organism = synthetic construct
```

```
SEQUENCE: 37
VKQTLNFDLL KLAGDVESNP GP                                          22

SEQ ID NO: 38          moltype = DNA  length = 282
FEATURE                Location/Qualifiers
misc_feature           1..282
                       note = RDE element
source                 1..282
                       mol_type = other DNA
                       organism = synthetic construct
SEQUENCE: 38
taattaagtg cttcccactt aaaacatatc aggccttcta tttatttaaa tatttaaatt  60
ttatatttat tgttgaatgt atggtttgct acctattgta actattattc ttaatcttaa  120
aactataaat atggatcttt tatgattctt tttgtaagcc ctaggggctc taaaatggtt  180
tcacttattt atcccaaaat atttattatt atgttgaatg ttaaatatag tatctatgta  240
gattggttag taaaactatt taataaattt gataaatata aa                    282

SEQ ID NO: 39          moltype = DNA  length = 282
FEATURE                Location/Qualifiers
misc_feature           1..282
                       note = RDE element
source                 1..282
                       mol_type = other DNA
                       organism = synthetic construct
SEQUENCE: 39
taattaagtg cttcccactt aaaacatatc aggccttcta tttatttaaa tatttaaatt  60
ttatatttat tgttgaatgt atggtttgct acctattgta actattattc ttaatcttaa  120
aactataaat atggatcttt tatgattgaa tttgtaagcc ctaggggctc taaaatggtt  180
tcacttattt atcccaaaat atttattatt atgttgaatg ttaaatatag tatctatgta  240
gattggttag taaaactatt taataaattt gataaatata aa                    282

SEQ ID NO: 40          moltype = DNA  length = 585
FEATURE                Location/Qualifiers
misc_feature           1..585
                       note = RDE element
source                 1..585
                       mol_type = other DNA
                       organism = synthetic construct
SEQUENCE: 40
tggttgtcct gcctgcaata tttgaatttt aaatctaaat ctatttatta atatttaaca  60
ttatttatat ggggaatata tttttagact catcaatcaa ataagtattt ataatagcaa  120
cttttgtgta atgaaaatga atatctatta atatatgtat tatttataat tcctatatcc  180
tgtgactgtc tcacttaatc ctttgttttc tgactaatta ggcaaggcta tgtgattaca  240
aggctttatc tcaggggcca actaggcagc caacctaagc aagatcccat gggttgtgtg  300
tttatttcac ttgatgatac aatgaacact tataagtgaa gtgatactat ccagttactg  360
ccggtttgaa aatatgcctg caatctgagc cagtgcttta atggcatgtc agacagaact  420
tgaatgtgtc aggtgaccct gatgaaaaca tagcatctca ggagatttca tgcctggtgc  480
ttccaaatat tgttgacaac tgtgactgta cccaaatgga aagtaactca tttgttaaaa  540
ttatcaatat ctaatatata tgaataaagt gtaagttcac aacta                 585

SEQ ID NO: 41          moltype = DNA  length = 32
FEATURE                Location/Qualifiers
misc_feature           1..32
                       note = Promoter
source                 1..32
                       mol_type = other DNA
                       organism = synthetic construct
SEQUENCE: 41
tagagggtat ataatggaag ctcgacttcc ag                               32

SEQ ID NO: 42          moltype = DNA  length = 131
FEATURE                Location/Qualifiers
misc_feature           1..131
                       note = Promoter
source                 1..131
                       mol_type = other DNA
                       organism = synthetic construct
SEQUENCE: 42
ggaggaaaaa ctgtttcata cagaaggcgt ggaggaaaaa ctgtttcata cagaaggcgt  60
ggaggaaaaa ctgtttcata cagaaggcgt agatctagac tctagagggt atataatgga  120
agctcgaatt c                                                      131
```

COMPOSITIONS AND METHODS FOR ANTI-TnMUC1 GOLD CAR T-CELLS

REFERENCE TO SEQUENCE LISTING, TABLE OR COMPUTER PROGRAM

The official copy of the Sequence Listing is submitted concurrently with the specification as an xml file, made with WIPO Sequence Version 2.1.0, via EFS-Web, with a file name of "CBI0079.xml", a creation date of Nov. 8, 2022, and a size of 151 kilobytes. The Sequence Listing filed via EFS-Web is part of the specification and is incorporated in its entirety by reference herein.

BACKGROUND OF THE INVENTION

Chimeric Antigen Receptors are human engineered receptors that may direct a T-cell to attack a target recognized by the CAR. For example, CAR T cell therapy has been shown to be effective at inducing complete responses against acute lymphoblastic leukemia and other B-cell-related malignancies and has been shown to be effective at achieving and sustaining remissions for refractory/relapsed acute lymphoblastic leukemia (Maude et al., NEJM, 371:1507, 2014). However, dangerous side effects related to cytokine release syndrome (CRS), tumor lysis syndrome (TLS), B-cell aplasia and on-tumor, off-target toxicities have been seen in some patients.

There are currently two extant strategies to control CAR technology. The first is an inducible "kill switch." In this approach, one or more "suicide" genes that initiate apoptotic pathways are incorporated into the CAR construct (Budde et al. PLoS1, 2013 doi:10.1371/journal.pone.0082742). Activation of these suicide genes is initiated by the addition of AP1903 (also known as rimiducid), a lipid-permeable tachrolimus analog that initiates homodimerization of the human protein FKBP12 (Fv), to which the apoptosis-inducing proteins are translationally fused. In the ideal scenario, these kill switches endeavor to sacrifice the long-term surveillance benefit of CAR technology to safeguard against toxicity. However, in vivo, these suicide switches are not likely to realize this goal, as they are operating against powerful selection pressures for CAR T-cells that do not respond to AP1903, a situation worsened by the inimical error-prone retroviral copying associated with the insertion of stable transgenes into patient T-cells. In this scenario, non-responsive CAR T-cell clones will continue to proliferate and kill target cells in an antigen-dependent manner. Thus, kill switch technology is unlikely to provide an adequate safeguard against toxicity.

The second CAR regulatory approach is transient CAR expression, which can be achieved in several ways. In one approach, T-cells are harvested from unrelated donors, the HLA genes are deleted by genome-editing technology and CAR-encoding transgenes are inserted into the genome of these cells. Upon adoptive transfer, these CAR T-cells will be recognized by the recipient's immune system as being foreign and destroyed, thus the CAR exposure in this system is transient. In another transient CAR exposure approach, mRNA of a CAR-encoding gene is introduced into harvested patient T-cells (Beatty, G L 2014. Cancer Immunology Research 2 (2): 112-20. doi:10.1158/2326-6066.CIR-13-0170). As mRNA has a short half-life and is not replicated in the cell or stably maintained, there is no permanent alteration of the CAR-expressing T-cell, thus the CAR expression and activity will be for a short period of time. However, as with the kill-switch approach, these transient CAR exposure approaches sacrifice the surveillance benefit of CARs. Additionally, with these transient systems acute toxicity can be difficult to control.

SUMMARY OF THE INVENTION

In an aspect, the description discloses methods, cells and nucleic acids for anti-TnMUC1 chimeric antigen receptors with various payloads under control of an RNA Destabilizing Element ("RDE") in immune cells, collectively used to target cancer cells. The Chimeric Antigen Receptor can be an anti-TnMUC1 CAR having the sequence of SEQ ID NO: 1 (amino acid sequence of SEQ ID NO: 2), which optionally can include a signal sequence such as SEQ ID NO: 3. Constructs with this anti-TnMUC1 CAR can include GC160 (SEQ ID NO: 4), GC213 (SEQ ID NO: 5), GC217 (SEQ ID NO: 6), GC219 (SEQ ID NO: 7), GC223 (SEQ ID NO: 8), SK062 (SEQ ID NO: 9), SK148 (SEQ ID NO: 10), SK072 (SEQ ID NO: 11), GC251, (SEQ ID NO: 12), PD007 (SEQ ID NO: 13), and PD009 (SEQ ID NO: 14). The payload can be one or more of a cytokine, a FasL, an antibody, a growth factor, a chemokine, an enzyme that cleaves a polypeptide or a polysaccharide, a granzyme, a perforin, or a checkpoint inhibitor. The payload can be one or more of IL-12, anti-4-1BB antibody, anti-CD11b antibody, anti-CTLA4 antibody, anti-IL1b antibody, a BiTE, CCL2, anti-CXCR4 antibody, anti-CXCL12 antibody, HAC, heparinase, hyaluronidase, Hsp60, Hsp70, IL-2, IL-15, IL-18, INFγ, miRNA (e.g., mir155), CD40 ligand, ApoE3, ApoE4, TNFα, CCR2, CCR4/CXCL12, CXCR3+CXCL9, CXCL9, ACLY, antagonists of CSF1 receptor, miRNA for Tox (e.g., hsa-mir-26b-5p (MIRT030248) hsa-mir-223-3p (MIRT054680)), miRNA for TCF-7 (e.g., mIR-192, mIR-34a, miR-133a, miR-138-5p, miR-342-5p, miR-491-5p, miR-541-3p), anti-CD28 antibody (including full length and fragments such as single chain antibodies) and/or anti-TGFb agents (e.g., anti-TGFb antibody, soluble TGFbR, anti-avB6 integrin antibody, natural TGFb binding proteins, dnTGFBR2, biglycan, decorin).

The TnMUC1 can be found on a number of cancers including, for example, ovarian cancers, breast cancers (e.g., certain triple negative breast cancers), pancreatic cancers, colorectal cancers, colon cancers, prostate cancer, non-small cell lung cancer (NSCLC), multiple myeloma, and/or T-cell acute lymphoblastic leukemia. Any of the foregoing cancers that are positive for TnMUC1 may be treated with the anti-TnMUC1 Gold CARs described herein. In an aspect, the binding domain of the chimeric antigen receptor recognizes the altered glycosylation of the Tn-MUC1 antigen, and can also recognize similar altered Tn-glycosylation at other antigens which because of the Tn-glycosylation can become tumor associated antigens. Such other, tumor associated antigens with altered Tn-glycosylation include, for example, MUC16 (uniprot Q8WXI7), CD43, LRP8 (uniprot Q14114), GALNT10 (uniprot Q86SR1), GXYLT2 (uniprot AOPJZ3), PODXL (uniprot 000592), TGOLN2 (uniprot 043493), CPD (uniprot 075976), LDLR (uniprot P01130), TFRC (uniprot P02786), PTPRC (uniprot P08575), CD7 (uniprot P09564), MIC2 (uniprot P14209), MGAT1 (uniprot P26572), CANX (uniprot P27824), GRN (uniprot P28799), TNFRSF8 (uniprot P28908), HCFC1 (uniprot P51610), GFRA1 (uniprot P56159), NUCB2 (uniprot P80303), FBLN2 (uniprot P98095), VLDLR (uniprot P98155), LRP1 (uniprot Q07954), MGAT2 (uniprot Q10469), GALNT2 (uniprot Q10471), OS9 (uniprot Q13438), DAG1 (uniprot Q14118), SELPLG (uniprot Q14242), CDON (uniprot Q4KMG0), PRRT3 (uniprot Q5FWE3), MIA3 (uniprot Q5JRA6), LAIR1 (uniprot Q6GTX8-2), PI16 (uniprot Q6UXB8), SEX6L2 (uniprot Q6UXD5-3), SRCAP (uniprot Q6ZRS2), GALNT7 (uniprot Q86SF2), RTN4RL2 (uniprot Q86UN3), LRP11 (uniprot Q86VZ4), AEBP1 (uniprot Q8IUX7), LEPREL2 (uniprot Q8IVL6), GALNT12 (uniprot Q8IXK2), KIAA2013 (uniprot Q8IYS2), XXYLT1 (uniprot Q8NBI6), TP53I13 (uniprot Q8NBR0), CHST14 (uniprot Q8NCH0), SORL1 (uniprot Q92673), SEMA4D (uniprot Q92854), DCBLD2 (uniprot Q96PD2), SLC29A1 (uniprot Q99808), SMO (uniprot Q99835), ERP44 (uniprot Q9BS26), YIPF3 (uniprot Q9GZM5), XYLT2 (uniprot Q9H1B5), MEGF9 (uniprot Q9H1U4), SLC38A10 (uniprot Q9HBR0), TMEM30A (uniprot Q9NV96), SEL1L (uniprot Q9UBV2), SAP30BP (uniprot Q9UHR5), MANIB1 (uniprot Q9UKM7), HEG1 (uniprot Q9ULI3), MINPP1 (uniprot Q9UNW1), CLEC11A (uniprot Q9Y240), BACE2 (uniprot Q9Y5Z0), CD99 (uniprot H7C2F2), NCOR1 (uniprot 075376), CTSD (uniprot P07339), FAS (uniprot P25445), CD27 (uniprot P26842), LRPAP1 (uniprot P30533), BMPR1A (uniprot P36894), FAM3A (uniprot P98173), GNPTAB (uniprot Q3T906), CASC4 (uniprot Q6P4E1), SEZ6L2 (uniprot Q6UXD5-3), XXYLT12 (uniprot Q8NBI6), TXNDC5 (uniprot Q8NBS9), ERGIC2 (uniprot Q96RQ1), CCDC134 (uniprot Q9H6E4), SDF2L1 (uniprot Q9HCN8), GPR108 (uniprot Q9NPR9), GNPTG (uniprot Q9UJJ9), CCDC64B (uniprot A1A5D9), LILRA5 (uniprot A6NI73), SPINT2 (043291), GDF11 (uniprot 095390), P4HA1 (uniprot P13674-2), IGLL1 (uniprot P15814), FXYD2 (uniprot P54710-2), HNRNPU (uniprot Q00839), PVRL1 (uniprot Q15223), ADRM1 (uniprot Q16186), XYLT1 (uniprot Q86Y38), PNPLA1 (uniprot Q8N8W4), TTN (uniprot Q8WZ42), IGSF8 (uniprot Q969P0), LY9 (uniprot Q9HBG7), SLC39A9 (uniprot Q9NUM3), B4GALT7 (uniprot Q9UBV7), MGAT4A (uniprot Q9UM21), TAF4 (uniprot 000268), VGF (uniprot 15240), TACSTD2 (uniprot P09758), HSPA5 (uniprot P11021), PRJCSH (uniprot P14314), LMAN1 (uniprot P49257), TMED10 (uniprot P49755), NUP153 (uniprot P49790), NUCB1 (uniprot Q02818), BPTF (uniprot Q12830), UBAP2L (uniprot Q14157), KLHDC10 (uniprot Q6PID8), LRRC8D (uniprot Q7L1W4), LYPD6 KIAA201 (uniprot Q86Y78), ZFR (uniprot Q96KR1), MUC5B (uniprot Q9HC84), CDK12 (uniprot Q9NYV4), HYOU1 (uniprot Q9Y4L1). The anti-TnMUC1 CARs disclosed herein can also target these other tumor associated antigens.

The payload can be a cytokine, an antibody, a reporter (e.g., for imaging), a receptor (such as a CAR), or other polypeptide that can have a desired effect at the target site. The payload can remain in the cell, or on the cell surface to modify the behavior of the cell. The payload can be an intracellular protein such as a kinase, phosphatase, metabolic enzyme, an epigenetic modifying enzyme, a gene editing enzyme, etc. The payload can be a gene regulatory RNA, such as, for example, siRNA, microRNAs (e.g., miR155), shRNA, antisense RNA, ribozymes, and the like, or guide RNAs for use with CRISPR systems. The payload can be a nucleic acid (e.g., a vector, or a human artificial chromosome (HAC)). The payload can also be a membrane bound protein such as GPCR, a transporter, etc. The payload can be an imaging agent that allows a target site to be imaged (target site has a desired amount of target antigen bound by the CAR). The payload can be a checkpoint inhibitor, and the CAR and/or other binding protein (e.g., T-cell receptor, antibody or innate immunity receptor) can recognize a tumor associated antigen so the eukaryotic cell preferentially delivers the checkpoint inhibitor at a tumor. The payload can be a cytotoxic compound including, for example, a granzyme, an apoptosis inducer, a cytotoxic small molecule, or complement. The payload can be an antibody, such as for example, an anti-4-1BB agonist antibody (an anti-CD137 antibody), an anti-IL1b antibody (anti-inflammatory), anti-CD29/anti-VEGF antibody, an anti-CTLA4 antibody, a bispecific antibody (e.g., BiTE), an anti-CD11b antibody, CCL2, anti-CXCR4 antibody, anti-CXCL12 antibody, HAC, heparinase, hyaluronidase, Hsp60, Hsp70, IL-2, IL-12, IL-15, IL-18, INFγ, miRNA (e.g., mir155), soluble CD40 ligand, ApoE3, ApoE4, TNFα, CCR2, CCR4/CXCL12, ACLY, antagonists of CSF1 receptor, siRNA, other antisense RNAs, and/or anti-CD28 antibody (including full length and fragments such as single chain antibodies). The payload can be presented as a fusion protein with a Small Leucine Rich Proteoglycans (SLRPs) such as Decorin, Biglycan and/or Lumican (all of which can anchor the fusion protein to the cellular matrix in or near the target site). Fusions with Decorin and/or Biglycan can also bind TGF-beta in and around the target site which can reduce immune suppression. Myeloid modifying payloads ("MM payloads") which reduce immune suppression or inhibition caused by myeloid cells may be delivered including, for example, ApoE3, ApoE4, Hsp60, Hsp70, TNFα, antagonists of CSF1 receptor, CD40L (CD154) and/or IL-12. Two or more MM payloads can also be delivered by the CAR, DE-CAR, side-CAR and/or other receptor cell (e.g., T-cell) using RDEs that produce different pharmacokinetics for delivery. For example, the different MM payloads could be controlled by different RDEs so that the Cmax of delivery for the different MM payloads occurs at different times. The payload can be an immune polypeptide, including for example, cytokines (e.g., IL-2, IL-12, IL-15, IL-18), chemokines (e.g., CXCL12), perforins, granzymes, and other immune polypeptides. The payload can be an enzyme including for example, hyaluronidase, or heparinase. The payload can be a polypeptide including for example, ApoE (e.g., ApoE2, ApoE3 and ApoE4), NO synthase (e.g., iNOS, nNOS, eNOS), HSV-thymidine kinase (HSV-TK), antagonists of CSF1 receptor, CCR2, and/or CCR4. The payload can be fused or associated with Decorin, Biglycan, fibromodulaon/Lumican so that the payload binds to the collagen near or in the target site. This strategy is particularly useful for keeping cytotoxic payloads localized to the target cells (e.g., a tumor). The payload can be a transgene(s) which delivers a virus as a payload. For example, the RDE can control a master control element that controls the expression of the virus genes for replication and coat/envelope proteins. Alternatively, the Rep and coat/envelope proteins can be placed under the control of inducible promoters that are controlled by a regulatory protein, and that regulatory protein can be controlled by an RDE. Still alternatively, the Rep proteins of the virus can be placed under the control of an RDE, and/or the coat/envelope proteins of the virus can be placed under the control of an RDE. As with other payloads this complex payload can use CAR T-cell regulation or any other regulation that induces glycolysis in a cell. Helper constructs in a T cell, or other delivery cell can encode the genes needed for viral replication and viral packaging.

The RDE may control multiple transgenes or multiple RDEs may control multiple transgenes. The multiple transgenes may be arranged serially and/or as a concatemer and/or in other arrangements. Multiple RDEs may be used to regulate a transgene, and these multiple RDEs can be organized as a concatemer, interspersed within a region of the transcript, or located in different parts of the transcript. Multiple transgenes can be regulated by an RDE or a combination of RDEs. The RDEs can be localized in the 3'-UTR, the 5'-UTR and/or an intron. RDEs can include, for example, the RDEs from AU 1 (CD40L), AU 2 (CSF2), AU 3 (CD247), AU 4 (CTLA4), AU 5 (EDN1), AU 6 (IL2RA), AU 7 (SLC2A1), AU 8 (TRAC), AU 9 (CD274), AU 10 (Myc), AU 11 (CD19), AU 12 (IL4), AU 13 (IL5), AU 14 (IL6), AU 15 (IL9), AU 16 (IL10), AU 17 (IL13), AU 18 (FOXP3), AU 19 (TMEM-219), AU 20 (TMEM-219snp), AU 21 (CCR7), AU 22 (SEM-A4D), AU 23 (CDC42-SE2), AU 24 (CD8), AU 27 (bGH), and/or AU 101 (Interferon gamma or IFNg). Other RDEs are disclosed in the following description. RDE control can also be combined with codon optimization of the transgene to increase the GC content of the wobble position (third position of the codon) in some or all of the codons of the transgene. This codon optimization can increase efficiency of expression (the on signal) by up to 100-fold. Such codon optimized transgenes can be linked to an RDE and produce a larger dynamic range of expression from the RDE control compared to the transgene-RDE without codon optimization.

In an aspect, a therapy utilizing an anti-TnMUC1 CAR T-cell with or without an RDE controlled payload(s) is combined with another therapy. The other therapy can include any therapeutic molecule including, for example, a polypeptide, lipid, carbohydrate, nucleic acid, small molecule drug, biological drug, antibody, antibody-drug-conjugate, or combinations of the foregoing. Suitable molecules are described below. The other therapy can be administered to a subject at the same time as the CAR therapy (with or without a RDE controlled transgene(s)), before the administration of the CAR therapy (with or without a RDE controlled transgene(s)), or after the administration of the CAR therapy (with or without a RDA controlled transgene(s)). For example, a subject could be treated with chemotherapy and/or an immunotherapy (e.g., an antibody-drug conjugate), followed by treatment with a CAR T-cell with optionally a RDE controlled payload. The CAR T-cell treatment can be given the subject at varying times after the chemotherapy and/or immunotherapy, e.g., one, two, three, four, five, or six weeks. The chemotherapy and/or immunotherapy (e.g., ADC) can be cycled with the CAR T-cell treatment for multiple cycles of treatment. Treatment with CAR T-cells may also be boosted with target X peptide, or virus or cells loaded with target X peptide (target X is the target bound by the CAR).

In an aspect, an RDE, combination of RDEs, and/or modified RDEs can be used to provide desired kinetic parameters to the regulation of the payload including, for example, amount of expression, steady state concentration, $C_{max}$ (maximal concentration of gene product obtained), $T_{max}$ (time to reach $C_{max}$), baseline expression, speed of induction (acceleration), induction rate (velocity), dynamic range also known as fold regulation (induced expression/basal expression), maximal dynamic range ($DR_{max}$), time to $DR_{max}$, area under the curve (AUC), etc. A RDE construct can be made that has a desired set of kinetic parameters to provide the level, degree, temporal, and amount of regulation that is desired. In addition, RDE concatemers can be used to alter the kinetic performance of a construct.

Combinations of RDEs can be used to provide temporal regulation between two or more payloads. RDEs can be selected to provide maximal rates of expression (and different amounts of maximal expression) at different times following activation of a cell (or induction of expression). This temporal control allows a first payload to alter the state of the cell so that the cell is prepared to be acted upon by a second payload with an RDE that provides later in time expression. This temporal control can also be used to time the expression of two, three or more transgenes following activation of a cell. If the transgene encoded polypeptides are secreted, they can act in a temporal fashion upon target cells. For example, a first payload (with an early expression RDE) could be secreted and act upon a target cell to change its state (e.g., induce the expression of receptor). The second payload is expressed at a later time (under the control of a later expression RDE) and acts upon the target cell with the changed state (e.g., the second protein can be a ligand for the induced receptor).

In an aspect, the anti-TnMUC1 CAR recognizes an antigen at the target site (e.g., tumor cell or other diseased tissue/cell) and this activates the cell. The payload can be another CAR that recognizes a second antigen at the target site and activation of the cell by the anti-TnMUC1 CAR induces the second CAR allowing the eukaryotic cell to recognize the target site by a second antigen. In an aspect, the eukaryotic cell has a anti-TnMUC1 CAR that recognizes an antigen at a target site and this activates a transgene (through an RDE) that encodes a polypeptide that directly or indirectly reduces the activation state of the cell. For example, the transgene may encode a second CAR that recognizes an antigen on healthy tissue so that when the first CAR reacts with antigen at a nontarget cell, the eukaryotic cell will be de-activated by the second CAR interaction with the healthy cell antigen (that is not present or is present in reduced amounts at the target site).

In some aspects, the cell with the anti-TnMUC1 CAR is an immune cell, e.g., a T-cell, a natural killer cell, a B-cell, a macrophage, a dendritic cell, or other antigen presenting cell. The immune cells (e.g., T-cells, NK cells, macrophages, B-cells etc.) can be allogeneic, autologous, or syngeneic. The immune cells (e.g., T-cells, NK cells, macrophages, B-cells etc.) may be primary immune cells, derived from primary immune cells, or from cell lines. In these aspects, activation of the cell by the anti-TnMUC1 CAR or changing the metabolic state of the immune cell in other ways can induce expression of the payload through the RDE. The RDE that controls the payload can have microRNA binding sites and can be engineered to remove one or more of these microRNA binding sites. The RDE can be bound by the Hu Protein R (HuR). Without wishing to be bound by theory it is expected that HuR can bind to some RDEs, and act to stabilize the mRNA, leading to enhanced translation. Some RDEs can be tied to the glycolytic state of the eukaryotic cell through the enzyme glyceraldehyde 3-phosphate dehydrogenase (GAPDH), other dehydrogenases, other oxidoreductases, or other glycolytic enzymes that can bind to an RDE when the eukaryotic cell is not activated (low glycolytic activity), quiescent, or at rest. When GAPDH or the other enzymes bind to the RDE this can reduce half-life of the RNA with the RDE. In this aspect, CAR activation of the eukaryotic cell (e.g., T-lymphocyte) can induce glycolysis in the cell which reduces GAPDH binding of the RNA, increases half-life of the RNA, which produces increased expression of the payload encoded in the RNA and controlled by the RDE. Without wishing to be bound by theory, as GAPDH vacates the RDE, HuR or other RDE binding proteins may subsequently bind either the same RDE, or a previously inaccessible RDE (sterically hindered by presence of GAPDH), further stabilizing the mRNA, increasing half-life of the mRNA, and producing further increased expression of the payload encoded by the RNA and controlled by said RDE. Thus, CAR activation can induce expression of the payload. In other aspects, other activation of the immune cell can cause GAPDH to engage in glycolysis and so induce expression of the payload under the control of the RDE. Examples of RDEs bound by GAPDH include, for example, AU 19 (TMEM-219), AU 20 (TMEM-219snp), AU 21 (CCR7), AU 22 (SEM-A4D), and AU 23 (CDC42-SE2).

Expression from the transcript with the RDE(s) can respond to the metabolic state of the cell. For example, the RDE can be bound by metabolic or glycolytic enzymes which couples expression of the transgene to the activation state of the cell through these metabolic or glycolytic enzymes. Some metabolic or glycolytic enzymes bind to RDEs in the transcript and degrade or target for degradation the transcript. When those metabolic or glycolytic enzymes become active, the enzymes no longer bind to the RDEs, the transcripts are stable for a longer period of time, and the transcripts can be translated for this longer period of time. Cells expressing transgenes under the control of such RDEs can also be engineered to express a CAR that can alter the metabolic state of the cell at desired times resulting in expression of the transgene at the desired time. Alternatively, other stimuli can be used to alter the metabolic state of the eukaryotic cell resulting in expression of the transgene. For example, the metabolic state of the cell can be altered to cause transgene expression (or to inhibit expression) by stimuli including, for example, small molecules (e.g., PMA/ionomycin), cytokines, a TCR and costimulatory domain engagement with ligand, oxygen levels, cellular stress, temperature, or light/radiation.

In an aspect, CAR T-lymphocytes are modified to reduce or prevent graft versus host reactions. This is done by knocking out the ability of the T-cell receptors to activate the T-lymphocyte. When a dominant CD3 epsilon chain mutant is introduced to the T-lymphocyte it can knockout the ability of the T-cell receptors to activate the T-lymphocyte. One such CD3 epsilon mutant is a double mutant that replaces the Cysteine residues of the C-X-X-C motif with Serine residues (a C119S and C122S mutant). This mutant CD3 epsilon chain disrupts signaling from the T-cell receptor and prevents ligand induced activation of the T-lymphocyte through the T-cell receptor. By expressing an excess of the CD3 epsilon C119S/C122S mutant in a T-lymphocyte, the T-lymphocyte will not activate in response to host antigens binding to the T-lymphocyte receptor of the CAR T-lymphocytes. This allows the use of allogenic CAR T-lymphocytes in a subject with reduced graft versus host reactions.

DETAILED DESCRIPTION OF THE INVENTION

Figure 1:
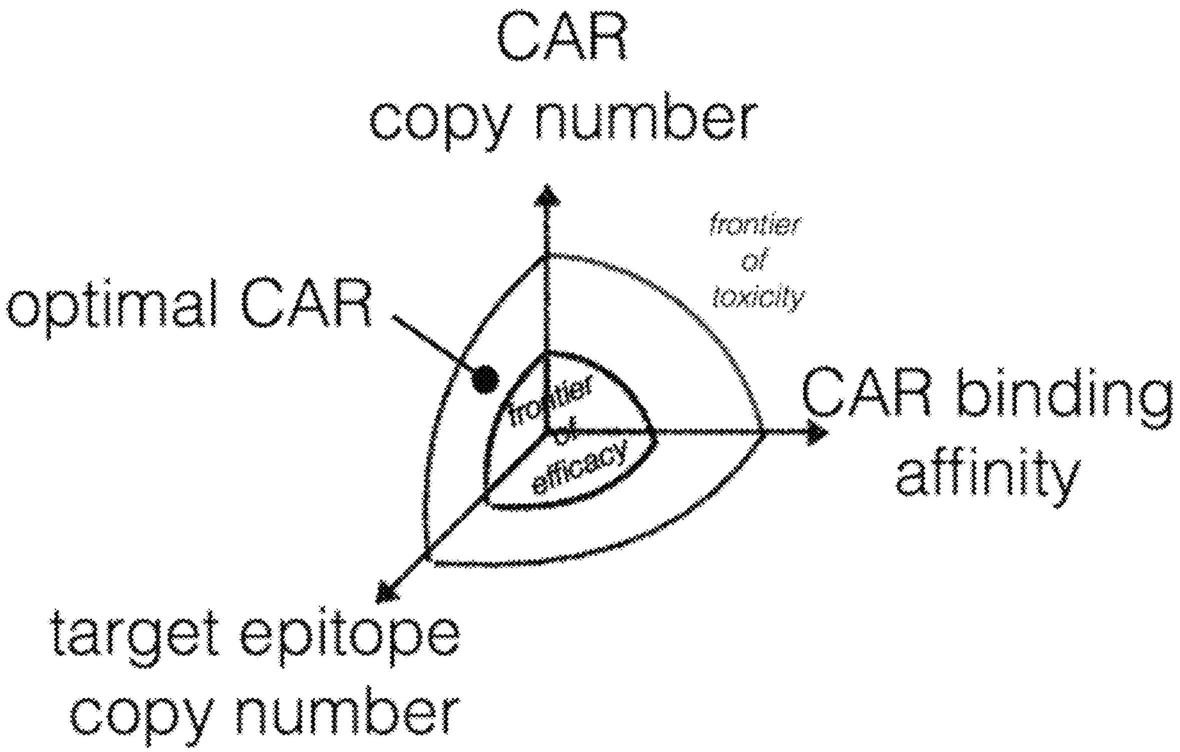
FIG. 1 shows a diagram for optimal CAR activity where the three variables are CAR copy number, target epitope copy number and CAR binding affinity.

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

It must be noted that as used herein and in the appended claims, the singular forms "a", "an", and "the" include plural referents unless the context clearly dictates otherwise. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation. Numerical limitations given with respect to concentrations or levels of a substance are intended to be approximate, unless the context clearly dictates otherwise. Thus, where a concentration is indicated to be (for example) 10 g, it is intended that the concentration be understood to be at least approximately or about 10 g.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

Definitions

In reference to the present disclosure, the technical and scientific terms used in the descriptions herein will have the meanings commonly understood by one of ordinary skill in the art, unless specifically defined otherwise. Accordingly, the following terms are intended to have the following meanings.

As used herein, an "antibody" is defined to be a protein functionally defined as a ligand-binding protein and structurally defined as comprising an amino acid sequence that is recognized by one of skill as being derived from the variable region of an immunoglobulin. An antibody can consist of one or more polypeptides substantially encoded by immunoglobulin genes, fragments of immunoglobulin genes, hybrid immunoglobulin genes (made by combining the genetic information from different animals), or synthetic immunoglobulin genes. The recognized, native, immunoglobulin genes include the kappa, lambda, alpha, gamma, delta, epsilon and mu constant region genes, as well as myriad immunoglobulin variable region genes and multiple D-segments and J-segments. Light chains are classified as either kappa or lambda. Heavy chains are classified as gamma, mu, alpha, delta, or epsilon, which in turn define the immunoglobulin classes, IgG, IgM, IgA, IgD and IgE, respectively. Antibodies exist as intact immunoglobulins, as a number of well characterized fragments produced by digestion with various peptidases, or as a variety of fragments made by recombinant DNA technology. Antibodies can derive from many different species (e.g., rabbit, sheep, camel, human, or rodent, such as mouse or rat), or can be synthetic. Antibodies can be chimeric, humanized, or humaneered. Antibodies can be monoclonal or polyclonal, multiple or single chained, fragments or intact immunoglobulins.

As used herein, an "antibody fragment" is defined to be at least one portion of an intact antibody, or recombinant variants thereof, and refers to the antigen binding domain, e.g., an antigenic determining variable region of an intact antibody, that is sufficient to confer recognition and specific binding of the antibody fragment to a target, such as an antigen. Examples of antibody fragments include, but are not limited to, Fab, Fab', $F(ab')_2$, and Fv fragments, scFv antibody fragments, linear antibodies, single domain antibodies such as sdAb (either $V_L$ or $V_H$), camelid VHH domains, and multi-specific antibodies formed from antibody fragments. The term "scFv" is defined to be a fusion protein comprising at least one antibody fragment comprising a variable region of a light chain and at least one antibody fragment comprising a variable region of a heavy chain, wherein the light and heavy chain variable regions are contiguously linked via a short flexible polypeptide linker, and capable of being expressed as a single chain polypeptide, and wherein the scFv retains the specificity of the intact antibody from which it is derived. Unless specified, as used herein an scFv may have the $V_L$ and $V_H$ variable regions in either order, e.g., with respect to the N-terminal and C-terminal ends of the polypeptide, the scFv may comprise $V_L$-linker-$V_H$ or may comprise $V_H$-linker-$V_L$.

As used herein, an "antigen" is defined to be a molecule that provokes an immune response. This immune response may involve either antibody production, or the activation of specific immunologically-competent cells, or both. The skilled artisan will understand that any macromolecule, including, but not limited to, virtually all proteins or peptides, including glycosylated polypeptides, phosphorylated polypeptides, and other post-translation modified polypeptides including polypeptides modified with lipids, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to encode polypeptides that elicit the desired immune response. Moreover, a skilled artisan will understand that an antigen need not be encoded by a "gene" at all. It is readily apparent that an antigen can be synthesized or can be derived from a biological sample, or can be a macromolecule besides a polypeptide. Such a biological sample can include, but is not limited to a tissue sample, a tumor sample, a cell or a fluid with other biological components.

As used herein, the terms "Chimeric Antigen Receptor" and the term "CAR" are used interchangeably. As used herein, a "CAR" is defined to be a fusion protein comprising antigen recognition moieties and cell-activation elements.

As used herein, a "CAR T-cell" or "CAR T-lymphocyte" are used interchangeably, and are defined to be a T-cell containing the capability of producing CAR polypeptide, regardless of actual expression level. For example a cell that is capable of expressing a CAR is a T-cell containing nucleic acid sequences for the expression of the CAR in the cell.

As used herein, a "costimulatory element" or "costimulatory signaling domain" or "costimulatory polypeptide" are defined to be the intracellular portion of a costimulatory polypeptide. A costimulatory polypeptide can be represented in the following protein families: TNF receptor proteins, Immunoglobulin-like proteins, cytokine receptors, integrins, signaling lymphocytic activation molecules (SLAM proteins), and activating natural killer cell receptors. Examples of such polypeptides include CD27, CD28, 4-1BB (CD137), OX40, GITR, CD30, CD40, ICOS, BAFFR, HVEM, lymphocyte function-associated antigen-1 (LFA-1), CD2, CD7, LIGHT, NKG2C, SLAMF7, NKp80, CD160, B7-H3, MyD88, and the like.

As used herein, a "$C_{max}$" is defined to mean the maximum concentration of a polypeptide produced by a cell after the cell is stimulated or activated to produce the polypeptide.

As used herein, a "cytokine $C_{max}$" is defined to mean the maximum concentration of cytokine produced by an immune cell after stimulation or activation to produce the cytokine.

As used herein, a "cytotoxic polypeptide $C_{max}$" is defined to mean the maximum concentration of cytotoxic polypeptide produced by an immune cell after stimulation or activation to produce the cytotoxic polypeptide.

As used herein, an "effective amount" or "therapeutically effective amount" are used interchangeably, and defined to be an amount of a compound, formulation, material, or composition, as described herein effective to achieve a particular biological result.

As used herein, an "epitope" is defined to be the portion of an antigen capable of eliciting an immune response, or the portion of an antigen that binds to an antibody. Epitopes can be a protein sequence or subsequence that is recognized by an antibody.

As used herein, an "expression vector" and an "expression construct" are used interchangeably, and are both defined to be a plasmid, virus, or other nucleic acid designed for protein expression in a cell. The vector or construct is used to introduce a gene into a host cell whereby the vector will interact with polymerases in the cell to express the protein encoded in the vector/construct. The expression vector and/or expression construct may exist in the cell extrachromosomally or integrated into the chromosome. When integrated into the chromosome the nucleic acids comprising the expression vector or expression construct will be an expression vector or expression construct.

As used herein, an "extracellular element" is defined as the antigen binding or recognition element of a Chimeric Antigen Receptor.

As used herein, a "hematopoietic cell" is defined to be a cell that arises from a hematopoietic stem cell. This includes but is not limited to myeloid progenitor cells, lymphoid progenitor cells, megakaryocytes, erythrocytes, mast cells, myeloblasts, basophils, neutrophils, eosinophils, macrophages, thrombocytes, monocytes, natural killer cells, T lymphocytes, B lymphocytes and plasma cells.

As used herein, "heterologous" is defined to mean the nucleic acid and/or polypeptide are not homologous to the host cell. For example, a construct is heterologous to a host cell if it contains some homologous sequences arranged in a manner not found in the host cell and/or the construct contains some heterologous sequences not found in the host cell.

As used herein, an "intracellular element" is defined as the portion of a Chimeric Antigen Receptor that resides on the cytoplasmic side of the eukaryotic cell's cytoplasmic membrane, and transmits a signal into the eukaryotic cell. The "intracellular signaling element" is that portion of the intracellular element which transduces the effector function signal which directs the eukaryotic cell to perform a specialized function.

As used herein, "RNA destabilizing element" or "RDE" are used interchangeably and both are defined as a nucleic acid sequence in an RNA that is bound by proteins and which protein binding changes the stability and/or translation of the RNA. Examples of RDEs include Class I AU rich elements (ARE), Class II ARE, Class III ARE, U rich elements, GU rich elements, and stem-loop destabilizing elements (SLDE). Without wishing to be bound by theory, RDE's may also bind RNA stabilizing polypeptides like HuR.

As used herein, a "single chain antibody" (scFv) is defined as an immunoglobulin molecule with function in antigen-binding activities. An antibody in scFv (single chain fragment variable) format consists of variable regions of heavy ($V_H$) and light ($V_L$) chains, which are joined together by a flexible peptide linker.

As used herein, a "T-lymphocyte" or T-cell" is defined to be a hematopoietic cell that normally develops in the thymus. T-lymphocytes or T-cells include, but are not limited to, natural killer T cells, regulatory T cells, helper T cells, cytotoxic T cells, memory T cells, gamma delta T cells and mucosal invariant T cells.

As used herein, "transfected" or "transformed" or "transduced" are defined to be a process by which exogenous nucleic acid is transferred or introduced into a host cell. A "transfected" or "transformed" or "transduced" cell is one which has been transfected, transformed or transduced with exogenous nucleic acid. The cell includes the primary subject cell and its progeny.

As used herein, a "transmembrane element" is defined as the element between the extracellular element and the intracellular element. A portion of the transmembrane element exists within the cell membrane.

Anti-TnMUC1 CARs

The Chimeric Antigen Receptor can be an anti-TnMUC1 CAR having the sequence of SEQ ID NO: 1.

(SEQ ID NO: 1)

```
GACATCGTGATGACCCAGAGCCCCGACAGCCTGGCCGTGAGCCTGGGCG
AGAGGGCCACCATCAACTGCAAGAGCAGCCAGAGCCTGCTGAACAGCGG
CGACCAGAAGAACTACCTGACCTGGTACCAGCAGAAGCCCGGCCAGCCC
CCCAAGCTGCTGATCTACTGGGCCAGCACCAGGGAGAGCGGCGTGCCCG
ACAGGTTCAGCGGCAGCGGCAGCGGCACCGACTTCACCCTGACCATCAG
CAGCCTGCAGGCCGAGGACGTGGCCGTGTACTACTGCCAGAACGACTAC
AGCTACCCCCTGACCTTCGGCCAGGGCACCAAGGTGGAGATCAAGGGCG
GCGGCGGCAGCGGCGGCGGCGGCAGCGGCGGCGGCGGCAGCCAGGTGCA
GCTGGTGCAGAGCGGCGCCGAGGTGAAGAAGACCGGCAGCAGCGTGAAG
GTGAGCTGCAAGGCCAGCGGCTACACCTTCACCGACCACGCCATCCACT
GGGTGAGGCAGGCCCCCGGCCAGGCCCTGGAGTGGATGGGCCACTTCAG
CCCCGGCAACACCGACATCAAGTACAACGACAAGTTCAAGGGCAGGGTG
ACCCTGACCGTGGACAGGAGCATGAGCACCGCCTACATGGAGCTGAGCA
GCCTGAGGAGCGAGGACACCGCCATGTACTACTGCAAGACCAGCACCTT
CTTCTTCGACTACTGGGGCCAGGGCACCATGGTGACCGTGAGCAGCACC
ACGACGCCAGCGCCGCGACCACCAACACCGGCGCCCACCATCGCGTCGC
AGCCCCTGTCCCTGCGCCCAGAGGCGTGCCGGCCAGCGGCGGGGGGCGC
AGTGCACACGAGGGGGCTGGACTTCGCCTGTGATATCTACATCTGGGCG
CCCTTGGCCGGGACTTGTGGGGTCCTTCTCCTGTCACTGGTTATCACCC
TTTACTGCAAACGGGGCAGAAAGAAACTCCTGTATATATTCAAACAACC
ATTTATGAGACCAGTACAAACTACTCAAGAGGAAGATGGCTGTAGCTGC
```

-continued

CGATTTCCAGAAGAAGAAGAAGGAGGATGTGAACTGAGAGTGAAGTTCA

GCAGGAGCGCAGACGCCCCCGCGTACAAGCAGGGCCAGAACCAGCTCTA

TAACGAGCTCAATCTAGGACGAAGAGAGGAGTACGATGTTTTGGACAAG

AGACGTGGCCGGGACCCTGAGATGGGGGGAAAGCCGAGAAGGAAGAACC

CTCAGGAAGGCCTGTACAATGAACTGCAGAAAGATAAGATGGCGGAGGC

CTACAGTGAGATTGGGATGAAAGGCGAGCGCCGGAGGGGCAAGGGGCAC

GATGGCCTTTACCAGGGTCTCAGTACAGCCACCAAGGACACCTACGACG

CCCTTCACATGCAGGCCCTGCCCCCTCGC

The amino acid sequence of this anti-TnMUC1 CAR is:

(SEQ ID NO: 2)
MALPVTALLLPLALLLHAARPDIVMTQSPDSLAVSLGERATINCKSSQS

LLNSGDQKNYLTWYQQKPGQPPKLLIYWASTRESGVPDRFSGSGSGTDF

TLTISSLQAEDVAVYYCQNDYSYPLTFGQGTKVEIKGGGGSGGGGSGGG

GSQVQLVQSGAEVKKTGSSVKVSCKASGYTFTDHAIHWVRQAPGQALEW

-continued

MGHFSPGNTDIKYNDKFKGRVTLTVDRSMSTAYMELSSLRSEDTAMYYC

KTSTFFFDYWGQGTMVTVSSTTTPAPRPPTPAPTIASQPLSLRPEACRP

AAGGAVHTRGLDFACDIYIWAPLAGTCGVLLLSLVITLYCKRGRKKLLY

IFKQPFMRPVQTTQEEDGCSCRFPEEEEGGCELRVKFSRSADAPAYKQG

QNQLYNELNLGRREEYDVLDKRRGRDPEMGGKPRRKNPQEGLYNELQKD

KMAEAYSEIGMKGERRRGKGHDGLYQGLSTATKDTYDALHMQALPPR

Optionally, this anti-TnMUC1 chimeric antigen receptor sequence includes a signal sequence such as, for example:

(SEQ ID NO: 3)
GCCTTACCAGTGACCGCCTTGCTCCTGCCGCTGGCCTTGCTGCTCCACG
CCGCCAGGCCG

Constructs with this anti-TnMUC1 CAR can include GC160 (SEQ ID NO: 4), GC213 (SEQ ID NO: 5), GC217 (SEQ ID NO: 6), GC219 (SEQ ID NO: 7), GC223 (SEQ ID NO: 8), SK062 (SEQ ID NO: 9), SK148 (SEQ ID NO: 10), SK072 (SEQ ID NO: 11), GC251, (SEQ ID NO: 12), PD007 (SEQ ID NO: 13), and PD009 (SEQ ID NO: 14).

GC160

(SEQ ID NO: 4)
TCTGGTTAGACCAGATCTGAGCCTGGGAGCTCTCTGGCTAACTAGGGAACCCACTGC

TTAAGCCTCAATAAAGCTTGCCTTGAGTGCTTCAAGTAGTGTGTGCCCGTCTGTTGTG

TGACTCTGGTAACTAGAGATCCCTCAGACCCTTTTAGTCAGTGTGGAAAATCTCTAG

CAGTGGCGCCCGAACAGGGACCTGAAAGCGAAAGGGAAACCAGAGCTCTCTCGAC

GCAGGACTCGGCTTGCTGAAGCGCGCACGGCAAGAGGCGAGGGGCGGCGACTGGT

GAGTACGCCAAAAATTTTGACTAGCGGAGGCTAGAAGGAGAGAGATGGGTGCGAG

AGCGTCAGTATTAAGCGGGGGAGAATTAGATCGCGATGGGAAAAAATTCGGTTAAG

GCCAGGGGGAAAGAAAAAATATAAATTAAAACATATAGTATGGGCAAGCAGGGAG

CTAGAACGATTCGCAGTTAATCCTGGCCTGTTAGAAACATCAGAAGGCTGTAGACA

AATACTGGGACAGCTACAACCATCCCTTCAGACAGGATCAGAAGAACTTAGATCAT

TATATAATACAGTAGCAACCCTCTATTGTGTGCATCAAAGGATAGAGATAAAAGAC

ACCAAGGAAGCTTTAGACAAGATAGAGGAAGAGCAAAACAAAAGTAAGACCACCG

CACAGCAAGCGGCCACTGATCTTCAGACCTGGAGGAGGAGATATGAGGGACAATTG

GAGAAGTGAATTATATAAATATAAAGTAGTAAAAATTGAACCATTAGGAGTAGCAC

CCACCAAGGCAAAGAGAAGAGTGGTGCAGAGAGAAAAAAGAGCAGTGGGAATAGG

AGCTTTGTTCCTTGGGTTCTTGGGAGCAGCAGGAAGCACTATGGGCGCAGCCTCAAT

GACGCTGACGGTACAGGCCAGACAATTATTGTCTGGTATAGTGCAGCAGCAGAACA

ATTTGCTGAGGGCTATTGAGGCGCAACAGCATCTGTTGCAACTCACAGTCTGGGGCA

TCAAGCAGCTCCAGGCAAGAATCCTGGCTGTGGAAAGATACCTAAAGGATCAACAG

CTCCTGGGGATTTGGGGTTGCTCTGGAAAACTCATTTGCACCACTGCTGTGCCTTGG

AATGCTAGTTGGAGTAATAAATCTCTGGAACAGATTGGAATCACACGACCTGGATG

GAGTGGGACAGAGAAATTAACAATTACACAAGCTTAATACACTCCTTAATTGAAGA

ATCGCAAAACCAGCAAGAAAAGAATGAACAAGAATTATTGGAATTAGATAAATGGG

CAAGTTTGTGGAATTGGTTTAACATAACAAATTGGCTGTGGTATATAAAATTATTCA

-continued

TAATGATAGTAGGAGGCTTGGTAGGTTTAAGAATAGTTTTTGCTGTACTTTCTATAGT

GAATAGAGTTAGGCAGGGATATTCACCATTATCGTTTCAGACCCACCTCCCAACCCC

GAGGGGACCCGACAGGCCCGAAGGAATAGAAGAAGAAGGTGGAGAGAGAGACAG

AGACAGATCCATTCGATTAGTGAACGGATCTCGACGGTATCGGTTAACTTTTAAAAG

AAAAGGGGGGATTGGGGGGTACAGTGCAGGGGAAAGAATAGTAGACATAATAGCA

ACAGACATACAAACTAAAGAATTACAAAAACAAATTACAAAAATTCAAAATTTTAT

CTCGAGGTTTAAACGGGGTTGGGGTTGCGCCTTTTCCAAGGCAGCCCTGGGTTTGCG

CAGGGACGCGGCTGCTCTGGGCGTGGTTCCGGGAAACGCAGCGGCGCCGACCCTGG

GTCTCGCACATTCTTCACGTCCGTTCGCAGCGTCACCCGGATCTTCGCCGCTACCCTT

GTGGGCCCCCCGGCGACGCTTCCTGCTCCGCCCCTAAGTCGGGAAGGTTCCTTGCGG

TTCGCGGCGTGCCGGACGTGACAAACGGAAGCCGCACGTCTCACTAGTACCCTCGC

AGACGGACAGCGCCAGGGAGCAATGGCAGCGCGCCGACCGCGATGGGCTGTGGCC

AATAGCGGCTGCTCAGCAGGGCGCGCCGAGAGCAGCGGCCGGGAAGGGGCGGTGC

GGGAGGCGGGGTGTGGGGCGGTAGTGTGGGCCCTGTTCCTGCCCGCGCGGTGTTCC

GCATTCTGCAAGCCTCCGGAGCGCACGTCGGCAGTCGGCTCCCTCGTTGACCGAATC

ACCGACCTCTCTCCCCAGCGCTAGCGCTACCGGTCGCCAAGATGGCGGCGGTGAGC

AAGGGCGAGGAGGATAACATGGCCATCATCAAGGAGTTCATGCGCTTCAAGGTGCA

CATGGAGGGCTCCGTGAACGGCCACGAGTTCGAGATCGAGGGCGAGGGCGAGGGC

CGCCCCTACGAGGGCACCCAGACCGCCAAGCTGAAGGTGACCAAGGGTGGCCCCCT

GCCCTTCGCCTGGGACATCCTGTCCCCTCAGTTCATGTACGGCTCCAAGGCCTACGT

GAAGCACCCCGCCGACATCCCCGACTACTTGAAGCTGTCCTTCCCCGAGGGCTTCAA

GTGGGAGCGCGTGATGAACTTCGAGGACGGCGGCGTGGTGACCGTGACCCAGGACT

CCTCCCTGCAGGACGGCGAGTTCATCTACAAGGTGAAGCTGCGCGGCACCAACTTCC

CCTCCGACGGCCCCGTAATGCAGAAGAAGACCATGGGCTGGGAGGCCTCCTCCGAG

CGGATGTACCCCGAGGACGGCGCCCTGAAGGGCGAGATCAAGCAGAGGCTGAAGCT

GAAGGACGGCGGCCACTACGACGCTGAGGTCAAGACCACCTACAAGGCCAAGAAG

CCCGTGCAGCTGCCCGGCGCCTACAACGTCAACATCAAGTTGGACATCACCTCCCAC

AACGAGGACTACACCATCGTGGAACAGTACGAACGCGCCGAGGGCCGCCACTCCAC

CGGCGGCATGGACGAGCTGTACAAGGGCAGCGGAGAGGGTAGGGGTAGTCTTTTGA

CGTGTGGGGACGTCGAGGAAAATCCTGGGCCTGCCTTACCAGTGACCGCCTTGCTCC

TGCCGCTGGCCTTGCTGCTCCACGCCGCCAGGCCGGACATCGTGATGACCCAGAGCC

CCGACAGCCTGGCCGTGAGCCTGGGCGAGAGGGCCACCATCAACTGCAAGAGCAGC

CAGAGCCTGCTGAACAGCGGCGACCAGAAGAACTACCTGACCTGGTACCAGCAGAA

GCCCGGCCAGCCCCCCAAGCTGCTGATCTACTGGGCCAGCACCAGGGAGAGCGGCG

TGCCCGACAGGTTCAGCGGCAGCGGCAGCGGCACCGACTTCACCCTGACCATCAGC

AGCCTGCAGGCCGAGGACGTGGCCGTGTACTACTGCCAGAACGACTACAGCTACCC

CCTGACCTTCGGCCAGGGCACCAAGGTGGAGATCAAGGGCGGCGGCGGCAGCGGCG

GCGGCGGCAGCGGCGGCGGCGGCAGCCAGGTGCAGCTGGTGCAGAGCGGCGCCGA

GGTGAAGAAGACCGGCAGCAGCGTGAAGGTGAGCTGCAAGGCCAGCGGCTACACC

TTCACCGACCACGCCATCCACTGGGTGAGGCAGGCCCCCGGCCAGGCCCTGGAGTG

-continued

GATGGGCCACTTCAGCCCCGGCAACACCGACATCAAGTACAACGACAAGTTCAAGG

GCAGGGTGACCCTGACCGTGGACAGGAGCATGAGCACCGCCTACATGGAGCTGAGC

AGCCTGAGGAGCGAGGACACCGCCATGTACTACTGCAAGACCAGCACCTTCTTCTTC

GACTACTGGGGCCAGGGCACCATGGTGACCGTGAGCAGCACCACGACGCCAGCGCC

GCGACCACCAACACCGGCGCCCACCATCGCGTCGCAGCCCCTGTCCCTGCGCCCAG

AGGCGTGCCGGCCAGCGGCGGGGGGCGCAGTGCACACGAGGGGGCTGGACTTCGCC

TGTGATATCTACATCTGGGCGCCCTTGGCCGGGACTTGTGGGGTCCTTCTCCTGTCAC

TGGTTATCACCCTTTACTGCAAACGGGGCAGAAAGAAACTCCTGTATATATTCAAAC

AACCATTTATGAGACCAGTACAAACTACTCAAGAGGAAGATGGCTGTAGCTGCCGA

TTTCCAGAAGAAGAAGAAGGAGGATGTGAACTGAGAGTGAAGTTCAGCAGGAGCG

CAGACGCCCCCGCGTACAAGCAGGGCCAGAACCAGCTCTATAACGAGCTCAATCTA

GGACGAAGAGAGGAGTACGATGTTTTGGACAAGAGACGTGGCCGGGACCCTGAGAT

GGGGGGAAAGCCGAGAAGGAAGAACCCTCAGGAAGGCCTGTACAATGAACTGCAG

AAAGATAAGATGGCGGAGGCCTACAGTGAGATTGGGATGAAAGGCGAGCGCCGGA

GGGGCAAGGGGCACGATGGCCTTTACCAGGGTCTCAGTACAGCCACCAAGGACACC

TACGACGCCCTTCACATGCAGGCCCTGCCCCCTCGCTGAAGAGACGTCATAATCAGC

CAGCGGCCGCGTCGACAATCAACCTCTGGATTACAAAATTTGTGAAAGATTGACTGG

TATTCTTAACTATGTTGCTCCTTTTACGCTATGTGGATACGCTGCTTTAATGCCTTTGT

ATCATGCTATTGCTTCCCGTATGGCTTTCATTTTCTCCTCCTTGTATAAATCCTGGTTG

CTGTCTCTTTATGAGGAGTTGTGGCCCGTTGTCAGGCAACGTGGCGTGGTGTGCACT

GTGTTTGCTGACGCAACCCCCACTGGTTGGGGCATTGCCACCACCTGTCAGCTCCTT

TCCGGGACTTTCGCTTTCCCCCTCCCTATTGCCACGGCGGAACTCATCGCCGCCTGCC

TTGCCCGCTGCTGGACAGGGGCTCGGCTGTTGGGCACTGACAATTCCGTGGTGTTGT

CGGGGAAATCATCGTCCTTTCCTTGGCTGCTCGCCTGTGTTGCCACCTGGATTCTGCG

CGGGACGTCCTTCTGCTACGTCCCTTCGGCCCTCAATCCAGCGGACCTTCCTTCCCGC

GGCCTGCTGCCGGCTCTGCGGCCTCTTCCGCGTCTTCGCCTTCGCCCTCAGACGAGTC

GGATCTCCCTTTGGGCCGCCTCCCCGCCTGGTACCTTTAAGACCAATGACTTACAAG

GCAGCTGTAGATCTTAGCCACTTTTTAAAAGAAAAGGGGGGACTGGAAGGGCTAAT

TCACTCCCAACGAAAATAAGATCTGCTTTTTGCTTGTACTGGGTCTCTCTGGTTAGAC

CAGATCTGAGCCTGGGAGCTCTCTGGCTAACTAGGGAACCCACTGCTTAAGCCTCAA

TAAAGCTTGCCTTGAGTGCTTCAAGTAGTGTGTGCCCGTCTGTTGTGTGACTCTGGTA

ACTAGAGATCCCTCAGACCCTTTTAGTCAGTGTGGAAAATCTCTAGCA

GC213

(SEQ ID NO: 5)

TCTGGTTAGACCAGATCTGAGCCTGGGAGCTCTCTGGCTAACTAGGGAACCCACTGC

TTAAGCCTCAATAAAGCTTGCCTTGAGTGCTTCAAGTAGTGTGTGCCCGTCTGTTGTG

TGACTCTGGTAACTAGAGATCCCTCAGACCCTTTTAGTCAGTGTGGAAAATCTCTAG

CAGTGGCGCCCGAACAGGGACCTGAAAGCGAAAGGGAAACCAGAGCTCTCTCGAC

GCAGGACTCGGCTTGCTGAAGCGCGCACGGCAAGAGGCGAGGGGCGGCGACTGGT

GAGTACGCCAAAAATTTTGACTAGCGGAGGCTAGAAGGAGAGAGATGGGTGCGAG

AGCGTCAGTATTAAGCGGGGGAGAATTAGATCGCGATGGGAAAAAATTCGGTTAAG

GCCAGGGGGAAAGAAAAAATATAAATTAAAACATATAGTATGGGCAAGCAGGGAG

-continued

CTAGAACGATTCGCAGTTAATCCTGGCCTGTTAGAAACATCAGAAGGCTGTAGACA

AATACTGGGACAGCTACAACCATCCCTTCAGACAGGATCAGAAGAACTTAGATCAT

TATATAATACAGTAGCAACCCTCTATTGTGTGCATCAAAGGATAGAGATAAAAGAC

ACCAAGGAAGCTTTAGACAAGATAGAGGAAGAGCAAAACAAAAGTAAGACCACCG

CACAGCAAGCGGCCACTGATCTTCAGACCTGGAGGAGGAGATATGAGGGACAATTG

GAGAAGTGAATTATATAAATATAAAGTAGTAAAAATTGAACCATTAGGAGTAGCAC

CCACCAAGGCAAAGAGAAGAGTGGTGCAGAGAGAAAAAAGAGCAGTGGGAATAGG

AGCTTTGTTCCTTGGGTTCTTGGGAGCAGCAGGAAGCACTATGGGCGCAGCCTCAAT

GACGCTGACGGTACAGGCCAGACAATTATTGTCTGGTATAGTGCAGCAGCAGAACA

ATTTGCTGAGGGCTATTGAGGCGCAACAGCATCTGTTGCAACTCACAGTCTGGGGCA

TCAAGCAGCTCCAGGCAAGAATCCTGGCTGTGGAAAGATACCTAAAGGATCAACAG

CTCCTGGGGATTTGGGGTTGCTCTGGAAAACTCATTTGCACCACTGCTGTGCCTTGG

AATGCTAGTTGGAGTAATAAATCTCTGGAACAGATTGGAATCACACGACCTGGATG

GAGTGGGACAGAGAAATTAACAATTACACAAGCTTAATACACTCCTTAATTGAAGA

ATCGCAAAACCAGCAAGAAAAGAATGAACAAGAATTATTGGAATTAGATAAATGGG

CAAGTTTGTGGAATTGGTTTAACATAACAAATTGGCTGTGGTATATAAAATTATTCA

TAATGATAGTAGGAGGCTTGGTAGGTTTAAGAATAGTTTTTGCTGTACTTTCTATAGT

GAATAGAGTTAGGCAGGGATATTCACCATTATCGTTTCAGACCCACCTCCCAACCCC

GAGGGGACCCGACAGGCCCGAAGGAATAGAAGAAGAAGGTGGAGAGAGAGACAG

AGACAGATCCATTCGATTAGTGAACGGATCTCGACGGTATCGGTTAACTTTTAAAAG

AAAAGGGGGGATTGGGGGGTACAGTGCAGGGGAAAGAATAGTAGACATAATAGCA

ACAGACATACAAACTAAAGAATTACAAAAACAAATTACAAAAATTCAAAATTTTAT

CTCGAGTAGTTGTGAACTTACACTTTATTCATATATATTAGATATTGATAATTTTAAC

AAATGAGTTACTTTCCATTTGGGTACAGTCACAGTTGTCAACAATATTTGGAAGCAC

CAGGCATGAAATCTCCTGAGATGCTATGTTTTCATCAGGGTCACCTGACACATTCAA

GTTCTGTCTGACATGCCATTAAAGCACTGGCTCAGATTGCAGGCATATTTTCAAACC

GGCAGTAACTGGATAGTATCACTTCACTTATAAGTGTTCATTGTATCATCAAGTGAA

ATAAACACACAACCCATGGGATCTTGCTTAGGTTGGCTGCCTAGTTGGCCCCTGAGA

TAAAGCCTTGTAATCACATAGCCTTGCCTAATTAGTCAGAAAACAAAGGATTAAGTG

AGACAGTCACAGGATATAGGAATTATAAATAATACATATATTAATAGATATTCATTT

TCATTACACAAAAGTTGCTATTATAAATACTTATTTGATTGATGAGTCTAAAAATAT

ATTCCCCATATAAATAATGTTAAATATTAATAAATAGATTTAGATTTAAAATTCAAA

TATTGCAGGCAGGACAACCACCCGGGTTAACTTGCATTCAAATATGACATTACCCTA

TCAATTGTAACGGCCCTGATTCTAAAAGCATGCAAAAGTATACACAGCTTTATTTTT

GTCTTGTAAAAATCAGGTTCTTCAAGAGAGCTTTTTTGAGGAACCGTTTCAGAATTA

AAATTAAGAGCTTGCATCAGCTCATCAATAACGGCAAGCATATTCTGATCAAGGAAT

ATCTGTCGCTTGGGGTCCATCAAAAGTTTTGCGTTCATTGTCTTGAACTCAACCTGGT

ACATCTTAAGATCTTCATATATAGAAGACAAGCACAGGGCCATCATAAAGCTTGTTT

TGCGGCTGGCCAAACAAGATCCATTGGTAATGAAAGAAGTCTCTCTGGAATTGAGA

CAAGATTCGTTTTTAGTGAGTTCCAGTGGCAGGCATGCCTCCACGGTGGATGTTTTG

-continued

TCCTTAGTAATATCTTCGTGGTCTATTTCCTCACTTGTGCAAGGGTAAAATTCAAGTG

TTTGTCGGGCCTTCTGGAGCATGTTGGAGACAGCCCTAAGCAAGTTTTGAGAGTGGT

GAAGACATGGGAACATGCCTGGGTCTGGGGTTGCAACAGGCAAGTTCCGAGAACCG

CCCCCACCACCACCTGAGCATGGGACAGATGCCCATTCGCTCCAGCTAGATGAGTA

GTATCTGTCTTGGGCTCTGACACTTATGCTTGCGTTCTTTCTGCAAATGACTGTTGCA

GACGTTTTATCAGTGAAAACCCGATCTTTCTTTTCCCTTTTTGATTTTCCTTGCACCTG

GACACAAAATGTCAAACTAAAGTAAGAGTGCGGAGTTGACCAGGTGTCGGGGTACT

CCCAAGAAACTTCAACCTGGCGTGAGTTCTTCAAAGGCTTAAGCTGCAGATTCTTCG

GAGGATCGGGCTTGATAATGTCCCGGATAAAAAAGCTGCTCGTGTAATTTTCATACT

TCAACTTGTGTACGGCGTCAACCATCACCTCTATTGGCAGGCTCTCCTCTGCTGCGG

GGCAAGCGGAGTCTTCCTGGCATTCCACGCTATATTCGTATTCTTTGTTGTCCCCCCG

TACCCTCTCCGCAGAAAGCGTAGCAGCACCGCACGTTACACCTTGTGGGTCACTGGA

ACCCCTACTAGACTTAACAGAAAACGTAAGATCCGTAGAGATTGTTGTCAACCACCA

GCAAGTAAAGCGTCCGGAGTAATTTTTTGCTTCACAGCGCAGAAACGTTTTGTTTTT

GGGTTCTTTCTGATCCTTAAGGATATCTGTACTCCAAATGCCATCCTCTTTTTTGTGC

AGGAGCAGCAGGCTGTGAGAAAGGACCTCGCCTCCCTTATGGCACGTATACTGCCC

GGCATCTCCAAACTCTTTTACCTGGATAGTAAGTGTTTTGCCGCTGCCAAGCACCTCT

GAGCTTTGGTCCAGGGTCCAGGTTATCCCATCTTCTTCAGGTGTATCGCAGGTGAGG

ACCACCATCTCGCCCGGTGCGTCGGGATACCAATCCAATTCAACAACATATACGTCT

TTCTTAAGTTCCCAAATAGCGACCAATGGTGACGCCAGAAAAACAAGTGAGAACCA

AGAGATTACCAGTTGTTGATGGCACATGGTGGGAATTCCTGGAATTCGAGCTTCCAT

TATATACCCTCTAGAGTCTAGATCTACGCCTTCTGTATGAAACAGTTTTTCCTCCACG

CCTTCTGTATGAAACAGTTTTTCCTCCACGCCTTCTGTATGAAACAGTTTTTCCTCCG

TTTAAACGTAAGTCATTGGTCTTAAAGGTAGCTTTATTTAGTCTCCAGAAAAAGGGG

GGAATGAAAGACCCCACCTGTAGGTTTGGCAAGCTAGGATCAAGGTTAGGAACAGA

GAGACAGCAGAATATGGGCCAAACAGGATATCTGTGGTAAGCAGTTCCTGCCCCGG

CTCAGGGCCAAGAACAGTTGGAACAGCAGAATATGGGCCAAACAGGATATCTGTGG

TAAGCAGTTCCTGCCCCGGCTCAGGGCCAAGAACAGATGGTCCCCAGATGCGGTCC

CGCCCTCAGCAGTTTCTAGAGAACCATCAGATGTTTCCAGGGTGCCCCAAGGACCTG

AAATGACCCTGTGCCTTATTTGAACTAACCAATCAGTTCGCTTCTCGCTTCTGTTCGC

GCGCTTCTGCTCCCCGAGCTCAATAAAAGAGCCCACGCTAGCGCTACCGGTCGCCAA

GATGGGGGCAGGTGCCACCGGCCGCGCAATGGATGGTCCGCGTCTACTGCTGTTACT

ACTTCTGGGTGTGTCCCTTGGAGGTGCCAAAGAGGCATGCCCCACAGGTCTATACAC

ACATAGCGGTGAATGCTGCAAAGCATGCAACCTGGGCGAAGGTGTGGCCCAACCTT

GTGGAGCCAATCAAACCGTTTGTGAGCCATGTCTGGACAGCGTGACGTTCTCCGATG

TTGTTAGCGCGACCGAGCCATGCAAACCGTGTACCGAGTGTGTTGGTCTCCAAAGTA

TGTCGGCGCCGTGCGTGGAGGCCGACGACGCCGTGTGTCGCTGTGCCTACGGTTATT

ACCAGGATGAAACTACTGGTCGCTGTGAAGCGTGCCGCGTGTGTGAGGCGGGCTCA

GGCCTCGTGTTCTCCTGTCAGGACAAACAGAACACTGTGTGTGAAGAATGCCCCGAC

GGTACTTATTCCGACGAGGCCAACCATGTGGACCCGTGTCTGCCCTGCACCGTTTGC

GAGGATACCGAGCGCCAGCTACGTGAGTGCACACGTTGGGCCGACGCCGAGTGCGA

-continued

GGAAATCCCTGGCCGTTGGATTACACGGTCCACACCACCAGAAGGCTCGGACAGCA

CAGCACCCAGCACTCAGGAACCTGAGGCACCTCCAGAACAAGACCTAATAGCCAGC

ACTGTGGCAGGTGTTGTGACTACAGTGATGGGTAGCTCACAACCCGTTGTTACTCGA

GGCACCACCGACAATCTAATTCCTGTCTATTGTTCCATCCTGGCTGCTGTGGTTGTGG

GTCTTGTTGCATATATAGCCTTCAAGAGGGGCAGCGGAGAGGGTAGGGGTAGTCTTT

TGACGTGTGGGGACGTCGAGGAAAATCCTGGGCCTGCCTTACCAGTGACCGCCTTGC

TCCTGCCGCTGGCCTTGCTGCTCCACGCCGCCAGGCCGGACATCGTGATGACCCAGA

GCCCCGACAGCCTGGCCGTGAGCCTGGGCGAGAGGGCCACCATCAACTGCAAGAGC

AGCCAGAGCCTGCTGAACAGCGGCGACCAGAAGAACTACCTGACCTGGTACCAGCA

GAAGCCCGGCCAGCCCCCCAAGCTGCTGATCTACTGGGCCAGCACCAGGGAGAGCG

GCGTGCCCGACAGGTTCAGCGGCAGCGGCAGCGGCACCGACTTCACCCTGACCATC

AGCAGCCTGCAGGCCGAGGACGTGGCCGTGTACTACTGCCAGAACGACTACAGCTA

CCCCCTGACCTTCGGCCAGGGCACCAAGGTGGAGATCAAGGGCGGCGGCGGCAGCG

GCGGCGGCGGCAGCGGCGGCGGCGGCAGCCAGGTGCAGCTGGTGCAGAGCGGCGC

CGAGGTGAAGAAGACCGGCAGCAGCGTGAAGGTGAGCTGCAAGGCCAGCGGCTAC

ACCTTCACCGACCACGCCATCCACTGGGTGAGGCAGGCCCCCGGCCAGGCCCTGGA

GTGGATGGGCCACTTCAGCCCCGGCAACACCGACATCAAGTACAACGACAAGTTCA

AGGGCAGGGTGACCCTGACCGTGGACAGGAGCATGAGCACCGCCTACATGGAGCTG

AGCAGCCTGAGGAGCGAGGACACCGCCATGTACTACTGCAAGACCAGCACCTTCTT

CTTCGACTACTGGGGCCAGGGCACCATGGTGACCGTGAGCAGCACCACGACGCCAG

CGCCGCGACCACCAACACCGGCGCCCACCATCGCGTCGCAGCCCCTGTCCCTGCGCC

CAGAGGCGTGCCGGCCAGCGGCGGGGGGCGCAGTGCACACGAGGGGGCTGGACTT

CGCCTGTGATATCTACATCTGGGCGCCCTTGGCCGGGACTTGTGGGGTCCTTCTCCTG

TCACTGGTTATCACCCTTTACTGCAAACGGGGCAGAAAGAAACTCCTGTATATATTC

AAACAACCATTTATGAGACCAGTACAAACTACTCAAGAGGAAGATGGCTGTAGCTG

CCGATTTCCAGAAGAAGAAGAAGGAGGATGTGAACTGAGAGTGAAGTTCAGCAGG

AGCGCAGACGCCCCCGCGTACAAGCAGGGCCAGAACCAGCTCTATAACGAGCTCAA

TCTAGGACGAAGAGAGGAGTACGATGTTTTGGACAAGAGACGTGGCCGGGACCCTG

AGATGGGGGGAAAGCCGAGAAGGAAGAACCCTCAGGAAGGCCTGTACAATGAACT

GCAGAAAGATAAGATGGCGGAGGCCTACAGTGAGATTGGGATGAAAGGCGAGCGC

CGGAGGGGCAAGGGGCACGATGGCCTTTACCAGGGTCTCAGTACAGCCACCAAGGA

CACCTACGACGCCCTTCACATGCAGGCCCTGCCCCCTCGCTGAAGAGACGTCATAAT

CAGCCAGCGGCCGCGTCGACAATCAACCTCTGGATTACAAAATTTGTGAAAGATTG

ACTGGTATTCTTAACTATGTTGCTCCTTTTACGCTATGTGGATACGCTGCTTTAATGC

CTTTGTATCATGCTATTGCTTCCCGTATGGCTTTCATTTTCTCCTCCTTGTATAAATCC

TGGTTGCTGTCTCTTTATGAGGAGTTGTGGCCCGTTGTCAGGCAACGTGGCGTGGTG

TGCACTGTGTTTGCTGACGCAACCCCCACTGGTTGGGGCATTGCCACCACCTGTCAG

CTCCTTTCCGGGACTTTCGCTTTCCCCCTCCCTATTGCCACGGCGGAACTCATCGCCG

CCTGCCTTGCCCGCTGCTGGACAGGGGCTCGGCTGTTGGGCACTGACAATTCCGTGG

TGTTGTCGGGGAAATCATCGTCCTTTCCTTGGCTGCTCGCCTGTGTTGCCACCTGGAT

-continued

TCTGCGCGGGACGTCCTTCTGCTACGTCCCTTCGGCCCTCAATCCAGCGGACCTTCCT

TCCCGCGGCCTGCTGCCGGCTCTGCGGCCTCTTCCGCGTCTTCGCCTTCGCCCTCAGA

CGAGTCGGATCTCCCTTTGGGCCGCCTCCCCGCCTGGTACCTTTAAGACCAATGACT

TACAAGGCAGCTGTAGATCTTAGCCACTTTTTAAAAGAAAAGGGGGGACTGGAAGG

GCTAATTCACTCCCAACGAAAATAAGATCTGCTTTTTGCTTGTACTGGGTCTCTCTGG

TTAGACCAGATCTGAGCCTGGGAGCTCTCTGGCTAACTAGGGAACCCACTGCTTAAG

CCTCAATAAAGCTTGCCTTGAGTGCTTCAAGTAGTGTGTGCCCGTCTGTTGTGTGACT

CTGGTAACTAGAGATCCCTCAGACCCTTTTAGTCAGTGTGGAAAATCTCTAGCA

GC217

(SEQ ID NO: 6)

TCTGGTTAGACCAGATCTGAGCCTGGGAGCTCTCTGGCTAACTAGGGAACCCACTGC

TTAAGCCTCAATAAAGCTTGCCTTGAGTGCTTCAAGTAGTGTGTGCCCGTCTGTTGTG

TGACTCTGGTAACTAGAGATCCCTCAGACCCTTTTAGTCAGTGTGGAAAATCTCTAG

CAGTGGCGCCCGAACAGGGACCTGAAAGCGAAAGGGAAACCAGAGCTCTCTCGAC

GCAGGACTCGGCTTGCTGAAGCGCGCACGGCAAGAGGCGAGGGGCGGCGACTGGT

GAGTACGCCAAAAATTTTGACTAGCGGAGGCTAGAAGGAGAGAGATGGGTGCGAG

AGCGTCAGTATTAAGCGGGGGAGAATTAGATCGCGATGGGAAAAAATTCGGTTAAG

GCCAGGGGGAAAGAAAAAATATAAATTAAAACATATAGTATGGGCAAGCAGGGAG

CTAGAACGATTCGCAGTTAATCCTGGCCTGTTAGAAACATCAGAAGGCTGTAGACA

AATACTGGGACAGCTACAACCATCCCTTCAGACAGGATCAGAAGAACTTAGATCAT

TATATAATACAGTAGCAACCCTCTATTGTGTGCATCAAAGGATAGAGATAAAAGAC

ACCAAGGAAGCTTTAGACAAGATAGAGGAAGAGCAAAACAAAAGTAAGACCACCG

CACAGCAAGCGGCCACTGATCTTCAGACCTGGAGGAGGAGATATGAGGGACAATTG

GAGAAGTGAATTATATAAATATAAAGTAGTAAAAATTGAACCATTAGGAGTAGCAC

CCACCAAGGCAAAGAGAAGAGTGGTGCAGAGAGAAAAAAGAGCAGTGGGAATAGG

AGCTTTGTTCCTTGGGTTCTTGGGAGCAGCAGGAAGCACTATGGGCGCAGCCTCAAT

GACGCTGACGGTACAGGCCAGACAATTATTGTCTGGTATAGTGCAGCAGCAGAACA

ATTTGCTGAGGGCTATTGAGGCGCAACAGCATCTGTTGCAACTCACAGTCTGGGGCA

TCAAGCAGCTCCAGGCAAGAATCCTGGCTGTGGAAAGATACCTAAAGGATCAACAG

CTCCTGGGGATTTGGGGTTGCTCTGGAAAACTCATTTGCACCACTGCTGTGCCTTGG

AATGCTAGTTGGAGTAATAAATCTCTGGAACAGATTGGAATCACACGACCTGGATG

GAGTGGGACAGAGAAATTAACAATTACACAAGCTTAATACACTCCTTAATTGAAGA

ATCGCAAAACCAGCAAGAAAAGAATGAACAAGAATTATTGGAATTAGATAAATGGG

CAAGTTTGTGGAATTGGTTTAACATAACAAATTGGCTGTGGTATATAAAATTATTCA

TAATGATAGTAGGAGGCTTGGTAGGTTTAAGAATAGTTTTTGCTGTACTTTCTATAGT

GAATAGAGTTAGGCAGGGATATTCACCATTATCGTTTCAGACCCACCTCCCAACCCC

GAGGGGACCCGACAGGCCCGAAGGAATAGAAGAAGAAGGTGGAGAGAGAGACAG

AGACAGATCCATTCGATTAGTGAACGGATCTCGACGGTATCGGTTAACTTTTAAAAG

AAAAGGGGGGATTGGGGGGTACAGTGCAGGGGAAAGAATAGTAGACATAATAGCA

ACAGACATACAAACTAAAGAATTACAAAAACAAATTACAAAAATTCAAAATTTTAT

CTCGAGTAGTTGTGAACTTACACTTTATTCATATATATTAGATATTGATAATTTTAAC

AAATGAGTTACTTTCCATTTGGGTACAGTCACAGTTGTCAACAATATTTGGAAGCAC

-continued

```
CAGGCATGAAATCTCCTGAGATGCTATGTTTTCATCAGGGTCACCTGACACATTCAA

GTTCTGTCTGACATGCCATTAAAGCACTGGCTCAGATTGCAGGCATATTTTCAAACC

GGCAGTAACTGGATAGTATCACTTCACTTATAAGTGTTCATTGTATCATCAAGTGAA

ATAAACACACAACCCATGGGATCTTGCTTAGGTTGGCTGCCTAGTTGGCCCCTGAGA

TAAAGCCTTGTAATCACATAGCCTTGCCTAATTAGTCAGAAAACAAAGGATTAAGTG

AGACAGTCACAGGATATAGGAATTATAAATAATACATATATTAATAGATATTCATTT

TCATTACACAAAGTTGCTATTATAAATACTTATTTGATTGATGAGTCTAAAAATAT

ATTCCCCATATAAATAATGTTAAATATTAATAAATAGATTTAGATTTAAAATTCAAA

TATTGCAGGCAGGACAACCACCCGGGTCACACGCGGTAGCAGTAGAAGATGATGAT

GACGGAGATGGCCACGCCCAGGGGGGGCAGGAGGCTGATGCCGGTCACCTGGAAG

ATGACCAGCAACAAGTCGGGGTTGCTGGTGTTGTACTCCTCGGAGAAGATGATGTTG

TCGTTGCACTCGTCGGAGCTGCAGGAGCACATGAAGAAGGTCTCGCCGGGCTTCTTC

TTCTCCTTCATGATGCACTTGGGGGAGGCGGCGTCCTCCAGGATGAAGTCGTGGTAG

GGGAGCTTGGGGTCGTGGCACACGGTCTCCAGGGTGATGTTCTCGTCGTTCTTCCTC

CACACGGCCACGCAGACCTCCTGGGGCTTCTCGCAGATGGAGGTGATGCTGCAGTT

GCTCATGCAGGACTTCTGGTTGTCGCAGGTGGAGAACCTCACGTCGCAGAACTTGCA

CAGCTGGGGGAACTTGACGGCGCCGTTGTTGTCGGTGACGATCATGTCGTTGTTCAC

CGACTTCTGCACGTGCGGGGGGATCGTGCTGGCGATCCGCGTCCACAGGACGATGT

GCAGCGGCCACAGGCCCCTGAGCAGCCCCCGGCCCATGGTGGGAATTCCTGGAATT

CGAGCTTCCATTATATACCCTCTAGAGTCTAGATCTACGCCTTCTGTATGAAACAGTT

TTTCCTCCACGCCTTCTGTATGAAACAGTTTTTCCTCCACGCCTTCTGTATGAAACAG

TTTTTCCTCCGTTTAAACGTAAGTCATTGGTCTTAAAGGTAGCTTTATTTAGTCTCCA

GAAAAAGGGGGGAATGAAAGACCCCACCTGTAGGTTTGGCAAGCTAGGATCAAGGT

TAGGAACAGAGAGACAGCAGAATATGGGCCAAACAGGATATCTGTGGTAAGCAGTT

CCTGCCCCGGCTCAGGGCCAAGAACAGTTGGAACAGCAGAATATGGGCCAAACAGG

ATATCTGTGGTAAGCAGTTCCTGCCCCGGCTCAGGGCCAAGAACAGATGGTCCCCA

GATGCGGTCCCGCCCTCAGCAGTTTCTAGAGAACCATCAGATGTTTCCAGGGTGCCC

CAAGGACCTGAAATGACCCTGTGCCTTATTTGAACTAACCAATCAGTTCGCTTCTCG

CTTCTGTTCGCGCGCTTCTGCTCCCCGAGCTCAATAAAAGAGCCCACGCTAGCGCTA

CCGGTCGCCAAGATGGGGGCAGGTGCCACCGGCCGCGCAATGGATGGTCCGCGTCT

ACTGCTGTTACTACTTCTGGGTGTGTCCCTTGGAGGTGCCAAAGAGGCATGCCCCAC

AGGTCTATACACACATAGCGGTGAATGCTGCAAAGCATGCAACCTGGGCGAAGGTG

TGGCCCAACCTTGTGGAGCCAATCAAACCGTTTGTGAGCCATGTCTGGACAGCGTGA

CGTTCTCCGATGTTGTTAGCGCGACCGAGCCATGCAAACCGTGTACCGAGTGTGTTG

GTCTCCAAAGTATGTCGGCGCCGTGCGTGGAGGCCGACGACGCCGTGTGTCGCTGTG

CCTACGGTTATTACCAGGATGAAACTACTGGTCGCTGTGAAGCGTGCCGCGTGTGTG

AGGCGGGCTCAGGCCTCGTGTTCTCCTGTCAGGACAAACAGAACACTGTGTGTGAA

GAATGCCCCGACGGTACTTATTCCGACGAGGCCAACCATGTGGACCCGTGTCTGCCC

TGCACCGTTTGCGAGGATACCGAGCGCCAGCTACGTGAGTGCACACGTTGGGCCGA

CGCCGAGTGCGAGGAAATCCCTGGCCGTTGGATTACACGGTCCACACCACCAGAAG
```

-continued

GCTCGGACAGCACAGCACCCAGCACTCAGGAACCTGAGGCACCTCCAGAACAAGAC

CTAATAGCCAGCACTGTGGCAGGTGTTGTGACTACAGTGATGGGTAGCTCACAACCC

GTTGTTACTCGAGGCACCACCGACAATCTAATTCCTGTCTATTGTTCCATCCTGGCTG

CTGTGGTTGTGGGTCTTGTTGCATATATAGCCTTCAAGAGGGGCAGCGGAGAGGGTA

GGGGTAGTCTTTTGACGTGTGGGGACGTCGAGGAAAATCCTGGGCCTGCCTTACCAG

TGACCGCCTTGCTCCTGCCGCTGGCCTTGCTGCTCCACGCCGCCAGGCCGGACATCG

TGATGACCCAGAGCCCCGACAGCCTGGCCGTGAGCCTGGGCGAGAGGGCCACCATC

AACTGCAAGAGCAGCCAGAGCCTGCTGAACAGCGGCGACCAGAAGAACTACCTGAC

CTGGTACCAGCAGAAGCCCGGCCAGCCCCCCAAGCTGCTGATCTACTGGGCCAGCA

CCAGGGAGAGCGGCGTGCCCGACAGGTTCAGCGGCAGCGGCAGCGGCACCGACTTC

ACCCTGACCATCAGCAGCCTGCAGGCCGAGGACGTGGCCGTGTACTACTGCCAGAA

CGACTACAGCTACCCCCTGACCTTCGGCCAGGGCACCAAGGTGGAGATCAAGGGCG

GCGGCGGCAGCGGCGGCGGCGGCAGCGGCGGCGGCGGCAGCCAGGTGCAGCTGGT

GCAGAGCGGCGCCGAGGTGAAGAAGACCGGCAGCAGCGTGAAGGTGAGCTGCAAG

GCCAGCGGCTACACCTTCACCGACCACGCCATCCACTGGGTGAGGCAGGCCCCCGG

CCAGGCCCTGGAGTGGATGGGCCACTTCAGCCCCGGCAACACCGACATCAAGTACA

ACGACAAGTTCAAGGGCAGGGTGACCCTGACCGTGGACAGGAGCATGAGCACCGCC

TACATGGAGCTGAGCAGCCTGAGGAGCGAGGACACCGCCATGTACTACTGCAAGAC

CAGCACCTTCTTCTTCGACTACTGGGGCCAGGGCACCATGGTGACCGTGAGCAGCAC

CACGACGCCAGCGCCGCGACCACCAACACCGGCGCCCACCATCGCGTCGCAGCCCC

TGTCCCTGCGCCCAGAGGCGTGCCGGCCAGCGGCGGGGGGCGCAGTGCACACGAGG

GGGCTGGACTTCGCCTGTGATATCTACATCTGGGCGCCCTTGGCCGGGACTTGTGGG

GTCCTTCTCCTGTCACTGGTTATCACCCTTTACTGCAAACGGGGCAGAAAGAAACTC

CTGTATATATTCAAACAACCATTTATGAGACCAGTACAAACTACTCAAGAGGAAGAT

GGCTGTAGCTGCCGATTTCCAGAAGAAGAAGAAGGAGGATGTGAACTGAGAGTGAA

GTTCAGCAGGAGCGCAGACGCCCCCGCGTACAAGCAGGGCCAGAACCAGCTCTATA

ACGAGCTCAATCTAGGACGAAGAGAGGAGTACGATGTTTTGGACAAGAGACGTGGC

CGGGACCCTGAGATGGGGGGAAAGCCGAGAAGGAAGAACCCTCAGGAAGGCCTGT

ACAATGAACTGCAGAAAGATAAGATGGCGGAGGCCTACAGTGAGATTGGGATGAA

AGGCGAGCGCCGGAGGGGCAAGGGGCACGATGGCCTTTACCAGGGTCTCAGTACAG

CCACCAAGGACACCTACGACGCCCTTCACATGCAGGCCCTGCCCCCTCGCTGAAGA

GACGTCATAATCAGCCAGCGGCCGCGTCGACAATCAACCTCTGGATTACAAAATTTG

TGAAAGATTGACTGGTATTCTTAACTATGTTGCTCCTTTTACGCTATGTGGATACGCT

GCTTTAATGCCTTTGTATCATGCTATTGCTTCCCGTATGGCTTTCATTTTCTCCTCCTT

GTATAAATCCTGGTTGCTGTCTCTTTATGAGGAGTTGTGGCCCGTTGTCAGGCAACG

TGGCGTGGTGTGCACTGTGTTTGCTGACGCAACCCCCACTGGTTGGGGCATTGCCAC

CACCTGTCAGCTCCTTTCCGGGACTTTCGCTTTCCCCCTCCCTATTGCCACGGCGGAA

CTCATCGCCGCCTGCCTTGCCCGCTGCTGGACAGGGGCTCGGCTGTTGGGCACTGAC

AATTCCGTGGTGTTGTCGGGGAAATCATCGTCCTTTCCTTGGCTGCTCGCCTGTGTTG

CCACCTGGATTCTGCGCGGGACGTCCTTCTGCTACGTCCCTTCGGCCCTCAATCCAG

CGGACCTTCCTTCCCGCGGCCTGCTGCCGGCTCTGCGGCCTCTTCCGCGTCTTCGCCT

-continued

TCGCCCTCAGACGAGTCGGATCTCCCTTTGGGCCGCCTCCCCGCCTGGTACCTTTAA

GACCAATGACTTACAAGGCAGCTGTAGATCTTAGCCACTTTTTAAAAGAAAAGGGG

GGACTGGAAGGGCTAATTCACTCCCAACGAAAATAAGATCTGCTTTTTGCTTGTACT

GGGTCTCTCTGGTTAGACCAGATCTGAGCCTGGGAGCTCTCTGGCTAACTAGGGAAC

CCACTGCTTAAGCCTCAATAAAGCTTGCCTTGAGTGCTTCAAGTAGTGTGTGCCCGT

CTGTTGTGTGACTCTGGTAACTAGAGATCCCTCAGACCCTTTTAGTCAGTGTGGAAA

ATCTCTAGCA

GC219

(SEQ ID NO: 7)

TCTGGTTAGACCAGATCTGAGCCTGGGAGCTCTCTGGCTAACTAGGGAACCCACTGC

TTAAGCCTCAATAAAGCTTGCCTTGAGTGCTTCAAGTAGTGTGTGCCCGTCTGTTGTG

TGACTCTGGTAACTAGAGATCCCTCAGACCCTTTTAGTCAGTGTGGAAAATCTCTAG

CAGTGGCGCCCGAACAGGGACCTGAAAGCGAAAGGGAAACCAGAGCTCTCTCGAC

GCAGGACTCGGCTTGCTGAAGCGCGCACGGCAAGAGGCGAGGGGCGGCGACTGGT

GAGTACGCCAAAAATTTTGACTAGCGGAGGCTAGAAGGAGAGAGATGGGTGCGAG

AGCGTCAGTATTAAGCGGGGGAGAATTAGATCGCGATGGGAAAAAATTCGGTTAAG

GCCAGGGGGAAAGAAAAAATATAAATTAAAACATATAGTATGGGCAAGCAGGGAG

CTAGAACGATTCGCAGTTAATCCTGGCCTGTTAGAAACATCAGAAGGCTGTAGACA

AATACTGGGACAGCTACAACCATCCCTTCAGACAGGATCAGAAGAACTTAGATCAT

TATATAATACAGTAGCAACCCTCTATTGTGTGCATCAAAGGATAGAGATAAAAGAC

ACCAAGGAAGCTTTAGACAAGATAGAGGAAGAGCAAAACAAAAGTAAGACCACCG

CACAGCAAGCGGCCACTGATCTTCAGACCTGGAGGAGGAGATATGAGGGACAATTG

GAGAAGTGAATTATATAAATATAAAGTAGTAAAAATTGAACCATTAGGAGTAGCAC

CCACCAAGGCAAAGAGAAGAGTGGTGCAGAGAGAAAAAAGAGCAGTGGGAATAGG

AGCTTTGTTCCTTGGGTTCTTGGGAGCAGCAGGAAGCACTATGGGCGCAGCCTCAAT

GACGCTGACGGTACAGGCCAGACAATTATTGTCTGGTATAGTGCAGCAGCAGAACA

ATTTGCTGAGGGCTATTGAGGCGCAACAGCATCTGTTGCAACTCACAGTCTGGGGCA

TCAAGCAGCTCCAGGCAAGAATCCTGGCTGTGGAAAGATACCTAAAGGATCAACAG

CTCCTGGGGATTTGGGGTTGCTCTGGAAAACTCATTTGCACCACTGCTGTGCCTTGG

AATGCTAGTTGGAGTAATAAATCTCTGGAACAGATTGGAATCACACGACCTGGATG

GAGTGGGACAGAGAAATTAACAATTACACAAGCTTAATACACTCCTTAATTGAAGA

ATCGCAAAACCAGCAAGAAAAGAATGAACAAGAATTATTGGAATTAGATAAATGGG

CAAGTTTGTGGAATTGGTTTAACATAACAAATTGGCTGTGGTATATAAAATTATTCA

TAATGATAGTAGGAGGCTTGGTAGGTTTAAGAATAGTTTTTGCTGTACTTTCTATAGT

GAATAGAGTTAGGCAGGGATATTCACCATTATCGTTTCAGACCCACCTCCCAACCCC

GAGGGGACCCGACAGGCCCGAAGGAATAGAAGAAGAAGGTGGAGAGAGAGACAG

AGACAGATCCATTCGATTAGTGAACGGATCTCGACGGTATCGGTTAACTTTTAAAAG

AAAAGGGGGGATTGGGGGGTACAGTGCAGGGGAAAGAATAGTAGACATAATAGCA

ACAGACATACAAACTAAAGAATTACAAAAACAAATTACAAAAATTCAAAATTTTAT

CTCGAGTAGTTGTGAACTTACACTTTATTCATATATATTAGATATTGATAATTTTAAC

AAATGAGTTACTTTCCATTTGGGTACAGTCACAGTTGTCAACAATATTTGGAAGCAC

-continued

CAGGCATGAAATCTCCTGAGATGCTATGTTTTCATCAGGGTCACCTGACACATTCAA

GTTCTGTCTGACATGCCATTAAAGCACTGGCTCAGATTGCAGGCATATTTTCAAACC

GGCAGTAACTGGATAGTATCACTTCACTTATAAGTGTTCATTGTATCATCAAGTGAA

ATAAACACACAACCCATGGGATCTTGCTTAGGTTGGCTGCCTAGTTGGCCCCTGAGA

TAAAGCCTTGTAATCACATAGCCTTGCCTAATTAGTCAGAAAACAAAGGATTAAGTG

AGACAGTCACAGGATATAGGAATTATAAATAATACATATATTAATAGATATTCATTT

TCATTACACAAAAGTTGCTATTATAAATACTTATTTGATTGATGAGTCTAAAAATAT

ATTCCCCATATAAATAATGTTAAATATTAATAAATAGATTTAGATTTAAAATTCAAA

TATTGCAGGCAGGACAACCACCCGGGCTAGTCCTCGTTCTGCACGGTGAACATGATG

GACCTGTCCCCCAACTCGTCCTCCTTCTTCAAGATGAGCTTGAACAGGTCCCTCTCCT

TCTCGCAGGCCAGGAAGTAGCCCTCGTAGGAGGAGGACTCGAACTGCATCTTGTTGT

CGTGGCCGGGGACGCTCCTCTGGAAGAAGATGATGTCGCTCTTGGTGTCCTTGATGT

TGTCGGGGGGGTTCATCTCCTTGAAGGAGATGATCTTGTTCTCGCAGGAGAGGGTGG

AGATCTTCTCGCACTTCACGGAGATGGTCACGGCCTTGCCCCTGGCCCTGCTGTCGC

CGTAGGCGCTGATGATGAAGATGGTCCGGGGGGCGTTGTCCCTGCAGTCGGAGTCG

GTCATGTCCTCGAACAGGGGCCGGTTGCCCTGGTCGATGAAGAGCACCTGGTCGTTC

AAGTTCCTGATGACGGACAACTTGGACTCCAGCTTGCCGAAGTAGTCGGACTCCAGG

TTCTCGTCGTCCTCGGCGATGAAGTACAGCGTGTTGTCGATGAACTTCATGGCCACG

AAGTTGATGCAGTTGTCCTCCACGGGCTCGGCGGCCATGGTGGGAATTCCTGGAATT

CGAGCTTCCATTATATACCCTCTAGAGTCTAGATCTACGCCTTCTGTATGAAACAGTT

TTTCCTCCACGCCTTCTGTATGAAACAGTTTTTCCTCCACGCCTTCTGTATGAAACAG

TTTTTCCTCCGTTTAAACGTAAGTCATTGGTCTTAAAGGTAGCTTTATTTAGTCTCCA

GAAAAAGGGGGGAATGAAAGACCCCACCTGTAGGTTTGGCAAGCTAGGATCAAGGT

TAGGAACAGAGAGACAGCAGAATATGGGCCAAACAGGATATCTGTGGTAAGCAGTT

CCTGCCCCGGCTCAGGGCCAAGAACAGTTGGAACAGCAGAATATGGGCCAAACAGG

ATATCTGTGGTAAGCAGTTCCTGCCCCGGCTCAGGGCCAAGAACAGATGGTCCCCA

GATGCGGTCCCGCCCTCAGCAGTTTCTAGAGAACCATCAGATGTTTCCAGGGTGCCC

CAAGGACCTGAAATGACCCTGTGCCTTATTTGAACTAACCAATCAGTTCGCTTCTCG

CTTCTGTTCGCGCGCTTCTGCTCCCCGAGCTCAATAAAAGAGCCCACGCTAGCGCTA

CCGGTCGCCAAGATGGGGGCAGGTGCCACCGGCCGCGCAATGGATGGTCCGCGTCT

ACTGCTGTTACTACTTCTGGGTGTGTCCCTTGGAGGTGCCAAAGAGGCATGCCCCAC

AGGTCTATACACACATAGCGGTGAATGCTGCAAAGCATGCAACCTGGGCGAAGGTG

TGGCCCAACCTTGTGGAGCCAATCAAACCGTTTGTGAGCCATGTCTGGACAGCGTGA

CGTTCTCCGATGTTGTTAGCGCGACCGAGCCATGCAAACCGTGTACCGAGTGTGTTG

GTCTCCAAAGTATGTCGGCGCCGTGCGTGGAGGCCGACGACGCCGTGTGTCGCTGTG

CCTACGGTTATTACCAGGATGAAACTACTGGTCGCTGTGAAGCGTGCCGCGTGTGTG

AGGCGGGCTCAGGCCTCGTGTTCTCCTGTCAGGACAAACAGAACACTGTGTGTGAA

GAATGCCCCGACGGTACTTATTCCGACGAGGCCAACCATGTGGACCCGTGTCTGCCC

TGCACCGTTTGCGAGGATACCGAGCGCCAGCTACGTGAGTGCACACGTTGGGCCGA

CGCCGAGTGCGAGGAAATCCCTGGCCGTTGGATTACACGGTCCACACCACCAGAAG

GCTCGGACAGCACAGCACCCAGCACTCAGGAACCTGAGGCACCTCCAGAACAAGAC

-continued

CTAATAGCCAGCACTGTGGCAGGTGTTGTGACTACAGTGATGGGTAGCTCACAACCC

GTTGTTACTCGAGGCACCACCGACAATCTAATTCCTGTCTATTGTTCCATCCTGGCTG

CTGTGGTTGTGGGTCTTGTTGCATATATAGCCTTCAAGAGGGGCAGCGGAGAGGGTA

GGGGTAGTCTTTTGACGTGTGGGGACGTCGAGGAAAATCCTGGGCCTGCCTTACCAG

TGACCGCCTTGCTCCTGCCGCTGGCCTTGCTGCTCCACGCCGCCAGGCCGGACATCG

TGATGACCCAGAGCCCCGACAGCCTGGCCGTGAGCCTGGGCGAGAGGGCCACCATC

AACTGCAAGAGCAGCCAGAGCCTGCTGAACAGCGGCGACCAGAAGAACTACCTGAC

CTGGTACCAGCAGAAGCCCGGCCAGCCCCCCAAGCTGCTGATCTACTGGGCCAGCA

CCAGGGAGAGCGGCGTGCCCGACAGGTTCAGCGGCAGCGGCAGCGGCACCGACTTC

ACCCTGACCATCAGCAGCCTGCAGGCCGAGGACGTGGCCGTGTACTACTGCCAGAA

CGACTACAGCTACCCCCTGACCTTCGGCCAGGGCACCAAGGTGGAGATCAAGGGCG

GCGGCGGCAGCGGCGGCGGCGGCAGCGGCGGCGGCGGCAGCCAGGTGCAGCTGGT

GCAGAGCGGCGCCGAGGTGAAGAAGACCGGCAGCAGCGTGAAGGTGAGCTGCAAG

GCCAGCGGCTACACCTTCACCGACCACGCCATCCACTGGGTGAGGCAGGCCCCCGG

CCAGGCCCTGGAGTGGATGGGCCACTTCAGCCCCGGCAACACCGACATCAAGTACA

ACGACAAGTTCAAGGGCAGGGTGACCCTGACCGTGGACAGGAGCATGAGCACCGCC

TACATGGAGCTGAGCAGCCTGAGGAGCGAGGACACCGCCATGTACTACTGCAAGAC

CAGCACCTTCTTCTTCGACTACTGGGGCCAGGGCACCATGGTGACCGTGAGCAGCAC

CACGACGCCAGCGCCGCGACCACCAACACCGGCGCCCACCATCGCGTCGCAGCCCC

TGTCCCTGCGCCCAGAGGCGTGCCGGCCAGCGGCGGGGGGCGCAGTGCACACGAGG

GGGCTGGACTTCGCCTGTGATATCTACATCTGGGCGCCCTTGGCCGGGACTTGTGGG

GTCCTTCTCCTGTCACTGGTTATCACCCTTTACTGCAAACGGGGCAGAAAGAAACTC

CTGTATATATTCAAACAACCATTTATGAGACCAGTACAAACTACTCAAGAGGAAGAT

GGCTGTAGCTGCCGATTTCCAGAAGAAGAAGAAGGAGGATGTGAACTGAGAGTGAA

GTTCAGCAGGAGCGCAGACGCCCCCGCGTACAAGCAGGGCCAGAACCAGCTCTATA

ACGAGCTCAATCTAGGACGAAGAGAGGAGTACGATGTTTTGGACAAGAGACGTGGC

CGGGACCCTGAGATGGGGGGAAAGCCGAGAAGGAAGAACCCTCAGGAAGGCCTGT

ACAATGAACTGCAGAAAGATAAGATGGCGGAGGCCTACAGTGAGATTGGGATGAA

AGGCGAGCGCCGGAGGGGCAAGGGGCACGATGGCCTTTACCAGGGTCTCAGTACAG

CCACCAAGGACACCTACGACGCCCTTCACATGCAGGCCCTGCCCCCTCGCTGAAGA

GACGTCATAATCAGCCAGCGGCCGCGTCGACAATCAACCTCTGGATTACAAAATTTG

TGAAAGATTGACTGGTATTCTTAACTATGTTGCTCCTTTTACGCTATGTGGATACGCT

GCTTTAATGCCTTTGTATCATGCTATTGCTTCCCGTATGGCTTTCATTTTCTCCTCCTT

GTATAAATCCTGGTTGCTGTCTCTTTATGAGGAGTTGTGGCCCGTTGTCAGGCAACG

TGGCGTGGTGTGCACTGTGTTTGCTGACGCAACCCCCACTGGTTGGGGCATTGCCAC

CACCTGTCAGCTCCTTTCCGGGACTTTCGCTTTCCCCCTCCCTATTGCCACGGCGGAA

CTCATCGCCGCCTGCCTTGCCCGCTGCTGGACAGGGGCTCGGCTGTTGGGCACTGAC

AATTCCGTGGTGTTGTCGGGGAAATCATCGTCCTTTCCTTGGCTGCTCGCCTGTGTTG

CCACCTGGATTCTGCGCGGGACGTCCTTCTGCTACGTCCCTTCGGCCCTCAATCCAG

CGGACCTTCCTTCCCGCGGCCTGCTGCCGGCTCTGCGGCCTCTTCCGCGTCTTCGCCT

-continued

TCGCCCTCAGACGAGTCGGATCTCCCTTTGGGCCGCCTCCCCGCCTGGTACCTTTAA

GACCAATGACTTACAAGGCAGCTGTAGATCTTAGCCACTTTTTAAAAGAAAAGGGG

GGACTGGAAGGGCTAATTCACTCCCAACGAAAATAAGATCTGCTTTTTGCTTGTACT

GGGTCTCTCTGGTTAGACCAGATCTGAGCCTGGGAGCTCTCTGGCTAACTAGGGAAC

CCACTGCTTAAGCCTCAATAAAGCTTGCCTTGAGTGCTTCAAGTAGTGTGTGCCCGT

CTGTTGTGTGACTCTGGTAACTAGAGATCCCTCAGACCCTTTTAGTCAGTGTGGAAA

ATCTCTAGCA

GC223

(SEQ ID NO: 8)

TCTGGTTAGACCAGATCTGAGCCTGGGAGCTCTCTGGCTAACTAGGGAACCCACTGC

TTAAGCCTCAATAAAGCTTGCCTTGAGTGCTTCAAGTAGTGTGTGCCCGTCTGTTGTG

TGACTCTGGTAACTAGAGATCCCTCAGACCCTTTTAGTCAGTGTGGAAAATCTCTAG

CAGTGGCGCCCGAACAGGGACCTGAAAGCGAAAGGGAAACCAGAGCTCTCTCGAC

GCAGGACTCGGCTTGCTGAAGCGCGCACGGCAAGAGGCGAGGGGCGGCGACTGGT

GAGTACGCCAAAAATTTTGACTAGCGGAGGCTAGAAGGAGAGAGATGGGTGCGAG

AGCGTCAGTATTAAGCGGGGGAGAATTAGATCGCGATGGGAAAAAATTCGGTTAAG

GCCAGGGGGAAAGAAAAAATATAAATTAAAACATATAGTATGGGCAAGCAGGGAG

CTAGAACGATTCGCAGTTAATCCTGGCCTGTTAGAAACATCAGAAGGCTGTAGACA

AATACTGGGACAGCTACAACCATCCCTTCAGACAGGATCAGAAGAACTTAGATCAT

TATATAATACAGTAGCAACCCTCTATTGTGTGCATCAAAGGATAGAGATAAAAGAC

ACCAAGGAAGCTTTAGACAAGATAGAGGAAGAGCAAAACAAAAGTAAGACCACCG

CACAGCAAGCGGCCACTGATCTTCAGACCTGGAGGAGGAGATATGAGGGACAATTG

GAGAAGTGAATTATATAAATATAAAGTAGTAAAAATTGAACCATTAGGAGTAGCAC

CCACCAAGGCAAAGAGAAGAGTGGTGCAGAGAGAAAAAAGAGCAGTGGGAATAGG

AGCTTTGTTCCTTGGGTTCTTGGGAGCAGCAGGAAGCACTATGGGCGCAGCCTCAAT

GACGCTGACGGTACAGGCCAGACAATTATTGTCTGGTATAGTGCAGCAGCAGAACA

ATTTGCTGAGGGCTATTGAGGCGCAACAGCATCTGTTGCAACTCACAGTCTGGGGCA

TCAAGCAGCTCCAGGCAAGAATCCTGGCTGTGGAAAGATACCTAAAGGATCAACAG

CTCCTGGGGATTTGGGGTTGCTCTGGAAAACTCATTTGCACCACTGCTGTGCCTTGG

AATGCTAGTTGGAGTAATAAATCTCTGGAACAGATTGGAATCACACGACCTGGATG

GAGTGGGACAGAGAAATTAACAATTACACAAGCTTAATACACTCCTTAATTGAAGA

ATCGCAAAACCAGCAAGAAAAGAATGAACAAGAATTATTGGAATTAGATAAATGGG

CAAGTTTGTGGAATTGGTTTAACATAACAAATTGGCTGTGGTATATAAAATTATTCA

TAATGATAGTAGGAGGCTTGGTAGGTTTAAGAATAGTTTTTGCTGTACTTTCTATAGT

GAATAGAGTTAGGCAGGGATATTCACCATTATCGTTTCAGACCCACCTCCCAACCCC

GAGGGGACCCGACAGGCCCGAAGGAATAGAAGAAGAAGGTGGAGAGAGAGACAG

AGACAGATCCATTCGATTAGTGAACGGATCTCGACGGTATCGGTTAACTTTTAAAAG

AAAAGGGGGGATTGGGGGGTACAGTGCAGGGGAAAGAATAGTAGACATAATAGCA

ACAGACATACAAACTAAAGAATTACAAAAACAAATTACAAAAATTCAAAATTTTAT

CTCGAGTAGTTGTGAACTTACACTTTATTCATATATATTAGATATTGATAATTTTAAC

AAATGAGTTACTTTCCATTTGGGTACAGTCACAGTTGTCAACAATATTTGGAAGCAC

CAGGCATGAAATCTCCTGAGATGCTATGTTTTCATCAGGGTCACCTGACACATTCAA

-continued

GTTCTGTCTGACATGCCATTAAAGCACTGGCTCAGATTGCAGGCATATTTTCAAACC

GGCAGTAACTGGATAGTATCACTTCACTTATAAGTGTTCATTGTATCATCAAGTGAA

ATAAACACACAACCCATGGGATCTTGCTTAGGTTGGCTGCCTAGTTGGCCCCTGAGA

TAAAGCCTTGTAATCACATAGCCTTGCCTAATTAGTCAGAAAACAAAGGATTAAGTG

AGACAGTCACAGGATATAGGAATTATAAATAATACATATATTAATAGATATTCATTT

TCATTACACAAAAGTTGCTATTATAAATACTTATTTGATTGATGAGTCTAAAAATAT

ATTCCCCATATAAATAATGTTAAATATTAATAAATAGATTTAGATTTAAAATTCAAA

TATTGCAGGCAGGACAACCACCCGGGTCAGGTCAGGGTGGAGATGATGCTCTGGCA

GAAGGTGATCCACCTGTTCAGGAACTCCACGATGGTGGCGGTCTCGTCGGCGTACTC

GCACATGAAGGTGGTCTCGGAGCCCTTCAGCTCCAGCACGATCACGTTGATGTTGCT

GATCAGGTCCCTGGGCCTCAGGTGGAAGTTCTTGCTCTGGGCCAGGTTCAGCACCTC

CTCCAGGGGCTTCAGCTCCTCCTCCAGGCACTGCAGGTGCTTCAGCTCGGTGGCCTT

CTTGGGCATGTAGAACTTGAAGGTCAGCATCCTGGTCAGCTTGGGGTTCTTGTAGTT

GTTGATGCCGTTCAGGATCATCTGCAGGTCCAGCAGCAGGTGCTCCAGCTGCAGCTG

GGTCTTCTTGGTGGAGCTGGAGGTGGGGGCGCTGTTGGTCACCAGGGCCAGGCTCA

GGGCGATGCAGGACAGCAGCTGCATCCGGTACATGGTGGGAATTCCTGGAATTCGA

GCTTCCATTATATACCCTCTAGAGTCTAGATCTACGCCTTCTGTATGAAACAGTTTTT

CCTCCACGCCTTCTGTATGAAACAGTTTTTCCTCCACGCCTTCTGTATGAAACAGTTT

TTCCTCCGTTTAAACGTAAGTCATTGGTCTTAAAGGTAGCTTTATTTAGTCTCCAGAA

AAAGGGGGGAATGAAAGACCCCACCTGTAGGTTTGGCAAGCTAGGATCAAGGTTAG

GAACAGAGAGACAGCAGAATATGGGCCAAACAGGATATCTGTGGTAAGCAGTTCCT

GCCCCGGCTCAGGGCCAAGAACAGTTGGAACAGCAGAATATGGGCCAAACAGGAT

ATCTGTGGTAAGCAGTTCCTGCCCCGGCTCAGGGCCAAGAACAGATGGTCCCCAGA

TGCGGTCCCGCCCTCAGCAGTTTCTAGAGAACCATCAGATGTTTCCAGGGTGCCCCA

AGGACCTGAAATGACCCTGTGCCTTATTTGAACTAACCAATCAGTTCGCTTCTCGCTT

CTGTTCGCGCGCTTCTGCTCCCCGAGCTCAATAAAAGAGCCCACGCTAGCGCTACCG

GTCGCCAAGATGGGGGCAGGTGCCACCGGCCGCGCAATGGATGGTCCGCGTCTACT

GCTGTTACTACTTCTGGGTGTGTCCCTTGGAGGTGCCAAAGAGGCATGCCCCACAGG

TCTATACACACATAGCGGTGAATGCTGCAAAGCATGCAACCTGGGCGAAGGTGTGG

CCCAACCTTGTGGAGCCAATCAAACCGTTTGTGAGCCATGTCTGGACAGCGTGACGT

TCTCCGATGTTGTTAGCGCGACCGAGCCATGCAAACCGTGTACCGAGTGTGTTGGTC

TCCAAAGTATGTCGGCGCCGTGCGTGGAGGCCGACGACGCCGTGTGTCGCTGTGCCT

ACGGTTATTACCAGGATGAAACTACTGGTCGCTGTGAAGCGTGCCGCGTGTGTGAGG

CGGGCTCAGGCCTCGTGTTCTCCTGTCAGGACAAACAGAACACTGTGTGTGAAGAAT

GCCCCGACGGTACTTATTCCGACGAGGCCAACCATGTGGACCCGTGTCTGCCCTGCA

CCGTTTGCGAGGATACCGAGCGCCAGCTACGTGAGTGCACACGTTGGGCCGACGCC

GAGTGCGAGGAAATCCCTGGCCGTTGGATTACACGGTCCACACCACCAGAAGGCTC

GGACAGCACAGCACCCAGCACTCAGGAACCTGAGGCACCTCCAGAACAAGACCTAA

TAGCCAGCACTGTGGCAGGTGTTGTGACTACAGTGATGGGTAGCTCACAACCCGTTG

TTACTCGAGGCACCACCGACAATCTAATTCCTGTCTATTGTTCCATCCTGGCTGCTGT

-continued

GGTTGTGGGTCTTGTTGCATATATAGCCTTCAAGAGGGGCAGCGGAGAGGGTAGGG

GTAGTCTTTTGACGTGTGGGGACGTCGAGGAAAATCCTGGGCCTGCCTTACCAGTGA

CCGCCTTGCTCCTGCCGCTGGCCTTGCTGCTCCACGCCGCCAGGCCGGACATCGTGA

TGACCCAGAGCCCCGACAGCCTGGCCGTGAGCCTGGGCGAGAGGGCCACCATCAAC

TGCAAGAGCAGCCAGAGCCTGCTGAACAGCGGCGACCAGAAGAACTACCTGACCTG

GTACCAGCAGAAGCCCGGCCAGCCCCCCAAGCTGCTGATCTACTGGGCCAGCACCA

GGGAGAGCGGCGTGCCCGACAGGTTCAGCGGCAGCGGCAGCGGCACCGACTTCACC

CTGACCATCAGCAGCCTGCAGGCCGAGGACGTGGCCGTGTACTACTGCCAGAACGA

CTACAGCTACCCCCTGACCTTCGGCCAGGGCACCAAGGTGGAGATCAAGGGCGGCG

GCGGCAGCGGCGGCGGCGGCAGCGGCGGCGGCGGCAGCCAGGTGCAGCTGGTGCA

GAGCGGCGCCGAGGTGAAGAAGACCGGCAGCAGCGTGAAGGTGAGCTGCAAGGCC

AGCGGCTACACCTTCACCGACCACGCCATCCACTGGGTGAGGCAGGCCCCCGGCCA

GGCCCTGGAGTGGATGGGCCACTTCAGCCCCGGCAACACCGACATCAAGTACAACG

ACAAGTTCAAGGGCAGGGTGACCCTGACCGTGGACAGGAGCATGAGCACCGCCTAC

ATGGAGCTGAGCAGCCTGAGGAGCGAGGACACCGCCATGTACTACTGCAAGACCAG

CACCTTCTTCTTCGACTACTGGGGCCAGGGCACCATGGTGACCGTGAGCAGCACCAC

GACGCCAGCGCCGCGACCACCAACACCGGCGCCCACCATCGCGTCGCAGCCCCTGT

CCCTGCGCCCAGAGGCGTGCCGGCCAGCGGCGGGGGGCGCAGTGCACACGAGGGG

GCTGGACTTCGCCTGTGATATCTACATCTGGGCGCCCTTGGCCGGGACTTGTGGGGT

CCTTCTCCTGTCACTGGTTATCACCCTTTACTGCAAACGGGGCAGAAAGAAACTCCT

GTATATATTCAAACAACCATTTATGAGACCAGTACAAACTACTCAAGAGGAAGATG

GCTGTAGCTGCCGATTTCCAGAAGAAGAAGAAGGAGGATGTGAACTGAGAGTGAAG

TTCAGCAGGAGCGCAGACGCCCCCGCGTACAAGCAGGGCCAGAACCAGCTCTATAA

CGAGCTCAATCTAGGACGAAGAGAGGAGTACGATGTTTTGGACAAGAGACGTGGCC

GGGACCCTGAGATGGGGGGAAAGCCGAGAAGGAAGAACCCTCAGGAAGGCCTGTA

CAATGAACTGCAGAAAGATAAGATGGCGGAGGCCTACAGTGAGATTGGGATGAAA

GGCGAGCGCCGGAGGGGCAAGGGGCACGATGGCCTTTACCAGGGTCTCAGTACAGC

CACCAAGGACACCTACGACGCCCTTCACATGCAGGCCCTGCCCCCTCGCTGAAGAG

ACGTCATAATCAGCCAGCGGCCGCGTCGACAATCAACCTCTGGATTACAAAATTTGT

GAAAGATTGACTGGTATTCTTAACTATGTTGCTCCTTTTACGCTATGTGGATACGCTG

CTTTAATGCCTTTGTATCATGCTATTGCTTCCCGTATGGCTTTCATTTTCTCCTCCTTG

TATAAATCCTGGTTGCTGTCTCTTTATGAGGAGTTGTGGCCCGTTGTCAGGCAACGT

GGCGTGGTGTGCACTGTGTTTGCTGACGCAACCCCCACTGGTTGGGGCATTGCCACC

ACCTGTCAGCTCCTTTCCGGGACTTTCGCTTTCCCCCTCCCTATTGCCACGGCGGAAC

TCATCGCCGCCTGCCTTGCCCGCTGCTGGACAGGGGCTCGGCTGTTGGGCACTGACA

ATTCCGTGGTGTTGTCGGGGAAATCATCGTCCTTTCCTTGGCTGCTCGCCTGTGTTGC

CACCTGGATTCTGCGCGGGACGTCCTTCTGCTACGTCCCTTCGGCCCTCAATCCAGC

GGACCTTCCTTCCCGCGGCCTGCTGCCGGCTCTGCGGCCTCTTCCGCGTCTTCGCCTT

CGCCCTCAGACGAGTCGGATCTCCCTTTGGGCCGCCTCCCCGCCTGGTACCTTTAAG

ACCAATGACTTACAAGGCAGCTGTAGATCTTAGCCACTTTTTAAAAGAAAAGGGGG

GACTGGAAGGGCTAATTCACTCCCAACGAAAATAAGATCTGCTTTTTGCTTGTACTG

-continued

GGTCTCTCTGGTTAGACCAGATCTGAGCCTGGGAGCTCTCTGGCTAACTAGGGAACC

CACTGCTTAAGCCTCAATAAAGCTTGCCTTGAGTGCTTCAAGTAGTGTGTGCCCGTC

TGTTGTGTGACTCTGGTAACTAGAGATCCCTCAGACCCTTTTAGTCAGTGTGGAAAA

TCTCTAGCA

SK062

(SEQ ID NO: 9)

TCTGGTTAGACCAGATCTGAGCCTGGGAGCTCTCTGGCTAACTAGGGAACCCACTGC

TTAAGCCTCAATAAAGCTTGCCTTGAGTGCTTCAAGTAGTGTGTGCCCGTCTGTTGTG

TGACTCTGGTAACTAGAGATCCCTCAGACCCTTTTAGTCAGTGTGGAAAATCTCTAG

CAGTGGCGCCCGAACAGGGACCTGAAAGCGAAAGGGAAACCAGAGCTCTCTCGAC

GCAGGACTCGGCTTGCTGAAGCGCGCACGGCAAGAGGCGAGGGGCGGCGACTGGT

GAGTACGCCAAAAATTTTGACTAGCGGAGGCTAGAAGGAGAGAGATGGGTGCGAG

AGCGTCAGTATTAAGCGGGGGAGAATTAGATCGCGATGGGAAAAAATTCGGTTAAG

GCCAGGGGGAAAGAAAAAATATAAATTAAAACATATAGTATGGGCAAGCAGGGAG

CTAGAACGATTCGCAGTTAATCCTGGCCTGTTAGAAACATCAGAAGGCTGTAGACA

AATACTGGGACAGCTACAACCATCCCTTCAGACAGGATCAGAAGAACTTAGATCAT

TATATAATACAGTAGCAACCCTCTATTGTGTGCATCAAAGGATAGAGATAAAAGAC

ACCAAGGAAGCTTTAGACAAGATAGAGGAAGAGCAAAACAAAAGTAAGACCACCG

CACAGCAAGCGGCCACTGATCTTCAGACCTGGAGGAGGAGATATGAGGGACAATTG

GAGAAGTGAATTATATAAATATAAAGTAGTAAAAATTGAACCATTAGGAGTAGCAC

CCACCAAGGCAAAGAGAAGAGTGGTGCAGAGAGAAAAAAGAGCAGTGGGAATAGG

AGCTTTGTTCCTTGGGTTCTTGGGAGCAGCAGGAAGCACTATGGGCGCAGCCTCAAT

GACGCTGACGGTACAGGCCAGACAATTATTGTCTGGTATAGTGCAGCAGCAGAACA

ATTTGCTGAGGGCTATTGAGGCGCAACAGCATCTGTTGCAACTCACAGTCTGGGGCA

TCAAGCAGCTCCAGGCAAGAATCCTGGCTGTGGAAAGATACCTAAAGGATCAACAG

CTCCTGGGGATTTGGGGTTGCTCTGGAAAACTCATTTGCACCACTGCTGTGCCTTGG

AATGCTAGTTGGAGTAATAAATCTCTGGAACAGATTGGAATCACACGACCTGGATG

GAGTGGGACAGAGAAATTAACAATTACACAAGCTTAATACACTCCTTAATTGAAGA

ATCGCAAAACCAGCAAGAAAAGAATGAACAAGAATTATTGGAATTAGATAAATGGG

CAAGTTTGTGGAATTGGTTTAACATAACAAATTGGCTGTGGTATATAAAATTATTCA

TAATGATAGTAGGAGGCTTGGTAGGTTTAAGAATAGTTTTTGCTGTACTTTCTATAGT

GAATAGAGTTAGGCAGGGATATTCACCATTATCGTTTCAGACCCACCTCCCAACCCC

GAGGGGACCCGACAGGCCCGAAGGAATAGAAGAAGAAGGTGGAGAGAGAGACAG

AGACAGATCCATTCGATTAGTGAACGGATCTCGACGGTATCGGTTAACTTTTAAAAG

AAAAGGGGGGATTGGGGGGTACAGTGCAGGGGAAAGAATAGTAGACATAATAGCA

ACAGACATACAAACTAAAGAATTACAAAAACAAATTACAAAAATTCAAAATTTTAT

CTCGAGTAGTTGTGAACTTACACTTTATTCATATATATTAGATATTGATAATTTTAAC

AAATGAGTTACTTTCCATTTGGGTACAGTCACAGTTGTCAACAATATTTGGAAGCAC

CAGGCATGAAATCTCCTGAGATGCTATGTTTTCATCAGGGTCACCTGACACATTCAA

GTTCTGTCTGACATGCCATTAAAGCACTGGCTCAGATTGCAGGCATATTTTCAAACC

GGCAGTAACTGGATAGTATCACTTCACTTATAAGTGTTCATTGTATCATCAAGTGAA

-continued

ATAAACACACAACCCATGGGATCTTGCTTAGGTTGGCTGCCTAGTTGGCCCCTGAGA

TAAAGCCTTGTAATCACATAGCCTTGCCTAATTAGTCAGAAAACAAAGGATTAAGTG

AGACAGTCACAGGATATAGGAATTATAAATAATACATATATTAATAGATATTCATTT

TCATTACACAAAAGTTGCTATTATAAATACTTATTTGATTGATGAGTCTAAAAATAT

ATTCCCCATATAAATAATGTTAAATATTAATAAATAGATTTAGATTTAAAATTCAAA

TATTGCAGGCAGGACAACCACCCGGGTCACGCCAGAATGCGTTCGCACAGCCGCCA

GCCGGTCACTCCGTTGATGGTTACTCGGAACAGCAGGGAGCCGTCGGGGTTGATCA

GGCGCTCGTCGATAATTTTGTTGCCGTTCCACAGGGTCCCTGTTACAGTGATCTTTTT

GCCGTCGAACACGGCGATGCCTTCATACGGCCGTCCGAAATAGTCGATCATGTTCGG

CGTAACCCCGTCGATTACCAGTGTGCCATAGTGCAGGATCACCTTAAAGTGATGATC

ATCCACAGGGTACACCACCTTAAAAATTTTTTCGATCTGGCCCATTTGGTCGCCGCTC

AGACCTTCATACGGGATGATGACATGGATGTCGATCTTCAGCCCATTTTCACCGCTC

AGGACAATCCTTTGGATCGGAGTTACGGACACCCCGAGATTCTGAAACAAACTGGA

CACACCTCCCTGTTCAAGGACTTGGTCCAGGTTGTAGCCGGCTGTCTGTCGCCAGTC

CCCAACGAAATCTTCGAGTGTGAAGACTGGGGCAGGGAAGGCAGCAGGCAACACC

AGGAGCAGGCCCAGGGAGAAGGCAACTGGACCGAAGGCGCTTGTGGAGAAGGAGT

TCATGGTGGGAATTCCTGGAATTCGAGCTTCCATTATATACCCTCTAGAGTCTAGAT

CTACGCCTTCTGTATGAAACAGTTTTTCCTCCACGCCTTCTGTATGAAACAGTTTTTC

CTCCACGCCTTCTGTATGAAACAGTTTTTCCTCCGTTTAAACGTAAGTCATTGGTCTT

AAAGGTAGCTTTATTTAGTCTCCAGAAAAAGGGGGGAATGAAAGACCCCACCTGTA

GGTTTGGCAAGCTAGGATCAAGGTTAGGAACAGAGAGACAGCAGAATATGGGCCAA

ACAGGATATCTGTGGTAAGCAGTTCCTGCCCCGGCTCAGGGCCAAGAACAGTTGGA

ACAGCAGAATATGGGCCAAACAGGATATCTGTGGTAAGCAGTTCCTGCCCCGGCTC

AGGGCCAAGAACAGATGGTCCCCAGATGCGGTCCCGCCCTCAGCAGTTTCTAGAGA

ACCATCAGATGTTTCCAGGGTGCCCCAAGGACCTGAAATGACCCTGTGCCTTATTTG

AACTAACCAATCAGTTCGCTTCTCGCTTCTGTTCGCGCGCTTCTGCTCCCCGAGCTCA

ATAAAAGAGCCCACGCTAGCGCTACCGGTCGCCAAGATGGGGGCAGGTGCCACCGG

CCGCGCCATGGACGGGCCGCGCCTGCTGCTGTTGCTGCTTCTGGGGGTGTCCCTTGG

AGGTGCCAAGGAGGCATGCCCCACAGGCCTGTACACACACAGCGGTGAGTGCTGCA

AAGCCTGCAACCTGGGCGAGGGTGTGGCCCAGCCTTGTGGAGCCAACCAGACCGTG

TGTGAGCCCTGCCTGGACAGCGTGACGTTCTCCGACGTGGTGAGCGCGACCGAGCC

GTGCAAGCCGTGCACCGAGTGCGTGGGGCTCCAGAGCATGTCGGCGCCGTGCGTGG

AGGCCGACGACGCCGTGTGCCGCTGCGCCTACGGCTACTACCAGGATGAGACGACT

GGGCGCTGCGAGGCGTGCCGCGTGTGCGAGGCGGGCTCGGGCCTCGTGTTCTCCTGC

CAGGACAAGCAGAACACCGTGTGCGAGGAGTGCCCCGACGGCACGTATTCCGACGA

GGCCAACCACGTGGACCCGTGCCTGCCCTGCACCGTGTGCGAGGACACCGAGCGCC

AGCTCCGCGAGTGCACACGCTGGGCCGACGCCGAGTGCGAGGAGATCCCTGGCCGT

TGGATTACACGGTCCACACCCCCAGAGGGCTCGGACAGCACAGCCCCCAGCACCCA

GGAGCCTGAGGCACCTCCAGAACAAGACCTCATAGCCAGCACGGTGGCAGGTGTGG

TGACCACAGTGATGGGCAGCTCCCAGCCCGTGGTGACCCGAGGCACCACCGACAAC

CTCATCCCTGTCTATTGCTCCATCCTGGCTGCTGTGGTTGTGGGTCTTGTGGCCTACA

-continued

TAGCCTTCAAGAGGGGCAGCGGAGAGGGTAGGGGTAGTCTTTTGACGTGTGGGGAC

GTCGAGGAAAATCCTGGGCCTGCCTTACCAGTGACCGCCTTGCTCCTGCCGCTGGCC

TTGCTGCTCCACGCCGCCAGGCCGGACATCGTGATGACCCAGAGCCCCGACAGCCT

GGCCGTGAGCCTGGGCGAGAGGGCCACCATCAACTGCAAGAGCAGCCAGAGCCTGC

TGAACAGCGGCGACCAGAAGAACTACCTGACCTGGTACCAGCAGAAGCCCGGCCAG

CCCCCCAAGCTGCTGATCTACTGGGCCAGCACCAGGGAGAGCGGCGTGCCCGACAG

GTTCAGCGGCAGCGGCAGCGGCACCGACTTCACCCTGACCATCAGCAGCCTGCAGG

CCGAGGACGTGGCCGTGTACTACTGCCAGAACGACTACAGCTACCCCCTGACCTTCG

GCCAGGGCACCAAGGTGGAGATCAAGGGCGGCGGCGGCAGCGGCGGCGGCGGCAG

CGGCGGCGGCGGCAGCCAGGTGCAGCTGGTGCAGAGCGGCGCCGAGGTGAAGAAG

ACCGGCAGCAGCGTGAAGGTGAGCTGCAAGGCCAGCGGCTACACCTTCACCGACCA

CGCCATCCACTGGGTGAGGCAGGCCCCCGGCCAGGCCCTGGAGTGGATGGGCCACT

TCAGCCCCGGCAACACCGACATCAAGTACAACGACAAGTTCAAGGGCAGGGTGACC

CTGACCGTGGACAGGAGCATGAGCACCGCCTACATGGAGCTGAGCAGCCTGAGGAG

CGAGGACACCGCCATGTACTACTGCAAGACCAGCACCTTCTTCTTCGACTACTGGGG

CCAGGGCACCATGGTGACCGTGAGCAGCACCACGACGCCAGCGCCGCGACCACCAA

CACCGGCGCCCACCATCGCGTCGCAGCCCCTGTCCCTGCGCCCAGAGGCGTGCCGGC

CAGCGGCGGGGGGCGCAGTGCACACGAGGGGGCTGGACTTCGCCTGTGATATCTAC

ATCTGGGCGCCCTTGGCCGGGACTTGTGGGGTCCTTCTCCTGTCACTGGTTATCACCC

TTTACTGCAAACGGGGCAGAAAGAAACTCCTGTATATATTCAAACAACCATTTATGA

GACCAGTACAAACTACTCAAGAGGAAGATGGCTGTAGCTGCCGATTTCCAGAAGAA

GAAGAAGGAGGATGTGAACTGAGAGTGAAGTTCAGCAGGAGCGCAGACGCCCCCG

CGTACAAGCAGGGCCAGAACCAGCTCTATAACGAGCTCAATCTAGGACGAAGAGAG

GAGTACGATGTTTTGGACAAGAGACGTGGCCGGGACCCTGAGATGGGGGGAAAGCC

GAGAAGGAAGAACCCTCAGGAAGGCCTGTACAATGAACTGCAGAAAGATAAGATG

GCGGAGGCCTACAGTGAGATTGGGATGAAAGGCGAGCGCCGGAGGGGCAAGGGGC

ACGATGGCCTTTACCAGGGTCTCAGTACAGCCACCAAGGACACCTACGACGCCCTTC

ACATGCAGGCCCTGCCCCCTCGCTGAAGAGACGTCATAATCAGCCAGCGGCCGCGT

CGACAATCAACCTCTGGATTACAAAATTTGTGAAAGATTGACTGGTATTCTTAACTA

TGTTGCTCCTTTTACGCTATGTGGATACGCTGCTTTAATGCCTTTGTATCATGCTATT

GCTTCCCGTATGGCTTTCATTTTCTCCTCCTTGTATAAATCCTGGTTGCTGTCTCTTTA

TGAGGAGTTGTGGCCCGTTGTCAGGCAACGTGGCGTGGTGTGCACTGTGTTTGCTGA

CGCAACCCCCACTGGTTGGGGCATTGCCACCACCTGTCAGCTCCTTTCCGGGACTTT

CGCTTTCCCCCTCCCTATTGCCACGGCGGAACTCATCGCCGCCTGCCTTGCCCGCTGC

TGGACAGGGGCTCGGCTGTTGGGCACTGACAATTCCGTGGTGTTGTCGGGGAAATCA

TCGTCCTTTCCTTGGCTGCTCGCCTGTGTTGCCACCTGGATTCTGCGCGGGACGTCCT

TCTGCTACGTCCCTTCGGCCCTCAATCCAGCGGACCTTCCTTCCCGCGGCCTGCTGCC

GGCTCTGCGGCCTCTTCCGCGTCTTCGCCTTCGCCCTCAGACGAGTCGGATCTCCCTT

TGGGCCGCCTCCCCGCCTGGTACCTTTAAGACCAATGACTTACAAGGCAGCTGTAGA

TCTTAGCCACTTTTTAAAAGAAAAGGGGGGACTGGAAGGGCTAATTCACTCCCAAC

-continued

GAAAATAAGATCTGCTTTTTGCTTGTACTGGGTCTCTCTGGTTAGACCAGATCTGAG

CCTGGGAGCTCTCTGGCTAACTAGGGAACCCACTGCTTAAGCCTCAATAAAGCTTGC

CTTGAGTGCTTCAAGTAGTGTGTGCCCGTCTGTTGTGTGACTCTGGTAACTAGAGAT

CCCTCAGACCCTTTTAGTCAGTGTGGAAAATCTCTAGCA

SK0148

(SEQ ID NO: 10)

TCTGGTTAGACCAGATCTGAGCCTGGGAGCTCTCTGGCTAACTAGGGAACCCACTGC

TTAAGCCTCAATAAAGCTTGCCTTGAGTGCTTCAAGTAGTGTGTGCCCGTCTGTTGTG

TGACTCTGGTAACTAGAGATCCCTCAGACCCTTTTAGTCAGTGTGGAAAATCTCTAG

CAGTGGCGCCCGAACAGGGACCTGAAAGCGAAAGGGAAACCAGAGCTCTCTCGAC

GCAGGACTCGGCTTGCTGAAGCGCGCACGGCAAGAGGCGAGGGGCGGCGACTGGT

GAGTACGCCAAAAATTTTGACTAGCGGAGGCTAGAAGGAGAGAGATGGGTGCGAG

AGCGTCAGTATTAAGCGGGGGAGAATTAGATCGCGATGGGAAAAAATTCGGTTAAG

GCCAGGGGGAAAGAAAAAATATAAATTAAAACATATAGTATGGGCAAGCAGGGAG

CTAGAACGATTCGCAGTTAATCCTGGCCTGTTAGAAACATCAGAAGGCTGTAGACA

AATACTGGGACAGCTACAACCATCCCTTCAGACAGGATCAGAAGAACTTAGATCAT

TATATAATACAGTAGCAACCCTCTATTGTGTGCATCAAAGGATAGAGATAAAAGAC

ACCAAGGAAGCTTTAGACAAGATAGAGGAAGAGCAAAACAAAAGTAAGACCACCG

CACAGCAAGCGGCCACTGATCTTCAGACCTGGAGGAGGAGATATGAGGGACAATTG

GAGAAGTGAATTATATAAATATAAAGTAGTAAAAATTGAACCATTAGGAGTAGCAC

CCACCAAGGCAAAGAGAAGAGTGGTGCAGAGAGAAAAAAGAGCAGTGGGAATAGG

AGCTTTGTTCCTTGGGTTCTTGGGAGCAGCAGGAAGCACTATGGGCGCAGCCTCAAT

GACGCTGACGGTACAGGCCAGACAATTATTGTCTGGTATAGTGCAGCAGCAGAACA

ATTTGCTGAGGGCTATTGAGGCGCAACAGCATCTGTTGCAACTCACAGTCTGGGGCA

TCAAGCAGCTCCAGGCAAGAATCCTGGCTGTGGAAAGATACCTAAAGGATCAACAG

CTCCTGGGGATTTGGGGTTGCTCTGGAAAACTCATTTGCACCACTGCTGTGCCTTGG

AATGCTAGTTGGAGTAATAAATCTCTGGAACAGATTGGAATCACACGACCTGGATG

GAGTGGGACAGAGAAATTAACAATTACACAAGCTTAATACACTCCTTAATTGAAGA

ATCGCAAAACCAGCAAGAAAAGAATGAACAAGAATTATTGGAATTAGATAAATGGG

CAAGTTTGTGGAATTGGTTTAACATAACAAATTGGCTGTGGTATATAAAATTATTCA

TAATGATAGTAGGAGGCTTGGTAGGTTTAAGAATAGTTTTTGCTGTACTTTCTATAGT

GAATAGAGTTAGGCAGGGATATTCACCATTATCGTTTCAGACCCACCTCCCAACCCC

GAGGGGACCCGACAGGCCCGAAGGAATAGAAGAAGAAGGTGGAGAGAGAGACAG

AGACAGATCCATTCGATTAGTGAACGGATCTCGACGGTATCGGTTAACTTTTAAAAG

AAAAGGGGGGATTGGGGGGTACAGTGCAGGGGAAAGAATAGTAGACATAATAGCA

ACAGACATACAAACTAAAGAATTACAAAAACAAATTACAAAAATTCAAAATTTTAT

CTCGAGTAGTTGTGAACTTACACTTTATTCATATATATTAGATATTGATAATTTTAAC

AAATGAGTTACTTTCCATTTGGGTACAGTCACAGTTGTCAACAATATTTGGAAGCAC

CAGGCATGAAATCTCCTGAGATGCTATGTTTTCATCAGGGTCACCTGACACATTCAA

GTTCTGTCTGACATGCCATTAAAGCACTGGCTCAGATTGCAGGCATATTTTCAAACC

GGCAGTAACTGGATAGTATCACTTCACTTATAAGTGTTCATTGTATCATCAAGTGAA

ATAAACACACAACCCATGGGATCTTGCTTAGGTTGGCTGCCTAGTTGGCCCCTGAGA

-continued

TAAAGCCTTGTAATCACATAGCCTTGCCTAATTAGTCAGAAAACAAAGGATTAAGTG

AGACAGTCACAGGATATAGGAATTATAAATAATACATATATTAATAGATATTCATTT

TCATTACACAAAAGTTGCTATTATAAATACTTATTTGATTGATGAGTCTAAAAATAT

ATTCCCCATATAAATAATGTTAAATATTAATAAATAGATTTAGATTTAAAATTCAAA

TATTGCAGGCAGGACAACCACCCGGGTTAACTTGCATTCAAATATGACATTACCCTA

TCAATTGTAACGGCCCTGATTCTAAAAGCATGCAAAAGTATACACAGCTTTATTTTT

GTCTTGTAAAAATCAGGTTCTTCAAGAGAGCTTTTTTGAGGAACCGTTTCAGAATTA

AAATTAAGAGCTTGCATCAGCTCATCAATAACGGCAAGCATATTCTGATCAAGGAAT

ATCTGTCGCTTGGGGTCCATCAAAAGTTTTGCGTTCATTGTCTTGAACTCAACCTGGT

ACATCTTAAGATCTTCATATATAGAAGACAAGCACAGGGCCATCATAAAGCTTGTTT

TGCGGCTGGCCAAACAAGATCCATTGGTAATGAAAGAAGTCTCTCTGGAATTGAGA

CAAGATTCGTTTTTAGTGAGTTCCAGTGGCAGGCATGCCTCCACGGTGGATGTTTTG

TCCTTAGTAATATCTTCGTGGTCTATTTCCTCACTTGTGCAAGGGTAAAATTCAAGTG

TTTGTCGGGCCTTCTGGAGCATGTTGGAGACAGCCCTAAGCAAGTTTTGAGAGTGGT

GAAGACATGGGAACATGCCTGGGTCTGGGGTTGCAACAGGCAAGTTCCGAGAACCG

CCCCCACCACCACCTGAGCATGGGACAGATGCCCATTCGCTCCAGCTAGATGAGTA

GTATCTGTCTTGGGCTCTGACACTTATGCTTGCGTTCTTTCTGCAAATGACTGTTGCA

GACGTTTTATCAGTGAAAACCCGATCTTTCTTTTCCCTTTTTGATTTTCCTTGCACCTG

GACACAAAATGTCAAACTAAAGTAAGAGTGCGGAGTTGACCAGGTGTCGGGGTACT

CCCAAGAAACTTCAACCTGGCGTGAGTTCTTCAAAGGCTTAAGCTGCAGATTCTTCG

GAGGATCGGGCTTGATAATGTCCCGGATAAAAAAGCTGCTCGTGTAATTTTCATACT

TCAACTTGTGTACGGCGTCAACCATCACCTCTATTGGCAGGCTCTCCTCTGCTGCGG

GGCAAGCGGAGTCTTCCTGGCATTCCACGCTATATTCGTATTCTTTGTTGTCCCCCCG

TACCCTCTCCGCAGAAAGCGTAGCAGCACCGCACGTTACACCTTGTGGGTCACTGGA

ACCCCTACTAGACTTAACAGAAAACGTAAGATCCGTAGAGATTGTTGTCAACCACCA

GCAAGTAAAGCGTCCGGAGTAATTTTTTGCTTCACAGCGCAGAAACGTTTTGTTTTT

GGGTTCTTTCTGATCCTTAAGGATATCTGTACTCCAAATGCCATCCTCTTTTTTGTGC

AGGAGCAGCAGGCTGTGAGAAAGGACCTCGCCTCCCTTATGGCACGTATACTGCCC

GGCATCTCCAAACTCTTTTACCTGGATAGTAAGTGTTTTGCCGCTGCCAAGCACCTCT

GAGCTTTGGTCCAGGGTCCAGGTTATCCCATCTTCTTCAGGTGTATCGCAGGTGAGG

ACCACCATCTCGCCCGGTGCGTCGGGATACCAATCCAATTCAACAACATATACGTCT

TTCTTAAGTTCCCAAATAGCGACCAATGGTGACGCCAGAAAAACAAGTGAGAACCA

AGAGATTACCAGTTGTTGATGGCACATGGTGGGAATTCCTGGAATTCGAGCTTCCAT

TATATACCCTCTAGAGTCTAGATCTACGCCTTCTGTATGAAACAGTTTTTCCTCCACG

CCTTCTGTATGAAACAGTTTTTCCTCCACGCCTTCTGTATGAAACAGTTTTTCCTCCG

TTTAAACGTAAGTCATTGGTCTTAAAGGTAGCTTTATTTAGTCTCCAGAAAAAGGGG

GGAATGAAAGACCCCACCTGTAGGTTTGGCAAGCTAGGATCAAGGTTAGGAACAGA

GAGACAGCAGAATATGGGCCAAACAGGATATCTGTGGTAAGCAGTTCCTGCCCCGG

CTCAGGGCCAAGAACAGTTGGAACAGCAGAATATGGGCCAAACAGGATATCTGTGG

TAAGCAGTTCCTGCCCCGGCTCAGGGCCAAGAACAGATGGTCCCCAGATGCGGTCC

-continued

CGCCCTCAGCAGTTTCTAGAGAACCATCAGATGTTTCCAGGGTGCCCCAAGGACCTG

AAATGACCCTGTGCCTTATTTGAACTAACCAATCAGTTCGCTTCTCGCTTCTGTTCGC

GCGCTTCTGCTCCCCGAGCTCAATAAAAGAGCCCACGCTAGCGCTACCGGTCGCCAA

GATGGGGGCAGGTGCCACCGGCCGCGCCATGGACGGGCCGCGCCTGCTGCTGTTGC

TGCTTCTGGGGGTGTCCCTTGGAGGTGCCAAGGAGGCATGCCCCACAGGCCTGTACA

CACACAGCGGTGAGTGCTGCAAAGCCTGCAACCTGGGCGAGGGTGTGGCCCAGCCT

TGTGGAGCCAACCAGACCGTGTGTGAGCCCTGCCTGGACAGCGTGACGTTCTCCGAC

GTGGTGAGCGCGACCGAGCCGTGCAAGCCGTGCACCGAGTGCGTGGGGCTCCAGAG

CATGTCGGCGCCGTGCGTGGAGGCCGACGACGCCGTGTGCCGCTGCGCCTACGGCT

ACTACCAGGATGAGACGACTGGGCGCTGCGAGGCGTGCCGCGTGTGCGAGGCGGGC

TCGGGCCTCGTGTTCTCCTGCCAGGACAAGCAGAACACCGTGTGCGAGGAGTGCCC

CGACGGCACGTATTCCGACGAGGCCAACCACGTGGACCCGTGCCTGCCCTGCACCG

TGTGCGAGGACACCGAGCGCCAGCTCCGCGAGTGCACACGCTGGGCCGACGCCGAG

TGCGAGGAGATCCCTGGCCGTTGGATTACACGGTCCACACCCCCAGAGGGCTCGGA

CAGCACAGCCCCCAGCACCCAGGAGCCTGAGGCACCTCCAGAACAAGACCTCATAG

CCAGCACGGTGGCAGGTGTGGTGACCACAGTGATGGGCAGCTCCCAGCCCGTGGTG

ACCCGAGGCACCACCGACAACCTCATCCCTGTCTATTGCTCCATCCTGGCTGCTGTG

GTTGTGGGTCTTGTGGCCTACATAGCCTTCAAGAGGGGGCAGCGGAGAGGGTAGGGG

TAGTCTTTTGACGTGTGGGGACGTCGAGGAAAATCCTGGGCCTGCCTTACCAGTGAC

CGCCTTGCTCCTGCCGCTGGCCTTGCTGCTCCACGCCGCCAGGCCGGACATCGTGAT

GACCCAGAGCCCCGACAGCCTGGCCGTGAGCCTGGGCGAGAGGGCCACCATCAACT

GCAAGAGCAGCCAGAGCCTGCTGAACAGCGGCGACCAGAAGAACTACCTGACCTGG

TACCAGCAGAAGCCCGGCCAGCCCCCCAAGCTGCTGATCTACTGGGCCAGCACCAG

GGAGAGCGGCGTGCCCGACAGGTTCAGCGGCAGCGGCAGCGGCACCGACTTCACCC

TGACCATCAGCAGCCTGCAGGCCGAGGACGTGGCCGTGTACTACTGCCAGAACGAC

TACAGCTACCCCCTGACCTTCGGCCAGGGCACCAAGGTGGAGATCAAGGGCGGCGG

CGGCAGCGGCGGCGGCGGCAGCGGCGGCGGCGGCAGCCAGGTGCAGCTGGTGCAG

AGCGGCGCCGAGGTGAAGAAGACCGGCAGCAGCGTGAAGGTGAGCTGCAAGGCCA

GCGGCTACACCTTCACCGACCACGCCATCCACTGGGTGAGGCAGGCCCCCGGCCAG

GCCCTGGAGTGGATGGGCCACTTCAGCCCCGGCAACACCGACATCAAGTACAACGA

CAAGTTCAAGGGCAGGGTGACCCTGACCGTGGACAGGAGCATGAGCACCGCCTACA

TGGAGCTGAGCAGCCTGAGGAGCGAGGACACCGCCATGTACTACTGCAAGACCAGC

ACCTTCTTCTTCGACTACTGGGGCCAGGGCACCATGGTGACCGTGAGCAGCACCACG

ACGCCAGCGCCGCGACCACCAACACCGGCGCCCACCATCGCGTCGCAGCCCCTGTC

CCTGCGCCCAGAGGCGTGCCGGCCAGCGGCGGGGGGCGCAGTGCACACGAGGGGG

CTGGACTTCGCCTGTGATATCTACATCTGGGCGCCCTTGGCCGGGACTTGTGGGGTC

CTTCTCCTGTCACTGGTTATCACCCTTTACTGCAAACGGGGCAGAAAGAAACTCCTG

TATATATTCAAACAACCATTTATGAGACCAGTACAAACTACTCAAGAGGAAGATGG

CTGTAGCTGCCGATTTCCAGAAGAAGAAGAAGGAGGATGTGAACTGAGAGTGAAGT

TCAGCAGGAGCGCAGACGCCCCCGCGTACAAGCAGGGCCAGAACCAGCTCTATAAC

GAGCTCAATCTAGGACGAAGAGAGGAGTACGATGTTTTGGACAAGAGACGTGGCCG

-continued

GGACCCTGAGATGGGGGGAAAGCCGAGAAGGAAGAACCCTCAGGAAGGCCTGTAC
AATGAACTGCAGAAAGATAAGATGGCGGAGGCCTACAGTGAGATTGGGATGAAAG
GCGAGCGCCGGAGGGGCAAGGGGCACGATGGCCTTTACCAGGGTCTCAGTACAGCC
ACCAAGGACACCTACGACGCCCTTCACATGCAGGCCCTGCCCCCTCGCTGAAGAGA
CGTCATAATCAGCCAGCGGCCGCGTCGACAATCAACCTCTGGATTACAAAATTTGTG
AAAGATTGACTGGTATTCTTAACTATGTTGCTCCTTTTACGCTATGTGGATACGCTGC
TTTAATGCCTTTGTATCATGCTATTGCTTCCCGTATGGCTTTCATTTTCTCCTCCTTGT
ATAAATCCTGGTTGCTGTCTCTTTATGAGGAGTTGTGGCCCGTTGTCAGGCAACGTG
GCGTGGTGTGCACTGTGTTTGCTGACGCAACCCCCACTGGTTGGGGCATTGCCACCA
CCTGTCAGCTCCTTTCCGGGACTTTCGCTTTCCCCCTCCCTATTGCCACGGCGGAACT
CATCGCCGCCTGCCTTGCCCGCTGCTGGACAGGGGCTCGGCTGTTGGGCACTGACAA
TTCCGTGGTGTTGTCGGGGAAATCATCGTCCTTTCCTTGGCTGCTCGCCTGTGTTGCC
ACCTGGATTCTGCGCGGGACGTCCTTCTGCTACGTCCCTTCGGCCCTCAATCCAGCG
GACCTTCCTTCCCGCGGCCTGCTGCCGGCTCTGCGGCCTCTTCCGCGTCTTCGCCTTC
GCCCTCAGACGAGTCGGATCTCCCTTTGGGCCGCCTCCCCGCCTGGTACCTTTAAGA
CCAATGACTTACAAGGCAGCTGTAGATCTTAGCCACTTTTTAAAAGAAAAGGGGGG
ACTGGAAGGGCTAATTCACTCCCAACGAAAATAAGATCTGCTTTTTGCTTGTACTGG
GTCTCTCTGGTTAGACCAGATCTGAGCCTGGGAGCTCTCTGGCTAACTAGGGAACCC
ACTGCTTAAGCCTCAATAAAGCTTGCCTTGAGTGCTTCAAGTAGTGTGTGCCCGTCT
GTTGTGTGACTCTGGTAACTAGAGATCCCTCAGACCCTTTTAGTCAGTGTGGAAAAT
CTCTAGCA

SK072

(SEQ ID NO: 11)

ACGCGTGTAGTCTTATGCAATACTCTTGTAGTCTTGCAACATGGTAACGATGAGTTA
GCAACATGCCTTACAAGGAGAGAAAAAGCACCGTGCATGCCGATTGGTGGAAGTAA
GGTGGTACGATCGTGCCTTATTAGGAAGGCAACAGACGGGTCTGACATGGATTGGA
CGAACCACTGAATTGCCGCATTGCAGAGATATTGTATTTAAGTGCCTAGCTCGATAC
AATAAACGGGTCTCTCTGGTTAGACCAGATCTGAGCCTGGGAGCTCTCTGGCTAACT
AGGGAACCCACTGCTTAAGCCTCAATAAAGCTTGCCTTGAGTGCTTCAAGTAGTGTG
TGCCCGTCTGTTGTGTGACTCTGGTAACTAGAGATCCCTCAGACCCTTTTAGTCAGTG
TGGAAAATCTCTAGCAGTGGCGCCCGAACAGGGACCTGAAAGCGAAAGGGAAACC
AGAGCTCTCTCGACGCAGGACTCGGCTTGCTGAAGCGCGCACGGCAAGAGGCGAGG
GGCGGCGACTGGTGAGTACGCCAAAAATTTTGACTAGCGGAGGCTAGAAGGAGAGA
GATGGGTGCGAGAGCGTCAGTATTAAGCGGGGGAGAATTAGATCGCGATGGGAAAA
AATTCGGTTAAGGCCAGGGGGAAAGAAAAAATATAAATTAAAACATATAGTATGGG
CAAGCAGGGAGCTAGAACGATTCGCAGTTAATCCTGGCCTGTTAGAAACATCAGAA
GGCTGTAGACAAATACTGGGACAGCTACAACCATCCCTTCAGACAGGATCAGAAGA
ACTTAGATCATTATATAATACAGTAGCAACCCTCTATTGTGTGCATCAAAGGATAGA
GATAAAAGACACCAAGGAAGCTTTAGACAAGATAGAGGAAGAGCAAAACAAAAGT
AAGACCACCGCACAGCAAGCGGCCACTGATCTTCAGACCTGGAGGAGGAGATATGA
GGGACAATTGGAGAAGTGAATTATATAAATATAAAGTAGTAAAAATTGAACCATTA

-continued

GGAGTAGCACCCACCAAGGCAAAGAGAAGAGTGGTGCAGAGAGAAAAAAGAGCAG

TGGGAATAGGAGCTTTGTTCCTTGGGTTCTTGGGAGCAGCAGGAAGCACTATGGGCG

CAGCCTCAATGACGCTGACGGTACAGGCCAGACAATTATTGTCTGGTATAGTGCAGC

AGCAGAACAATTTGCTGAGGGCTATTGAGGCGCAACAGCATCTGTTGCAACTCACA

GTCTGGGGCATCAAGCAGCTCCAGGCAAGAATCCTGGCTGTGGAAAGATACCTAAA

GGATCAACAGCTCCTGGGGATTTGGGGTTGCTCTGGAAAACTCATTTGCACCACTGC

TGTGCCTTGGAATGCTAGTTGGAGTAATAAATCTCTGGAACAGATTGGAATCACACG

ACCTGGATGGAGTGGGACAGAGAAATTAACAATTACACAAGCTTAATACACTCCTT

AATTGAAGAATCGCAAAACCAGCAAGAAAAGAATGAACAAGAATTATTGGAATTAG

ATAAATGGGCAAGTTTGTGGAATTGGTTTAACATAACAAATTGGCTGTGGTATATAA

AATTATTCATAATGATAGTAGGAGGCTTGGTAGGTTTAAGAATAGTTTTTGCTGTAC

TTTCTATAGTGAATAGAGTTAGGCAGGGATATTCACCATTATCGTTTCAGACCCACC

TCCCAACCCCGAGGGGACCCGACAGGCCCGAAGGAATAGAAGAAGAAGGTGGAGA

GAGAGACAGAGACAGATCCATTCGATTAGTGAACGGATCTCGACGGTATCGGTTAA

CTTTTAAAAGAAAAGGGGGGATTGGGGGGTACAGTGCAGGGGAAAGAATAGTAGA

CATAATAGCAACAGACATACAAACTAAAGAATTACAAAAACAAATTACAAAAATTC

AAAATTTTATCTCGAGTAGTTGTGAACTTACACTTTATTCATATATATTAGATATTGA

TAATTTTAACAAATGAGTTACTTTCCATTTGGGTACAGTCACAGTTGTCAACAATATT

TGGAAGCACCAGGCATGAAATCTCCTGAGATGCTATGTTTTCATCAGGGTCACCTGA

CACATTCAAGTTCTGTCTGACATGCCATTAAAGCACTGGCTCAGATTGCAGGCATAT

TTTCAAACCGGCAGTAACTGGATAGTATCACTTCACTTATAAGTGTTCATTGTATCAT

CAAGTGAAATAAACACACAACCCATGGGATCTTGCTTAGGTTGGCTGCCTAGTTGGC

CCCTGAGATAAAGCCTTGTAATCACATAGCCTTGCCTAATTAGTCAGAAAACAAAGG

ATTAAGTGAGACAGTCACAGGATATAGGAATTATAAATAATACATATATTAATAGA

TATTCATTTTCATTACACAAAAGTTGCTATTATAAATACTTATTTGATTGATGAGTCT

AAAAATATATTCCCCATATAAATAATGTTAAATATTAATAAATAGATTTAGATTTAA

AATTCAAATATTGCAGGCAGGACAACCACCCGGGTCACGCCAGAATGCGTTCGCAC

AGCCGCCAGCCGGTCACTCCGTTGATGGTTACTCGGAACAGCAGGGAGCCGTCGGG

GTTGATCAGGCGCTCGTCGATAATTTTGTTGCCGTTCCACAGGGTCCCTGTTACAGTG

ATCTTTTTGCCGTCGAACACGGCGATGCCTTCATACGGCCGTCCGAAATAGTCGATC

ATGTTCGGCGTAACCCCGTCGATTACCAGTGTGCCATAGTGCAGGATCACCTTAAAG

TGATGATCATCCACAGGGTACACCACCTTAAAAATTTTTTCGATCTGGCCCATTTGGT

CGCCGCTCAGACCTTCATACGGGATGATGACATGGATGTCGATCTTCAGCCCATTTT

CACCGCTCAGGACAATCCTTTGGATCGGAGTTACGGACACCCCGAGATTCTGAAAC

AAACTGGACACACCTCCCTGTTCAAGGACTTGGTCCAGGTTGTAGCCGGCTGTCTGT

CGCCAGTCCCCAACGAAATCTTCGAGTGTGAAGACTGGGGCAGGGAAGGCAGCAGG

CAACACCAGGAGCAGGCCCAGGGAGAAGGCAACTGGACCGAAGGCGCTTGTGGAG

AAGGAGTTCATGGTGGGAATTCCTGGAATTCGAGCTTCCATTATATACCCTCTAGAG

TCTAGATCTACGCCTTCTGTATGAAACAGTTTTTCCTCCACGCCTTCTGTATGAAACA

GTTTTTCCTCCACGCCTTCTGTATGAAACAGTTTTTCCTCCGTTTAAACGTAAGTCAT

TGGTCTTAAAGGTAGCTTTATTTAGTCTCCAGAAAAAGGGGGGAATGAAAGACCCC

-continued

ACCTGTAGGTTTGGCAAGCTAGGATCAAGGTTAGGAACAGAGAGACAGCAGAATAT

GGGCCAAACAGGATATCTGTGGTAAGCAGTTCCTGCCCCGGCTCAGGGCCAAGAAC

AGTTGGAACAGCAGAATATGGGCCAAACAGGATATCTGTGGTAAGCAGTTCCTGCC

CCGGCTCAGGGCCAAGAACAGATGGTCCCCAGATGCGGTCCCGCCCTCAGCAGTTT

CTAGAGAACCATCAGATGTTTCCAGGGTGCCCCAAGGACCTGAAATGACCCTGTGC

CTTATTTGAACTAACCAATCAGTTCGCTTCTCGCTTCTGTTCGCGCGCTTCTGCTCCC

CGAGCTCAATAAAAGAGCCCACGCTAGCGCTACCGGTCGCCAAGATGGGGGCAGGT

GCCACCGGCCGCGCAATGGATGGTCCGCGTCTACTGCTGTTACTACTTCTGGGTGTG

TCCCTTGGAGGTGCCAAAGAGGCATGCCCCACAGGTCTATACACACATAGCGGTGA

ATGCTGCAAAGCATGCAACCTGGGCGAAGGTGTGGCCCAACCTTGTGGAGCCAATC

AAACCGTTTGTGAGCCATGTCTGGACAGCGTGACGTTCTCCGATGTTGTTAGCGCGA

CCGAGCCATGCAAACCGTGTACCGAGTGTGTTGGTCTCCAAAGTATGTCGGCGCCGT

GCGTGGAGGCCGACGACGCCGTGTGTCGCTGTGCCTACGGTTATTACCAGGATGAA

ACTACTGGTCGCTGTGAAGCGTGCCGCGTGTGTGAGGCGGGCTCAGGCCTCGTGTTC

TCCTGTCAGGACAAACAGAACACTGTGTGTGAAGAATGCCCCGACGGTACTTATTCC

GACGAGGCCAACCATGTGGACCCGTGTCTGCCCTGCACCGTTTGCGAGGATACCGA

GCGCCAGCTACGTGAGTGCACACGTTGGGCCGACGCCGAGTGCGAGGAAATCCCTG

GCCGTTGGATTACACGGTCCACACCACCAGAAGGCTCGGACAGCACAGCACCCAGC

ACTCAGGAACCTGAGGCACCTCCAGAACAAGACCTAATAGCCAGCACTGTGGCAGG

TGTTGTGACTACAGTGATGGGTAGCTCACAACCCGTTGTTACTCGAGGCACCACCGA

CAATCTAATTCCTGTCTATTGTTCCATCCTGGCTGCTGTGGTTGTGGGTCTTGTTGCA

TATATAGCCTTCAAGAGGGGCAGCGGAGAGGGTAGGGGTAGTCTTTTGACGTGTGG

GGACGTCGAGGAAAATCCTGGGCCTGCCTTACCAGTGACCGCCTTGCTCCTGCCGCT

GGCCTTGCTGCTCCACGCCGCCAGGCCGGACATCGTGATGACCCAGAGCCCCGACA

GCCTGGCCGTGAGCCTGGGCGAGAGGGCCACCATCAACTGCAAGAGCAGCCAGAGC

CTGCTGAACAGCGGCGACCAGAAGAACTACCTGACCTGGTACCAGCAGAAGCCCGG

CCAGCCCCCCAAGCTGCTGATCTACTGGGCCAGCACCAGGGAGAGCGGCGTGCCCG

ACAGGTTCAGCGGCAGCGGCAGCGGCACCGACTTCACCCTGACCATCAGCAGCCTG

CAGGCCGAGGACGTGGCCGTGTACTACTGCCAGAACGACTACAGCTACCCCCTGAC

CTTCGGCCAGGGCACCAAGGTGGAGATCAAGGGCGGCGGCGGCAGCGGCGGCGGC

GGCAGCGGCGGCGGCGGCAGCCAGGTGCAGCTGGTGCAGAGCGGCGCCGAGGTGA

AGAAGACCGGCAGCAGCGTGAAGGTGAGCTGCAAGGCCAGCGGCTACACCTTCACC

GACCACGCCATCCACTGGGTGAGGCAGGCCCCCGGCCAGGCCCTGGAGTGGATGGG

CCACTTCAGCCCCGGCAACACCGACATCAAGTACAACGACAAGTTCAAGGGCAGGG

TGACCCTGACCGTGGACAGGAGCATGAGCACCGCCTACATGGAGCTGAGCAGCCTG

AGGAGCGAGGACACCGCCATGTACTACTGCAAGACCAGCACCTTCTTCTTCGACTAC

TGGGGCCAGGGCACCATGGTGACCGTGAGCAGCACCACGACGCCAGCGCCGCGACC

ACCAACACCGGCGCCCACCATCGCGTCGCAGCCCCTGTCCCTGCGCCCAGAGGCGT

GCCGGCCAGCGGCGGGGGGCGCAGTGCACACGAGGGGGCTGGACTTCGCCTGTGAT

ATCTACATCTGGGCGCCCTTGGCCGGGACTTGTGGGGTCCTTCTCCTGTCACTGGTTA

-continued

TCACCCTTTACTGCAAACGGGGCAGAAAGAAACTCCTGTATATATTCAAACAACCAT

TTATGAGACCAGTACAAACTACTCAAGAGGAAGATGGCTGTAGCTGCCGATTTCCA

GAAGAAGAAGAAGGAGGATGTGAACTGAGAGTGAAGTTCAGCAGGAGCGCAGACG

CCCCCGCGTACAAGCAGGGCCAGAACCAGCTCTATAACGAGCTCAATCTAGGACGA

AGAGAGGAGTACGATGTTTTGGACAAGAGACGTGGCCGGGACCCTGAGATGGGGGG

AAAGCCGAGAAGGAAGAACCCTCAGGAAGGCCTGTACAATGAACTGCAGAAAGAT

AAGATGGCGGAGGCCTACAGTGAGATTGGGATGAAAGGCGAGCGCCGGAGGGGCA

AGGGGCACGATGGCCTTTACCAGGGTCTCAGTACAGCCACCAAGGACACCTACGAC

GCCCTTCACATGCAGGCCCTGCCCCCTCGCTGAAGAGACGTCATAATCAGCCAGCGG

CCGCGTCGACAATCAACCTCTGGATTACAAAATTTGTGAAAGATTGACTGGTATTCT

TAACTATGTTGCTCCTTTTACGCTATGTGGATACGCTGCTTTAATGCCTTTGTATCAT

GCTATTGCTTCCCGTATGGCTTTCATTTTCTCCTCCTTGTATAAATCCTGGTTGCTGTC

TCTTTATGAGGAGTTGTGGCCCGTTGTCAGGCAACGTGGCGTGGTGTGCACTGTGTT

TGCTGACGCAACCCCCACTGGTTGGGGCATTGCCACCACCTGTCAGCTCCTTTCCGG

GACTTTCGCTTTCCCCCTCCCTATTGCCACGGCGGAACTCATCGCCGCCTGCCTTGCC

CGCTGCTGGACAGGGGCTCGGCTGTTGGGCACTGACAATTCCGTGGTGTTGTCGGGG

AAATCATCGTCCTTTCCTTGGCTGCTCGCCTGTGTTGCCACCTGGATTCTGCGCGGGA

CGTCCTTCTGCTACGTCCCTTCGGCCCTCAATCCAGCGGACCTTCCTTCCCGCGGCCT

GCTGCCGGCTCTGCGGCCTCTTCCGCGTCTTCGCCTTCGCCCTCAGACGAGTCGGAT

CTCCCTTTGGGCCGCCTCCCCGCCTGGTACCTTTAAGACCAATGACTTACAAGGCAG

CTGTAGATCTTAGCCACTTTTTAAAAGAAAAGGGGGGACTGGAAGGGCTAATTCACT

CCCAACGAAAATAAGATCTGCTTTTTGCTTGTACTGGGTCTCTCTGGTTAGACCAGA

TCTGAGCCTGGGAGCTCTCTGGCTAACTAGGGAACCCACTGCTTAAGCCTCAATAAA

GCTTGCCTTGAGTGCTTCAAGTAGTGTGTGCCCGTCTGTTGTGTGACTCTGGTAACTA

GAGATCCCTCAGACCCTTTTAGTCAGTGTGGAAAATCTCTAGCAGTAGTAGTTCATG

TCATCTTATTATTCAGTATTTATAACTTGCAAAGAAATGAATATCAGAGAGTGAGAG

GAACTTGTTTATTGCAGCTTATAATGGTTACAAATAAAGCAATAGCATCACAAATTT

CACAAATAAAGCATTTTTTTCACTGCATTCTAGTTGTGGTTTGTCCAAACTCATCAAT

GTATCTTATCATGTCTGGCTCTAGCTATCCCGCCCCTAACTCCGCCCAGTTCCGCCCA

TTCTCCGCCCCATGGCTGACTAATTTTTTTTATTTATGCAGAGGCCGAGGCCGCCTCG

GCCTCTGAGCTATTCCAGAAGTAGTGAGGAGGCTTTTTTGGAGGCCTAGACTTTTGC

AGAGACGGCCCAAATTCGTAATCATGGTCATAGCTGTTTCCTGTGTGAAATTGTTAT

CCGCTCACAATTCCACACAACATACGAGCCGGAAGCATAAAGTGTAAAGCCTGGGG

TGCCTAATGAGTGAGCTAACTCACATTAATTGCGTTGCGCTCACTGCCCGCTTTCCA

GTCGGGAAACCTGTCGTGCCAGCTGCATTAATGAATCGGCCAACGCGCGGGGAGAG

GCGGTTTGCGTATTGGGCGCTCTTCCGCTTCCTCGCTCACTGACTCGCTGCGCTCGGT

CGTTCGGCTGCGGCGAGCGGTATCAGCTCACTCAAAGGCGGTAATACGGTTATCCAC

AGAATCAGGGGATAACGCAGGAAAGAACATGTGAGCAAAAGGCCAGCAAAAGGCC

AGGAACCGTAAAAAGGCCGCGTTGCTGGCGTTTTTCCATAGGCTCCGCCCCCCTGAC

GAGCATCACAAAAATCGACGCTCAAGTCAGAGGTGGCGAAACCCGACAGGACTATA

AAGATACCAGGCGTTTCCCCCTGGAAGCTCCCTCGTGCGCTCTCCTGTTCCGACCCT

-continued

GCCGCTTACCGGATACCTGTCCGCCTTTCTCCCTTCGGGAAGCGTGGCGCTTTCTCAT

AGCTCACGCTGTAGGTATCTCAGTTCGGTGTAGGTCGTTCGCTCCAAGCTGGGCTGT

GTGCACGAACCCCCCGTTCAGCCCGACCGCTGCGCCTTATCCGGTAACTATCGTCTT

GAGTCCAACCCGGTAAGACACGACTTATCGCCACTGGCAGCAGCCACTGGTAACAG

GATTAGCAGAGCGAGGTATGTAGGCGGTGCTACAGAGTTCTTGAAGTGGTGGCCTA

ACTACGGCTACACTAGAAGGACAGTATTTGGTATCTGCGCTCTGCTGAAGCCAGTTA

CCTTCGGAAAAAGAGTTGGTAGCTCTTGATCCGGCAAACAAACCACCGCTGGTAGC

GGTGGTTTTTTTGTTTGCAAGCAGCAGATTACGCGCAGAAAAAAAGGATCTCAAGA

AGATCCTTTGATCTTTTCTACGGGGTCTGACGCTCAGTGGAACGAAAACTCACGTTA

AGGGATTTTGGTCATGAGATTATCAAAAAGGATCTTCACCTAGATCCTTTTAAATTA

AAAATGAAGTTTTAAATCAATCTAAAGTATATATGAGTAAACTTGGTCTGACAGTTA

CCAATGCTTAATCAGTGAGGCACCTATCTCAGCGATCTGTCTATTTCGTTCATCCATA

GTTGCCTGACTCCCCGTCGTGTAGATAACTACGATACGGGAGGGCTTACCATCTGGC

CCCAGTGCTGCAATGATACCGCGAGACCCACGCTCACCGGCTCCAGATTTATCAGCA

ATAAACCAGCCAGCCGGAAGGGCCGAGCGCAGAAGTGGTCCTGCAACTTTATCCGC

CTCCATCCAGTCTATTAATTGTTGCCGGGAAGCTAGAGTAAGTAGTTCGCCAGTTAA

TAGTTTGCGCAACGTTGTTGCCATTGCTACAGGCATCGTGGTGTCACGCTCGTCGTTT

GGTATGGCTTCATTCAGCTCCGGTTCCCAACGATCAAGGCGAGTTACATGATCCCCC

ATGTTGTGCAAAAAAGCGGTTAGCTCCTTCGGTCCTCCGATCGTTGTCAGAAGTAAG

TTGGCCGCAGTGTTATCACTCATGGTTATGGCAGCACTGCATAATTCTCTTACTGTCA

TGCCATCCGTAAGATGCTTTTCTGTGACTGGTGAGTACTCAACCAAGTCATTCTGAG

AATAGTGTATGCGGCGACCGAGTTGCTCTTGCCCGGCGTCAATACGGGATAATACCG

CGCCACATAGCAGAACTTTAAAAGTGCTCATCATTGGAAAACGTTCTTCGGGGCGAA

AACTCTCAAGGATCTTACCGCTGTTGAGATCCAGTTCGATGTAACCCACTCGTGCAC

CCAACTGATCTTCAGCATCTTTTACTTTCACCAGCGTTTCTGGGTGAGCAAAAACAG

GAAGGCAAAATGCCGCAAAAAAGGGAATAAGGGCGACACGGAAATGTTGAATACT

CATACTCTTCCTTTTTCAATATTATTGAAGCATTTATCAGGGTTATTGTCTCATGAGC

GGATACATATTTGAATGTATTTAGAAAAATAAACAAATAGGGGTTCCGCGCACATTT

CCCCGAAAAGTGCCACCTGACGTCTAAGAAACCATTATTATCATGACATTAACCTAT

AAAAATAGGCGTATCACGAGGCCCTTTCGTCTCGCGCGTTTCGGTGATGACGGTGAA

AACCTCTGACACATGCAGCTCCCGGAGACGGTCACAGCTTGTCTGTAAGCGGATGCC

GGGAGCAGACAAGCCCGTCAGGGCGCGTCAGCGGGTGTTGGCGGGTGTCGGGGCTG

GCTTAACTATGCGGCATCAGAGCAGATTGTACTGAGAGTGCACCATATGCGGTGTGA

AATACCGCACAGATGCGTAAGGAGAAAATACCGCATCAGGCGCCATTCGCCATTCA

GGCTGCGCAACTGTTGGGAAGGGCGATCGGTGCGGGCCTCTTCGCTATTACGCCAGC

TGGCGAAAGGGGGATGTGCTGCAAGGCGATTAAGTTGGGTAACGCCAGGGTTTTCC

CAGTCACGACGTTGTAAAACGACGGCCAGTGCCAAGCTG

GC251

(SEQ ID NO: 12)

ACGCGTGTAGTCTTATGCAATACTCTTGTAGTCTTGCAACATGGTAACGATGAGTTA

GCAACATGCCTTACAAGGAGAGAAAAAGCACCGTGCATGCCGATTGGTGGAAGTAA

-continued

GGTGGTACGATCGTGCCTTATTAGGAAGGCAACAGACGGGTCTGACATGGATTGGA

CGAACCACTGAATTGCCGCATTGCAGAGATATTGTATTTAAGTGCCTAGCTCGATAC

AATAAACGGGTCTCTCTGGTTAGACCAGATCTGAGCCTGGGAGCTCTCTGGCTAACT

AGGGAACCCACTGCTTAAGCCTCAATAAAGCTTGCCTTGAGTGCTTCAAGTAGTGTG

TGCCCGTCTGTTGTGTGACTCTGGTAACTAGAGATCCCTCAGACCCTTTTAGTCAGTG

TGGAAAATCTCTAGCAGTGGCGCCCGAACAGGGACCTGAAAGCGAAAGGGAAACC

AGAGCTCTCTCGACGCAGGACTCGGCTTGCTGAAGCGCGCACGGCAAGAGGCGAGG

GGCGGCGACTGGTGAGTACGCCAAAAATTTTGACTAGCGGAGGCTAGAAGGAGAGA

GATGGGTGCGAGAGCGTCAGTATTAAGCGGGGGAGAATTAGATCGCGATGGGAAAA

AATTCGGTTAAGGCCAGGGGGAAAGAAAAAATATAAATTAAAACATATAGTATGGG

CAAGCAGGGAGCTAGAACGATTCGCAGTTAATCCTGGCCTGTTAGAAACATCAGAA

GGCTGTAGACAAATACTGGGACAGCTACAACCATCCCTTCAGACAGGATCAGAAGA

ACTTAGATCATTATATAATACAGTAGCAACCCTCTATTGTGTGCATCAAAGGATAGA

GATAAAAGACACCAAGGAAGCTTTAGACAAGATAGAGGAAGAGCAAAACAAAAGT

AAGACCACCGCACAGCAAGCGGCCACTGATCTTCAGACCTGGAGGAGGAGATATGA

GGGACAATTGGAGAAGTGAATTATATAAATATAAAGTAGTAAAAATTGAACCATTA

GGAGTAGCACCCACCAAGGCAAAGAGAAGAGTGGTGCAGAGAGAAAAAAGAGCAG

TGGGAATAGGAGCTTTGTTCCTTGGGTTCTTGGGAGCAGCAGGAAGCACTATGGGCG

CAGCCTCAATGACGCTGACGGTACAGGCCAGACAATTATTGTCTGGTATAGTGCAGC

AGCAGAACAATTTGCTGAGGGCTATTGAGGCGCAACAGCATCTGTTGCAACTCACA

GTCTGGGGCATCAAGCAGCTCCAGGCAAGAATCCTGGCTGTGGAAAGATACCTAAA

GGATCAACAGCTCCTGGGGATTTGGGGTTGCTCTGGAAAACTCATTTGCACCACTGC

TGTGCCTTGGAATGCTAGTTGGAGTAATAAATCTCTGGAACAGATTGGAATCACACG

ACCTGGATGGAGTGGGACAGAGAAATTAACAATTACACAAGCTTAATACACTCCTT

AATTGAAGAATCGCAAAACCAGCAAGAAAAGAATGAACAAGAATTATTGGAATTAG

ATAAATGGGCAAGTTTGTGGAATTGGTTTAACATAACAAATTGGCTGTGGTATATAA

AATTATTCATAATGATAGTAGGAGGCTTGGTAGGTTTAAGAATAGTTTTTGCTGTAC

TTTCTATAGTGAATAGAGTTAGGCAGGGATATTCACCATTATCGTTTCAGACCCACC

TCCCAACCCCGAGGGGACCCGACAGGCCCGAAGGAATAGAAGAAGAAGGTGGAGA

GAGAGACAGAGACAGATCCATTCGATTAGTGAACGGATCTCGACGGTATCGGTTAA

CTTTTAAAAGAAAAGGGGGGATTGGGGGGTACAGTGCAGGGGAAAGAATAGTAGA

CATAATAGCAACAGACATACAAACTAAAGAATTACAAAAACAAATTACAAAAATTC

AAAATTTTATCTCGAGTAGTTGTGAACTTACACTTTATTCATATATATTAGATATTGA

TAATTTTAACAAATGAGTTACTTTCCATTTGGGTACAGTCACAGTTGTCAACAATATT

TGGAAGCACCAGGCATGAAATCTCCTGAGATGCTATGTTTTCATCAGGGTCACCTGA

CACATTCAAGTTCTGTCTGACATGCCATTAAAGCACTGGCTCAGATTGCAGGCATAT

TTTCAAACCGGCAGTAACTGGATAGTATCACTTCACTTATAAGTGTTCATTGTATCAT

CAAGTGAAATAAACACACAACCCATGGGATCTTGCTTAGGTTGGCTGCCTAGTTGGC

CCCTGAGATAAAGCCTTGTAATCACATAGCCTTGCCTAATTAGTCAGAAAACAAAGG

ATTAAGTGAGACAGTCACAGGATATAGGAATTATAAATAATACATATATTAATAGA

TATTCATTTTCATTACACAAAAGTTGCTATTATAAATACTTATTTGATTGATGAGTCT

-continued

AAAAATATATTCCCCATATAAATAATGTTAAATATTAATAAATAGATTTAGATTTAA

AATTCAAATATTGCAGGCAGGACAACCACCCGGGTTAACTTGCATTCAAATATGACA

TTACCCTATCAATTGTAACGGCCCTGATTCTAAAAGCATGCAAAAGTATACACAGCT

TTATTTTTGTCTTGTAAAAATCAGGTTCTTCAAGAGAGCTTTTTTGAGGAACCGTTTC

AGAATTAAAATTAAGAGCTTGCATCAGCTCATCAATAACGGCAAGCATATTCTGATC

AAGGAATATCTGTCGCTTGGGGTCCATCAAAAGTTTTGCGTTCATTGTCTTGAACTC

AACCTGGTACATCTTAAGATCTTCATATATAGAAGACAAGCACAGGGCCATCATAA

AGCTTGTTTTGCGGCTGGCCAAACAAGATCCATTGGTAATGAAAGAAGTCTCTCTGG

AATTGAGACAAGATTCGTTTTTAGTGAGTTCCAGTGGCAGGCATGCCTCCACGGTGG

ATGTTTTGTCCTTAGTAATATCTTCGTGGTCTATTTCCTCACTTGTGCAAGGGTAAAA

TTCAAGTGTTTGTCGGGCCTTCTGGAGCATGTTGGAGACAGCCCTAAGCAAGTTTTG

AGAGTGGTGAAGACATGGGAACATGCCTGGGTCTGGGGTTGCAACAGGCAAGTTCC

GAGAACCGCCCCCACCACCACCTGAGCATGGGACAGATGCCCATTCGCTCCAGCTA

GATGAGTAGTATCTGTCTTGGGCTCTGACACTTATGCTTGCGTTCTTTCTGCAAATGA

CTGTTGCAGACGTTTTATCAGTGAAAACCCGATCTTTCTTTTCCCTTTTTGATTTTCCT

TGCACCTGGACACAAAATGTCAAACTAAAGTAAGAGTGCGGAGTTGACCAGGTGTC

GGGGTACTCCCAAGAAACTTCAACCTGGCGTGAGTTCTTCAAAGGCTTAAGCTGCAG

ATTCTTCGGAGGATCGGGCTTGATAATGTCCCGGATAAAAAAGCTGCTCGTGTAATT

TTCATACTTCAACTTGTGTACGGCGTCAACCATCACCTCTATTGGCAGGCTCTCCTCT

GCTGCGGGGCAAGCGGAGTCTTCCTGGCATTCCACGCTATATTCGTATTCTTTGTTGT

CCCCCCGTACCCTCTCCGCAGAAAGCGTAGCAGCACCGCACGTTACACCTTGTGGGT

CACTGGAACCCCTACTAGACTTAACAGAAAACGTAAGATCCGTAGAGATTGTTGTCA

ACCACCAGCAAGTAAAGCGTCCGGAGTAATTTTTTGCTTCACAGCGCAGAAACGTTT

TGTTTTTGGGTTCTTTCTGATCCTTAAGGATATCTGTACTCCAAATGCCATCCTCTTTT

TTGTGCAGGAGCAGCAGGCTGTGAGAAAGGACCTCGCCTCCCTTATGGCACGTATAC

TGCCCGGCATCTCCAAACTCTTTTACCTGGATAGTAAGTGTTTTGCCGCTGCCAAGC

ACCTCTGAGCTTTGGTCCAGGGTCCAGGTTATCCCATCTTCTTCAGGTGTATCGCAGG

TGAGGACCACCATCTCGCCCGGTGCGTCGGGATACCAATCCAATTCAACAACATATA

CGTCTTTCTTAAGTTCCCAAATAGCGACCAATGGTGACGCCAGAAAAACAAGTGAG

AACCAAGAGATTACCAGTTGTTGATGGCACATGGTGGGAATTCGGCTGTCCCAGCAC

CTCAGCGCAGAGCAAGTGGTGGTCAGGGGAGCGTCTCAAATCCTGCGCAGCCCAAC

GTCCGGCGCCGCCAAGTGACGCACGAGGTGCTGTGACTCGTGCCAGCCCCCTAATCT

GCGGAAGTGGAGTGCGGGGAGTGCGCCGGAAGAGGGGTACGGAAGTGCGCCGGAA

GTGGGGTGCGGAGGTGTGCAGCGCGCTGTCAGACTGGCTCGCAGGCGGCGCGGCCG

GCGGACCCGTTCGAGACAGCGCGGGCGGCTCGGGTCCCCTGGGGCTCCGCAGCAGG

AGGACGCCGCTAGCGCTACCGGTCGCCAAGATGGGGGCAGGTGCCACCGGCCGCGC

CATGGACGGGCCGCGCCTGCTGCTGTTGCTGCTTCTGGGGGTGTCCCTTGGAGGTGC

CAAGGAGGCATGCCCCACAGGCCTGTACACACACAGCGGTGAGTGCTGCAAAGCCT

GCAACCTGGGCGAGGGTGTGGCCCAGCCTTGTGGAGCCAACCAGACCGTGTGTGAG

CCCTGCCTGGACAGCGTGACGTTCTCCGACGTGGTGAGCGCGACCGAGCCGTGCAA

-continued
GCCGTGCACCGAGTGCGTGGGGCTCCAGAGCATGTCGGCGCCGTGCGTGGAGGCCG
ACGACGCCGTGTGCCGCTGCGCCTACGGCTACTACCAGGATGAGACGACTGGGCGC
TGCGAGGCGTGCCGCGTGTGCGAGGCGGGCTCGGGCCTCGTGTTCTCCTGCCAGGAC
AAGCAGAACACCGTGTGCGAGGAGTGCCCCGACGGCACGTATTCCGACGAGGCCAA
CCACGTGGACCCGTGCCTGCCCTGCACCGTGTGCGAGGACACCGAGCGCCAGCTCC
GCGAGTGCACACGCTGGGCCGACGCCGAGTGCGAGGAGATCCCTGGCCGTTGGATT
ACACGGTCCACACCCCCAGAGGGCTCGGACAGCACAGCCCCCAGCACCCAGGAGCC
TGAGGCACCTCCAGAACAAGACCTCATAGCCAGCACGGTGGCAGGTGTGGTGACCA
CAGTGATGGGCAGCTCCCAGCCCGTGGTGACCCGAGGCACCACCGACAACCTCATC
CCTGTCTATTGCTCCATCCTGGCTGCTGTGGTTGTGGGTCTTGTGGCCTACATAGCCT
TCAAGAGGGGCAGCGGAGAGGGTAGGGGTAGTCTTTTGACGTGTGGGGACGTCGAG
GAAAATCCTGGGCCTGCCTTACCAGTGACCGCCTTGCTCCTGCCGCTGGCCTTGCTG
CTCCACGCCGCCAGGCCGGACATCGTGATGACCCAGAGCCCCGACAGCCTGGCCGT
GAGCCTGGGCGAGAGGGCCACCATCAACTGCAAGAGCAGCCAGAGCCTGCTGAACA
GCGGCGACCAGAAGAACTACCTGACCTGGTACCAGCAGAAGCCCGGCCAGCCCCCC
AAGCTGCTGATCTACTGGGCCAGCACCAGGGAGAGCGGCGTGCCCGACAGGTTCAG
CGGCAGCGGCAGCGGCACCGACTTCACCCTGACCATCAGCAGCCTGCAGGCCGAGG
ACGTGGCCGTGTACTACTGCCAGAACGACTACAGCTACCCCCTGACCTTCGGCCAGG
GCACCAAGGTGGAGATCAAGGGCGGCGGCGGCAGCGGCGGCGGCGGCAGCGGCGG
CGGCGGCAGCCAGGTGCAGCTGGTGCAGAGCGGCGCCGAGGTGAAGAAGACCGGC
AGCAGCGTGAAGGTGAGCTGCAAGGCCAGCGGCTACACCTTCACCGACCACGCCAT
CCACTGGGTGAGGCAGGCCCCCGGCCAGGCCCTGGAGTGGATGGGCCACTTCAGCC
CCGGCAACACCGACATCAAGTACAACGACAAGTTCAAGGGCAGGGTGACCCTGACC
GTGGACAGGAGCATGAGCACCGCCTACATGGAGCTGAGCAGCCTGAGGAGCGAGG
ACACCGCCATGTACTACTGCAAGACCAGCACCTTCTTCTTCGACTACTGGGGCCAGG
GCACCATGGTGACCGTGAGCAGCACCACGACGCCAGCGCCGCGACCACCAACACCG
GCGCCCACCATCGCGTCGCAGCCCCTGTCCCTGCGCCCAGAGGCGTGCCGGCCAGC
GGCGGGGGGCGCAGTGCACACGAGGGGGCTGGACTTCGCCTGTGATATCTACATCT
GGGCGCCCTTGGCCGGGACTTGTGGGGTCCTTCTCCTGTCACTGGTTATCACCCTTTA
CTGCAAACGGGGCAGAAAGAAACTCCTGTATATATTCAAACAACCATTTATGAGAC
CAGTACAAACTACTCAAGAGGAAGATGGCTGTAGCTGCCGATTTCCAGAAGAAGAA
GAAGGAGGATGTGAACTGAGAGTGAAGTTCAGCAGGAGCGCAGACGCCCCCGCGTA
CAAGCAGGGCCAGAACCAGCTCTATAACGAGCTCAATCTAGGACGAAGAGAGGAGT
ACGATGTTTTGGACAAGAGACGTGGCCGGGACCCTGAGATGGGGGGAAAGCCGAGA
AGGAAGAACCCTCAGGAAGGCCTGTACAATGAACTGCAGAAAGATAAGATGGCGG
AGGCCTACAGTGAGATTGGGATGAAAGGCGAGCGCCGGAGGGGCAAGGGGCACGA
TGGCCTTTACCAGGGTCTCAGTACAGCCACCAAGGACACCTACGACGCCCTTCACAT
GCAGGCCCTGCCCCCTCGCTGAAGAGACGTCATAATCAGCCAGCGGCCGCGTCGAC
AATCAACCTCTGGATTACAAAATTTGTGAAAGATTGACTGGTATTCTTAACTATGTT
GCTCCTTTTACGCTATGTGGATACGCTGCTTTAATGCCTTTGTATCATGCTATTGCTT
CCCGTATGGCTTTCATTTTCTCCTCCTTGTATAAATCCTGGTTGCTGTCTCTTTATGAG -continued GAGTTGTGGCCCGTTGTCAGGCAACGTGGCGTGGTGTGCACTGTGTTTGCTGACGCA
ACCCCCACTGGTTGGGGCATTGCCACCACCTGTCAGCTCCTTTCCGGGACTTTCGCTT
TCCCCCTCCCTATTGCCACGGCGGAACTCATCGCCGCCTGCCTTGCCCGCTGCTGGA
CAGGGGCTCGGCTGTTGGGCACTGACAATTCCGTGGTGTTGTCGGGGAAATCATCGT
CCTTTCCTTGGCTGCTCGCCTGTGTTGCCACCTGGATTCTGCGCGGGACGTCCTTCTG
CTACGTCCCTTCGGCCCTCAATCCAGCGGACCTTCCTTCCCGCGGCCTGCTGCCGGCT
CTGCGGCCTCTTCCGCGTCTTCGCCTTCGCCCTCAGACGAGTCGGATCTCCCTTTGGG
CCGCCTCCCCGCCTGGTACCTTTAAGACCAATGACTTACAAGGCAGCTGTAGATCTT
AGCCACTTTTTAAAAGAAAAGGGGGGACTGGAAGGGCTAATTCACTCCCAACGAAA
ATAAGATCTGCTTTTTGCTTGTACTGGGTCTCTCTGGTTAGACCAGATCTGAGCCTGG
GAGCTCTCTGGCTAACTAGGGAACCCACTGCTTAAGCCTCAATAAAGCTTGCCTTGA
GTGCTTCAAGTAGTGTGTGCCCGTCTGTTGTGTGACTCTGGTAACTAGAGATCCCTC
AGACCCTTTTAGTCAGTGTGGAAAATCTCTAGCAGTAGTAGTTCATGTCATCTTATTA
TTCAGTATTTATAACTTGCAAAGAAATGAATATCAGAGAGTGAGAGGAACTTGTTTA
TTGCAGCTTATAATGGTTACAAATAAAGCAATAGCATCACAAATTTCACAAATAAAG
CATTTTTTTCACTGCATTCTAGTTGTGGTTTGTCCAAACTCATCAATGTATCTTATCAT
GTCTGGCTCTAGCTATCCCGCCCCTAACTCCGCCCAGTTCCGCCCATTCTCCGCCCCA
TGGCTGACTAATTTTTTTTATTTATGCAGAGGCCGAGGCCGCCTCGGCCTCTGAGCTA
TTCCAGAAGTAGTGAGGAGGCTTTTTTGGAGGCCTAGACTTTTGCAGAGACGGCCCA
AATTCGTAATCATGGTCATAGCTGTTTCCTGTGTGAAATTGTTATCCGCTCACAATTC
CACACAACATACGAGCCGGAAGCATAAAGTGTAAAGCCTGGGGTGCCTAATGAGTG
AGCTAACTCACATTAATTGCGTTGCGCTCACTGCCCGCTTTCCAGTCGGGAAACCTG
TCGTGCCAGCTGCATTAATGAATCGGCCAACGCGCGGGGAGAGGCGGTTTGCGTATT
GGGCGCTCTTCCGCTTCCTCGCTCACTGACTCGCTGCGCTCGGTCGTTCGGCTGCGGC
GAGCGGTATCAGCTCACTCAAAGGCGGTAATACGGTTATCCACAGAATCAGGGGAT
AACGCAGGAAAGAACATGTGAGCAAAAGGCCAGCAAAAGGCCAGGAACCGTAAAA
AGGCCGCGTTGCTGGCGTTTTTCCATAGGCTCCGCCCCCCTGACGAGCATCACAAAA
ATCGACGCTCAAGTCAGAGGTGGCGAAACCCGACAGGACTATAAAGATACCAGGCG
TTTCCCCCTGGAAGCTCCCTCGTGCGCTCTCCTGTTCCGACCCTGCCGCTTACCGGAT
ACCTGTCCGCCTTTCTCCCTTCGGGAAGCGTGGCGCTTTCTCATAGCTCACGCTGTAG
GTATCTCAGTTCGGTGTAGGTCGTTCGCTCCAAGCTGGGCTGTGTGCACGAACCCCC
CGTTCAGCCCGACCGCTGCGCCTTATCCGGTAACTATCGTCTTGAGTCCAACCCGGT
AAGACACGACTTATCGCCACTGGCAGCAGCCACTGGTAACAGGATTAGCAGAGCGA
GGTATGTAGGCGGTGCTACAGAGTTCTTGAAGTGGTGGCCTAACTACGGCTACACTA
GAAGGACAGTATTTGGTATCTGCGCTCTGCTGAAGCCAGTTACCTTCGGAAAAAGAG
TTGGTAGCTCTTGATCCGGCAAACAAACCACCGCTGGTAGCGGTGGTTTTTTTGTTTG
CAAGCAGCAGATTACGCGCAGAAAAAAAGGATCTCAAGAAGATCCTTTGATCTTTT
CTACGGGGTCTGACGCTCAGTGGAACGAAAACTCACGTTAAGGGATTTTGGTCATGA
GATTATCAAAAAGGATCTTCACCTAGATCCTTTTAAATTAAAAATGAAGTTTTAAAT
CAATCTAAAGTATATATGAGTAAACTTGGTCTGACAGTTACCAATGCTTAATCAGTG -continued

AGGCACCTATCTCAGCGATCTGTCTATTTCGTTCATCCATAGTTGCCTGACTCCCCGT

CGTGTAGATAACTACGATACGGGAGGGCTTACCATCTGGCCCCAGTGCTGCAATGAT

ACCGCGAGACCCACGCTCACCGGCTCCAGATTTATCAGCAATAAACCAGCCAGCCG

GAAGGGCCGAGCGCAGAAGTGGTCCTGCAACTTTATCCGCCTCCATCCAGTCTATTA

ATTGTTGCCGGGAAGCTAGAGTAAGTAGTTCGCCAGTTAATAGTTTGCGCAACGTTG

TTGCCATTGCTACAGGCATCGTGGTGTCACGCTCGTCGTTTGGTATGGCTTCATTCAG

CTCCGGTTCCCAACGATCAAGGCGAGTTACATGATCCCCCATGTTGTGCAAAAAAGC

GGTTAGCTCCTTCGGTCCTCCGATCGTTGTCAGAAGTAAGTTGGCCGCAGTGTTATC

ACTCATGGTTATGGCAGCACTGCATAATTCTCTTACTGTCATGCCATCCGTAAGATG

CTTTTCTGTGACTGGTGAGTACTCAACCAAGTCATTCTGAGAATAGTGTATGCGGCG

ACCGAGTTGCTCTTGCCCGGCGTCAATACGGGATAATACCGCGCCACATAGCAGAA

CTTTAAAAGTGCTCATCATTGGAAAACGTTCTTCGGGGCGAAAACTCTCAAGGATCT

TACCGCTGTTGAGATCCAGTTCGATGTAACCCACTCGTGCACCCAACTGATCTTCAG

CATCTTTTACTTTCACCAGCGTTTCTGGGTGAGCAAAAACAGGAAGGCAAAATGCCG

CAAAAAAGGGAATAAGGGCGACACGGAAATGTTGAATACTCATACTCTTCCTTTTTC

AATATTATTGAAGCATTTATCAGGGTTATTGTCTCATGAGCGGATACATATTTGAAT

GTATTTAGAAAAATAAACAAATAGGGGTTCCGCGCACATTTCCCCGAAAAGTGCCA

CCTGACGTCTAAGAAACCATTATTATCATGACATTAACCTATAAAAATAGGCGTATC

ACGAGGCCCTTTCGTCTCGCGCGTTTCGGTGATGACGGTGAAAACCTCTGACACATG

CAGCTCCCGGAGACGGTCACAGCTTGTCTGTAAGCGGATGCCGGGAGCAGACAAGC

CCGTCAGGGCGCGTCAGCGGGTGTTGGCGGGTGTCGGGGCTGGCTTAACTATGCGG

CATCAGAGCAGATTGTACTGAGAGTGCACCATATGCGGTGTGAAATACCGCACAGA

TGCGTAAGGAGAAAATACCGCATCAGGCGCCATTCGCCATTCAGGCTGCGCAACTG

TTGGGAAGGGCGATCGGTGCGGGCCTCTTCGCTATTACGCCAGCTGGCGAAAGGGG

GATGTGCTGCAAGGCGATTAAGTTGGGTAACGCCAGGGTTTTCCCAGTCACGACGTT

GTAAAACGACGGCCAGTGCCAAGCTG

PD007

(SEQ ID NO: 13)

GCGATCGCAGTAATCAATTACGGGGTCATTAGTTCATAGCCCATATATGGAGTTCCG

CGTTACATAACTTACGGTAAATGGCCCGCCTGGCTGACCGCCCAACGACCCCCGCCC

ATTGACGTCAATAATGACGTATGTTCCCATAGTAACGCCAATAGGGACTTTCCATTG

ACGTCAATGGGTGGAGTATTTACGGTAAACTGCCCACTTGGCAGTACATCAAGTGTA

TCATATGCCAAGTACGCCCCCTATTGACGTCAATGACGGTAAATGGCCCGCCTGGCA

TTATGCCCAGTACATGACCTTATGGGACTTTCCTACTTGGCAGTACATCTACGTATTA

GTCATCGCTATTACCATGGTGATGCGGTTTTGGCAGTACATCAATGGGCGTGGATAG

CGGTTTGACTCACGGGGATTTCCAAGTCTCCACCCCATTGACGTCAATGGGAGTTTG

TTTTGGCACCAAAATCAACGGGACTTTCCAAAATGTCGTAACAACTCCGCCCCATTG

ACGCAAATGGGCGGTAGGCGTGTACGGTGGGAGGTCTATATAAGCAGAGCTCGTTT

AGTGAACCGGGGTCTCTCTGGTTAGACCAGATCTGAGCCTGGGAGCTCTCTGGCTAA

CTAGGGAACCCACTGCTTAAGCCTCAATAAAGCTTGCCTTGAGTGCTTCAAGTAGTG

TGTGCCCGTCTGTTGTGTGACTCTGGTAACTAGAGATCCCTCAGACCCTTTTAGTCAG

TGTGGAAAATCTCTAGCAGTGGCGCCCGAACAGGGACCTGAAAGCGAAAGGGAAAC

-continued

CAGAGCTCTCTCGACGCAGGACTCGGCTTGCTGAAGCGCGCACGGCAAGAGGCGAG

GGGCGGCGACTGGTGAGTACGCCAAAAATTTTGACTAGCGGAGGCTAGAAGGAGAG

AGATGGGTGCGAGAGCGTCAGTATTAAGCGGGGGAGAATTAGATCGCGATGGGAAA

AAATTCGGTTAAGGCCAGGGGGAAAGAAAAAATATAAATTAAAACATATAGTATGG

GCAAGCAGGGAGCTAGAACGATTCGCAGTTAATCCTGGCCTGTTAGAAACATCAGA

AGGCTGTAGACAAATACTGGGACAGCTACAACCATCCCTTCAGACAGGATCAGAAG

AACTTAGATCATTATATAATACAGTAGCAACCCTCTATTGTGTGCATCAAAGGATAG

AGATAAAAGACACCAAGGAAGCTTTAGACAAGATAGAGGAAGAGCAAAACAAAAG

TAAGACCACCGCACAGCAAGCGGCCGCTGATCTTCAGACCTGGAGGAGGAGATATG

AGGGACAATTGGAGAAGTGAATTATATAAATATAAAGTAGTAAAAATTGAACCATT

AGGAGTAGCACCCACCAAGGCAAAGAGAAGAGTGGTGCAGAGAGAAAAAAGAGCA

GTGGGAATAGGAGCTTTGTTCCTTGGGTTCTTGGGAGCAGCAGGAAGCACTATGGGC

GCAGCCTCAATGACGCTGACGGTACAGGCCAGACAATTATTGTCTGGTATAGTGCAG

CAGCAGAACAATTTGCTGAGGGCTATTGAGGCGCAACAGCATCTGTTGCAACTCAC

AGTCTGGGGCATCAAGCAGCTCCAGGCAAGAATCCTGGCTGTGGAAAGATACCTAA

AGGATCAACAGCTCCTGGGGATTTGGGGTTGCTCTGGAAAACTCATTTGCACCACTG

CTGTGCCTTGGAATGCTAGTTGGAGTAATAAATCTCTGGAACAGATTTGGAATCACA

CGACCTGGATGGAGTGGGACAGAGAAATTAACAATTACACAAGCTTAATACACTCC

TTAATTGAAGAATCGCAAAACCAGCAAGAAAAGAATGAACAAGAATTATTGGAATT

AGATAAATGGGCAAGTTTGTGGAATTGGTTTAACATAACAAATTGGCTGTGGTATAT

AAAATTATTCATAATGATAGTAGGAGGCTTGGTAGGTTTAAGAATAGTTTTTGCTGT

ACTTTCTATAGTGAATAGAGTTAGGCAGGGATATTCACCATTATCGTTTCAGACCCA

CCTCCCAACCCCGAGGGGACCCGACAGGCCCGAAGGAATAGAAGAAGAAGGTGGA

GAGAGAGACAGAGACAGATCCATTCGATTAGTGAACGGATCTCGACGGTATCGGTT

AACTTTTAAAAGAAAAGGGGGGATTGGGGGGTACAGTGCAGGGGAAAGAATAGTA

GACATAATAGCAACAGACATACAAACTAAAGAATTACAAAAACAAATTACAAAAAT

TCAAAATTTTGGCTCCCGATCGTTGCGTTACACACACAATTACTGCTGATCGAGTGT

AGCCTTCGAACTCGAGTAGTTGTGAACTTACACTTTATTCATATATATTAGATATTGA

TAATTTTAACAAATGAGTTACTTTCCATTTGGGTACAGTCACAGTTGTCAACAATATT

TGGAAGCACCAGGCATGAAATCTCCTGAGATGCTATGTTTTCATCAGGGTCACCTGA

CACATTCAAGTTCTGTCTGACATGCCATTAAAGCACTGGCTCAGATTGCAGGCATAT

TTTCAAACCGGCAGTAACTGGATAGTATCACTTCACTTATAAGTGTTCATTGTATCAT

CAAGTGAAATAAACACACAACCCATGGGATCTTGCTTAGGTTGGCTGCCTAGTTGGC

CCCTGAGATAAAGCCTTGTAATCACATAGCCTTGCCTAATTAGTCAGAAAACAAAGG

ATTAAGTGAGACAGTCACAGGATATAGGAATTATAAATAATACATATATTAATAGA

TATTCATTTTCATTACACAAAAGTTGCTATTATAAATACTTATTTGATTGATGAGTCT

AAAAATATATTCCCCATATAAATAATGTTAAATATTAATAAATAGATTTAGATTTAA

AATTCAAATATTGCAGGCAGGACAACCACCCGGGTTAACTTGCATTCAAATATGACA

TTACCCTATCAATTGTAACGGCCCTGATTCTAAAAGCATGCAAAAGTATACACAGCT

TTATTTTTGTCTTGTAAAAATCAGGTTCTTCAAGAGAGCTTTTTGAGGAACCGTTTC

-continued

AGAATTAAAATTAAGAGCTTGCATCAGCTCATCAATAACGGCAAGCATATTCTGATC
AAGGAATATCTGTCGCTTGGGGTCCATCAAAAGTTTTGCGTTCATTGTCTTGAACTC
AACCTGGTACATCTTAAGATCTTCATATATAGAAGACAAGCACAGGGCCATCATAA
AGCTTGTTTTGCGGCTGGCCAAACAAGATCCATTGGTAATGAAAGAAGTCTCTCTGG
AATTGAGACAAGATTCGTTTTTAGTGAGTTCCAGTGGCAGGCATGCCTCCACGGTGG
ATGTTTTGTCCTTAGTAATATCTTCGTGGTCTATTTCCTCACTTGTGCAAGGGTAAAA
TTCAAGTGTTTGTCGGGCCTTCTGGAGCATGTTGGAGACAGCCCTAAGCAAGTTTTG
AGAGTGGTGAAGACATGGGAACATGCCTGGGTCTGGGGTTGCAACAGGCAAGTTCC
GAGAACCGCCCCCACCACCACCTGAGCATGGGACAGATGCCCATTCGCTCCAGCTA
GATGAGTAGTATCTGTCTTGGGCTCTGACACTTATGCTTGCGTTCTTTCTGCAAATGA
CTGTTGCAGACGTTTTATCAGTGAAAACCCGATCTTTCTTTTCCCTTTTTGATTTTCCT
TGCACCTGGACACAAAATGTCAAACTAAAGTAAGAGTGCGGAGTTGACCAGGTGTC
GGGGTACTCCCAAGAAACTTCAACCTGGCGTGAGTTCTTCAAAGGCTTAAGCTGCAG
ATTCTTCGGAGGATCGGGCTTGATAATGTCCCGGATAAAAAAGCTGCTCGTGTAATT
TTCATACTTCAACTTGTGTACGGCGTCAACCATCACCTCTATTGGCAGGCTCTCCTCT
GCTGCGGGGCAAGCGGAGTCTTCCTGGCATTCCACGCTATATTCGTATTCTTTGTTGT
CCCCCCGTACCCTCTCCGCAGAAAGCGTAGCAGCACCGCACGTTACACCTTGTGGGT
CACTGGAACCCCTACTAGACTTAACAGAAAACGTAAGATCCGTAGAGATTGTTGTCA
ACCACCAGCAAGTAAAGCGTCCGGAGTAATTTTTTGCTTCACAGCGCAGAAACGTTT
TGTTTTTGGGTTCTTTCTGATCCTTAAGGATATCTGTACTCCAAATGCCATCCTCTTTT
TTGTGCAGGAGCAGCAGGCTGTGAGAAAGGACCTCGCCTCCCTTATGGCACGTATAC
TGCCCGGCATCTCCAAACTCTTTTACCTGGATAGTAAGTGTTTTGCCGCTGCCAAGC
ACCTCTGAGCTTTGGTCCAGGGTCCAGGTTATCCCATCTTCTTCAGGTGTATCGCAGG
TGAGGACCACCATCTCGCCCGGTGCGTCGGGATACCAATCCAATTCAACAACATATA
CGTCTTTCTTAAGTTCCCAAATAGCGACCAATGGTGACGCCAGAAAAACAAGTGAG
AACCAAGAGATTACCAGTTGTTGATGGCACATGGTGGGAATTCCTGGAATTCGAGCT
TCCATTATATACCCTCTAGAGTCTAGATCTACGCCTTCTGTATGAAACAGTTTTTCCT
CCACGCCTTCTGTATGAAACAGTTTTTCCTCCACGCCTTCTGTATGAAACAGTTTTTC
CTCCGTTTAAACGTAAGTCATTGGTCTTAAAGGTAGCTTTATTTAGTCTCCAGAAAA
AGGGGGGAATGAAAGACCCCACCTGTAGGTTTGGCAAGCTAGGATCAAGGTTAGGA
ACAGAGAGACAGCAGAATATGGGCCAAACAGGATATCTGTGGTAAGCAGTTCCTGC
CCCGGCTCAGGGCCAAGAACAGTTGGAACAGCAGAATATGGGCCAAACAGGATATC
TGTGGTAAGCAGTTCCTGCCCCGGCTCAGGGCCAAGAACAGATGGTCCCCAGATGC
GGTCCCGCCCTCAGCAGTTTCTAGAGAACCATCAGATGTTTCCAGGGTGCCCCAAGG
ACCTGAAATGACCCTGTGCCTTATTTGAACTAACCAATCAGTTCGCTTCTCGCTTCTG
TTCGCGCGCTTCTGCTCCCCGAGCTCAATAAAAGAGCCCACGCTAGCGCTACCGGTC
GCCAAGATGGGGGCAGGTGCCACCGGCCGCGCAATGGATGGTCCGCGTCTACTGCT
GTTACTACTTCTGGGTGTGTCCCTTGGAGGTGCCAAAGAGGCATGCCCCACAGGTCT
ATACACACATAGCGGTGAATGCTGCAAAGCATGCAACCTGGGCGAAGGTGTGGCCC
AACCTTGTGGAGCCAATCAAACCGTTTGTGAGCCATGTCTGGACAGCGTGACGTTCT
CCGATGTTGTTAGCGCGACCGAGCCATGCAAACCGTGTACCGAGTGTGTTGGTCTCC

-continued

AAAGTATGTCGGCGCCGTGCGTGGAGGCCGACGACGCCGTGTGTCGCTGTGCCTAC

GGTTATTACCAGGATGAAACTACTGGTCGCTGTGAAGCGTGCCGCGTGTGTGAGGCG

GGCTCAGGCCTCGTGTTCTCCTGTCAGGACAAACAGAACACTGTGTGTGAAGAATGC

CCCGACGGTACTTATTCCGACGAGGCCAACCATGTGGACCCGTGTCTGCCCTGCACC

GTTTGCGAGGATACCGAGCGCCAGCTACGTGAGTGCACACGTTGGGCCGACGCCGA

GTGCGAGGAAATCCCTGGCCGTTGGATTACACGGTCCACACCACCAGAAGGCTCGG

ACAGCACAGCACCCAGCACTCAGGAACCTGAGGCACCTCCAGAACAAGACCTAATA

GCCAGCACTGTGGCAGGTGTTGTGACTACAGTGATGGGTAGCTCACAACCCGTTGTT

ACTCGAGGCACCACCGACAATCTAATTCCTGTCTATTGTTCCATCCTGGCTGCTGTGG

TTGTGGGTCTTGTTGCATATATAGCCTTCAAGAGGGGCAGCGGAGAGGGTAGGGGT

AGTCTTTTGACGTGTGGGGACGTCGAGGAAAATCCTGGGCCTGCCTTACCAGTGACC

GCCTTGCTCCTGCCGCTGGCCTTGCTGCTCCACGCCGCCAGGCCGGACATCGTGATG

ACCCAGAGCCCCGACAGCCTGGCCGTGAGCCTGGGCGAGAGGGCCACCATCAACTG

CAAGAGCAGCCAGAGCCTGCTGAACAGCGGCGACCAGAAGAACTACCTGACCTGGT

ACCAGCAGAAGCCCGGCCAGCCCCCCAAGCTGCTGATCTACTGGGCCAGCACCAGG

GAGAGCGGCGTGCCCGACAGGTTCAGCGGCAGCGGCAGCGGCACCGACTTCACCCT

GACCATCAGCAGCCTGCAGGCCGAGGACGTGGCCGTGTACTACTGCCAGAACGACT

ACAGCTACCCCCTGACCTTCGGCCAGGGCACCAAGGTGGAGATCAAGGGCGGCGGC

GGCAGCGGCGGCGGCGGCAGCGGCGGCGGCGGCAGCCAGGTGCAGCTGGTGCAGA

GCGGCGCCGAGGTGAAGAAGACCGGCAGCAGCGTGAAGGTGAGCTGCAAGGCCAG

CGGCTACACCTTCACCGACCACGCCATCCACTGGGTGAGGCAGGCCCCCGGCCAGG

CCCTGGAGTGGATGGGCCACTTCAGCCCCGGCAACACCGACATCAAGTACAACGAC

AAGTTCAAGGGCAGGGTGACCCTGACCGTGGACAGGAGCATGAGCACCGCCTACAT

GGAGCTGAGCAGCCTGAGGAGCGAGGACACCGCCATGTACTACTGCAAGACCAGCA

CCTTCTTCTTCGACTACTGGGGCCAGGGCACCATGGTGACCGTGAGCAGCACCACGA

CGCCAGCGCCGCGACCACCAACACCGGCGCCCACCATCGCGTCGCAGCCCCTGTCC

CTGCGCCCAGAGGCGTGCCGGCCAGCGGCGGGGGGCGCAGTGCACACGAGGGGGC

TGGACTTCGCCTGTGATATCTACATCTGGGCGCCCTTGGCCGGGACTTGTGGGGTCC

TTCTCCTGTCACTGGTTATCACCCTTTACTGCAAACGGGGCAGAAAGAAACTCCTGT

ATATATTCAAACAACCATTTATGAGACCAGTACAAACTACTCAAGAGGAAGATGGC

TGTAGCTGCCGATTTCCAGAAGAAGAAGAAGGAGGATGTGAACTGAGAGTGAAGTT

CAGCAGGAGCGCAGACGCCCCCGCGTACAAGCAGGGCCAGAACCAGCTCTATAACG

AGCTCAATCTAGGACGAAGAGAGGAGTACGATGTTTTGGACAAGAGACGTGGCCGG

GACCCTGAGATGGGGGGAAAGCCGAGAAGGAAGAACCCTCAGGAAGGCCTGTACA

ATGAACTGCAGAAAGATAAGATGGCGGAGGCCTACAGTGAGATTGGGATGAAAGG

CGAGCGCCGGAGGGGCAAGGGGCACGATGGCCTTTACCAGGGTCTCAGTACAGCCA

CCAAGGACACCTACGACGCCCTTCACATGCAGGCCCTGCCCCCTCGCTGAAGAGAC

GTCATAATCAGCCAGCGGCCGCGTCGACAATCAACCTCTGGATTACAAAATTTGTGA

AAGATTGACTGGTATTCTTAACTATGTTGCTCCTTTTACGCTATGTGGATACGCTGCT

TTAATGCCTTTGTATCATGCTATTGCTTCCCGTATGGCTTTCATTTTCTCCTCCTTGTA

-continued

```
TAAATCCTGGTTGCTGTCTCTTTATGAGGAGTTGTGGCCCGTTGTCAGGCAACGTGG

CGTGGTGTGCACTGTGTTTGCTGACGCAACCCCCACTGGTTGGGGCATTGCCACCAC

CTGTCAGCTCCTTTCCGGGACTTTCGCTTTCCCCCTCCCTATTGCCACGGCGGAACTC

ATCGCCGCCTGCCTTGCCCGCTGCTGGACAGGGGCTCGGCTGTTGGGCACTGACAAT

TCCGTGGTGTTGTCGGGGAAGCTGACGTCCTTTCCATGGCTGCTCGCCTGTGTTGCCA

CCTGGATTCTGCGCGGGACGTCCTTCTGCTACGTCCCTTCGGCCCTCAATCCAGCGG

ACCTTCCTTCCCGCGGCCTGCTGCCGGCTCTGCGGCCTCTTCCGCGTCTTCGCCTTCG

CCCTCAGACGAGTCGGATCTCCCTTTGGGCCGCCTCCCCGCCTGGAATTCGAGCTCG

GTACCTTTAAGACCAATGACTTACAAGGCAGCTGTAGATCTTAGCCACTTTTTAAAA

GAAAAGGGGGGACTGGAAGGGCTAATTCACTCCCAACGAAGACAAGATCTGCTTTT

TGCTTGTACTGGGTCTCTCTGGTTAGACCAGATCTGAGCCTGGGAGCTCTCTGGCTA

ACTAGGGAACCCACTGCTTAAGCCTCAATAAAGCTTGCCTTGAGTGCTTCAAGTAGT

GTGTGCCCGTCTGTTGTGTGACTCTGGTAACTAGAGATCCCTCAGACCCTTTTAGTCA

GTGTGGAAAATCTCTAGCAGTCCTGGCCAACGTGAGCACCGTGCTGACCTCCAAATA

TCGTTAAGCTGGAGCCTGGGAGCCGGCCTGGCCCTCCGCCCCCCCCACCCCCGCAGC

CCACCCCTGGTCTTTGAATAAAGTCTGAGTGAGTGGCCGACAGTGCCCGTGGAGTTC

TCGTGACCTGAGGTGCAGGGCCGGCGCTAGGGACACGTCCGTGCACGTGCCGAGGC

CCCCTGTGCAGCTGCAAGGGACAGGCCTAGCCCTGCAGGCCTAACTCCGCCCATCCC

GCCCCTAACTCCGCCCAGTTCCGCCCATTCTCCGCCTCATGGCTGACTAATTTTTTTT

ATTTATGCAGAGGCCGAGGCCGCCTCGGCCTCTGAGCTATTCCAGAAGTAGTGAGG

ACGCTTTTTTGGAGGCCGAGGCTTTTGCAAAGATCGAACAAGAGACAGGACCTGCA

GGTTAATTAAATTTAAATCATGTGAGCAAAAGGCCAGCAAAAGGCCAGGAACCGTA

AAAAGGCCGCGTTGCTGGCGTTTTTCCATAGGCTCCGCCCCCCTGACGAGCATCACA

AAAATCGACGCTCAAGTCAGAGGTGGCGAAACCCGACAGGACTATAAAGATACCAG

GCGTTTCCCCCTGGAAGCTCCCTCGTGCGCTCTCCTGTTCCGACCCTGCCGCTTACCG

GATACCTGTCCGCCTTTCTCCCTTCGGGAAGCGTGGCGCTTTCTCATAGCTCACGCTG

TAGGTATCTCAGTTCGGTGTAGGTCGTTCGCTCCAAGCTGGGCTGTGTGCACGAACC

CCCCGTTCAGCCCGACCGCTGCGCCTTATCCGGTAACTATCGTCTTGAGTCCAACCC

GGTAAGACACGACTTATCGCCACTGGCAGCAGCCACTGGTAACAGGATTAGCAGAG

CGAGGTATGTAGGCGGTGCTACAGAGTTCTTGAAGTGGTGGCCTAACTACGGCTACA

CTAGAAGAACAGTATTTGGTATCTGCGCTCTGCTGAAGCCAGTTACCTTCGGAAAAA

GAGTTGGTAGCTCTTGATCCGGCAAACAAACCACCGCTGGTAGCGGTGGTTTTTTTG

TTTGCAAGCAGCAGATTACGCGCAGAAAAAAAGGATCTCAAGAAGATCCTTTGATC

TTTTCTACGGGGTCTGACGCTCAGTGGAACGAAAACTCACGTTAAGGGATTTTGGTC

ATGAGATTATCAAAAAGGATCTTCACCTAGATCCTTTTAAATTAAAAATGAAGTTTT

AAATCAATCTAAAGTATATATGAGTAAACTTGGTCTGACAGTTACCAATGCTTAATC

AGTGAGGCACCTATCTCAGCGATCTGTCTATTTCGTTCATCCATAGTTGCATTTAAAT

GGCCGGCCTGGCGCGCCGTTTAAACCTAGATATTGATAGTCTGATCGGTCAACGTAT

AATCGAGTCCTAGCTTTTGCAAACATCTATCAAGAGACAGGATCAGCAGGAGGCTTT

CGCATGATTGAACAAGATGGATTGCACGCAGGTTCTCCGGCGGCTTGGGTGGAGAG

GCTATTCGGCTATGACTGGGCACAACAGACAATCGGCTGCTCTGATGCCGCCGTGTT
```

-continued

CCGGCTGTCAGCGCAGGGGCGTCCGGTTCTTTTTGTCAAGACCGACCTGTCCGGTGC

CCTGAATGAACTGCAAGACGAGGCAGCGCGGCTATCGTGGCTGGCGACGACGGGCG

TTCCTTGCGCGGCTGTGCTCGACGTTGTCACTGAAGCGGGAAGGGACTGGCTGCTAT

TGGGCGAAGTGCCGGGGCAGGATCTCCTGTCATCTCACCTTGCTCCTGCCGAGAAAG

TATCCATCATGGCTGATGCAATGCGGCGGCTGCATACGCTTGATCCGGCTACCTGCC

CATTCGACCACCAAGCGAAACATCGCATCGAGCGAGCACGTACTCGGATGGAAGCC

GGTCTTGTCGATCAGGATGATCTGGACGAAGAGCATCAGGGGCTCGCGCCAGCCGA

ACTGTTCGCCAGGCTCAAGGCGTCTATGCCCGACGGCGAGGATCTCGTCGTGACCCA

CGGCGATGCCTGCTTGCCGAATATCATGGTGGAAAATGGCCGCTTTTCTGGATTCAT

CGACTGTGGCCGTCTGGGTGTGGCGGACCGCTATCAGGACATAGCGTTGGCTACCCG

TGATATTGCTGAAGAGCTTGGCGGCGAATGGGCTGACCGCTTCCTTGTGCTTTACGG

TATCGCCGCGCCCGATTCGCAGCGCATCGCCTTCTATCGCCTTCTTGACGAGTTCTTC

TGACCGATTCTAGGTGCATTGGCGCAGAAAAAAATGCCTGATGCGACGCTGCGCGT

CTTATACTCCCACATATGCCAGATTCAGCAACGGATACGGCTTCCCCAACTTGCCCA

CTTCCATACGTGTCCTCCTTACCAGAAATTTATCCTTAAGGTCGTTTAAAC

PD009

(SEQ ID NO: 14)

GCGATCGCAGTAATCAATTACGGGGTCATTAGTTCATAGCCCATATATGGAGTTCCG

CGTTACATAACTTACGGTAAATGGCCCGCCTGGCTGACCGCCCAACGACCCCCGCCC

ATTGACGTCAATAATGACGTATGTTCCCATAGTAACGCCAATAGGGACTTTCCATTG

ACGTCAATGGGTGGAGTATTTACGGTAAACTGCCCACTTGGCAGTACATCAAGTGTA

TCATATGCCAAGTACGCCCCCTATTGACGTCAATGACGGTAAATGGCCCGCCTGGCA

TTATGCCCAGTACATGACCTTATGGGACTTTCCTACTTGGCAGTACATCTACGTATTA

GTCATCGCTATTACCATGGTGATGCGGTTTTGGCAGTACATCAATGGGCGTGGATAG

CGGTTTGACTCACGGGGATTTCCAAGTCTCCACCCCATTGACGTCAATGGGAGTTTG

TTTTGGCACCAAAATCAACGGGACTTTCCAAAATGTCGTAACAACTCCGCCCCATTG

ACGCAAATGGGCGGTAGGCGTGTACGGTGGGAGGTCTATATAAGCAGAGCTCGTTT

AGTGAACCGGGGTCTCTCTGGTTAGACCAGATCTGAGCCTGGGAGCTCTCTGGCTAA

CTAGGGAACCCACTGCTTAAGCCTCAATAAAGCTTGCCTTGAGTGCTTCAAGTAGTG

TGTGCCCGTCTGTTGTGTGACTCTGGTAACTAGAGATCCCTCAGACCCTTTTAGTCAG

TGTGGAAAATCTCTAGCAGTGGCGCCCGAACAGGGACCTGAAAGCGAAAGGGAAAC

CAGAGCTCTCTCGACGCAGGACTCGGCTTGCTGAAGCGCGCACGGCAAGAGGCGAG

GGGCGGCGACTGGTGAGTACGCCAAAAATTTTGACTAGCGGAGGCTAGAAGGAGAG

AGATGGGTGCGAGAGCGTCAGTATTAAGCGGGGGAGAATTAGATCGCGATGGGAAA

AAATTCGGTTAAGGCCAGGGGGAAAGAAAAAATATAAATTAAAACATATAGTATGG

GCAAGCAGGGAGCTAGAACGATTCGCAGTTAATCCTGGCCTGTTAGAAACATCAGA

AGGCTGTAGACAAATACTGGGACAGCTACAACCATCCCTTCAGACAGGATCAGAAG

AACTTAGATCATTATATAATACAGTAGCAACCCTCTATTGTGTGCATCAAAGGATAG

AGATAAAAGACACCAAGGAAGCTTTAGACAAGATAGAGGAAGAGCAAAACAAAAG

TAAGACCACCGCACAGCAAGCGGCCGCTGATCTTCAGACCTGGAGGAGGAGATATG

AGGGACAATTGGAGAAGTGAATTATATAAATATAAAGTAGTAAAAATTGAACCATT

-continued

AGGAGTAGCACCCACCAAGGCAAAGAGAAGAGTGGTGCAGAGAGAAAAAAGAGCA

GTGGGAATAGGAGCTTTGTTCCTTGGGTTCTTGGGAGCAGCAGGAAGCACTATGGGC

GCAGCCTCAATGACGCTGACGGTACAGGCCAGACAATTATTGTCTGGTATAGTGCAG

CAGCAGAACAATTTGCTGAGGGCTATTGAGGCGCAACAGCATCTGTTGCAACTCAC

AGTCTGGGGCATCAAGCAGCTCCAGGCAAGAATCCTGGCTGTGGAAAGATACCTAA

AGGATCAACAGCTCCTGGGGATTTGGGGTTGCTCTGGAAAACTCATTTGCACCACTG

CTGTGCCTTGGAATGCTAGTTGGAGTAATAAATCTCTGGAACAGATTTGGAATCACA

CGACCTGGATGGAGTGGGACAGAGAAATTAACAATTACACAAGCTTAATACACTCC

TTAATTGAAGAATCGCAAAACCAGCAAGAAAAGAATGAACAAGAATTATTGGAATT

AGATAAATGGGCAAGTTTGTGGAATTGGTTTAACATAACAAATTGGCTGTGGTATAT

AAAATTATTCATAATGATAGTAGGAGGCTTGGTAGGTTTAAGAATAGTTTTTGCTGT

ACTTTCTATAGTGAATAGAGTTAGGCAGGGATATTCACCATTATCGTTTCAGACCCA

CCTCCCAACCCCGAGGGGACCCGACAGGCCCGAAGGAATAGAAGAAGAAGGTGGA

GAGAGAGACAGAGACAGATCCATTCGATTAGTGAACGGATCTCGACGGTATCGGTT

AACTTTTAAAAGAAAAGGGGGGATTGGGGGGTACAGTGCAGGGGAAAGAATAGTA

GACATAATAGCAACAGACATACAAACTAAAGAATTACAAAAACAAATTACAAAAAT

TCAAAATTTTGGCTCCCGATCGTTGCGTTACACACACAATTACTGCTGATCGAGTGT

AGCCTTCGAACTCGAGTAGTTGTGAACTTACACTTTATTCATATATATTAGATATTGA

TAATTTTAACAAATGAGTTACTTTCCATTTGGGTACAGTCACAGTTGTCAACAATATT

TGGAAGCACCAGGCATGAAATCTCCTGAGATGCTATGTTTTCATCAGGGTCACCTGA

CACATTCAAGTTCTGTCTGACATGCCATTAAAGCACTGGCTCAGATTGCAGGCATAT

TTTCAAACCGGCAGTAACTGGATAGTATCACTTCACTTATAAGTGTTCATTGTATCAT

CAAGTGAAATAAACACACAACCCATGGGATCTTGCTTAGGTTGGCTGCCTAGTTGGC

CCCTGAGATAAAGCCTTGTAATCACATAGCCTTGCCTAATTAGTCAGAAAACAAAGG

ATTAAGTGAGACAGTCACAGGATATAGGAATTATAAATAATACATATATTAATAGA

TATTCATTTTCATTACACAAAAGTTGCTATTATAAATACTTATTTGATTGATGAGTCT

AAAAATATATTCCCCATATAAATAATGTTAAATATTAATAAATAGATTTAGATTTAA

AATTCAAATATTGCAGGCAGGACAACCACCCGGGTTAACTTGCATTCAAATATGACA

TTACCCTATCAATTGTAACGGCCCTGATTCTAAAAGCATGCAAAAGTATACACAGCT

TTATTTTTGTCTTGTAAAAATCAGGTTCTTCAAGAGAGCTTTTTTGAGGAACCGTTTC

AGAATTAAAATTAAGAGCTTGCATCAGCTCATCAATAACGGCAAGCATATTCTGATC

AAGGAATATCTGTCGCTTGGGGTCCATCAAAAGTTTTGCGTTCATTGTCTTGAACTC

AACCTGGTACATCTTAAGATCTTCATATATAGAAGACAAGCACAGGGCCATCATAA

AGCTTGTTTTGCGGCTGGCCAAACAAGATCCATTGGTAATGAAAGAAGTCTCTCTGG

AATTGAGACAAGATTCGTTTTTAGTGAGTTCCAGTGGCAGGCATGCCTCCACGGTGG

ATGTTTTGTCCTTAGTAATATCTTCGTGGTCTATTTCCTCACTTGTGCAAGGGTAAAA

TTCAAGTGTTTGTCGGGCCTTCTGGAGCATGTTGGAGACAGCCCTAAGCAAGTTTTG

AGAGTGGTGAAGACATGGGAACATGCCTGGGTCTGGGGTTGCAACAGGCAAGTTCC

GAGAACCGCCCCCACCACCACCTGAGCATGGGACAGATGCCCATTCGCTCCAGCTA

GATGAGTAGTATCTGTCTTGGGCTCTGACACTTATGCTTGCGTTCTTTCTGCAAATGA

CTGTTGCAGACGTTTTATCAGTGAAAACCCGATCTTTCTTTTCCCTTTTTGATTTTCCT

-continued

TGCACCTGGACACAAAATGTCAAACTAAAGTAAGAGTGCGGAGTTGACCAGGTGTC

GGGGTACTCCCAAGAAACTTCAACCTGGCGTGAGTTCTTCAAAGGCTTAAGCTGCAG

ATTCTTCGGAGGATCGGGCTTGATAATGTCCCGGATAAAAAAGCTGCTCGTGTAATT

TTCATACTTCAACTTGTGTACGGCGTCAACCATCACCTCTATTGGCAGGCTCTCCTCT

GCTGCGGGGCAAGCGGAGTCTTCCTGGCATTCCACGCTATATTCGTATTCTTTGTTGT

CCCCCCGTACCCTCTCCGCAGAAAGCGTAGCAGCACCGCACGTTACACCTTGTGGGT

CACTGGAACCCCTACTAGACTTAACAGAAAACGTAAGATCCGTAGAGATTGTTGTCA

ACCACCAGCAAGTAAAGCGTCCGGAGTAATTTTTTGCTTCACAGCGCAGAAACGTTT

TGTTTTTGGGTTCTTTCTGATCCTTAAGGATATCTGTACTCCAAATGCCATCCTCTTTT

TTGTGCAGGAGCAGCAGGCTGTGAGAAAGGACCTCGCCTCCCTTATGGCACGTATAC

TGCCCGGCATCTCCAAACTCTTTTACCTGGATAGTAAGTGTTTTGCCGCTGCCAAGC

ACCTCTGAGCTTTGGTCCAGGGTCCAGGTTATCCCATCTTCTTCAGGTGTATCGCAGG

TGAGGACCACCATCTCGCCCGGTGCGTCGGGATACCAATCCAATTCAACAACATATA

CGTCTTTCTTAAGTTCCCAAATAGCGACCAATGGTGACGCCAGAAAAACAAGTGAG

AACCAAGAGATTACCAGTTGTTGATGGCACATGGTGGGAATTCGGCTGTCCCAGCAC

CTCAGCGCAGAGCAAGTGGTGGTCAGGGGAGCGTCTCAAATCCTGCGCAGCCCAAC

GTCCGGCGCCGCCAAGTGACGCACGAGGTGCTGTGACTCGTGCCAGCCCCCTAATCT

GCGGAAGTGGAGTGCGGGGAGTGCGCCGGAAGAGGGGTACGGAAGTGCGCCGGAA

GTGGGGTGCGGAGGTGTGCAGCGCGCTGTCAGACTGGCTCGCAGGCGGCGCGGCCG

GCGGACCCGTTCGAGACAGCGCGGGCGGCTCGGGTCCCCTGGGGCTCCGCAGCAGG

AGGACGCCGCTAGCGCTACCGGTCGCCAAGATGGGGGCAGGTGCCACCGGCCGCGC

CATGGACGGGCCGCGCCTGCTGCTGTTGCTGCTTCTGGGGGTGTCCCTTGGAGGTGC

CAAGGAGGCATGCCCCACAGGCCTGTACACACACAGCGGTGAGTGCTGCAAAGCCT

GCAACCTGGGCGAGGGTGTGGCCCAGCCTTGTGGAGCCAACCAGACCGTGTGTGAG

CCCTGCCTGGACAGCGTGACGTTCTCCGACGTGGTGAGCGCGACCGAGCCGTGCAA

GCCGTGCACCGAGTGCGTGGGGCTCCAGAGCATGTCGGCGCCGTGCGTGGAGGCCG

ACGACGCCGTGTGCCGCTGCGCCTACGGCTACTACCAGGATGAGACGACTGGGCGC

TGCGAGGCGTGCCGCGTGTGCGAGGCGGGCTCGGGCCTCGTGTTCTCCTGCCAGGAC

AAGCAGAACACCGTGTGCGAGGAGTGCCCCGACGGCACGTATTCCGACGAGGCCAA

CCACGTGGACCCGTGCCTGCCCTGCACCGTGTGCGAGGACACCGAGCGCCAGCTCC

GCGAGTGCACACGCTGGGCCGACGCCGAGTGCGAGGAGATCCCTGGCCGTTGGATT

ACACGGTCCACACCCCCAGAGGGCTCGGACAGCACAGCCCCCAGCACCCAGGAGCC

TGAGGCACCTCCAGAACAAGACCTCATAGCCAGCACGGTGGCAGGTGTGGTGACCA

CAGTGATGGGCAGCTCCCAGCCCGTGGTGACCCGAGGCACCACCGACAACCTCATC

CCTGTCTATTGCTCCATCCTGGCTGCTGTGGTTGTGGGTCTTGTGGCCTACATAGCCT

TCAAGAGGGGCAGCGGAGAGGGTAGGGGTAGTCTTTTGACGTGTGGGGACGTCGAG

GAAAATCCTGGGCCTGCCTTACCAGTGACCGCCTTGCTCCTGCCGCTGGCCTTGCTG

CTCCACGCCGCCAGGCCGGACATCGTGATGACCCAGAGCCCCGACAGCCTGGCCGT

GAGCCTGGGCGAGAGGGCCACCATCAACTGCAAGAGCAGCCAGAGCCTGCTGAACA

GCGGCGACCAGAAGAACTACCTGACCTGGTACCAGCAGAAGCCCGGCCAGCCCCCC

-continued

AAGCTGCTGATCTACTGGGCCAGCACCAGGGAGAGCGGCGTGCCCGACAGGTTCAG

CGGCAGCGGCAGCGGCACCGACTTCACCCTGACCATCAGCAGCCTGCAGGCCGAGG

ACGTGGCCGTGTACTACTGCCAGAACGACTACAGCTACCCCCTGACCTTCGGCCAGG

GCACCAAGGTGGAGATCAAGGGCGGCGGCGGCAGCGGCGGCGGCGGCAGCGGCGG

CGGCGGCAGCCAGGTGCAGCTGGTGCAGAGCGGCGCCGAGGTGAAGAAGACCGGC

AGCAGCGTGAAGGTGAGCTGCAAGGCCAGCGGCTACACCTTCACCGACCACGCCAT

CCACTGGGTGAGGCAGGCCCCCGGCCAGGCCCTGGAGTGGATGGGCCACTTCAGCC

CCGGCAACACCGACATCAAGTACAACGACAAGTTCAAGGGCAGGGTGACCCTGACC

GTGGACAGGAGCATGAGCACCGCCTACATGGAGCTGAGCAGCCTGAGGAGCGAGG

ACACCGCCATGTACTACTGCAAGACCAGCACCTTCTTCTTCGACTACTGGGGCCAGG

GCACCATGGTGACCGTGAGCAGCACCACGACGCCAGCGCCGCGACCACCAACACCG

GCGCCCACCATCGCGTCGCAGCCCCTGTCCCTGCGCCCAGAGGCGTGCCGGCCAGC

GGCGGGGGGCGCAGTGCACACGAGGGGGCTGGACTTCGCCTGTGATATCTACATCT

GGGCGCCCTTGGCCGGGACTTGTGGGGTCCTTCTCCTGTCACTGGTTATCACCCTTTA

CTGCAAACGGGGCAGAAAGAAACTCCTGTATATATTCAAACAACCATTTATGAGAC

CAGTACAAACTACTCAAGAGGAAGATGGCTGTAGCTGCCGATTTCCAGAAGAAGAA

GAAGGAGGATGTGAACTGAGAGTGAAGTTCAGCAGGAGCGCAGACGCCCCCGCGTA

CAAGCAGGGCCAGAACCAGCTCTATAACGAGCTCAATCTAGGACGAAGAGAGGAGT

ACGATGTTTTGGACAAGAGACGTGGCCGGGACCCTGAGATGGGGGGAAAGCCGAGA

AGGAAGAACCCTCAGGAAGGCCTGTACAATGAACTGCAGAAAGATAAGATGGCGG

AGGCCTACAGTGAGATTGGGATGAAAGGCGAGCGCCGGAGGGGCAAGGGGCACGA

TGGCCTTTACCAGGGTCTCAGTACAGCCACCAAGGACACCTACGACGCCCTTCACAT

GCAGGCCCTGCCCCCTCGCTGAAGAGACGTCATAATCAGCCAGCGGCCGCGTCGAC

AATCAACCTCTGGATTACAAAATTTGTGAAAGATTGACTGGTATTCTTAACTATGTT

GCTCCTTTTACGCTATGTGGATACGCTGCTTTAATGCCTTTGTATCATGCTATTGCTT

CCCGTATGGCTTTCATTTTCTCCTCCTTGTATAAATCCTGGTTGCTGTCTCTTTATGAG

GAGTTGTGGCCCGTTGTCAGGCAACGTGGCGTGGTGTGCACTGTGTTTGCTGACGCA

ACCCCCACTGGTTGGGGCATTGCCACCACCTGTCAGCTCCTTTCCGGGACTTTCGCTT

TCCCCCTCCCTATTGCCACGGCGGAACTCATCGCCGCCTGCCTTGCCCGCTGCTGGA

CAGGGGCTCGGCTGTTGGGCACTGACAATTCCGTGGTGTTGTCGGGGAAGCTGACGT

CCTTTCCATGGCTGCTCGCCTGTGTTGCCACCTGGATTCTGCGCGGGACGTCCTTCTG

CTACGTCCCTTCGGCCCTCAATCCAGCGGACCTTCCTTCCCGCGGCCTGCTGCCGGCT

CTGCGGCCTCTTCCGCGTCTTCGCCTTCGCCCTCAGACGAGTCGGATCTCCCTTTGGG

CCGCCTCCCCGCCTGGAATTCGAGCTCGGTACCTTTAAGACCAATGACTTACAAGGC

AGCTGTAGATCTTAGCCACTTTTTAAAAGAAAAGGGGGGACTGGAAGGGCTAATTC

ACTCCCAACGAAGACAAGATCTGCTTTTTGCTTGTACTGGGTCTCTCTGGTTAGACC

AGATCTGAGCCTGGGAGCTCTCTGGCTAACTAGGGAACCCACTGCTTAAGCCTCAAT

AAAGCTTGCCTTGAGTGCTTCAAGTAGTGTGTGCCCGTCTGTTGTGTGACTCTGGTA

ACTAGAGATCCCTCAGACCCTTTTAGTCAGTGTGGAAAATCTCTAGCAGTCCTGGCC

AACGTGAGCACCGTGCTGACCTCCAAATATCGTTAAGCTGGAGCCTGGGAGCCGGC

CTGGCCCTCCGCCCCCCCCACCCCCGCAGCCCACCCCTGGTCTTTGAATAAAGTCTG

-continued

AGTGAGTGGCCGACAGTGCCCGTGGAGTTCTCGTGACCTGAGGTGCAGGGCCGGCG

CTAGGGACACGTCCGTGCACGTGCCGAGGCCCCCTGTGCAGCTGCAAGGGACAGGC

CTAGCCCTGCAGGCCTAACTCCGCCCATCCCGCCCCTAACTCCGCCCAGTTCCGCCC

ATTCTCCGCCTCATGGCTGACTAATTTTTTTTATTTATGCAGAGGCCGAGGCCGCCTC

GGCCTCTGAGCTATTCCAGAAGTAGTGAGGACGCTTTTTTGGAGGCCGAGGCTTTTG

CAAAGATCGAACAAGAGACAGGACCTGCAGGTTAATTAAATTTAAATCATGTGAGC

AAAAGGCCAGCAAAAGGCCAGGAACCGTAAAAAGGCCGCGTTGCTGGCGTTTTTCC

ATAGGCTCCGCCCCCCTGACGAGCATCACAAAAATCGACGCTCAAGTCAGAGGTGG

CGAAACCCGACAGGACTATAAAGATACCAGGCGTTTCCCCCTGGAAGCTCCCTCGT

GCGCTCTCCTGTTCCGACCCTGCCGCTTACCGGATACCTGTCCGCCTTTCTCCCTTCG

GGAAGCGTGGCGCTTTCTCATAGCTCACGCTGTAGGTATCTCAGTTCGGTGTAGGTC

GTTCGCTCCAAGCTGGGCTGTGTGCACGAACCCCCCGTTCAGCCCGACCGCTGCGCC

TTATCCGGTAACTATCGTCTTGAGTCCAACCCGGTAAGACACGACTTATCGCCACTG

GCAGCAGCCACTGGTAACAGGATTAGCAGAGCGAGGTATGTAGGCGGTGCTACAGA

GTTCTTGAAGTGGTGGCCTAACTACGGCTACACTAGAAGAACAGTATTTGGTATCTG

CGCTCTGCTGAAGCCAGTTACCTTCGGAAAAAGAGTTGGTAGCTCTTGATCCGGCAA

ACAAACCACCGCTGGTAGCGGTGGTTTTTTTGTTTGCAAGCAGCAGATTACGCGCAG

AAAAAAAGGATCTCAAGAAGATCCTTTGATCTTTTCTACGGGGTCTGACGCTCAGTG

GAACGAAAACTCACGTTAAGGGATTTTGGTCATGAGATTATCAAAAAGGATCTTCAC

CTAGATCCTTTTAAATTAAAAATGAAGTTTTAAATCAATCTAAAGTATATATGAGTA

AACTTGGTCTGACAGTTACCAATGCTTAATCAGTGAGGCACCTATCTCAGCGATCTG

TCTATTTCGTTCATCCATAGTTGCATTTAAATGGCCGGCCTGGCGCGCCGTTTAAACC

TAGATATTGATAGTCTGATCGGTCAACGTATAATCGAGTCCTAGCTTTTGCAAACAT

CTATCAAGAGACAGGATCAGCAGGAGGCTTTCGCATGATTGAACAAGATGGATTGC

ACGCAGGTTCTCCGGCGGCTTGGGTGGAGAGGCTATTCGGCTATGACTGGGCACAA

CAGACAATCGGCTGCTCTGATGCCGCCGTGTTCCGGCTGTCAGCGCAGGGGCGTCCG

GTTCTTTTTGTCAAGACCGACCTGTCCGGTGCCCTGAATGAACTGCAAGACGAGGCA

GCGCGGCTATCGTGGCTGGCGACGACGGGCGTTCCTTGCGCGGCTGTGCTCGACGTT

GTCACTGAAGCGGGAAGGGACTGGCTGCTATTGGGCGAAGTGCCGGGGCAGGATCT

CCTGTCATCTCACCTTGCTCCTGCCGAGAAAGTATCCATCATGGCTGATGCAATGCG

GCGGCTGCATACGCTTGATCCGGCTACCTGCCCATTCGACCACCAAGCGAAACATCG

CATCGAGCGAGCACGTACTCGGATGGAAGCCGGTCTTGTCGATCAGGATGATCTGG

ACGAAGAGCATCAGGGGCTCGCGCCAGCCGAACTGTTCGCCAGGCTCAAGGCGTCT

ATGCCCGACGGCGAGGATCTCGTCGTGACCCACGGCGATGCCTGCTTGCCGAATATC

ATGGTGGAAAATGGCCGCTTTTCTGGATTCATCGACTGTGGCCGTCTGGGTGTGGCG

GACCGCTATCAGGACATAGCGTTGGCTACCCGTGATATTGCTGAAGAGCTTGGCGGC

GAATGGGCTGACCGCTTCCTTGTGCTTTACGGTATCGCCGCGCCCGATTCGCAGCGC

ATCGCCTTCTATCGCCTTCTTGACGAGTTCTTCTGACCGATTCTAGGTGCATTGGCGC

-continued

AGAAAAAAATGCCTGATGCGACGCTGCGCGTCTTATACTCCCACATATGCCAGATTC

AGCAACGGATACGGCTTCCCCAACTTGCCCACTTCCATACGTGTCCTCCTTACCAGA

AATTTATCCTTAAGGTCGTTTAAAC

The GC160 (SEQ ID NO: 4) construct is a monocistronic construct encoding a PGK promoter expressing mCherry T2A SEQ ID NO: 3 (signal sequence) and SEQ ID NO: 1 (CAR).

The GC213 (SEQ ID NO: 5) construct is a bicistronic construct encoding a NFAT promoter expressing IL-12 under the control of an IFNg gold element in one strand, and a MND promoter expressing LNGFR (53) T2A SEQ ID NO: 3 (signal sequence) and SEQ ID NO: 1 (CAR). The nucleic acid encoding LNGFR in GC213 has been modified to decrease the GC content of the third position in all the codons to 53%. This reduction in GC content of the LNGFR reduces expression of LNGFR, and this also reduces the expression of the CAR.

The GC217 (SEQ ID NO: 6) construct is a NFAT promoter expressing dominant negative TGFBR2 (TGF beta receptor 2) under the control of an IFNg gold element in one strand, and a MND promoter expressing LNGFR (53% GC content of the third position of all codons) T2A SEQ ID NO: 3 (signal sequence) and SEQ ID NO: 1 (CAR).

The GC219 (SEQ ID NO: 7) construct is a bicistronic construct encoding a NFAT promoter expressing mutant IL18 (TL18 modified to reduce its affinity for IL-18 binding protein, e.g., SEQ ID NO: 15) under the control of an IFNg gold element in one strand, and a MND promoter expressing LNGFR (53% GC content of the third position of all codons) T2A SEQ ID NO: 3 (signal sequence) and SEQ ID NO: 1 (CAR).

Mature Variant IL-18

(SEQ ID NO: 15)

YFGKLESKLSVIRNLNDQVLFIDQGNRPLFEDMTDSDCRDNAPRTIFII

SMYKDSQPRGMAVTISVKCEKISTLSCENKIISFKEMNPPDNIKDTKSD

IIFFQRSVPGHDNKMQFESSSYEGYFLACEKERDLFKLILKKEDELGDR

SIMFTVQNED

Prepro-Variant IL-18

(SEQ ID NO: 16)

MAAEPVEDNCINFVAMKFIDNTLYFIAEDDENLESDYFGKLESKLSVIR

NLNDQVLFIDQGNRPLFEDMTDSDCRDNAPRTIFIISMYKDSQPRGMAV

TISVKCEKISTLSCENKIISFKEMNPPDNIKDTKSDIIFFQRSVPGHDN

KMQFESSSYEGYFLACEKERDLFKLILKKEDELGDRSIMFTVQNED

The IL-18 variants have one or more of the following changes in SEQ ID NO: 15, M51A, K53G, Q56R, P57A and/or M60K (numbering is for the mature, active IL-18, after secretion expression and caspase-1 processing). Alternative numbering from the full-length, unprocessed protein of SEQ ID NO: 16 are M87A, K89G, Q92R, P93A and/or M96K.

The GC223 (SEQ ID NO: 8) construct is a bicistronic construct encoding a NFAT promoter expressing eIL-2 (GC3 enriched) under the control of an IFNg gold element in one strand, and a MND promoter expressing LNGFR (53% GC content of the third position of all codons) T2A SEQ ID NO: 3 (signal sequence) and SEQ ID NO: 1 (CAR).

The SK062 (SEQ ID NO: 9) construct is a bicistronic construct encoding a NFAT promoter expressing secreted luciferase under the control of an IFNg gold element in one strand, and a MND promoter expressing LNGFR (83) T2A SEQ ID NO: 3 (signal sequence) and SEQ ID NO: 1 (CAR). The LNGFR in SK062 has 83% GC content in the third position of the codons.

The SK148 (SEQ ID NO: 10) construct is a bicistronic construct encoding a NFAT promoter expressing IL-12 under the control of an IFNg gold element in one strand, and a MND promoter expressing LNGFR (83) T2A SEQ ID NO: 3 (signal sequence) and SEQ ID NO: 1 (CAR). The LNGFR in SK148 has 83% GC content in the third position of the codons.

The SK072 (SEQ ID NO: 11) construct is a bicistronic construct encoding a NFAT promoter expressing secreted luciferase under the control of an IFNg gold element in one strand, and a MND promoter expressing LNGFR (53) T2A SEQ ID NO: 3 (signal sequence) and SEQ ID NO: 1 (CAR). The LNGFR in SK062 has 53% GC content in the third position of the codons.

The GC251 (SEQ ID NO: 12) construct is a bicistronic construct encoding an eIF2B1 promoter expressing IL-12 under the control of an IFNg gold element in one strand, and a GTF2H3 promoter expressing LNGFR (83) T2A SEQ ID NO: 3 (signal sequence) and SEQ ID NO: 1 (CAR). The nucleic acid encoding LNGFR in GC251 has been modified to increase the GC content of the third position in all the codons to 83%. This increase in GC content of the LNGFR increases expression of LNGFR, and this also increases the expression of the CAR.

PD007 (SEQ ID NO: 13) is a bicistronic construct encoding a NFAT promoter expressing IL-12 under the control of an IFNg gold element in one strand, and a MND promoter expressing LNGFR (53) T2A SEQ ID NO: 3 (signal sequence) and SEQ ID NO: 1 (CAR). The nucleic acid encoding LNGFR in PD007 has been modified to decrease the GC content of the third position in all the codons to 53%. This reduction in GC content of the LNGFR reduces expression of LNGFR, and this also reduces the expression of the CAR.

The PD009 (SEQ ID NO: 14) construct is a bicistronic construct encoding an eIF2B1 promoter expressing IL-12 under the control of an IFNg gold element in one strand, and a GTF2H3 promoter expressing LNGFR (83) T2A SEQ ID NO: 3 (signal sequence) and SEQ ID NO: 1 (CAR). The nucleic acid encoding LNGFR in GC251 has been modified to increase the GC content of the third position in all the codons to 83%. This increase in GC content of the LNGFR increases expression of LNGFR, and this also increases the expression of the CAR.

In an aspect, the bidirectional promoters in the above constructs can be replaced by the mol2 bidirectional promoter that has the promoter from EIF2B1 (eukaryotic translation initiation factor 2B subunit alpha) and the promoter from GTF2H3 (General transcription factor IIH subunit 3). In these constructs, the EIF2B1 promoter transcribes the payload, and the GTF2H3 promoter transcribes the CAR (and LNGFR). The smol2 bidirectional promoter reduces the baseline expression of the payload, and increases the dynamic range of expression (the fold increase in expression from non-induced to induced expression).

Notch Inhibitors and Modulators

Notch can be an immunological checkpoint in T-cells. The methods and compositions for modifying Notch related suppression of T-cells can be combined with other checkpoint inhibitors and/or other immune-therapies to treat many solid tumors. In a context dependent manner, Notch signals can promote or suppress cell proliferation, cell death, acquisition of specific cell fates, or activation of differentiation programs.

Binding of ligand to Notch receptors on T-cells has been shown to inhibit activation and proliferation of the T-cells. Notch receptor can be phosphorylated at multiple sites, and phosphorylation can play a role in signal transduction. Notch receptor signaling in T-cells can suppress activation and proliferation of naïve T-cells. The phosphorylation of GSK-3β and AKT are inhibited with rapid kinetics after Notch receptors engage ligand. GSK-3β is a component of Notch signaling and its phosphorylation is dependent on AKT. AKT is also essential to T-cell activation, proliferation and cytokine production. Antagonists of GSK-3β activity may be used to prevent Notch-mediated activation of GSK-3β. Some examples of GSK-3β antagonists are dominant negative GSK-3β mutants (Taelman V F, et al., 2010, Cell 143(7):1136-48), or inhibitory phosphoserine mimetics such as GSK-3β_S9D.

Notch receptor activity can be inhibited by a number of different classes of agents including, for example, receptor antagonists, dominant negative receptor mutants, ADAM17 protease inhibitors, and gamma secretase inhibitors. Notch antagonists can include, for example, soluble Notch ligands such as soluble, high affinity DLL4 (Luca et al, 2015 Science 347:847-53, which is incorporated by reference in its entirety for all purposes), soluble, high affinity Jagged1, antibodies for Notch receptor (Wu et al, 2010, Nature 464:1052-57; Tran et al., 2013, J. Clin. Invest. 123:1590-1604, both of which are incorporated by reference in their entirety for all purposes), and antibodies for Notch receptor made by Merck or Oncomed.

Dominant negative mutants include, for example, PSEN1 (a component of the gamma secretase complex) mutants disclosed in Zhou et al., 2017, Proc. Natl Acad Sci 114: 12731-36, which is incorporated by reference in its entirety for all purposes. Other dominant negative mutants include, for example, the PSEN1 mutant D257A/D385A and other mutants disclosed in Zhou et al, 2017, ADAM17ΔMP (e.g., Peng et al, 2010, Immunology 130:83-91, which is incorporated by reference in its entirety for all purposes), ADAM10ΔMP (Bozkulak et al, 2009, Molecular and Cellular Biology 29:5679-95, which is incorporated by reference in its entirety for all purposes).

ADAM17 protease inhibitors include, for example, TAPI-2 (Santa Cruz Biotechnology Catalog #sc-205851), 1-Propyl-1H-imidazole (Santa Cruz Biotechnology Catalog #sc-471932), Secalciferol (Santa Cruz Biotechnology Catalog #sc-473270), Secophenol (Santa Cruz Biotechnology Catalog #sc-473288), (7R,8S,9R,10S)-rel-7,8,9,10-Tetrahydrobenzo[a]pyrene-7,8,9,10-tetrol (Santa Cruz Biotechnology Catalog #sc-474274), Boc-L-glutamic acid gamma-benzyl ester 4-oxymethylphenylacetamidomethyl resin (Santa Cruz Biotechnology Catalog #sc-476580), 3-[(4-Methyl-1-piperazinyllimino)methyl]rifamycin O (Santa Cruz Biotechnology Catalog #sc-487922), GI 254023X (Santa Cruz Biotechnology Catalog #sc-490114), (2Z)-6-Chloro-2-[(2,4-dimethoxyphenyl)imino]-N-(tetrahydrofuran-2-ylmethyl)-2H-chromene-3-carboxamide (Santa Cruz Biotechnology Catalog #sc-491865), {[4-(2-Oxo-2H-chromen-3-yl)-1,3-thiazol-2-yl]thio}acetic acid (Santa Cruz Biotechnology Catalog #sc-493593), 4-(Dimethylamino)-N-{1-[3-(2-thienyl)-1H-pyrazol-5-yl]piperidin-4-yl}benzamide (Santa Cruz Biotechnology Catalog #sc-495081), 2-{[(2,5-Diethoxyphenyl)amino]methyl}-6-ethoxyphenol (Santa Cruz Biotechnology Catalog #sc-495315), Etozolin-d3 Hydrochloride (Santa Cruz Biotechnology Catalog #sc-497422), Erythrolosamine (Santa Cruz Biotechnology Catalog #sc-498341), Desmethyl doxylamine-d5 (Santa Cruz Biotechnology Catalog #sc-500285), N-Demethyl N-acetyl alogliptin-2,2,2-trifluoroacetate (Santa Cruz Biotechnology Catalog #sc-500411), GI 254023X (Tocris Catalog #3995), TAPI 0 (Tocris Catalog #5523), TAPI-1 (Tocris Catalog #6162), TAPI-2 (Tocris Catalog #6013), and TMI-1 (Tocris Catalog #5960).

Gamma secretase inhibitors fall into a number of classes and subclasses: peptide isosteres (e.g., aspartyl proteinase transition-state analogs) and small molecules (e.g., azepines, sulfonamides). Many gamma secretase inhibitors are commercially available including, for example, DAPT (GSI-IX) (Selleckchem Catalog #S2215), R04929097 (Selleckchem Catalog #S1575), Semagacestat (LY450139) (Selleckchem Catalog #S1594), MK-0752 (Selleckchem Catalog #S2660), Avagacestat (BMS-708163) (Selleckchem Catalog #S1262), MDL-28170 (Selleckchem Catalog #S7394), Debenzazepine (Selleckchem Catalog #S2711), LY411575 (Selleckchem Catalog #S2714), Nirogacestat (Selleckchem Catalog #S8018), L-685,458 (Selleckchem Catalog #S7673), FPS-ZM1 (Selleckchem Catalog #S8185), Crenigacestat (Selleckchem Catalog #S7169), CHF-5074 (Selleckchem Catalog #S7323), NGP-555 (Selleckchem Catalog #S8603).

Recombinant Notch antagonists (e.g., antibodies or soluble ligands) and/or dominant negative mutants can be delivered as a payload(s) by the eukaryotic cell (e.g., T-cell, NK cell, CAR NK cell, or CAR T-cell). The Notch antagonists (e.g., antibodies or soluble ligands) and/or dominant negative mutants can be constitutively expressed or can be inducibly expressed. Inducible expression can involve an inducible promoter and/or inducible post-transcriptional control such as, for example, an RDE, an RNA control device, or a degron.

The payload can be placed under the control of an RDE so that it is expressed upon activation of the eukaryotic cell (e.g., T-cell or NK cell). Some dominant negative mutants can be placed under the control of an RDE and when the T-cell is expanded with CD3/CD28 the T-cell expresses the dominant negative mutant prior administration to a subject.

An antibody or soluble ligand payload can be constitutively expressed or when under inducible expression, expression can be induced at a desired time. For example, expression can be induced prior to when the eukaryotic cell (e.g., T-cell of NK cell) reaches the target site (e.g., a tumor). Expression can also be induced when or after the eukaryotic cell (e.g., T-cell of NK cell) reaches the target site (e.g., a tumor). If expression has been placed under ligand inducible control, ligand can be added to the eukaryotic cell at the desired time.

Small molecule Notch inhibitors can be administered to a subject systemically (e.g., orally or via injection), or locally (e.g., intratumor). Many of the protease inhibitors have been formulated for oral administration and subjects can be dosed orally at an appropriate time to produce a desired amount of small molecule at the target site based on the known PK properties of the small molecule.

Rapalogs and Related Molecules

Rapalogs and related molecules can be used to turn off or suppress expression of transgenes under Gold control. Rapamycin is an immunosuppressive agent that acts through the master regulator mTOR (mammalian target of rapamycin). mTOR integrates cues from nutrients and growth factors, acting as a nexus point for cellular signals to control growth, metabolism and longevity. mTor is a master regulator of growth (aerobic glycolysis) versus quiescence (oxidative phosphorylation). Thus, following activation of a cell, and expression of a transgene under Gold control, rapalogs can be used to inhibit (turn off) expression of the transgene.

mTOR forms two structurally and functionally distinct complexes called the mammalian target of rapamycin complex 1 (mTORC1) and mammalian target of rapamycin complex 2 (mTORC2). mTORC1 is comprised of mTOR, raptor, GOL and deptor, while mTORC2 is composed of mTOR, Rictor, GOL, PRR5, deptor, and SIN1. mTORC1 integrates signals from multiple growth factors, oxygen and amino acids, and energy supply to promote cell growth when energy is sufficient and catabolism when the body is hungry. mTORC1 mainly regulates cell growth and metabolism, while mTORC2 mainly controls cell proliferation and survival.

mTORC1 positively regulates cell growth and proliferation by promoting many anabolic processes, including biosynthesis of proteins, lipids and organelles, and by limiting catabolic processes such as autophagy. Much of the knowledge about mTORC1 function comes from the use of the bacterial macrolide rapamycin. Upon entering the cell, rapamycin binds to FK506-binding protein of 12 kDa (FKBP12) and interacts with the FKBP12-rapamycin binding domain (FRB) of mTOR, thus inhibiting mTORC1 functions (reviewed by Guertin and Sabatini, 2007). Chronic rapamycin treatment can, in some cases, inhibit mTORC2 activity by blocking its assembly (Sarbassov et al., 2006).

Exemplary rapalogs include, for example, Everolimus (Eve, RAD-001), Deforolimus (Def, Ridaforolimus), Zotarolimus (Zot), Temsirolimus (Tem, CCI-779), WYE-592 rapalog, ILS-920 rapalog, and sirolimus.

A

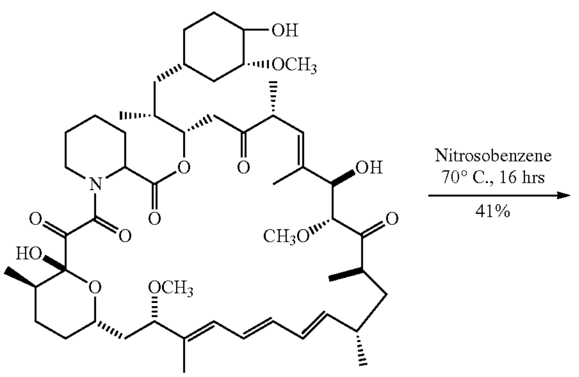

Rapamycin

-continued

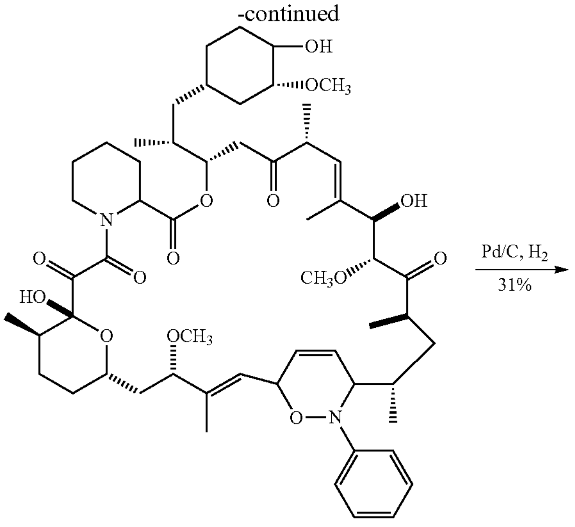

WYE-592

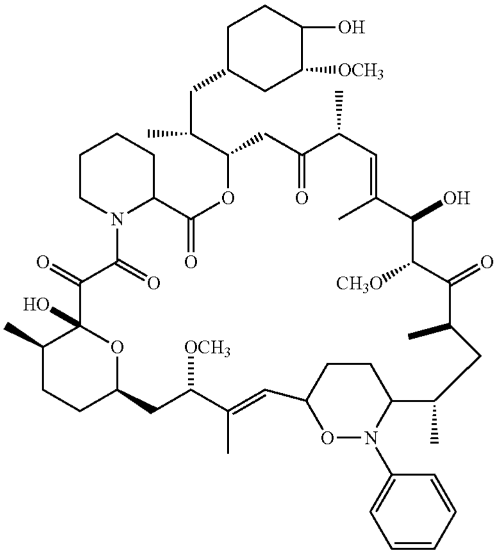

ILS-920 mTor inhibitors that can also be used to reduce or turn-off Gold controlled transgene expression include, for example, Torin 1, Torin 2, PP30, PP242, OSI-027, AZD8055, KU-0063794, WYE-125132, NVP-BEZ235, NVP-BBD130, XL765, and Wortmannin.

Example of TOR Inhibitors

| Type | Drug | $IC_{50}$ mTORC1 | $IC_{50}$ PI3K | Reference |
|---|---|---|---|---|
| Rapalog | Rapamycin/sirolimus | 0.4-0.9 nM | N/A | 119 |
| | Everolimus | 1.8-2.6 nM | N/A | 120 |

-continued

| Type | Drug | $IC_{50}$ mTORC1 | $IC_{50}$ PI3K | Reference |
|---|---|---|---|---|
| mTOR kinase inhibitors | Torin 1 | 0.29 nM | 250 nM | 121 |
| | Torin 2 | 2.1 nM | 4.68 nM | 122 |
| | PP30 | 80 nM | 3 uM | 123 |
| | PP242 | 8 nM | 1.96 μM | 123 |
| | OSI-027 | 22 nM | 1.3 μM | 124 |
| | AZD8055 | 0.8 nM | 3,590 nM | 125 |
| | KU-0063794 | 10 nM | >10 μM | 126 |
| | WYE-125132 | 0.19 nM | 1,179 nM | 127 |
| Dual mTOR/PI3K | NVP-BEZ235 | 20.7 nM | 4 nM | 128 |
| | NVP-BBD130 | 7.7 nM | 72 nM | 128 |
| | XL765 | 157 nM | 39 nM | 129 |
| | Wortmannin | ~200 nM | ~1 nM | 130, 131 |

Combination Therapies

This disclosure provides compositions and methods for providing a CAR T-lymphocyte expressing a transgene under the control of an RDE in combination or in an order of succession with another therapy. The other therapy can include, for example, a chemotherapeutic, an antibody, and antibody-drug conjugate, a radiotherapy, an alkylating agent, a plant alkaloid, an antitumor antibiotic, an antimetabolite, a topoisomerase inhibitor, and/or an anti-neoplastic. For example, the other therapy can be an antibody drug conjugate that has the same or different specificity as the CAR T-lymphocyte.

Antibodies and antibody-drug conjugates (ADC) can bind to a tumor associated antigen, including, for example, any of the tumor associate antigens described herein as targets for a CAR. The drug component of the ADC can be, for example, a chemotherapeutic, a radionucleotide, an alkylating agent, a plant alkaloid, an antitumor antibiotic, an antimetabolite, a topoisomerase inhibitor, and/or an anti-neoplastic. The drug component of the ADC can be attached to the antibody through a linker which can be cleavable or non-cleavable in nature.

Alkylating agents can include, for example, mustard gas derivatives (e.g., mechlorethamine, cyclophosphamide, chlorambucil, melphalan, or ifosfamide), ethylenimines (e.g., thiotepa or hexamethylmelamine), alkylsulfonates (e.g., busulfan), hydrazines and triazines (e.g., altretamine, procarbazine, dacarbazine, or temozolomide), nitrosoureas (e.g., carmustine, lomustine or streptozocin), and metal salts (e.g., carboplatin, cisplatin, or oxaliplatin). Plant alkaloids can include, for example, Vinca alkaloids (e.g., vincristine, vinblastine, or vinorelbine), taxanes (e.g., paclitaxel or docetaxel), podophyllotoxins (e.g., etoposide or tenisopide), and camptothecan analogs (e.g., irinotecan or topotecan). Antitumor antibiotics can include, for example, anthracyclines (e.g., doxorubicin, daunorubicin, epirubicin, mixoantrone, or idarubicin), and chromomycins (e.g., dactinomycin or plicamycin). Antimetabolites can include, for example, folic acid antagonists (e.g., methotrexate), pyrimidine antagonists (e.g., 5-flurouracil, foxuridine, cytarabine, capecitabine, or gemcitabine), purine antagonists (e.g., 6-mercaptopurine or 6-thioguanine), and adenosine deaminase inhibitors (e.g., cladribine, fludarabine, nelarabine, or pentostatin). Topoisomerase inhibitors can include, for example, topoisomerase I inhibitors (e.g., irinotecan or topotecan) and topoisomerase II inhibitors (e.g., amsacrine, etoposide, etoposide phosphate, or teniposide). Anti-neoplastics can include, for example, ribonucleotide reductase inhibitors (e.g., hydroxyurea), adrenocortical steroid inhibitors (e.g., mitotane), enzymes (e.g., asparaginase or pegaspargase), antimicrotubule agents (e.g., estramustine), and retinoids (e.g., bexarotene, isotretinoin, or tretinoin).

The drug component can also be an anthracycline, a camptothecin, a tubulin inhibitor, a maytansinoid, a calicheamycin, a pyrrolobenzodiazepine dimer (PBD), an auristatin, a nitrogen mustard, an ethylenimine derivative, an alkyl sulfonate, a nitrosourea, a triazene, a folic acid analog, a taxane, a COX-2 inhibitor, a pyrimidine analog, a purine analog, an antibiotic, an enzyme inhibitor, an epipodophyllotoxin, a platinum coordination complex, a vnca alkaloid, a substituted urea, a methyl hydrazine derivative, an adrenocortical suppressant, a hormone antagonist, an antimetabolite, an alkylating agent, an antimitotic, an anti-angiogenic agent, a tyrosine kinase inhibitor, an mTOR inhibitor, a heat shock protein (HSP90) inhibitor, a proteosome inhibitor, an HDAC inhibitor, a pro-apoptotic agent, and a combination thereof.

Specific drugs of use may be selected from the group consisting of 5-fluorouracil, afatinib, aplidin, azaribine, anastrozole, anthracyclines, axitinib, AVL-101, AVL-291, bendamustine, bleomycin, bortezomib, bosutinib, bryostatin-1, busulfan, calicheamycin, camptothecin, carboplatin, 10-hydroxycamptothecin, carmustine, celecoxib, chlorambucil, cisplatinum, COX-2 inhibitors, irinotecan (CPT-11), SN-38, carboplatin, cladribine, camptothecans, crizotinib, cyclophosphamide, cytarabine, dacarbazine, dasatinib, dinaciclib, docetaxel, dactinomycin, daunorubicin, DM1, DM3, DM4, doxorubicin, 2-pyrrolinodoxorubicine (2-PDox), a pro-drug form of 2-PDox (pro-2-PDox), cyanomorpholino doxorubicin, doxorubicin glucuronide, endostatin, epirubicin glucuronide, erlotinib, estramustine, epidophyllotoxin, erlotinib, entinostat, estrogen receptor binding agents, etoposide (VP16), etoposide glucuronide, etoposide phosphate, exemestane, fingolimod, floxuridine (FUdR), 3',5'-O-dioleoyl-FudR (FUdR-dO), fludarabine, flutamide, farnesyl-protein transferase inhibitors, flavopiridol, fostamatinib, ganetespib, GDC-0834, GS-1101, gefitinib, gemcitabine, hydroxyurea, ibrutinib, idarubicin, idelalisib, ifosfamide, imatinib, lapatinib, lenolidamide, leucovorin, LFM-A13, lomustine, mechlorethamine, melphalan, mercaptopurine, 6-mercaptopurine, methotrexate, mitoxantrone, mithramycin, mitomycin, mitotane, monomethylauristatin F (MMAF), monomethylauristatin D (MMAD), monomethylauristatin E (MMAE), navelbine, neratinib, nilotinib, nitrosurea, olaparib, plicomycin, procarbazine, paclitaxel, PCI-32765, pentostatin, PSI-341, raloxifene, semustine, SN-38, sorafenib, streptozocin, SU11248, sunitinib, tamoxifen, temazolomide, transplatinum, thalidomide, thioguanine, thiotepa, teniposide, topotecan, uracil mustard, vatalanib, vinorelbine, vinblastine, vincristine, vinca alkaloids and ZD1839. Preferably, the drug is SN-38.

In an aspect the combination therapy is a protein conjugate. The protein conjugate can carry a payload that can be a therapeutic, diagnostic, or a reporter. A single molecule of the therapeutic, diagnostic or reporter may be present or two or more molecules may be present. The therapeutic can be a chemotherapeutic including, for example, any of those described herein such as a radionucleotide, an alkylating agent, a plant alkaloid, an antitumor antibiotic, an antimetabolite, a topoisomerase inhibitor, and/or an anti-neoplastic. The payload of the conjugate can be any one or more of these therapeutics, diagnostics and/or reporters. The protein can be a fragment, a monomer, a dimer, or a multimeric protein. The protein can be an antibody, an antibody fragment or derivative, a single chain antibody, an enzyme, cytokine, chemokine, receptor, blood factor, peptide hormone, toxin, and/or transcription factor.

Many conjugating reagents can be used to conjugate a payload to a protein. Such reagents may contain at least one functional group capable of reacting with a protein or peptide. For example, the conjugating reagent may comprise a functional group capable of reacting with at least one electrophile or, especially, nucleophile, present in the protein, the functional group being attached to the payload via the linker. Any type of known conjugation reaction may be used to form the conjugate. For example, the reaction can be carried out using the known methods of thiol bonding, amine conjugation, or click chemistry. The reagent may contain a maleimide group, an N-hydroxysuccinimide group, a click-chemistry group, for example an azide or alkyne group, an amine group, a carboxyl group, a carbonyl group, or an active ester group. Other possible approaches include the use of proteins that have been recombinantly engineered with an amino acid specifically for conjugation such as engineered cysteines or non-natural amino acids, and enzymatic conjugation through a specific enzymatic reaction such as with transglutaminase. The reaction site on the protein may be either nucleophilic or electrophilic in nature. Common protein conjugation sites are at lysine or cysteine amino acid residues or carbohydrate moieties. Alternatively, conjugation may occur at a polyhistidine tag which has been attached to a binding protein.

A conjugating reagent can be advantageously capable of reacting with a nucleophile in a protein and hence becoming chemically bonded thereto. In these examples, the conjugating reagent typically includes at least one leaving group which is lost on reaction with a nucleophile. The conjugating reagent may, for example, include two or more leaving groups. The conjugating reagent can be capable of reacting with two nucleophiles. The conjugating reagent can comprise at least two leaving groups. When two or more leaving groups are present, these may be the same or different. Alternatively, a conjugating reagent may contain a single group which is chemically equivalent to two leaving groups and which single group is capable of reacting with two nucleophiles. Nucleophilic groups include, for example, sulfur atoms and amine groups, and nucleophilic groups in proteins are for example provided by cysteine, lysine or histidine residues. Nucleophilic groups can be a sulfur atom present in a cysteine residue of a protein. Such structures may be obtained by reduction of a disulfide bond in the protein. The nucleophilic group may be an imidazole group in a histidine residue of the protein, e.g., as present in a polyhistidine tag.

The conjugates can contain a linker which connects the therapeutic, diagnostic or labelling agent to the protein or peptide in the conjugate. The backbone of the linker can be a continuous chain of atoms which runs from the therapeutic, diagnostic or labelling agent at one end to the protein or peptide at the other end. The linker may contain a degradable group, i.e. it may contain a group which breaks under physiological conditions, separating the payload from the protein to which it is, or will be, bonded. Alternatively, the linker is not cleavable under physiological conditions. Where a linker breaks under physiological conditions, it is preferably cleavable under intracellular conditions. Where the target is intracellular, preferably the linker is substantially insensitive to extracellular conditions (i.e. so that delivery to the intracellular target of a sufficient dose of the therapeutic agent is not prohibited).

Where the linker contains a degradable group, this is generally sensitive to hydrolytic conditions, for example it may be a group which degrades at certain pH values (e.g. acidic conditions). Hydrolytic/acidic conditions may for example be found in endosomes or lysosomes. Examples of groups susceptible to hydrolysis under acidic conditions include hydrazones, semicarbazones, thiosemicarbazones, cis-aconitic amides, orthoesters and ketals. The degradable linker can also be an acid-cleavable linker or a reducible linker. The reducible linker may comprise a disulfide group. The linker may also contain a group which is susceptible to enzymatic degradation, for example it may be susceptible to cleavage by a protease (e.g. a lysosomal or endosomal protease) or peptidase. For example, it may contain a peptidyl group comprising at least one, for example at least two, or at least three amino acid residues (e.g. Phe-Leu, Gly-Phe-Leu-Gly, Val-Ala, Val-Cit, Phe-Lys, Glu-Glu-Glu). For example, it may include an amino acid chain having from 1 to 5, for example 2 to 4, amino acids. The enzyme cleavable linker can also comprise a chemical group which can be cleaved or degraded by one or more lysosomal enzymes. Suitable groups include, for example, a valine-citrulline dipeptide group, a phenylalanine-lysine dipeptide group, and a P-glucuronide group.

When the protein in the protein conjugate is an antibody (e.g., full length, fragment, and/or single chain) one end of the first linker can be covalently attached to the antibody. The antibody-reactive end of the linker can be a site that is capable of conjugation to the antibody through a cysteine thiol or lysine amine group on the antibody, and so can be a thiol-reactive group such as a double bond (as in maleimide) or a leaving group such as a chloro, bromo, or iodo, or an R-sulfanyl group, or an amine-reactive group such as a carboxyl group.

The CAR therapy (e.g., with a GOLD-controlled transgene) and the other therapy can be provided to a subject at the same time, or one can be provided to the subject before the other, or the CAR therapy and the other therapy can be provided in alternating cycles, or the CAR therapy together with the other therapy can be provided in cycles, or other combinations of administration can be used. The CAR therapy can be combined with an antibody conjugate (ADC) therapy where the CAR and the ADC bind to the same antigen or bind to different antigens. When the CAR and ADC bind to the same antigen, the CAR and the ADC can bind to the same or different epitopes on the antigen. One of the ADC or the CAR therapy can be provided to the subject first, and followed by the other after a period of treatment with the first. The ADC, either alone or in combination with another approved therapy (e.g. chemotherapy and/or immume checkpoint inhibitors) can be provided to the subject first to reduce the tumor burden in the subject prior to the administration of the CAR therapy. Alternatively, the ADC and CAR therapy can be provided to the subject at the same time. Or the CAR therapy can be provided first followed by the ADC therapy.

RNA Destabilizing Elements

RNA destabilizing elements (RDE) are nucleic acids that affect or maintain the stability of an RNA molecule or the translation kinetics of an RNA molecule. Some RDEs are bound by polypeptides which destabilize (e.g., cleave) the RNA, or prevent translation, leading to loss of function for the RNA. Some RDE binding polypeptide stabilizes the RNA increasing the half-life of the RNA. RDEs can be used to control the expression of a transgene, e.g., a transgene encoding a chimeric antigen receptors. RDEs can be used with RNA control devices, DEs, and/or Side CARs to regulate the expression of a transgene. The RDEs can also be used to control expression of transgenes encoding polypeptides other than a CAR. Other transgenes may encode, for example, a cytokine, an antibody, a checkpoint inhibitor, a granzyme, an apoptosis inducer, complement, a cytotoxic small molecule, other cytotoxic compounds, a polypeptide for imaging, or other polypeptide that can have a desired effect. The RDE can control the delivery of a transgene payload. Examples of RDEs include, for example, AU rich elements, U rich elements, GU rich elements, and certain stem-loop elements. Exemplary RDEs are described in Kovarik et al., Cytokine 89:21-26 (2017); Ray et al., Nature 499:172-177 (2013); Castello et al., Cell 149:1393-1406 (2012); Vlasova et al., Molc. Cell. 29:263-270 (2008); Barreau et al., Nucl. Acids Res. vol 33, doi:10.1093/nar/gki1012 (2006); Meisner et al., ChemBioChem 5:1432-1447 (2004); Guhaniyogi et al., Gene 265:11-23 (2001), all of which are incorporated by reference in their entirety for all purposes.

The RDE can be a Class I AU rich element (dispersed AUUUA in U rich context), a Class II AU rich element (overlapping (AUUUA)~), a Class III AU rich element (U-rich stretch), a stem-loop destabilizing element (SLDE), a cytokine 3' UTR (e.g., INF-7, IL-2, T-cell receptor a chain, TNFα, IL-6, IL-8, GM-CSF, G-CSF etc.), and a sequence of AUUUAUUUAUUUA (SEQ ID NO: 17). Khabar, WIREs RNA 2016, doi: 10.1002/wrna.1368 (2016); Palanisamy et al, J. Dent. Res. 91:651-658 (2012), both of which are incorporated by reference in their entirety for all purposes. The RDE can also be a GU rich element comprised of one or more of, for example, UUGUU, UGGGGAU, or GUUUG. The RDE can be a U-rich element comprised of one or more of, for example, UUUGUUU, NNUUNNUUU, UUUAUUU, UUUUUUU, UUAGA, or AGUUU. In some aspects, multiple RDEs can be combined to make a regulatory unit, for example, multiple RDEs that have the same sequence can be arranged in a concatemer or can be arranged with intervening sequence in between some or all of the RDEs. The RDE sequence can be modified to increase or decrease the affinity of an RNA binding protein(s) for the RDE. For example, an AU rich RDE can be changed to alter the affinity of glyceraldehyde phosphate dehydrogenase (GAPDH) to the RDE. This change in affinity can alter the GAPDH-activation threshold for expression of a transgene regulated by the RDE to which GAPDH binds.

The disclosure assigns AU #designations to some RDEs and these RDEs can be referred to by the AU #or the gene name from which the RDE is derived. Some AU #s and the corresponding gene from which the RDE is derived include, for example, AU 1 (CD40LG), AU 2 (CSF2), AU 3 (CD247), AU 4 (CTLA4), AU 5 (EDN1), AU 6 (IL2RA), AU 7 (SLC2A1), AU 8 (TRAC), AU 9 (CD274), AU 10 (Myc), AU 11 (CD19), AU 12 (IL4), AU 13 (IL5), AU 14 (IL6), AU 15 (IL9), AU 16 (IL10), AU 17 (IL13), AU 18 (FOXP3), AU 19 (TMEM-219), AU 20 (TMEM-219snp), AU 21 (CCR7), AU 22 (SEM-A4D), AU 23 (CDC42-SE2), AU 24 (CD8), AU 27 (bGH), and AU 101 (IFNg).

The RDE can be from the 3' UTR of a gene encoding, for example, IL-1, IL-2, IL-3, IL-4, IL-6, IL-8, IL-10, GM-CSF, G-CSF, VEG F, $PGE_2$, COX-2, MMP (matrix metalloproteinases), bFGF, c-myc, c-fos, betal-AR, PTH, interferon-gamma, MyoD, p21, Cyclin A, Cyclin B1, Cyclin D1, PAI-2, NOS HANOS, TNF-alpha, interferon-alpha, bcl-2, interferon-beta, c-jun, GLUT1, p53, Myogenin, NF-M, or GAP-43, lymphocyte antigen 96, SUPV3L1, SFtPA2, BLOC1S2, OR10A6, OR8D1, TRPT1, CIP29, EP400, PLE2, H3ST3A1, ZNF571, PPP1R14A, SPAG4L, OR10A6 and KIR3DL. Other RDEs are found in, for example, the 3'-UTRs from GLMN, AMY2B, AMY2A, AMY2A, AMY1A, TRIM33, TRIM33, TRIM33, CSRP1, PPP1R12B, KCNH1, Reticulon_4, MRPL30, Navl.2, Tissue_factorpathway inhibitor, EEF1B2, CRYGB, ARMC9, RPL15, EAF2, MRPS22, MRPS22, COPB2, PDCD10, RE1-silencing_transcription_factor, Amphiregulin, AP1AR, TLR3, SKP2, Peptidylglycine_alpha-amidating_monooxygenase, TNFAIP8, Interleukin_9, PCDHA2, PCDHA12, Aldehyde_dehydrogenase_5_family, _member_A1, KCNQ5, COX7A2, Monocarboxylate_transporter_10, MLLT4, PHF10, PTPN12, MRNA_(guanine-N7-)-methyltransferase, WHSC1L1, Tricho-rhino-phalangeal_syndrome_Type_1, Interferon_alpha-1, ZCCHC6, Retinitis_pigmentosa_GTPase_regulator, MED14, CLCN5, DNA2L, OR52D1, NELL1, SLC22A25, SLC22A10, TRPC6, CACNA2D4, EPS8, CT2_(gene), Mitochondrial_ribosomal_protein_L42, TAOK3, NUPL1, Endothelin_receptor_type_B, Survival_of_motor_neuron_protein-interacting_protein_1, POLE2, Hepatic lipase, TPSG1, TRAP1, RPS15A, HS3ST3A1, CROP_(gene), Apolipoprotein_H, GRB2, CEP76, VPS4B, Interleukin_28B, IZUMO1, FGF21, PPP1R15A, LIN7B, hnRNPLL, Tox, and CDC45-related_protein.

Still other RDEs can be found in, for example, the 3'UTRs of SCFD1, MAL2, KHSRP, IQCB1, CAMP_responsive_element_modulator, MFAP5, SBF2, FKBP2, PDCD10, UBE2V2, NDUFAB1, Coiled-Coil_Domain_Containing_Protein, ALG13, TPTE, Enaptin, Thymopoietin, Delta-like_1, C11orf30, Actinin_alpha_4, TMEM59, SP110, Dicer, TARDBP, IFNA17, IFNA16, IFNA14, ZMYM3, Interleukin_9,_type_I, OPNISW, THSD1, ERGIC2, CAMK2B, WDR8, FXR1, Thymine-DNA_glycosylase, Parathyroid_hormone-related_protein, OSBPL3, Ran, GYPE, AKAP4, LOC642658, L2HGDH, AKAP1, Zinc_finger_protein_334, TC2N, FKBPL, GRB14, CXorf67, CXorf66, CEP76, Gastricsin, CEP70, CYP26A1, NAA35, Aryl_hydrocarbon_receptor_nuclear_translocator, KLC4, GPR112, LARP4, NOVAl, UBE2D3, ITGA6, GPR18, MGST_type_A, RE1-silencing_transcription_factor, ASPM, ZNF452, KIR2DS4, AHSA1, TMTC4, VSX1, P16, MRPL19, CCL20, TRPT1, Hepatic lipase, PDLIM5, CCDC53, 'CCDC55, GAPVD1, HOXB2, KCNQ5, BRCC3, GTF2IRD1, CDK5RAP3, Transcription_factor_II_B, ZEB1, IRGM, SLC39A6, RHEB, PSIP1, RPS6KA5, Urokinase_receptor, GFM1, DNAJC7, Phosphoinositide-dependent_kinase-1, LMOD3, TTC35, RRP12, ATXN2, ACSM3, SOAT1, FGF8, HNRPH3, CTAGE5, POLG2, DYRK3, POLK, Cyclin-dependent_kinase_inhibitor_1C, CD137, Calmodulin_1, ZNF571, CNOT2, CRYZL1, SMC3, SMC4, SLC36A1, Decorin, HKR1, ERC1, S100A6, RIMS1, TMEM67, Mitochondrial_ribosomal_protein_L42, MECP2, RNF111, SULTIA1, MYLK3, TINAG, PRKAR1A, RGPD5, UBE2V1, SAR1B, SLC27A6, ZNF638, RAB33A, TRIOBP, MUCL1, CADPS2, MCF2L, TBCA, SLC17A3, LEO1, IFNA21, RUNX1T1, PRKD2, ATP11B, MORC2, RBM6, KLRD1, MED31, PPHLN1, HMGB2, DNA_repair_and_recombination_protein_RAD54-like, RBM9', ARL 11, HuD, SPEF2, CBLL1, SLC38A1, 'Caspase_1', S100G, CA1_, CELA1, PTS, ITM2B, Natriuretic_peptide_precursor_C, TRPP3, IMPDH2, DPYS, CDCA3, EFCAB6, SLIT2, SIPA1L1, FIP1L1, ATP6V1B2, HSD17B4, HSD17B7, NDUFC1, CROP, CD48, APPBP1, CD44, CD46, Histone_deacetylase_2_type_XI, Interleukin_4, Tricho-rhino-phalangeal_syndrome_Type_1, SEC61G, TRIP12, PLEKHO1, SEC61B, ST6GALNAC1, CPVL, E2F7, UTP20, E2F5, PARD3, EXOC7, HEXB, Caspase_recruitment_domain-containing_protein_8, MBD4, PPP4C, Helicase, Phosducin, SPG11, CGGBP1, PSKH1, Cathepsin_S, orexin, IMMP2L, C2orf28, Laminin, EIF3S6, LRRC41 type_XII, Cathepsin_C, HPS6, ARAF, Zinc_finger_and_BTB_domain-containing_protein_16, Sex_hormone-binding_globulin, FBLN2, Suppressor_of cytokine_signaling_1, TMEM126A, DOM3Z, TSFM_POLQ-like, DYNLT3, CDH9, EAF2, MIPEP, NDUFA12, HDAC8, MKKS, FGG, IL36G, CDCA7, CRISPLD2, Olfactomedin-like_2b, MRPL32, MRPL33, AHII, SMARCAL1, UTP14A, SSH2, Dystonin, Contactin 6, PPFIBP1, THOC1, CNOT1, RHCE, SLC41A3, SLC2A9, SNAP23, RFX3, GNG4, MRPL40, LSR, Angiogenin, TRIP4, VRK1, COUP-TFII, FOXP2, SNX2, Nucleoporin_85, RPL37A, RPL27A, SEC62, Calcium-activated_potassium_channel_subunit alpha-1, SMARCEl, RPL17, CEP104, CEP290, VPS29, ANXA4, Zinc_finger_protein_737, DDX59, SAP30, NEK3, Exosome_component_9, Receptor_for_activated_C_kinase_1, Peptidylprolyl_isomerase_A, TINP1, CEACAMI, DISCI, LRRTM1, POP1_Lamin_B1, SREBP_cleavage-activating_protein, COX6C, TLR_1, ARID2, LACTB, MMS22L, UBE2E3, DAP3, ZNF23, SKP2, GPR113, IRF9 Ghrelin_O-acyltransferase, NEIL3, EEF1E1, COX17, ESD_, Dentin_sialophosphoprotein, HDAC9, RFC4, CYLD, RPLPO, EIF2B3, UGT2A1, FABP7, TRIP11, PLA2G4A, AKR1C3, INTS12, MYH1, ZBTB17, MYH4, NLRP2, MECOM, MYH8, Thermogenin_receptor_2, IFI16, THYN1, RAB17, ETFA, Cystic_fibrosis_transmembrane_conductance_regulator, F13B, RAB6A, ST8SIA1, SATB2, SATB1, HMG20B, UHRF1, CNOT3, Prostaglandin_EP2_receptor, FAM65B, Peroxisome_proliferator-activated_receptor_gamma, KvLQT2, GRIK5, SHOC2, Cortactin, FANCI, KIAA1199, Kynureninase, Decoy_receptor_1, NEU3, PHF10, Methyl-CpG-binding_domain_protein_2, RABGAP1, CEP55, SF3B1, MSH5, MSH6, CREB-binding_protein, LIMS1, SLC5A4, CCNB1IP1, RNF34, SORBS2, UIMC1, SOX5, YWHAZ, ICOSLG, NOP58, Zinc_finger_protein_679, PHKB, MED13, ABCB7, COQ9, C14orf104, Zinc_finger_protein_530, KLRC2, LSM8, NBR1, PRKCD, Long-chain-aldehyde_dehydrogenase, MTSS1, Somatostatin, Ubiquitin_ carboxyl-terminal_hydrolase_L5, WDR72, FERMT3, Nuclear_receptor_related-1_protein, Citrate_synthase, VPS11, KIZ, ZFYVE27, BCKDHB, Hypocretin, CACNG2, PTCH1, Carbonic_anhydrase_4, Nucleoporin_107, LDL_receptor, LEKTI, FBXO11, NDUFB3, FCHO2, CEP78, RAPGEF6, PPIL3, NIN, RAPGEF2, Growth_hormone_1, Growth_hormone 2, MNAT1, Nav1, MAP3K8, SUGT1, LAIR1, Hyaluronan-mediated_motility_receptor, MAP3K2, MPP2, TFB2M, CRB3, MPP5, CACNAlG, DLGAP2, INHBA, MAGI2, CIP29, SETDB1, Cytochrome_b5, TRPV2, Interleukin_1_receptor, HOXD8, TIMM10, ATXN2L, CLCN2, CREB1, TNIP1, CBLB, Factor_V, USP33, SON, RBBP8, SLC22A18, PTPN12, ADCY8, MYLK, KIF23, REXO2, BST1, TOP3B, COPB1, AXIN2, COPB2, TNRC6B, Guanidinoacetate_N-methyltransferase, Acyl-CoA_thioesterase_9, C4orf21, TSHB, FRS3, EPB41, Cyclin_T2, LAIR2, Nucleoporin_43, APLP2, TNFRSF19, Death-associated_protein_6, Epithelial_cell_adhesion_molecule, CLEC7A, Gephyrin, CLDND1, VPS37A, PCDHAC2, Bone_morphogenetic_protein_4, NVL, RBM33, RNF139, Sperm_associated_antigen_5, PLCB1, Glial_cell_line-derived_neurotrophic_factor, PARP4, PARP1, MAN2A1, Bone_morphogenetic_protein_1, PAX4, BCCIP, MMP7, Decoy_receptor_3, RAMP2, NCAPD3, LRRC37A, RWDD3, UBE2A, UBE2C, SLC3A1, MRPS22, CDC14A, ITSN1, POLE2, MYC-induced_nuclear_antigen, TMLHE, Glutamate_carboxypeptidase_II, GPR177, PPP2R5C, KIAA1333, RPP38, MYO1F, Farnesoid_X_receptor, Caldesmon, FBXO4, FBX05, OPN1MW, PIGN, ARNTL2, BCAS3, C6orf58, PHTF2, SEC23A, NUFIP2, OAZ1, Osteoprotegerin, ANAPC4, ATP6V0A2, SPAM1, PSMA6, TAS2R30, RABEP1, DPM3, SLC6A15, RPS26, RPS27, RPS24, RPS20, RPS21, ARHGAP24, Catechol-O-methyl_transferase, ERCC5, Transcription_initiation_protein_SPT3_homolog, OR1E1, ZNRF1, GMEB1, CCT2_GNAQ, Mucin_6, Mucin_4, LRP5, PDE9A, C2orf3, EZH2, Epidermal_growth_factor_receptor, TMTC2, PDE4A, EPH_receptor_A4, PPIB, DENND4A, ANTXR1, ANTXR2, Nucleoporin_88, SLCO1B3, COG8, RBMS1, MAP7, HIST2H2BE, AEBP2, DCLREIA, RPL24, HNRPA2B1, RPL21, RPL23, MAPKAP1, NIPBL, ATG7, SERPINI2, GYLTL1B, ATP5G2, DIP2A, AMY2A, CEP63, TDRD7, PIEZO1, CLDN20, GRXCR1, PMEL, NIF3L1, MCC_, PCNX, TMBIM4, DUSP12, ZMYND8, GOSR1, Interferon_gamma_receptor_1, LDB3, PON3, CID, ABCC8, COQ7, COQ6, AMELY, HAVCR1, PICALM, Sjogren_syndrome_antigen_B, PLK4, HBB, AKT1, PCDHGB7, C6orf10, UBR1, Retinoblastoma-like_protein_1, GRK6, WWC2, GRK4, INPP4B, SLC34A1, GOLGA2, MYCBP2, PTP4A2, NUCB2, MAGOH, RPP40, Alpha-2A_adrenergic_receptor, SPAGIiB, Nucleoporin_205, COG1, Motile_sperm_domain_containing_3, KCNMB3, Motile_sperm_domain_containing_1, KLHL7, KCNN2, TSPAN8, GPR21, Translocator_protein, HNRNPLL, ABHD5, CAB39L, Amphiregulin, GPR1, Interleukin_18, EIF4G3, Interleukin_15, CCDC80, CD2AP, NFS1, GRB2, ULBP2, Vascular_endothelial_growth_factor_C, RPS3, TLR8, BCL2-related_protein_A1, RHOT1, Collagen, Centromere_protein_E, STMN2, HESX1, RPL7, Kalirin, PCMT1, HLA-F, SUMO2, NOX3, EP400, DNM3, EED, NGLY1, NPRL2, PLAC1, Baculoviral_IAP_repeat-containing_protein_3, C7orf31, TUBAIC, HAUS3, IFNA10, MYST4, DCHS1, SIRT4, EFEMP1, ARPC2, MED30, IFT74, PAK1IP1, DYNC1LI2, POLR2B, POLR2H, KIF3A, PRDM16, PLSCR5, PEX5, Parathyroid_hormone_1_receptor, CDC23, RBPMS, MAST1, NRD1, BAT5, BAT2, Dockl1, GCSH, POF1B, USP15, POT1, MUTYH, CYP2E1, FAM122C, A1_polypeptide, Flavin_containing_monooxygenase_3, HPGD, LGALS13, MTHFD2L, Survival_motor_neuron_ domain_containing_1, PSMA3, MRPS35, MHC_class_I_polypeptide-related_sequence_A, SGCE, REPS1, PPP1R12A, PPP1R12B, PABPC1, MAPK8, PDCD5, Phosphoglucomutase_3, Ubiquitin_C, GABPB2, Mitochondrial_translational_release_factor_1, PFDN4, NUB1, SLC13A3, ZFP36L1, Galectin-3, CC2D2A, GCA, Tissue_factor_pathway_inhibitor, UCKL1, ITFG3, SOS1, WWTR1, GPR84, HSPA14, GJC3, TCF7L1, Matrix_metallopeptidase_12, ISG20, LILRA3, Serum_albumin, Phosducin-like, RPS13, UTP6, HP1BP3, IL12A, HtrA_serine_peptidase_2, LATS1, BMF_, Thymosin_beta-4, B-cell_linker, BCL2L11, Coagulation_factor_XIII, BCL2L12, PRPF19, SFRS5, Interleukin_23_subunit_alpha, NRAP, 60S_ribosomal_protein_L14, C9orf64, Testin, VPS13A, DGKD, PTPRB, ATP5C1, KCNJ16, KARS, GTF2H2, AMBN, USP13, ADAMTSL1, TRO_, RTF1, ATP6V1C2, SSBP1, SNRPN_upstream_reading_frame_protein, RPS29, SNRPG, ABCC10, PTPRU, APPL1, TINF2, TMEM22, UNC45A, RPL30, PCDH7, Galactosamine-6_sulfatase, UPF3A, ACTL6A, ACTL6B, IL3RA, SDHB, Cathepsin_L2, TAS2R7, Cathepsin_L1, Pituitary_adenylate_cyclase-activating_peptide, RPN2, DYNLL1, KLK13, NDUFB3, PRPF8, SPINT2, AHSA1, Glutamate_carboxypeptidase_II, DRAP1, RNASE1, Olfactomedin-like_2b, VRK1, IKK2, ERGIC2, TAS2R16, CAMK2G, CAMK2B, Estrogen_receptor_beta, NADH_dehydrogenase, RPL19, NUCB2, KCTD13, ubiquinone, H2AFY, CEP290, PABPC1, HLA-F, DHX38, KIAA0922, MPHOSPH8, DDX59, MIB2_, ZBP1, C16orf84, UACA, C6orf142, MRPL39, Cyclin-dependent_kinase_7, Far_upstream_element-binding_protein_1, SGOL1, GTF2IRD1, ATG10, Dermcidin, EPS8L2, Decorin, Nicotinamide_phosphoribosyltransferase, CDC20, MYB, WNT5A, RBPJ, DEFB103A, RPS15A, ATP5H, RPS3, FABP1, SLC4A8, Serum_amyloid_P_component, ALAS1, MAPK1, PDCD5, SULTIA1, CHRNA3, ATXN10, MNAT1, ALG13, Ataxin 3, LRRC39, ADH7, Delta-sarcoglycan, TACC1, IFNA4, Thymic_stromal_lymphopoietin, LGTN, KIAA1333, MSH6, MYOT, RIPK5, BCL2L11, RPL27, Rndl, Platelet_factor 4, HSD17B7, LSM8, CEP63, INTS8, CTNS, ASAHL, CELA3A, SMARCAL1, HEXB, SLC16A5, MAP3K12, FRMD6.

Additional RDEs are found in the 3'-UTRs of long noncoding RNAs, or primary transcripts encoding miRNAs. For example, RDEs from the 3'-UTR of THRIL (linc 1992), NIKILA lncRNA, SeT lncRNA, lncRNAs uc.197, RP11-172E9.2, LINC00598, lncRNAs LOC100128098, RP11-150012.3, and the primary transcripts encoding miR-146a, miR-let7e, miR-181c, miR-155, miR-125b, and miR-16.

A class of RDEs includes those which are bound by glycolytic enzymes such as glyceraldehyde phosphate dehydrogenase (GAPDH). This group of RDEs includes, for example, AU 19 (TMEM-219), AU 20 (TMEM-219snp), AU 21 (CCR7), AU 22 (SEM-A4D), and AU 23 (CDC42-SE2).

The RDE can be a Class I AU rich element that arises from the 3' UTR of a gene encoding, for example, c-myc, c-fos, betal-AR, PTH, interferon-gamma, MyoD, p21, Cyclin A, Cyclin B1, Cyclin D1, PAI-2, or NOS HANOS. The RDE can also be a Class II AU rich element and arises from the 3' UTR of a gene encoding, for example, GM-CSF, TNF-alpha, interferon-alpha, COX-2, IL-2, IL-3, bcl-2, interferon-beta, or VEG-F. The RDE can be a Class III AU rich element that arises from the 3' UTR of a gene encoding, for example, c-jun, GLUT1, p53, hsp 70, Myogenin, NF-M, or GAP-43. Other RDEs may be obtained from the 3'-UTRs of a T-cell receptor subunit (a, J, 7, or 6 chains), cytotoxic T-lymphocyte-associated antigen 4 (CTLA4), programmed cell death protein (PD-1), Killer-cell Immunoglobulin-like Receptors (KIR), and Lymphocyte Activation Gene-3 (LAG3), and other checkpoint inhibitors. Still other RDEs may be obtained from the 3'-LUTRs of senescence-associated secretory phenotype genes disclosed in Coppe et al., Ann. Rev. Pathol. 5:99-118 (2010), which is incorporated by reference in its entirety for all purposes (e.g., see Table 1).

The RDE can be bound by certain polypeptides including, for example, ARE poly(U) binding/degradation factor (AUF-1), tristetraprolin (TTP), human antigen-related protein (HuR), butyrate response factor 1 (BRF-1), butyrate response factor 2 (BRF-2), T-cell restricted intracellular antigen-1 (TIA-1), TIA-1 related protein (TIAR), CUG triplet repeat, RNA binding protein 1 (CUGBP-1), CUG triplet repeat, RNA binding protein 2 (CUGBP-2), human neuron specific RNA binding protein (Hel-N1, Hel-N2), RNA binding proteins HuA, HuB and HuC, KH-type splicing regulatory protein (KSRP), 3-methylglutaconyl-CoA hydratase (AUH), glyceraldehyde 3-phosphate dehydrogenase (GAPDH), heat shock protein 70 (Hsp70), heat shock protein 10 (Hsp10), heterogeneous nuclear ribonucleoprotein A1 (hnRNP A1), heterogeneous nuclear ribonucleoprotein A2 (hnRNP A2), heterogeneous nuclear ribonucleoprotein A3 (hnRNP A3), heterogeneous nuclear ribonucleoprotein C (hnRNP C), heterogeneous nuclear ribonucleoprotein L (hnRNP L), Bcl-2 AU-rich element RNA binding protein (TINO), Poly(A) Binding Protein Interacting Protein 2 (PAIP2), IRP1, pyruvate kinase, lactate dehydrogenase, enolase, and aldolase. The RDE binding protein also can be an enzyme involved in glycolysis or carbohydrate metabolism, such as, for example, Glyceraldehyde Phosphate Dehydrogenase (GAPDH), enolase (ENO1 or ENO3), Phosphoglycerate Kinase (PGK1), Triosephosphate Isomerase (TPI1), Aldolase A (ALDOA), Phosphoglycerate Mutase (PGAM1), Hexokinase (HK-2), or Lactate Dehydrogenase (LDH). The RDE binding protein can be an enzyme involved in the Pentose Phosphate Shunt, including for example, Transketolase (TKT) or Triosephosphate Isomerase (TPI1). Additional exemplary RNA binding proteins are those described in Castello et al., Molc. Cell 63:696-710 (2016); Kovarik et al., Cytokine 89:21-26 (2017); Ray et al., Nature 499:172-177 (2013); Castello et al., Cell 149:1393-1406 (2012); Vlasova et al., Molc. Cell. 29:263-270 (2008); Barreau et al., Nucl. Acids Res. vol 33, doi:10.1093/nar/gkil012 (2006); Meisner et al., ChemBioChem 5:1432-1447 (2004); Guhaniyogi et al., Gene 265:11-23 (2001), all of which are incorporated by reference in their entirety for all purposes.

The RDE binding protein can be TTP which can bind to RDEs including for example, one or more of UUAUUUAUU and AUUUA, or KSRP which binds AU-rich RDEs, or Aufl which binds RDEs including for example, one or more of UUGA, AGUUU, or GUUUG, or CELF-1 which binds RDEs including for example, one or more of UUGUU, or HuR which binds RDEs including for example, one or more of UUUAUUU, UUUUUUU, or UUUGUUU, or ESRP1 or ESRP2 which binds RDEs including for example, one or more of UGGGGAU, or ELAV which binds RDEs including for example, one or more of UUUGUUU. The RDE binding protein can be an enzyme involved in glycolysis, including for example, GAPDH which binds AU rich elements including for example, one or more of AUUUA elements, or ENO3/ENO1 which binds RDEs including for example, one or more of CUGCUGCUG, or ALDOA which binds RDEs including for example, one or more of AUUGA.

In an aspect, the RDE can be combined with an RNA control device to make the regulation by the RDE ligand inducible. For example, an RDE can be operably linked to an RNA control device where ligand binding by the RNA control device activates the regulatory element (e.g., a ribozyme or riboswitch) which inhibits the RDE (e.g., a ribozyme cleaves the RDE so RDE binding proteins no longer bind, or the riboswitch alters secondary structure). This places transcripts with the RDE and RNA control device under two types of control from the RDE, first the RDE can regulate the transcript subject to binding of RDE binding proteins as governed by conditions in the cell, and second, the RDE control can be removed by inducing the RNA control device with ligand. When ligand is added, the RNA control device renders the RDE unavailable for binding and RDE regulation is removed. When ligand is removed, new transcripts that are transcribed can be under the control of the RDE (as the RNA control device will not be activated). Alternatively, an RDE can be operable linked to an RNA control device where ligand binding turns off the regulatory element (e.g., a ribozyme). In this example, the presence of ligand inhibits the RNA control device and transcripts can be regulated by the RDE. When ligand is removed, the RNA control device renders the RDE unavailable for binding to RDE binding proteins and RDE regulation of the transcript is removed. The RNA control device could also cleave a polynucleotide that binds to the RDE to form a structure (e.g., a helix) that inhibits RDE proteins from binding to the RDE. In this example, the RNA control device can cleave the inhibitory polynucleotide which then does not bind or is inhibited for binding to the RDE. This cleavage by the RNA control device can be stimulated by ligand binding or inhibited by ligand binding.

Different RDEs have different kinetic parameters such as, for example, different steady expression levels, different $T_{max}$ (time to maximal expression level), different $C_{max}$ (maximum expression level), different dynamic range (expression/basal expression), different AUC, different kinetics of induction (acceleration of expression rate and velocity of expression rate), amount of expression, baseline expression, maximal dynamic range ($DR_{max}$), time to $DR_{max}$, area under the curve (AUC), etc. In addition, these kinetic properties of the RDEs can be altered by making concatemers of the same RDE, or combining different RDEs into regulatory units. Placing RDEs under the control of an operably linked RNA control device can also alter the kinetic properties of the RDE, RDE concatemer, or RDE combinations. Also, small molecules and other molecules that affect the availability of RDE binding proteins for binding RDEs can be used to alter the kinetic response of an RDE, RDE concatemer, and/or RDE combinations. The kinetic response of RDEs, RDE concatemers, and/or RDE combinations can be changed using constructs that express competitive RDEs in a transcript. Such transcripts with one or more competing RDEs can compete for RDE binding proteins and so alter the regulation of the desired gene by an RDE, RDE concatemer, and/or RDE combination. These competitive RDE transcripts can bind to RDE binding proteins reducing the amount of RDE binding protein available for binding to the RDE, RDE concatemer, and/or RDE combination. Thus, RDEs, RDE concatemers, and/or RDE combinations can be selected and/or combined with other conditions (discussed above) to provide a desired kinetic response to the expression of a transgene.

Table 2 in Example 20 shows that different RDEs (e.g., AU elements) provided different kinetics of expression. For example, different RDEs (e.g., AU elements) reached maximal induction (maximal dynamic range also known as fold induction) at different time points. The RDEs AU 2 and AU 101 reached maximal dynamic range ($DR_m$ax) at day 1 and then the dynamic range (DR) decreased showing reduced expression compared to basal expression. The RDEs AU 5 and AU 21 had a $DR_{max}$ at day 3/4 and this expression was maintained out to day 8. The RDEs AU 3, AU 7, AU 10, AU 20 and AU 23 had a $DR_{max}$ on day 6 and expression decreased on day 8. The RDEs AU 19 and AU 22 had $DR_{max}$ on day 8. The RDEs (e.g., AU elements) also had differences in the amount of expression covering a range of about 5500 fold comparing the expression of AU 7 to AU 10 (see Table 1). Thus, RDEs (AU elements) can be selected to provide maximal rates of expression at a desired time point and to provide a desired amount of polypeptide at that time point.

Some RNA binding proteins increase the rate of RNA degradation after binding to the RDE. Some RNA binding proteins decrease the rate of degradation of the RNA after binding to the RDE. More than one RNA binding protein binds can bind to an RDE. In some RDE regulatory units, more than one RNA binding protein binds to more than one RDE. Binding of one or more of the RNA binding proteins to the one or more RDEs can increase the degradation rate of the RNA. Binding of one or more of the RNA binding proteins can decrease the degradation rate of the RNA. RNA binding proteins that increase degradation may compete for binding to an RDE with RNA binding proteins that decrease degradation, so that the stability of the RNA is dependent of the relative binding of the two RNA binding proteins. Other proteins can bind to the RDE binding proteins and modulate the effect of the RNA binding protein on the RNA with the RDE. Binding of a protein to the RNA binding protein can increases RNA stability or decrease RNA stability. An RNA can have multiple RDEs that are bound by the proteins HuR and TTP. The HuR protein can stabilize the RNA and the TTP protein can destabilize the RNA. An RNA can have at least one RDE that interacts with the proteins KSRP, TTP and/or HuR. KSRP can destabilize the RNA and compete for binding with the HuR protein that can stabilize the RNA. The KSRP protein can bind to the RDE and destabilizes the RNA and the TTP protein can bind to KSRP and prevent degradation of the RNA. Different proteins may be bound to the same transcript and may have competing effects on degradation and stabilization rates. Different proteins may be bound to the same transcript and may have cooperative effects on degradation and stabilization rates. Different proteins may be bound to the same transcript at different times, conferring different effects on degradation and stabilization.

The RDE can be a Class II AU rich element, and the RNA binding protein can be GAPDH. The Class II AU rich element bound by GAPDH can be AUUUAUUUAUUUA (SEQ ID NO: 17). The Class II AU rich element and GADPH can be used to control the expression of a transgene, e.g., a CAR. The Class II AU rich element and GADPH also can be used to effect the expression of a transgene and/or a CAR in a T-lymphocyte. The Class II AU rich element and GADPH can be used to effect the expression of a transgene and/or a CAR in a CD8+T-lymphocyte. The Class II AU rich element and GADPH can be used to effect the expression of a transgene and/or a CAR in a CD4+T-lymphocyte. The Class II AU rich element and GADPH can be used to effect the expression of a transgene and/or a CAR in a natural killer cell.

The RDE may have microRNA binding sites. The RDE can be engineered to remove one or more of these microRNA binding sites. The removal of the microRNA binding sites can increase the on expression from a construct with an RDE by at least 5, 10, 15, 20, 50 or 100 fold. The RDE with the microRNA sites can be an RDE that is bound by GAPDH. The removal of microRNA sites from the RDE bound by GAPDH can increase the on expression of a construct with the GAPDH sensitive RDE by at least 5-10 fold. This GAPDH control through the RDE can be used to deliver a payload at a target site. The GAPDH control can be tied to activation of the eukaryotic cell by a CAR that recognizes an antigen found preferentially at the target site.

The RDE can be the 3'-UTR of IL-2 or IFN-γ, and removal of micro-RNA sites can increase the rate of expression and/or the dynamic range of expression from a transgene RNA with the RDE. The RDE can be the 3'-UTR of IL-2 and the removed micro-RNA sites can be the MIR-186 sites which deletion increases the kinetics of expression and increases the dynamic range of expression by about 50-fold. The RDE also can be the 3'-UTR of IFN-γ and the micro-RNA sites removed can be the MIR-125 sites.

The dynamic range of expression (control) with an RDE can be increased by optimizing the codons of the transgene controlled by the RDE. By increasing the GC content of the wobble position of the codons in a transgene the efficiency of translation can be increased by 1-2 logs (10-100 fold). The increased efficiency of translation means the amount of expression in the "on" state with the RDE is increased. If the "off" state expression rate is not changed or changed less, the overall dynamic range of control with the RDE is increased.

New RDEs can be obtained from synthetic libraries made by combinatorially mixing and matching parts of known RDEs by applying techniques such as molecular breeding and/or directed evolution to the 3'-UTRs of genes known to have an RDE. For example, multiple 3'-UTRs with different RDEs are fragmented and assembled into synthetic 3'-UTRs that are then screened or selected for RDE activity. RDEs with desired properties can be discovered from such libraries using positive and/or negative selections.

Alternative Splicing

Alternative splicing can link a change in metabolic state in a cell to the splicing of a pre-mRNA transcript into a mRNA that encodes and is translated into a desired polypeptide. For example, following a change in metabolic state of a cell, a pre-mRNA transcript can undergo alternative splicing to produce a payload in the cell. Prior to the alternative splicing the pre-mRNA transcript can be spliced into a transcript encoding a nonsense polypeptide or into an mRNA encoding a different polypeptide product.

hnRNPLL (heterogeneous nuclear ribonucleoprotein L like) is a RNA binding polypeptide that is made when immune cells (e.g., T-cells and B-cells) are activated (change in metabolic state). hnRNPLL is a master regulator of activation-induced alternative splicing in lymphocytes, including T cells and B-cells. In T-cells, hnRNPLL effects the splicing of a variety of transcripts including CD45, a tyrosine phosphatase essential for T-cell development and activation.

hnRNPLL binds to CA repeats and also to C rich motifs, A rich motifs, and T rich motifs including, for example, CACACA$(CA)_n$, CTTCCt/c, CATt/a, CATT, and TTTAt/aA. When hnRNPLL binding sites are in the 3'-UTRs of a transcript, binding of hnRNPLL to the site can stabilize the transcript. When hnRNPLL binding sites are within about 1 kilobase on the 5' side of an exon, hnRNPLL binding promotes inclusion of the exon during splicing. When hnRNPLL binding sites are within about 1 kilobase on the 3' side of an exon, hnRNPLL binding promotes exclusion of the exon. When hnRNPLL binds to a transcript it can alter the splicing pattern of the transcript resulting in a new mRNA transcript and new noncoding excision products (excised introns or introns plus exons). This alternative splicing pattern can produce an alternatively spliced mRNA that now encodes a desired polypeptide (e.g., a payload), and/or the new noncoding excision products can encode a miRNA or siRNA that is only produced upon alternative splicing.

hnRNPLL alternative splicing can be used alone or in combination with other regulatory signals such as RDEs. Together hnRNPLL alternative splicing and RDEs can control expression of a payload upon activation of a cell (change in metabolic state) when it reaches a target site having a ligand that binds to a CAR, T-cell receptor (TCR), or other receptor expressed on the cell. Binding of ligand to the receptor (e.g., CAR or TCR) activates the cell, increases expression of a payload by RDE mechanisms, and produces alternative splicing following hnRNPLL expression. Together the RDE control and alternative splicing produce desired amounts of a payload or other transgene.

hnRNPLL alternative splicing can also be used to turn off a gene that is being expressed while the cell is quiescent. When the quiescent cell is activated by ligand binding to a receptor (e.g., CAR or TCR) this changes the metabolic state of the cell and hnRNPLL is expressed. If a gene being expressed while the cell is quiescent has hnRNPLL binding sites the binding of hnRNPLL can alter the splicing of the transcript so that the mRNA no longer encodes the gene product. For example, a cell (e.g., T-cell or B-cell) can be engineered to express a stemness factor (e.g., Tox and/or TCF7) while the cell is quiescent. The nucleic acid encoding Tox and/or TCF7 can include intron(s) with hnRNPLL binding sites so that in the absence of hnRNPLL the transcripts are spliced to make the Tox and/or TCF7 polypeptides, but upon cell activation and expression of hnRNPLL these transcripts now undergo alternative splicing and no longer produce transcripts encoding Tox and/or TCF7.

hnRNPLL alternative splicing also produces new "introns" or noncoding excision products as well as new mRNAs. The new introns can encode active RNAs (e.g., miRNA, siRNA, etc.) that are only expressed in the new introns. This adds yet another level of control to hnRNPLL alternative splicing as the miRNAs or siRNAs can turn off genes in the activated cells that are detrimental to the effector state of the cell including, for example, Tox, SCF7, and other exhaustion factors. miRNAs and siRNAs that could be controlled in this manner include, for example, miR155, mIR-192, mIR-34a, miR-133a, miR-138-5p, miR-342-5p, miR-491-5p, miR-541-3p, hsa-mir-26b-5p (MIRT030248), and hsa-mir-223-3p (MIRT054680).

Chimeric Antigen Receptors

Chimeric antigen receptors (CARs) can be fused proteins comprising an extracellular antigen-binding/recognition element, a transmembrane element that anchors the receptor to the cell membrane and at least one intracellular element. These CAR elements are known in the art, for example as described in patent application US20140242701, which is incorporated by reference in its entirety for all purposes herein. The CAR can be a recombinant polypeptide expressed from a construct comprising at least an extracellular antigen binding element, a transmembrane element and an intracellular signaling element comprising a functional signaling element derived from a stimulatory molecule. The stimulatory molecule can be the zeta chain associated with the T cell receptor complex. The cytoplasmic signaling element may further comprise one or more functional signaling elements derived from at least one costimulatory molecule. The costimulatory molecule can be chosen from 4-1BB (i.e., CD137), CD27 and/or CD28. The CAR may be a chimeric fusion protein comprising an extracellular antigen recognition element, a transmembrane element and an intracellular signaling element comprising a functional signaling element derived from a stimulatory molecule. The CAR may comprise a chimeric fusion protein comprising an extracellular antigen recognition element, a transmembrane element and an intracellular signaling element comprising a functional signaling element derived from a co-stimulatory molecule and a functional signaling element derived from a stimulatory molecule. The CAR may be a chimeric fusion protein comprising an extracellular antigen recognition element, a transmembrane element and an intracellular signaling element comprising two functional signaling elements derived from one or more co-stimulatory molecule(s) and a functional signaling element derived from a stimulatory molecule. The CAR may comprise a chimeric fusion protein comprising an extracellular antigen recognition element, a transmembrane element and an intracellular signaling element comprising at least two functional signaling elements derived from one or more co-stimulatory molecule(s) and a functional signaling element derived from a stimulatory molecule. The CAR may comprise an optional leader sequence at the amino-terminus (N-term) of the CAR fusion protein. The CAR may further comprise a leader sequence at the N-terminus of the extracellular antigen recognition element, wherein the leader sequence is optionally cleaved from the antigen recognition element (e.g., a scFv) during cellular processing and localization of the CAR to the cellular membrane.

Chimeric Antigen Receptor—Extracellular Element

Exemplary extracellular elements useful in making CARs are described, for example, in U.S. patent application Ser. No. 15/070,352 filed on Mar. 15, 2016, and U.S. patent application Ser. No. 15/369,132 filed Dec. 5, 2016, both of which are incorporated by reference in their entirety for all purposes.

The extracellular element(s) can be obtained from the repertoire of antibodies obtained from the immune cells of a subject that has become immune to a disease, such as for example, as described in U.S. patent application Ser. No. 15/070,352 filed on Mar. 15, 2016, and U.S. patent application Ser. No. 15/369,132 filed Dec. 5, 2016, both of which are incorporated by reference in their entirety for all purposes.

The extracellular element may be obtained from any of the wide variety of extracellular elements or secreted proteins associated with ligand binding and/or signal transduction as described in U.S. patent application Ser. No. 15/070,352 filed on Mar. 15, 2016, U.S. patent application Ser. No. 15/369,132 filed Dec. 5, 2016, U.S. Pat. Nos. 5,359,046, 5,686,281 and 6,103,521, all of which are incorporated by reference in their entirety for all purposes.

The extracellular element can also be obtained from a variety of scaffold protein families which share the common feature of a protein scaffold core with protein loops that can confer binding specificity and which loops can be altered to provide different binding specificities. Knottins are one such scaffold protein that has peptide loops which can be engineered to produce different binding specificities. For example, knottins can be engineered to have high affinity for specific integrin peptides. See for example, Silverman et al., J. Mol. Biol. 385:1064-75 (2009) and Kimura et al, Proteins 77:359-69 (2009), which are incorporated by reference in their entirety for all purposes. Some cancers overexpress certain integrin peptides and such cancers can be targeted by CARs that have an extracellular element that is a knottin specific for the overexpressed integrin. One such integrin is the integrin avP6 which is upregulated in multiple solid tumors such as those derived from colon, lung, breast, cervix, ovary/fallopian tubes, pancreas, and head and neck. See for example, Whilding et al., Biochem. Soc. Trans. 44:349-355 (2016), which is incorporated by reference in its entirety for all purposes.

The extracellular element can also be derived from knottins, which are a family of peptides containing a disulfide bonded core that confers outstanding proteolytic resistance and thermal stability. Knottins, which naturally function as protease inhibitors, antimicrobials, and toxins, are composed of several loops that possess diverse sequences amongst family members. Knottins can be engineered to include additional diversity of sequence in the loops to increase and create new binding specificities. Engineered knottins can be made to bind desired targets (e.g., desired antigens) with a desired specificity. Some Knottins bind with nM specificity to integrins and can be used to target a CAR to a certain integrins (e.g., αvβ3/αvβ5, αvβ3/αvβ5/a5β1, or αvβ6 integrins). Integrins such as αvβ6 can be upregulated on solid tumors and so can be suitable targets for a CAR. Such αvβ6 integrin specific CARs can be made using a knottin specific for the αvβ6 integrin as the extracellular element of the CAR. Activation of an engineered cell (e.g., a T-cell) through the αvβ6 knottin-CAR can be used to deliver a pay load to a solid tumor under the control of an RDE that causes expression of the payload upon CAR cell activation.

In an aspect, the extracellular domain can be an antibody or other binding molecule that binds specifically to an onco-sialylated CD43 that is widely found on AML and MDS blasts. See Hazenberg et al., European Hematology Associate abstracts, Abst S511 (2016), which is incorporated by reference in its entirety for all purposes. The antibody AT14-013 binds a specific sialylated epitope on the onco-sialylated CD43 which epitope is not found on CD43 associated with normal cells and tissue. See WO 2016/209079 and WO 2015/093949, both of which are incorporated by reference in their entirety for all purposes. This antibody or antibodies or other binding molecules which compete for onco-sialylated CD43 binding with AT14-013 are used to make anti-onco sialylated CD43 CARs. For example, the variable regions of the heavy and light chain of AT14-013 can be taken and reformatted as a single chain antibody for use as the extracellular domain of a CAR. Such an extracellular domain on a CAR directs the CAR cell (e.g., anti-onco sialylated CD43 CAR T-lymphocyte) to the AML and/or MDS cells targeting them for cell killing or modification by the CAR cell.

In an aspect, the extracellular domain can be an antibody or other binding molecule that binds specifically to complement factor H (CFH), for example, the SCR19 epitope of CFH. Antibodies and CDRs that can be used to make extracellular domains specific for CFH are found, for example, in U.S. Patent Application 20190315842, which is incorporated by reference in its entirety for all purposes. CFH can be aberrantly expressed on many types of solid tumors including, for example, breast cancer, lung cancer, small cell lung cancer, and nonsmall cell lung cancer.

Other tumor associated antigens that can be the target of the CAR include, for example, complement factor H (e.g., lung cancer, breast cancer, other solid tumors), delta opioid receptor (e.g., small cell lung cancer), c-Met (e.g., NSCLC), gpNMB (e.g., melanoma, breast cancer, other solid tumors), TRAP-2 (e.g., epithelial tumors and other solid tumors), CEACAM5 (e.g., colorectal cancer), CD56 (e.g., SCLC), CD25 (e.g., hematological cancers), guanyl cyclase C (e.g., pancreatic cancer), CAG (e.g., solid tumors), LIV-1 (e.g., breast cancer), PTK7 (e.g., lung cancer, colorectal cancer, breast cancer, and ovarian cancer), LAMP-1 (e.g., colorectal cancer, melanoma, laryngeal cancer), P-cadherin 3 (e.g., epithelial tumors), HER-3 (e.g., breast cancer), CD133 (e.g., hepatocellular carcinoma, pancreatic cancer, colorectal cancer, cholangiocarcinoma), GPRC5D (e.g., multiple myeloma), BCMA (e.g., multiple myeloma), CD138 (e.g., multiple myeloma), Ig kappa light chain (e.g., leukemia, lymphoma, NHL, and multiple myeloma), CD30 (e.g., NHL, HD), IL13Ra2 (e.g., glioblastoma), and ligands for NKG2D (e.g., using the NKG2D receptor as the binding domain for, e.g., AML, MDS, and MM).

Other tumor associated antigens that can be the target of the CAR include, for example, mesothelin, disialoganglioside (GD2), Her-2, MUC1, GPC3, EGFRVIII, CEA, CD19, EGFR, PSMA, GPC2, folate receptor P, IgG Fc receptor, PSCA, PD-L1, EPCAM, Lewis Y Antigen, LiCAM, FOLR, CD30, CD20, EPHA2, PD-1, C-MET, ROR1, CLDN18.2, NKG2D, CD133, TSHR, CD70, ERBB, AXL, Death Receptor 5, VEGFR-2, CD123, CD80, CD86, TSHR, ROR2, CD147, kappa IGG, IL-13, MUC16, IL-13R, NY-ESO-1, IL13RA2, DLL3, FAP, LMP1, TSHR, BCMA, NECTIN-4, MG7, AFP (alpha-fetoprotein), GP100, B7-H3, Nectin-4, MAGE-A1, MAGE-A4, MART-1, HBV, MAGE-A3, TAA, GP100, Thyroglobulin, EBV, HPV E6, PRAME, HERV-E, WT1, GRAS G12V, p53, TRAIL, MAGE-A10, HPV-E7, KRAS G12D, MAGE-A6, CD19, BCMA, CD22, CD123, CD20, CD30, CD33, CD138, CD38, CD7, SLAMF7, IGG FC, MUC1, Lewis Y Antigen, CD133, ROR1, FLT3, NKG2D, Kappa light chain, CD34, CLL-1, TSLP, CD10, PD-L1, CD44V6, EBV, CD5, GPC3, CD56, integrin B7, CD70, MUCL, CKIT, CLDN18.2, TRBC1, TACi, CD56, and CD4.

Still other tumor associated antigens that can be the target of the CAR include, for example, CD2, CD18, CD27, CD37, CD72, CD79A, CD79B, CD83, CD117, CD172, ERBB3, ERBB4, DR5, HER2, CS1, IL-1RAP, ITGB7, SLC2A14, SLC4A1, SLC6A11, SLC7A3, SLC13A5, SLC19A1, SLC22A12, SLC34A1, slc45A3, SLC46A2, Fra, IL-13Ra2, ULBP3, ULBP1, CLD18, NANOG, CEACAM8, TSPANi6, GLRB, DYRK4, SV2C, SIGLEC8, RBMXL3, HISTIHIT, CCR8, CCNB3, ALPPL2, ZP2, OTUB2, LILRA4, GRM2, PGG1, NBIF3, GYPA, ALPP, SPATAi9, FCRLI, FCRLA, CACNG3, UPK3B, 12UMO4, MUC12, HEPACAM, BPI, ATP6V0A4, HMMR, UPK1A, ADGRVI, HERC5, C3AR1, FASLG, NGB, CELSR3, CD3G, CEACAM3, TNFRSFBC, MS4AB, S1PR5, EDNRB, SCN3A, ABCC8, ABCB1, ANO1, KCND2, HTR4, CACNB4, HTR4, CNR2, 26LRB, EXOC1, ENTPP1, ICAM3, ABCGB, SCN4B, SPN, CD68, ITGAL, ITGAM, SCTR, CYYR1, CLCN2, SLARA3, and JAG3.

Intracellular Element

The intracellular element can be a molecule that can transmit a signal into a cell when the extracellular element of the CAR and/or RDE-CAR (collectively "CARS") binds to (interacts with) an antigen. The intracellular signaling element can be generally responsible for activation of at least one of the normal effector functions of the immune cell in which the CAR(s) has been introduced. The term "effector function" refers to a specialized function of a cell. Effector function of a T cell, for example, may be cytolytic activity or helper activity including the secretion of cytokines. Thus the term "intracellular signaling element" refers to the portion of a protein which transduces the effector function signal and directs the cell to perform a specialized function. While the entire intracellular signaling domain can be employed, in many cases the intracellular element or intracellular signaling element need not consist of the entire domain. To the extent that a truncated portion of the intracellular signaling domain is used, such truncated portion may be used as long as it transduces the effector function signal. The term intracellular signaling element is thus also meant to include any truncated portion of the intracellular signaling domain sufficient to transduce the effector function signal. Examples of intracellular signaling elements for use in the CARS can include the cytoplasmic sequences of the T cell receptor (TCR) and co-receptors that act in concert to initiate signal transduction following antigen receptor engagement, as well as any derivative or variant of these sequences and any recombinant sequence that has the same functional capability.

Intracellular elements and combinations of polypeptides useful with or as intracellular elements are described, for example, in U.S. patent application Ser. No. 15/070,352 filed on Mar. 15, 2016, and U.S. patent application Ser. No. 15/369,132 filed Dec. 5, 2016, both of which are incorporated by reference in their entirety for all purposes.

Transmembrane Element and Spacer Element

The CAR, and/or RDE-CAR may comprise a transmembrane element. The transmembrane element can be attached to the extracellular element of CAR, and/or RDE-CAR. The transmembrane element can include one or more additional amino acids adjacent to the transmembrane region, e.g., one or more amino acid associated with the extracellular region of the protein from which the transmembrane was derived (e.g., 1, 2, 3, 4, 5, 6, 7, 8, 9, 10 up to 15 amino acids of the extracellular region) and/or one or more additional amino acids associated with the intracellular region of the protein from which the transmembrane protein is derived (e.g., 1, 2, 3, 4, 5, 6, 7, 8, 9, 10 up to 15 amino acids of the intracellular region). The transmembrane element can be associated with one of the other elements used in the CAR, and/or RDE-CAR. The transmembrane element can be selected or modified by amino acid substitution to avoid binding of such elements to the transmembrane elements of the same or different surface membrane proteins, e.g., to minimize interactions with other members of the receptor complex. The transmembrane element can be modified to remove cryptic splice sites (e.g., CARS made with a CD8 transmembrane domain can be engineered to remove a cryptic splice site) and/or a transmembrane element can be used in the CAR construct that does not have cryptic splice sites. The transmembrane element can be capable of homodimerization with another CAR, and/or RDE-CAR on the cell surface. The amino acid sequence of the transmembrane element may be modified or substituted so as to minimize interactions with the binding elements of the native binding partner present in the same cell.

Transmembrane elements useful in the present invention are described, for example, in U.S. patent application Ser. No. 15/070,352 filed on Mar. 15, 2016, and U.S. patent application Ser. No. 15/369,132 filed Dec. 5, 2016, both of which are incorporated by reference in their entirety for all purposes.

Receptors

CARS may be used as the receptor with the cell and the RDE-transgene. CARS are described above. In addition to CARS, other receptors may be used to activate or otherwise change conditions in a cell so that a transgene under the control of an RDE is expressed. Receptors that recognize and respond to a chemical signal can be coupled to expression of the transgene through the RDE. For example, ion channel-linked (ionotropic) receptors, G protein-linked (metabotropic) receptors, and enzyme-linked receptors can be coupled to the expression of the transgene.

One class of receptor that can be coupled to transgene expression are immune receptors such as, for example, T-cell receptors, B-cell receptors (aka antigen receptor or immunoglobulin receptor), and innate immunity receptors.

T-cell receptors are heterodimers of two different polypeptide chains. In humans, most T cells have a T-cell receptor made of an alpha (a) chain and a beta (β) chain have a T-cell receptor made of gamma and delta (γ/δ) chains (encoded by TRG and TRD, respectively). Techniques and primers for amplifying nucleic acids encoding the T-cell receptor chains from lymphocytes are well known in the art and are described in, for example, SMARTer Human TCR a/b Profiling Kits sold commercially by Clontech, Boria et al., BMC Immunol. 9:50-58 (2008); Moonka et al., J. Immunol. Methods 169:41-51 (1994); Kim et al., PLoS ONE 7:e37338 (2012); Seitz et al., Proc. Natl Acad. Sci. 103:12057-62 (2006), all of which are incorporated by reference in their entirety for all purposes. The TCR repertoires can be used as separate chains to form an antigen binding domain. The TCR repertoires can be converted to single chain antigen binding domains. Single chain TCRs can be made from nucleic acids encoding human alpha and beta chains using techniques well-known in the art including, for example, those described in U.S. Patent Application Publication No. US2012/0252742, Schodin et al., Mol. Immunol. 33:819-829 (1996); Aggen et al., "Engineering Human Single-Chain T Cell Receptors," Ph.D. Thesis with the University of Illinois at Urbana-Champaign (2010) a copy of which is found at ideals.illinois.edu/bitstream/handle/2142/18585/Aggen_David.pdf?sequence=1, all of which are incorporated by reference in their entirety for all purposes.

B-cell receptors include an immunoglobulin that is membrane bound, a signal transduction moiety, CD79, and an ITAM. Techniques and primers for amplifying nucleic acids encoding human antibody light and heavy chains are well-known in the art, and described in, for example, ProGen's Human IgG and IgM Library Primer Set, Catalog No. F2000; Andris-Widhopf et al., "Generation of Human Fab Antibody Libraries: PCR Amplification and Assembly of Light and Heavy Chain Coding Sequences," Cold Spring Harb. Protoc. 2011; Lim et al., Nat. Biotechnol. 31:108-117 (2010); Sun et al., World J. Microbiol. Biotechnol. 28:381-386 (2012); Coronella et al., Nucl. Acids. Res. 28:e85 (2000), all of which are incorporated by reference in their entirety for all purposes. Techniques and primers for amplifying nucleic acids encoding mouse antibody light and heavy chains are well-known in the art, and described in, for example, U.S. Pat. No. 8,143,007; Wang et al., BMC Bioinform. 7(Suppl):S9 (2006), both of which are incorporated by reference in their entirety for all purposes. The antibody repertoires can be used as separate chains in antigen binding domains, or converted to single chain antigen binding domains. Single chain antibodies can be made from nucleic acids encoding human light and heavy chains using techniques well-known in the art including, for example, those described in Pansri et al., BMC Biotechnol. 9:6 (2009); Peraldi-Roux, Methods Molc. Biol. 907:73-83 (2012), both of which are incorporated by reference in their entirety for all purposes. Single chain antibodies can be made from nucleic acids encoding mouse light and heavy chains using techniques well-known in the art including, for example, those described in Imai et al., Biol. Pharm. Bull. 29:1325-1330 (2006); Cheng et al., PLoS ONE 6:e27406 (2011), both of which are incorporated by reference in their entirety for all purposes.

Innate immunity receptors include, for example, the CD94/NKG2 receptor family (e.g., NKG2A, NKG2B, NKG2C, NKG2D, NKG2E, NKG2F, NKG2H), the 2B4 receptor, the NKp30, NKp44, NKp46, and NKp80 receptors, the Toll-like receptors (e.g., TLR1, TLR2, TLR3, TLR4, TLR5, TLR6, TLR7, TLR8, TLR9, TLR10, RP105).

G-protein linked receptors also known as seven-transmembrane domain receptors are a large family of receptors that couple receptor binding of ligand to cellular responses through G proteins. These G-proteins are trimers of α, β, and γ subunits (known as Ga, Go, and Gy, respectively) which are active when bound to GTP and inactive when bound to GDP. When the receptor binds ligand it undergoes a conformational change and allosterically activates the G-protein to exchange GTP for bound GDP. After GTP binding the G-protein dissociates from the receptor to yield a Gα-GTP monomer and a Gβγ dimer. G-protein linked receptors have been grouped together into classes which include, for example, Rhodopsin-like receptors, secretin receptors, metabotropic glutamate/pheromone receptors, fungal mating pheromone receptors, cyclic AMP receptors, and frizzled/smoothened receptors. G-protein receptors are used in a wide variety of physiological processes including detection of electromagnetic radiation, gustatory sense (taste), sense of smell, neurotransmission, immune system regulation, growth, cell density sensing, etc.

Enzyme linked receptors also known as a catalytic receptor, is a transmembrane receptor, where the binding of an extracellular ligand causes enzymatic activity on the intracellular side. Enzyme linked receptors have two domains joined together by a transmembrane portion (or domain) of the polypeptide. The two terminal domains are an extracellular ligand binding domain and an intracellular domain that has a catalytic function. There are multiple families of enzyme linked receptors including, for example, the Erb receptor family, the glial cell-derived neurotrophic factor receptor family, the natriuretic peptide receptor family, the trk neurotrophin receptor family, and the toll-like receptor family.

Ion channel linked receptors also known as ligand-gated ion channels are receptors that allow ions such as, for example, $Na^+$, $K^+$, $Ca^{2+}$ and $Cl^-$ to pass through the membrane in response to the binding of a ligand to the receptor. There are multiple families of ligand-gated ion channels including, for example, cationic cys-loop receptors, anionic cys-loop receptors, ionotropic glutamate receptors (AMPA receptors, NMDA receptors), GABA receptors, 5-HT receptors, ATP-gated channels, and $PIP_2$-gated channels.

Eukaryotic Cells

Various eukaryotic cells can be used as the eukaryotic cell. The eukaryotic cells can be animal cells. The eukaryotic cells can be mammalian cells, such as mouse, rat, rabbit, hamster, porcine, bovine, feline, or canine. The mammalian cells can be cells of primates, including but not limited to, monkeys, chimpanzees, gorillas, and humans. The mammalians cells can be mouse cells, as mice routinely function as a model for other mammals, most particularly for humans (see, e.g., Hanna, J. et al., *Science* 318:1920-23, 2007; Holtzman, D. M. et al., *J Clin Invest.* 103(6):R15-R21, 1999; Warren, R. S. et al., *J Clin Invest.* 95: 1789-1797, 1995; each publication is incorporated by reference in its entirety for all purposes). Animal cells include, for example, fibroblasts, epithelial cells (e.g., renal, mammary, prostate, lung), keratinocytes, hepatocytes, adipocytes, endothelial cells, and hematopoietic cells. The animal cells can be adult cells (e.g., terminally differentiated, dividing or non-dividing) or embryonic cells (e.g., blastocyst cells, etc.) or stem cells. The eukaryotic cell also can be a cell line derived from an animal or other source.

The eukaryotic cells can be stem cells. A variety of stem cells types are known in the art and can be used as the eukaryotic cell, including for example, embryonic stem cells, inducible pluripotent stem cells, hematopoietic stem cells, neural stem cells, epidermal neural crest stem cells, mammary stem cells, intestinal stem cells, mesenchymal stem cells, olfactory adult stem cells, testicular cells, and progenitor cells (e.g., neural, angioblast, osteoblast, chondroblast, pancreatic, epidermal, etc.). The stem cells can be stem cell lines derived from cells taken from a subject.

The eukaryotic cell can be a cell found in the circulatory system of a mammal, including humans. Exemplary circulatory system cells include, among others, red blood cells, platelets, plasma cells, T-cells, natural killer cells, B-cells, macrophages, neutrophils, or the like, and precursor cells of the same. As a group, these cells are defined to be circulating eukaryotic cells of the invention. The eukaryotic cell can be derived from any of these circulating eukaryotic cells. The eukaryotic cell can be a primary cell, derived from a primary cell, or a suitable cell line. The source of the eukaryotic cell may be allogeneic, syngeneic, or autologous. Transgenes may be used with any of these circulating cells or eukaryotic cells derived from the circulating cells. The eukaryotic cell can be a T-cell or T-cell precursor or progenitor cell. The eukaryotic cell can be a helper T-cell, a cytotoxic T-cell, a memory T-cell, a regulatory T-cell, a natural killer T-cell, a mucosal associated invariant T-cell, a gamma delta T cell, or a precursor or progenitor cell to the aforementioned. The eukaryotic cell can be a natural killer cell, or a precursor or progenitor cell to the natural killer cell. The eukaryotic cell can be a B-cell, or a B-cell precursor or progenitor cell. The eukaryotic cell can be a neutrophil or a neutrophil precursor or progenitor cell. The eukaryotic cell can be a megakaryocyte or a precursor or progenitor cell to the megakaryocyte. The eukaryotic cell can be a macrophage or a precursor or progenitor cell to a macrophage.

The eukaryotic cells can be obtained from a subject. The subject may be any living organisms. The cells can be derived from cells obtained from a subject. Examples of subjects include humans, dogs, cats, mice, rats, and transgenic species thereof. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. Any number of T cell lines available in the art also may be used. T-cells can be obtained from a unit of blood collected from a subject using any number of techniques known to the skilled artisan, such as Ficoll separation. Cells from the circulating blood of an individual can be obtained by apheresis. The apheresis product typically contains lymphocytes, including T cells, monocytes, granulocytes, B cells, other nucleated white blood cells, red blood cells, and platelets. The cells collected by apheresis may be washed to remove the plasma fraction and to place the cells in an appropriate buffer or media for subsequent processing steps. The cells can be washed with phosphate buffered saline (PBS). In an alternative aspect, the wash solution lacks calcium and may lack magnesium or may lack many if not all divalent cations. Initial activation steps in the absence of calcium can lead to magnified activation.

Enrichment of a T cell population by negative selection can be accomplished with a combination of antibodies directed to surface markers unique to the negatively selected cells. Cells can be enriched by cell sorting and/or selection via negative magnetic immunoadherence or flow cytometry using a cocktail of monoclonal antibodies directed to cell surface markers present on the cells. For example, to enrich for CD4+ cells, a monoclonal antibody cocktail typically includes antibodies to CD14, CD20, CD11b, CD16, HLA-DR, and CD8. It may be desirable to enrich for regulatory T cells which typically express CD4+, CD25+, CD62Lhi, GITR+, and FoxP3+. Alternatively, in certain aspects, T regulatory cells are depleted by anti-C25 conjugated beads or other similar method of selection.

T cells may be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005, each of which is incorporated by reference in its entirety for all purposes.

NK cells may be expanded in the presence of a myeloid cell line that has been genetically modified to express membrane bound IL-15 and 4-1BB ligand (CD137L). A cell line modified in this way which does not have MHC class I and II molecules is highly susceptible to NK cell lysis and activates NK cells. For example, K562 myeloid cells can be transduced with a chimeric protein construct consisting of human IL-15 mature peptide fused to the signal peptide and transmembrane domain of human CD8a and GFP. Transduced cells can then be single-cell cloned by limiting dilution and a clone with the highest GFP expression and surface IL-15 selected. This clone can then be transduced with human CD137L, creating a K562-mbl5-137L cell line. To preferentially expand NK cells, peripheral blood mononuclear cell cultures containing NK cells are cultured with a K562-mb15-137L cell line in the presence of 10 IU/mL of IL-2 for a period of time sufficient to activate and enrich for a population of NK cells. This period can range from 2 to 20 days, preferably about 5 days. Expanded NK cells may then be transduced with the anti-CD19-BB-(chimeric receptor.

Modification of CD3 Epsilon in T-Lymphocytes

T-lymphocytes can be modified to reduce graft versus host reactions. For example, allogenic T-lymphocytes can be modified so that upon transplantation graft versus host reactions are reduced. The allogenic T-lymphocytes can be used in a CAR therapy and/or can carry other transgenes for delivery by the T-lymphocyte at a target site. The T-lymphocytes can be modified by introducing a mutant that has a dominant effect on T-cell receptor function. For example, the mutant can knock out the T-cell receptor, or can disrupt signaling from the T-cell receptor. Mutations of the CD3 epsilon chain can have such dominant negative effects on T-cell receptor signaling. An example of a negative dominant mutant of CD3 epsilon is a C119S/C122S double mutant that alters the C-X-X-C motif in the CD3 epsilon to S-X-X-S. This double mutant is defective for signal transduction from an activated T-cell receptor and so binding of host antigens by a T-lymphocyte (e.g., an allogenic T-lymphocyte) does not activate the T-lymphocyte reducing graft versus host disease.

The CD3 epsilon double mutant (C119S/C122S) can be introduced into the T-lymphocyte by integrating it to the CD3 epsilon locus of the T-lymphocyte, or because this double mutant is a negative dominant it can be introduced at other sites in the T-lymphocyte genome or can be transiently transfected/transduced into the T-lymphocyte. Transient transfection can produce T-lymphocytes with CD3 epsilon double mutant associated with the T-cell receptors of the T-lymphocytes prior to activation by binding of a CAR (or other receptor) at the target site. If the transient expression has ended when the T-lymphocyte reaches target and interacts with its CAR, the CAR T-lymphocytes can kill through CAR reactions and through graft versus host/tumor cell reactions through the allogenic T-cell receptors.

In an example, T-lymphocytes are obtained from a host (e.g., an allogenic host) and activated with CD3/CD28 beads. These activated T-lymphocytes are transfected with a construct encoding a CAR (and/or other desired transgene) and a double mutant CD3 epsilon (C119S/C122S). T-lymphocytes transfected/transduced with the CAR are isolated (e.g., by affinity isolation with the CAR or a selection against active T-lymphocytes with active TCRs can be done) and administered to a subject.

Another mutation of CD3 epsilon can make deletions of one or more of the ITAM portions of the polypeptide. These ITAM deletions reduce the signaling capacity of CARS made with these ITAM mutants. The CD3 epsilon of the CAR can be engineered to have ITAM deletions of one or more ITAM sequences. T-cells engineered with a CAR and these CD3 epsilon genes with the ΔITAM(s) can be used with payloads under control of an RDE. When these T-cells are activated by the CAR the payload is expressed. The ΔITAMs reduce the responsiveness of the cell to the CAR (a crippled CAR) which can reduce or prevent T-cell exhaustion. This allows the T-cell to produce the transgene payload for a longer period of time.

Nucleic Acids

Also described in this disclosure are nucleic acids that encode, at least in part, the individual peptides, polypeptides, proteins, RDEs, and other post-transcriptional control devices described herein. The nucleic acids may be natural, synthetic or a combination thereof. The nucleic acids of the invention may be RNA, mRNA, DNA or cDNA.

The nucleic acids of the invention also include expression vectors, such as plasmids, or viral vectors, or linear vectors, or vectors that integrate into chromosomal DNA. Expression vectors can contain a nucleic acid sequence that enables the vector to replicate in one or more selected host cells. Such sequences are well known for a variety of cells. The origin of replication from the plasmid pBR322 is suitable for most Gram-negative bacteria. In eukaryotic host cells, e.g., mammalian cells, the expression vector can be integrated into the host cell chromosome and then replicate with the host chromosome. Similarly, vectors can be integrated into the chromosome of prokaryotic cells.

Expression vectors also generally contain a selection gene, also termed a selectable marker. Selectable markers are well-known in the art for prokaryotic and eukaryotic cells, including host cells of the invention. Generally, the selection gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli. An exemplary selection scheme can utilize a drug to arrest growth of a host cell. Those cells that are successfully transformed with a heterologous gene produce a protein conferring drug resistance and thus survive the selection regimen. Other selectable markers for use in bacterial or eukaryotic (including mammalian) systems are well-known in the art.

An example of a promoter that is capable of expressing a transgene (e.g., a RDE-CAR and/or a CAR) in a mammalian T cell is the EF1a promoter. The native EF1a promoter drives expression of the alpha subunit of the elongation factor-1 complex, which is responsible for the enzymatic delivery of aminoacyl tRNAs to the ribosome. The EF1a promoter has been extensively used in mammalian expression plasmids and has been shown to be effective in driving CAR expression from transgenes cloned into a lentiviral vector. See, e.g., Milone et al., Mol. Ther. 17(8): 1453-1464 (2009), which is incorporated by reference in its entirety for all purposes. Another example of a promoter is the immediate early cytomegalovirus (CMV) promoter sequence. This promoter sequence is a strong constitutive promoter sequence capable of driving high levels of expression of any polynucleotide sequence operatively linked thereto. Other constitutive promoter sequences may also be used, including, but not limited to the simian virus 40 (SV40) early promoter, mouse mammary tumor virus promoter (MMTV), human immunodeficiency virus (HIV) long terminal repeat (LTR) promoter, MoMuLV promoter, phosphoglycerate kinase (PGK) promoter, MND promoter (a synthetic promoter that contains the U3 region of a modified MoMuLV LTR with myeloproliferative sarcoma virus enhancer, see, e.g., Li et al., J. Neurosci. Methods vol. 189, pp. 56-64 (2010) which is incorporated by reference in its entirety for all purposes), an avian leukemia virus promoter, an Epstein-Barr virus immediate early promoter, a Rous sarcoma virus promoter, as well as human gene promoters such as, but not limited to, the actin promoter, the myosin promoter, the elongation factor-1a promoter, the hemoglobin promoter, and the creatine kinase promoter. Further, the invention is not limited to the use of constitutive promoters.

Inducible or repressible promoters are also contemplated for use in this disclosure. Examples of inducible promoters include, but are not limited to a Nuclear Factor of Activated T-cell inducible promoter (NFAT), a metallothionein promoter, a glucocorticoid promoter, a progesterone promoter, a tetracycline promoter, a c-fos promoter, the T-REx system of ThermoFisher which places expression from the human cytomegalovirus immediate-early promoter under the control of tetracycline operator(s), and RheoSwitch promoters of Intrexon. Macian et al., Oncogene 20:2476-2489 (2001); Karzenowski, D. et al., BioTechiques 39:191-196 (2005); Dai, X. et al., Protein Expr. Purif 42:236-245 (2005); Palli, S. R. et al., Eur. J. Biochem. 270:1308-1515 (2003); Dhadialla, T. S. et al., Annual Rev. Entomol. 43:545-569 (1998); Kumar, M. B, et al., J. Biol. Chem. 279:27211-27218 (2004); Verhaegent, M. et al., Annal. Chem. 74:4378-4385 (2002); Katalam, A. K., et al., Molecular Therapy 13:S103 (2006); and Karzenowski, D. et al., Molecular Therapy 13:S194 (2006), U.S. Pat. Nos. 8,895,306, 8,822,754, 8,748,125, 8,536,354, all of which are incorporated by reference in their entirety for all purposes. Inducible promoter also include promoters with heat shock elements that respond to mild hyperthermia. Heat shock elements are made of multiple inverted repeats of the consensus sequence 5'-nGAAn-3' located upstream of a promoter such as, for example, a promoter from a heat shock gene (e.g., HSPB1).

Expression vectors typically have promoter elements, e.g., enhancers, to regulate the frequency of transcriptional initiation. Typically, these are located in the region 30-110 bp upstream of the start site, although a number of promoters have been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

The expression vector may be a bi-cistronic construct or multiple cistronic construct. The two cistrons may be oriented in opposite directions with the control regions for the cistrons located in between the two cistrons. When the construct has more than two cistrons, the cistrons may be arranged in two groups with the two groups oriented in opposite directions for transcription. Exemplary bicistronic constructs are described in Amendola et al., Nat. Biotechnol. 23:108-116 (2005), which is incorporated by reference in its entirety for all purposes. The control region for one cistron may be capable of high transcription activity and the other may have low transcriptional activity under conditions of use. One or both control regions may be inducible. Examples of high transcription activity control regions include, for example, MND, EF1-alpha, PGK1, CMV, ubiquitin C, SV40 early promoter, tetracycline-responsive element promoter, cell-specific promoters, human beat-actin promoter, and CBG (chicken beta-globin), optionally including the CMV early enhancer. Examples of low transcription activity control regions include, for example, TRE3G (commercially sold by Clontech, a tetracycline-responsive element promoter with mutations that reduce basal expression), T-REx™ (commercially sold by ThermoFisher), and a minimal TATA promoter (Kiran et al., Plant Physiol. 142:364-376 (2006), which is incorporated by reference in its entirety for all purposes), HSP68, and a minimal CMV promoter. Examples of inducible control regions include, for example, NFAT control regions (Macian et al, Oncogene 20:2476-2489 (2001)), and the inducible control regions described above.

The bi-cistronic construct may encode a CAR and a polypeptide that is a payload (or makes a payload) to be delivered at a target site. Exemplary payloads are described above and below. The nucleic acid encoding the CAR can be operably linked to a strong promoter, a weak promoter, and/or an inducible promoter, and optionally, operably linked to a RNA control device, DE, RDE, or combination of the foregoing. The CAR can be encoded by nucleic acids in a Side-CAR format. The nucleic acid encoding the polypeptide can be operably linked to a strong promoter, a weak promoter, and/or an inducible promoter. The nucleic acid encoding the polypeptide that is a payload (or makes the payload) can be under the control of an RDE. The RDE may be one that responds to the activation state of the cell through, for example, glycolytic enzymes such as, for example, glyceraldehyde phosphate dehydrogenase (GAPDH), enolase (ENO1 or ENO3), phosphoglycerate kinase (PGK1), triose phosphate isomerase (TPI1), aldolase A (ALDOA), or phosphoglycerate mutase (PGAM1). The RDE may also be bound and regulated by other energy metabolism enzymes such as, for example, transketolase (TKT), malate dehydrogenase (MDH2), succinyl CoA Synthetase (SUGLG1), ATP citrate lyase (ACLY), or isocitrate dehydrogenase (IDH1/2). The host cell can express a CAR that binds to its antigen at a target site in a subject. This binding of antigen at the target site activates the cell causing the cell to increase glycolysis which induces expression of the nucleic acid encoding the polypeptide under the control of the RDE (bound by glycolytic or other energy metabolism enzymes).

Bidirectional promoters that can be used in constructs include, for example, smol2 described above. Additional bidirectional promoters include, for example, BDP1 that has the IDH3 promoter and SSR4 promoter, BDP3 that has the XPC promoter and LSM3 promoter, BDP4 that has the XPO5 promoter and the POLH promoter, BDP5 that has the DESI promoter and the XRCC6 promoter, BDP6 that has the TMEM167a promoter and the XRCC4 promoter, BDP7 that has the MBD4 promoter and the IFT122 promoter, BDP8 that has the PCNA promoter and the CDS2 promoter, BDP9 that has the CETN2 promoter and the DHL promoter, BDP10 that has the SMYD4 promoter and the RPA1 promoter, BDP11 that has the PMS2 promoter and the AIMP2 promoter, BDP12 that has the MCM7 promoter and the AP4M1 promoter, BDP13 that has the TPRA1 promoter and the MCM2 promoter, BDP14 that has the TIMM8 promoter and the SDHD promoter, BDP15 that has the IKZF5 promoter and the ACADSAB promoter, and BDP16 that has the STYXL1 promoter and the MDH2 promoter. Examples of the bidirectional promoters include, for example, a smol2 example is SEQ ID NO: 18, a BDP1 example is SEQ ID NO: 19, a BDP3 example is SEQ ID NO: 20, a BDP4 example is SEQ ID NO: 21, a BDP5 example is SEQ ID NO: 22, a BDP6 example is SEQ ID NO: 23, a BDP7 example is SEQ ID NO: 24, a BDP8 example is SEQ ID NO: 25, a BDP9 example is SEQ ID NO: 26, a BDP10 example is SEQ ID NO: 27, a BDP11 example is SEQ ID NO: 28, a BDP12 example is SEQ ID NO: 29, a BDP13 example is SEQ ID NO: 30, a BDP14 example is SEQ ID NO: 31, a BDP15 example is SEQ ID NO: 32, and a BDP16 example is SEQ ID NO: 33.

(SEQ ID NO: 33)

GGCTGTCCCAGCACCTCAGCGCAGAGCAAGTGGTGGTCAGGGGAGCGTCTCAAATC

CTGCGCAGCCCAACGTCCGGCGCCGCCAAGTGACGCACGAGGTGCTGTGACTCGTG

CCAGCCCCCTAATCTGCGGAAGTGGAGTGCGGGGAGTGCGCCGGAAGAGGGGTACG

GAAGTGCGCCGGAAGTGGGGTGCGGAGGTGTGCAGCGCGCTGTCAGACTGGCTCGC

AGGCGGCGCGGCCGGCGGACCCGTTCGAGACAGCGCGGGCGGCTCGGGTCCCCTGG

GGCTCCGCAGCAGGAGGACGCC (SEQ ID NO: 34)

CGCCTCTTCTCTGCCTAGAGGAAAAGAAAACGAGCTCCCATGAACACGAGGGGCAA

ACGAGGAAGAGCGACGCGTAAGTGGCAGCGGCAGCCAATCGCGCACCGAACGGCT

GGGCCGGCATTGTGACGTCTCTGGCAGCACTGACGTGGCCCCTCCCTGAGCCAGGG

GCCCAGCTGGTCGCGGTCCCCCCCTCAACATGGCGGCAGCGGTGCTCTAGGCGCCG

GAAGGGGGCGTGAATCGGTGCGACCGCGCGCGTGCGCAGTACCGGGTCCGCGCCTG

-continued

TCCCCGAAACTTCGCACCCCGTCGAACTCTCGCGAGAGCGGTATCTGCGTGTCGGGA

CGTGCGGAGGCTCTCACTTTCCGTC (SEQ ID NO: 35)

CATGTTGCTTGTCTGGGCAAATTCCACTTCGCGAGTGACGCACCCGGCCGCGATGCG

CTAGAACGCCGGCCCCGCCCCGAGGCGGTGCGCTTGGCCACGCCCCTTCGTTGGAG

GCCTAGTCACGCCCCTAAAGGAAGCTCCACCCCATACCCGTGGCCACTAAAAAACT

GCGGGAAGCAGGAAAGAGCACAACAGGTTTCTCTCTATTTCCGGTGTATTGTATCCT

CACGTTTCCGGAGATTGACGTTGCTCTTGTGTTCTCGCGAGAGGCGGGAAAGGGCGC

AGGGTTTGAAACATG (SEQ ID NO: 36)

CATGCCTAGCGCCACGCGCCGAGAGCGCACACCACTGCAGTCCCGGGACCACGAGG

CACGACAGCTCCCTCGGCGAGACCACCCGTTGGTACCGGGCCGCGGCGGGCGGCGG

GGGTGGGAAGCTGGAGGAGGAGCGTTAGCAGCAACTCGCGCTGGGAAGAAGCCGG

CGCTGCGCACGCGCCCGGCCCGCCACTGCGCACGCGCCCGCGGAAGTGGCGGCTCC

CGTGTGCAGGTTGAGCCTAGGTGGGCGGGGCGGGAGGCGGAAGGGCCGCGGTGCGC

AGCCGCGTCAACGGCCCTTCGCAGCGGGCGCGCTGTCAGACCTCA (SEQ ID NO: 37)

CATTGGGACCCGTGGCGACGGCGGCCACGACGGCCCTCGGGCACCCGGCAGCGGCT

TGGACCTTCCCGTACCCGACGGGAGTGCGAAGCGGAGGGAGAGGGGGGGACCGAG

CCCGGGCCCGGGCTGAGGGGTGGGGGAGAGGCCGCCCTGCGCTGCTCGCGCCCCCA

CACCCGCTACCGGCAACGACTACTGTGAGGTGACAGAGAGGGGACAGGGAGGGCC

CACACGGAAGAGGGGGCGGGGGCAGGGATGCACTTTTGCGCATGTGCTTACAGTCC

TGACGTAGGAAGGGGCGGGGCTTTGCCGAAGGGGGCGGGGCTCTCGCTGATGGGTT

GGCTTTCGTCAGGGACATAGGTAGAAGCTGGTTGGGGAGTGTGCGTGCCAGCCTGA

CGCGATATAGTGCGCACATGCGTGATGACGTAGAGGGCGTTGATTGGGA (SEQ ID NO: 38)

CATAGCGAGGCCGGCGATGCCGCAGCCACATCACCCTTCCGGGGCTCAGGCGGAAG

AGGCTGCATGTCCCGTCTGCCCTTCTCGCCCTCTCCAGCCGTCCGGTTGGGCTTGTCA

CGGCACCGCCTACCAAGACGGGCGGTTAAGACACTAGGATAGGCTCCTCTCCACCG

GAAAAGGCGGGATTTAGATCACGTCCCGCAGGCCGGCGGAAGTAGCTGATACTCTC

ATTGGTTGCAAAACCTTGATCTGTGAAAGCGGGCGTTTTGGAAGATACCGGAAGTA

GAGTCACGGAGAGGTAGGATCCG (SEQ ID NO: 39)

CATCGAGCAGGGTCCGGCTGCAGCAACGAGCCCAGCGCCGCAACGCCCAGGGTGTG

GGGCGGAGTAAGATGTGAAACCTCTTCAGCTCACGGCACCGGGCTGCAACCGAGGT

CTGAATGTTGCGAAAGCGCCCCAGACGCCGCCGCTGCTTTCCGGCCGCCCCCTCGGC

TACAGCCGCCATTTCCACGCTCCACCAATCAAATCCATTCTCGAGGAAGACGCACCG

CCCCCACACGCCCCGACCAATCGCTCGCGCTCTGGTTGCGCTGGCGCCTTAGGGGCT

CCAGTGCCACCATTGCTTTTGCTGCTTTTCTGGCTTTCCCTTTCGGACATGCGCGCTC

GGAGCAAGGCGCCCTCGCACTCAGCTTACCGCGCATGTACGTTGCCAGGGGTAACG

CAGGTAGCCAAAGTGGCTTGTGGAGTGGCGACCGTTAGTGAGGCGGTTGCTGAGAC

AGACGCTGAGGCGGGTAGGAGGAGCCCGAGCCGTAAGGGAAGCCGTGATG

-continued (SEQ ID NO: 40)
CAGGCTAGAGCCTCCGGGTGGCGCTTCTCGCCCTCAGTAACCGGTTACCTCCAGAAC

CAGGGCGCCAGCTCCGGCCATCCGCGGTTAAGCGGGAGCTCCCATTGGCTAATCGC

ACACTGAAACGCACGCCTTTTCCCGCCCCTGACGCTGCCGTCCAATGCGCGCCTCTC

GACTCTGCTCCGCCCCGCCCCGCCCCCGTCGCCCTGCCTCCCTGGCGTATTTGCGCCA

TTGGTGGATATTCCGGACCGTGATGGTGGCGCTGCGCGTGCGCACTCGCTCCGAGCC

CTGCTCCCGGGAGAGGGAGCTCTCGGGTCGGGGCTAGGGAAGGCTGACCCCGCTCG

GCCCGGGTGAAAGGGCGGTGACGGCACTGGGTGGGGCCGAGCTCCAGGGCTGGCTG

CTGGGCTGCTAAGGGAACTGTGAGCCGCTCAGAGCCGCGCGCCTCCCGGGCGGGGC

GGGGCCGGCCGTGGGAGTCCGCGCGTGCCCGCGCCGAGCTGCCTGCTCCGGCGGCT

TCGCTGCTAGCTCGCGGCGACGTCGGGCCGATTTTCCCAGGATG.

(SEQ ID NO: 41)
CATAGCCAAAGGAGTCCGCTGCCGGTTGTTAGGCAACCGACGTGTACACTGACTCG

GCGCCGTTCCCACCGCCCCGCGCGCGCAGCCCCGCTCCCCATTGGCCGTCCGCTCGT

CGCCGCCTCTCCCTATTGGTGCAGGGCCGAAGAGGGTGGGACTAACCTGGCAAAGC

CCCGGCCCAGCGCGGGGAGGGGCACGCTGGCGACAGAGCCCCGTCTTTATTGGGCA

AGATCACGCCGTGAGCGCCAATTGGCTGAGTCGTCGCCGAGCTGGGCCAATCCTCTT

GGTGGAGGAAGCTCGGCTGATTCTCGGCTCACGCGGGAGGGGAG (SEQ ID NO: 42)
GTGGGTCACGTGGGCCGCGCCTCGGCCAATGCGGCGGCTGCGTAGCGCCCGGGCCC

GCCCCTGAGCCGCGCGCACGTCGGGGGCGGGAGCGGTGCGCGCAACTTC (SEQ ID NO: 43)
CATGGATGCAACACCCGATCCGCCTCGGGGACTGGGAAAGTTCCCTCCAGGGCTCC

CACAGGCGCTCCGCCTCCTGAACTCCCATTGGCTGCTTTCGACGTTGTGCTCCACCCT

TTCCGGGCGGGGCGGCAAAAATACTTCCCGTCTCTCCTTTTCGCCTATTGGCTCTGTC

AAAGGTCGACTTCGTGACGTCAAAGAGCCTGGGCCAATCAGAGCACACCGGACTGC

GTTTTCCCGAACGCCCGCAGCAGGGTCAGAAGGGAGGTGGCCGGTCTCCGTCGTGA

CCTCTGACGGTTTCTGAGCGTTGGCCTTTGGCACGCGCTACCCCCTTTTGCTTTGGTT

CTGCCATG (SEQ ID NO: 44)
CATCGCTGCCGAGGGCCGTGCGGCCGCGCTTGGCGGGCTCAGAGGTCTTGCTCCTGG

GGAAGCTGAGAATCTCCGCGCGGTGGACTGTGGCCGGCCAACCGAAATTGGCGCGA

AACGTCGCCCCCCACGTGACCGGCGCCACTGCGTGCGGGCCAATCGGACAAGGCGG

CCTTCTTCACCTCCCGCTAGCCGCAAGCCAATCACCGTGCGGGCCTAGAATGAGTGA

CGGGGAGGCGGTGCGGGCGTCGGAAGGGAATCTCCGGGCGGGGTAGTGCAGGCGC

CGGGTTTCCCGCGGTCCGAGCTGGCGCGGGCGGAGGAGAATCGCTCTTAAAGGGCC

AGCGCACACGCGTTCTTTTGTTCCGGGGCCGCAGGGCGGGGCAGGCCCGACTTTCGC

CGTCTTCTTGTCTACTCTCCAGAACGGCCATG (SEQ ID NO: 45)
GCACGCGCACAGCGCCGGGCCGCACACCTCCGGGCTCTGGGCGGAGCGCCTCGGGC

GTTGTAGGCGGGACCGGACCCTCTGGCCCGCCCCTCCGTGTCCCTTCTGGTCGCCAG

TGGACGCCGACGTCATGACGTCGCGTTCCGTAGGGCTCTTCCCGGGCTTTGGTGGGT

-continued

CACGTGAACCACTTTTCGCGCGAAACCTGGTTGTTGCTGTAGTGGCGGAGAGGATCG

TGGTACTGCTATG (SEQ ID NO: 46)
CATTGTTCGCCTCAGGCTCGCCACCTTCCGACAGCTGTGTTTGCGCATGCGCGACGG

GTGTGCACCGCCTCTCGACTTCCGGTTCACCCAGCATTTCCTCTTCCCTGTTTTCTTTC

GTCGTCGTGGGTGGGAATTGTCGCCTAAGTGGTTCCGGGTTGGTGGATGACCTTGAG

CCCTCAGGAACGAGATG (SEQ ID NO: 47)
ACCACACCGCCTTGTTAAATGCCGTCGCCGCCGCCGCCGTCTTCGTCACCGTCACAG

TCGCCGCCGCCATCTTTGTTGTGTCTCCGACTCCCTTCCCGCCCCCCTGCCTTGCTCA

AGTCTCGCGTGAGCAGGATGGAGGGCGAAAGCGAGGAGGGGCCTGTTTGTCTCTCT

TGGGGTTCCGTAGGCAGCAGGGGGCAGGGATTAAGGGGGGGTGTGTGCGGGGCGG

GTACTGAGTGGGCGGGGCCTTGCTCGGGTAACTCCCAGGGGCTGGCTAGAGACCCA

GAGGCGCAGAGCGGAGAGGCCTGCGGCGAGGATG (SEQ ID NO: 48)
ACCACACCGCCTTGTTAAATGCCGTCGCCGCCGCCGCCGTCTTCGTCACCGTCACAG

TCGCCGCCGCCATCTTTGTTGTGTCTCCGACTCCCTTCCCGCCCCCCTGCCTTGCTCA

AGTCTCGCGTGAGCAGGATGGAGGGCGAAAGCGAGGAGGGGCCTGTTTGTCTCTCT

TGGGGTTCCGTAGGCAGCAGGGGGCAGGGATTAAGGGGGGGTGTGTGCGGGGCGG

GTACTGAGTGGGCGGGGCCTTGCTCGGGTAACTCCCAGGGGCTGGCTAGAGACCCA

GAGGCGCAGAGCGGAGAGGCCTGCGGCGAGGATG

Additional bidirectional promoters can be made by pairing one of the promoters from IDH3G, eIF2B1, XPC, XPO5, DESI, TMEM167a, MBD4, PCNA, CETN2, SMYD4, PMS2, MCM7, TPRA1, TIMM8, IKZF5, and STYXL1, and one of the promoters from SSR4, GTF2H3, LSM3, POLH, XRCC6, XRCC4, IFT122, CDS2, DHL, RPA1, AIMP2, AP4MA, MCM2, SDHD, ACADSAB, and MDH2.

The multicistronic constructs can have three or more cistrons with each having control regions (optionally inducible) and RDEs operably linked to some or all of the transgenes. These cassettes may be organized into two groups that are transcribed in opposite directions on the construct. Two or more transgenes can be transcribed from the same control region and the two or more transgenes may have IRES (internal ribosome entry site) sequences operably linked to the downstream transgenes. Alternatively, the two or more transgenes are operably linked together by 2A elements as described in Plasmids 101: Multicistronic Vectors found at blog.addgene.org/plasmids-101-multicistrnic-vectors. Commonly used 2A sequences include, for example, EGRGSLLTCGDVEENPGP (T2A) (SEQ ID NO: 34), ATNFSLLKQAGDVEENPGP (P2A) (SEQ ID NO: 35); QCTNYALLKLAGDVESNPGP (E2A) (SEQ ID NO: 36); and VKQTLNFDLLKLAGDVESNPGP (F2A) (SEQ ID NO: 37) all of which can optionally include the sequence GSG at the amino terminal end. This allows multiple transgenes to be transcribed onto a single transcript that is regulated by a 3'-UTR with an RDE (or multiple RDEs).

The bicistronic/multicistronic vector can increase the overall expression of the two or more cistrons (versus introducing the cistrons on separate constructs). The bicistronic/multicistronic construct can be derived from a *lentivirus* vector. The bicistronic/multicistronic construct can encode a CAR and a polypeptide(s) that is encoded on a transgene(s) (e.g., a payload), and the bicistronic construct may increase expression of the polypeptide encoded by the transgene(s) when the cell is activated by the CAR.

Expression constructs can be modified to remove an RNA splice site in a 5'-LTR of the construct so as to increase the transduction frequency of the expression construct. Many lentiviral transduction constructs have a residual splice site in the 5'-LTR that can reduce transduction frequency through splicing events with this site that alter the nucleic acids to be introduced. For example, lentiviral vectors represented by the pCDH vectors (System Biosciences), the lentiviral vectors pLVTH, pRRLSIN, pWPI, and pWPXL, as well as other lentiviral vectors contain a portion of the HIV 5'-LTR that includes a splice acceptor site. Removal of this splice site from the vectors increases transduction frequencies with the modified vectors (compared to the non-modified vectors). The splice donor site in the residual HIV 5'-LTR segment can be disrupted by making two nucleotide changes, G290C and U291A (numbering the HIV splice site according to Keane et al., *Science* 348:917-921 (2015), which is incorporated by reference in its entirety for all purposes). Other changes in this splice donor site could also be made to knock out this splice site. Other transduction vectors also include residual splice sites that can disrupt the desired sequence after transduction/transfection and removal of these splice sites should increase transduction/transfection frequencies with these vectors.

It may be desirable to modify polypeptides described herein. One of skill will recognize many ways of generating alterations in a given nucleic acid construct to generate variant polypeptides Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques (see, e.g., Gillam and Smith, Gene 8:81-97, 1979; Roberts et al., *Nature* 328:731-734, 1987, which is incorporated by reference in its entirety for all purposes). The recombinant nucleic acids encoding the polypeptides of the invention can be modified to provide preferred codons which enhance translation of the nucleic acid in a selected organism.

The polynucleotides can also include polynucleotides including nucleotide sequences that are substantially equivalent to other polynucleotides described herein. Polynucleotides can have at least about 80%, more typically at least about 90%, and even more typically at least about 95%, sequence identity to another polynucleotide. The nucleic acids also provide the complement of the polynucleotides including a nucleotide sequence that has at least about 80%, more typically at least about 90%, and even more typically at least about 95%, sequence identity to a polynucleotide encoding a polypeptide recited herein. The polynucleotide can be DNA (genomic, cDNA, amplified, or synthetic) or RNA. Methods and algorithms for obtaining such polynucleotides are well known to those of skill in the art and can include, for example, methods for determining hybridization conditions which can routinely isolate polynucleotides of the desired sequence identities.

Nucleic acids which encode protein analogs or variants (i.e., wherein one or more amino acids are designed to differ from the wild type polypeptide) may be produced using site directed mutagenesis or PCR amplification in which the primer(s) have the desired point mutations. For a detailed description of suitable mutagenesis techniques, see Sambrook et al., Molecular Cloning: A Laboratory Manual, Cold Spring Harbor Laboratory Press, Cold Spring Harbor, N.Y. (1989) and/or Current Protocols in Molecular Biology, Ausubel et al., eds, Green Publishers Inc. and Wiley and Sons, N.Y (1994), each of which is incorporated by reference in its entirety for all purposes. Chemical synthesis using methods well known in the art, such as that described by Engels et al., *Angew Chem IntlEd.* 28:716-34, 1989 (which is incorporated by reference in its entirety for all purposes), may also be used to prepare such nucleic acids.

Amino acid "substitutions" for creating variants are preferably the result of replacing one amino acid with another amino acid having similar structural and/or chemical properties, i.e., conservative amino acid replacements. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

Also disclosed herein are nucleic acids encoding a transgene, including a transgene encoding a CARS. The nucleic acid encoding the transgene can be easily prepared from an amino acid sequence of the specified CAR combined with the sequence of the RNA control device by a conventional method. A base sequence encoding an amino acid sequence can be obtained from the aforementioned NCBI RefSeq IDs or accession numbers of GenBenk for an amino acid sequence of each element, and the nucleic acid of the present invention can be prepared using a standard molecular biological and/or chemical procedure. For example, based on the base sequence, a nucleic acid can be synthesized, and the nucleic acid of the present invention can be prepared by combining DNA fragments which are obtained from a cDNA library using a polymerase chain reaction (PCR).

The nucleic acids can be linked to another nucleic acid so as to be expressed under control of a suitable promoter. The nucleic acid can be also linked to, in order to attain efficient transcription of the nucleic acid, other regulatory elements that cooperate with a promoter or a transcription initiation site, for example, a nucleic acid comprising an enhancer sequence, a polyA site, or a terminator sequence. In addition to the nucleic acid of the present invention, a gene that can be a marker for confirming expression of the nucleic acid (e.g. a drug resistance gene, a gene encoding a reporter enzyme, or a gene encoding a fluorescent protein) may be incorporated.

When the nucleic acid is introduced into a cell ex vivo, the nucleic acid of may be combined with a substance that promotes transference of a nucleic acid into a cell, for example, a reagent for introducing a nucleic acid such as a liposome or a cationic lipid, in addition to the aforementioned excipients. Alternatively, a vector carrying the nucleic acid of the present invention is also useful. Particularly, a composition in a form suitable for administration to a living body which contains the nucleic acid of the present invention carried by a suitable vector is suitable for in vivo gene therapy.

Introducing Nucleic Acids into Eukaryotic Cells

A process for producing a cell expressing a transgene includes a step of introducing the nucleic acid encoding the transgene described herein into a eukaryotic cell. This step can be carried out ex vivo. Exemplary methods for introducing nucleic acids to eukaryotic cells are described, for example, in U.S. patent application Ser. No. 15/070,352 filed on Mar. 15, 2016, and U.S. patent application Ser. No. 15/369,132 filed Dec. 5, 2016, both of which are incorporated by reference in their entirety for all purposes.

Virus Payloads

Viruses can be used to deliver transgenes to target cells. Viruses can carry nucleic acid constructs (e.g., transfer plasmids) as payloads and so deliver to a target cell desired nucleic acids for modification of the target cell genotype and/or phenotype (transiently or stably). In many of these transduction applications, the nucleic acid carried by the virus does not include all of the viral genome, and often includes the viral genome signals needed for packaging the nucleic acid construct into the virus without most or all of the rest of the viral genome. For example, lentiviral helper plasmid and transfer plasmids systems for transduction of target cells are available from addgene. Other helper and transfer plasmid systems are commercially available form a number of sources (e.g., Clontech/Takara).

When used as a payload, synthesis of viral capsids, packaging of payload nucleic acids, and release of virus with payload nucleic acids can be restricted to the target site by timing the expression of the virus genes for replication and coat proteins to binding of ligand by a receptor at the target site. Such control can be achieved using RDEs that induce expression when the cell undergoes a change in metabolic state (e.g., activation of glycolysis after receptor binding to target). This RDE control can regulate expression of master switch factors for expression of the virus genes. For example, a transcription regulatory factor can be placed under the control of a suitable RDE, and the viral genes for replication, coat proteins etc can be placed under the control of this transcription factor. When the host cell binds to ligand at the target site through an appropriate receptor (e.g., a CAR) this activates the cell, induces expression of the transcription factor with the appropriate RDE leading to expression of the viral replication proteins, coat proteins, etc.

Transduction can be accomplished with a virus vector such as a retrovirus vector (including an oncoretrovirus vector, a lentivirus vector, and a pseudo type vector), an adenovirus vector, an adeno-associated virus (AAV) vector, a simian virus vector, a vaccinia virus vector or a sendai virus vector, an Epstein-Barr virus (EBV) vector, and a HSV vector can be used. The virus vector can lack replicating ability so as not to self-replicate in an infected cell.

When a retrovirus vector is used to transduce the host cell, the process can be carried out by selecting a suitable packaging cell based on a LTR sequence and a packaging signal sequence possessed by the vector and preparing a retrovirus particle using the packaging cell. Examples of the packaging cell include PG13 (ATCC CRL-10686), PA317 (ATCC CRL-9078), GP+E-86 and GP+envAm-12 (U.S. Pat. No. 5,278,056, which is incorporated by reference in its entirety for all purposes), and Psi-Crip (Proceedings of the National Academy of Sciences of the United States of America, vol. 85, pp. 6460-6464 (1988), which is incorporated by reference in its entirety for all purposes). A retrovirus particle can also be prepared using a 293 cell or a T cell having high transfection efficiency. Many kinds of retrovirus vectors produced based on retroviruses and packaging cells that can be used for packaging of the retrovirus vectors are widely commercially available from many companies.

A number of viral based systems have been developed for gene transfer into mammalian cells. A selected gene can be inserted into a vector and packaged in viral particles using techniques known in the art. The recombinant virus can then be isolated and delivered to cells of the subject either in vivo or ex vivo. A number of viral systems are known in the art. Adenovirus vectors can be used. A number of adenovirus vectors are known in the art and can be used. In addition, lentivirus vectors can be used.

Pharmaceutical Compositions

Pharmaceutical compositions of the present invention may comprise a CARS and/or transgene-RDE expressing cell, e.g., a plurality of CARS and/or transgene-RDE expressing cells, as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are in one aspect formulated for intravenous administration.

Pharmaceutical compositions may be administered in a manner appropriate to the disease to be treated (or prevented). The quantity and frequency of administration will be determined by such factors as the condition of the patient, and the type and severity of the patient's disease, although appropriate dosages may be determined by clinical trials.

Suitable pharmaceutically acceptable excipients are well known to a person skilled in the art. Examples of the pharmaceutically acceptable excipients include phosphate buffered saline (e.g. 0.01 M phosphate, 0.138 M NaCl, 0.0027 M KCl, pH 7.4), an aqueous solution containing a mineral acid salt such as a hydrochloride, a hydrobromide, a phosphate, or a sulfate, saline, a solution of glycol or ethanol, and a salt of an organic acid such as an acetate, a propionate, a malonate or a benzoate. An adjuvant such as a wetting agent or an emulsifier, and a pH buffering agent can also be used. The pharmaceutically acceptable excipients described in Remington's Pharmaceutical Sciences (Mack Pub. Co., N.J. 1991) (which is incorporated herein by reference in its entirety for all purposes) can be appropriately used. The composition can be formulated into a known form suitable for parenteral administration, for example, injection or infusion. The composition may comprise formulation additives such as a suspending agent, a preservative, a stabilizer and/or a dispersant, and a preservation agent for extending a validity term during storage.

A composition comprising the eukaryotic cells described herein as an active ingredient can be administered for treatment of, for example, a cancer (blood cancer (leukemia), solid tumor (ovarian cancer) etc.), an inflammatory disease/autoimmune disease (pemphigus vulgaris, lupus erythematosus, rheumatoid arthritis, asthma, eczema), hepatitis, and an infectious disease the cause of which is a virus such as influenza and HIV, a bacterium, or a fungus, for example, a disease such as tuberculosis, MRSA, VRE, or deep mycosis, depending on an antigen to which a CAR, DE-CAR, and/or Side-CAR polypeptide binds.

The administration of the subject compositions may be carried out in any convenient manner, including by aerosol inhalation, injection, ingestion, transfusion, implantation or transplantation. The compositions described herein may be administered to a patient trans arterially, subcutaneously, intradermally, intratumorally, intranodally, intramedullary, intramuscularly, intranasally, intraarterially, intratumorally, into an afferent lymph vessel, by intravenous (i.v.) injection, or intraperitoneally. In one aspect, the T cell compositions of the present invention are administered to a patient by intradermal or subcutaneous injection. In one aspect, the T-cell compositions of the present invention are administered by i.v. injection. The compositions of T-cells may be injected directly into a tumor, lymph node, or site of infection. The administration can be done by adoptive transfer.

When "an immunologically effective amount," "an anti-tumor effective amount," "a tumor-inhibiting effective amount," or "therapeutic amount" is indicated, the precise amount of the compositions of the present invention to be administered can be determined by a physician with consideration of individual differences in age, weight, tumor size, extent of infection or metastasis, and condition of the patient (subject). A pharmaceutical composition comprising the eukaryotic cells described herein may be administered at a dosage of $10^4$ to $10^9$ cells/kg body weight, in some instances $10^5$ to $10^6$ cells/kg body weight, including all integer values within those ranges. A eukaryotic cell composition may also be administered multiple times at these dosages. Eukaryotic cells can also be administered by using infusion techniques that are commonly known in immunotherapy (see, e.g., Rosenberg et al., *New Eng. J. of Med.* 319:1676, 1988, which is incorporated by reference in its entirety for all purposes).

Uses of Eukaryotic Cells

Nucleic acids encoding CARS and/or transgene-RDE(s) can be used to express CARs and/or transgene polypeptides in eukaryotic cells. The eukaryotic cell can be a mammalian cell, including for example human cells or murine cells. The eukaryotic cells may also be, for example, hematopoietic cells including, e.g., T-cells, natural killer cells, B-cells, or macrophages.

T-cells (e.g., CD4+ or CD8+) or natural killer cells can be engineered with a polynucleotide encoding a CAR. The desired amount of effector function can be an optimized amount of effector function with a known amount (and/or density) of target antigen on target cells. Effector function can be target cell killing, activation of host immune cells, cytokine secretion, production of granzymes, production of apoptosis inducing ligands, production of other ligands that modulate the immune system, etc. The effector function can be secretion of cytokines such as, for example, IL-2, IFN-γ, TNF-α, TGF-β, and/or IL-10. Effector function can be the killing of target cells. Target cells can be killed with granzymes. Target cells can be induced to undergo apoptosis. Eukaryotic cells with CARs can kill target cells through apoptosis and granzymes.

The RDE regulatory element can be used to control expression of a transgene. This transgene expression can deliver a payload at a target site. These transgenes can also be carried by viral constructs, or viruses when the payload is a virus. Expression of the transgene can cause a desired change in the eukaryotic cell. An RDE regulated by GAPDH can be used for payload delivery, and the eukaryotic cell (e.g., T-cell, natural killer cell, B-cell, macrophage, dendritic cell, or other antigen presenting cell) can be activated (e.g., by a CAR) when it reaches the target site. Upon activation of the eukaryotic cell at the target site through the CAR, the cell induces glycolysis and the GAPDH releases from the RDE allowed payload expression and delivery. The target site can be a tumor or infection and the transgene could encode a cytokine, a chemokine, an antibody, a checkpoint inhibitor, a granzyme, an apoptosis inducer, complement, an enzyme for making a cytotoxic small molecule, an enzyme that cleaves peptides or saccharides (e.g., for digesting a biofilm), other cytotoxic compounds, or other polypeptides that can have a desired effect at the target site. Checkpoint inhibitors include agents that act at immune checkpoints including, for example, cytotoxic T-lymphocyte-associated antigen 4 (CTLA4), programmed cell death protein (PD-1), Killer-cell Immunoglobulin-like Receptors (KIR), and Lymphocyte Activation Gene-3 (LAG3). Examples of checkpoint inhibitors that may be used as payloads include, for example, Nivolumab (Opdivo®), Pembrolizumab (Keytruda®), Cemiplimab (Libtayo®), Atezolizumab (Tecentriq®), Avelumab (Bavencio®), Durvalumab (Imfinzi®), Ipilimumab (Yervoy®), Lirilumab, and BMS-986016. Nivolumab, Atezolizumab and Pembrolizumab act at the checkpoint protein PD-1 and inhibit apoptosis of anti-tumor immune cells. Some checkpoint inhibitors prevent the interaction between PD-1 and its ligand PD-L1. Ipilimumab acts at CTLA4 and prevents CTLA4 from downregulating activated T-cells in the tumor. Lirilumab acts at KIR and facilitates activation of Natural Killer cells. BMS-986016 acts at LAG3 and activates antigen-specific T-lymphocytes and enhances cytotoxic T cell-mediated lysis of tumor cells.

The payload can be one or more of an anti-IL33 antibody, anti-LAG3 antibody, anti-TIM3 antibody, anti-TIGIT antibody, anti-MARCO antibody, anti-VISTA antibody, anti-CD39 antibody, anti-41BB antibody, IL-15, IL-21, IL-12, CD40L, and/or Leptin. The IL-33 receptor is upregulated in $T_{regs}$ (regulatory T-cells) and anti-IL33 antibody reduces proliferation and activation of $T_{regs}$. Anti-LAG3 antibody can also decrease activity of $T_{regs}$. Anti-1133 antibody and anti-LAG3 antibody can be used alone or together to reduce the activity of $T_{regs}$ which can reduce the suppression of CAR T-cells and other anti-cancer T-cells. Anti-TIM-3 antibody allows co-localization of CD8+ T-cells and DC-1 cells (which improves anti-tumor response). MARCO is expressed on macrophages and in the tumor microenvironment this can be suppressive to T-cells. Anti-MARCO antibody prevents this tumor suppression by macrophages. Anti-VISTA antibody reduces the amount of neutrophils in the tumor microenvironment. A high neutrophil to T-cell ratio in the tumor microenvironment correlates with poor patient outcomes. Decreasing the neutrophils in the tumor can improve patient outcomes and tumor cell killing. IL-15 and Il-21 increase the expansion of natural killer cells and Il-15 can rescue CD8+ T-cells and may prevent T-cell exhaustion. CD40L plays a central role in priming, co-stimulation and activation of T-cells in an immune response. Anti-CD39 antibody can reduce adenosine levels in the tumor microenvironment. High levels of adenosine in the tumor microenvironment can induce immunosuppression. Anti-CD39 antibody can reduce this immunosuppression. Anti-41BB antibody can prevent T-cells from undergoing apoptosis and can also cause tumor cells to upregulate expression of PD1 (so can be combined with anti-PD1 therapies).

Cytokines can include, for example, IL-2, IL-12, IL-15, IL-18, IL-21, IFN-γ, TNF-α, TGF-β, and/or IL-10. Cytotoxic agents can include, for example, granzymes, apoptosis inducers, complement, or a cytotoxic small molecule. The payload can be a gene regulatory RNA, such as, for example, siRNA, microRNAs (e.g., miR155), shRNA, antisense RNA, ribozymes, and the like, or guide RNAs for use with CRISPR systems. The payload can be an anti-4-1BB antibody, anti-CD11b antibody, anti-CTLA4 antibody, anti-IL1b antibody, anti-IL33 antibody, anti-LAG3 antibody, anti-TIM3 antibody, anti-TIGIT antibody, anti-MARCO antibody, anti-VISTA antibody, anti-CD39 antibody, PGC-alpha, Leptin, a BiTE, CCL2, anti-CXCR4 antibody, anti-CXCL12 antibody, HAC, heparinase, hyaluronidase, Hsp60, Hsp70, IL-2, IL-15, IL-18, INFγ, miRNA (e.g., mir155), CD40 ligand, ApoE3, ApoE4, TNFα, CCR2, CCR4/CXCL12, CXCR3+CXCL9, CXCL9, ACLY, antagonists of CSF1 receptor, Ox40-41BB, miRNA for Tox (e.g., hsa-mir-26b-5p (MIRT030248) hsa-mir-223-3p (MIRT054680)), miRNA for TCF-7 (e.g., mIR-192, mIR-34a, miR-133a, miR-138-5p, miR-342-5p, miR-491-5p, miR-541-3p), anti-CD28 antibody (including full length and fragments such as single chain antibodies), IL-21, Leptin, GOT2, NAMPT, CD56, IL-2 superkine, anti-REGNASE-1 payloads (e.g., miRNA), C-jun, cysteinase enzyme, cystinase enzyme, PCBP1 (poly(RC) binding protein 1), complement (one or more of B, C1-C9, D, C5b, C3b, C4b, C2a), BMP-1, anti-TGFb agents (e.g., anti-TGFb antibody, soluble TGFbR, anti-avB6 integrin antibody, natural TGFb binding proteins, small molecules such as GW788388, Tranilast, Losartan, HMG CoA reductase inhibitors, Imatinib mesylate, PPAR-g agonists, rosiglitazone, Pirfenidone, Halofuginone), IL7 combined with CCL19 (e.g., IL7-t2A-CCL19), dnTNFR2, dnTGFBR2, DCN, DKK1, OKT3, NOS2, CCL5, anti-4-1BB agonist Antibody, anti-CD11b, anti-CD28 agonist Ab, anti-CD29/anti-VEGF, anti-CTLA4 Ab, anti-IL1b Ab, BiTE, CCR2, CCR4/CXCL12 disruption, HAC, heparinase, HSP60, HSP70, hyaluronidase, IL-12, IL15, IL18, IL2, anti-CSF1R and anti-IGF1, anti-IL4, IL4 receptor antagonists, IL4 binders (e.g., soluble IL4R), soluble CD40 ligand (e.g., secreted ecto-CD40L), membrane CD40 ligand, a TGFBR antagonist, and/or 4-1BB ligand. An anti-TGFb payloads may be combined with CAR T-cells directed at multiple myeloma (e.g., an anti-GPRC5D CAR). The payloads can also include those found in US20190183932, which is incorporated by reference in its entirety for all purposes. The payload delivered at a target site (e.g., non-tumor target site) can be a factor that protects the target site such as, for example, an anti-inflammatory, a factor that attracts T-regulatory cells to the site, or cytokines or other factors that cause suppression and reduction in immune activity. The payload can be an enzyme that cleaves peptides or saccharides, for example hyaluronidase, heparanase, metalloproteinases and other proteinases which can be used, for example, to digest an undesired biofilm. Myeloid modifying payloads ("MM payloads") which reduce immune suppression or inhibition caused by myeloid cells may be delivered including, for example, ApoE3, ApoE4, Hsp60, Hsp70, TNFα, antagonists of CSF1 receptor, CD40L (CD154) and/or IL-12. Two or more MM payloads can also be delivered by the CAR, DE-CAR, side-CAR and/or other receptor cell (e.g., T-cell) using RDEs that produce different pharmacokinetics for delivery. For example, the different MM payloads could be controlled by different RDEs so that the $C_{max}$ of delivery for the different MM payloads occurs at different times. For example, Myeloid modifying payloads can promote activated M1 macrophages that are proinflammatory and tumoricidal. A MM payload that promotes M1 phenotypes are antagonists of CSF1R (antagonists that block and do not activate the CSF1 receptor and agents that bind CSF1 and prevent it from interacting with the CSF1R). Such antagonists of CSF1R include, for example, small-molecule inhibitors, PLX3397 (Pexidartinib, Plexxikon), PLX7486 (Plexxikon), ARRY-382 (Array Biopharma), JNJ-40346527 (Johnson & Johnson), and BLZ945 (Novartis). Exemplary antibodies which are antagonists of CSF1R include, for example, Ernacuzunab (Roche), AMG820 (Amgen), IMC-CS4 (LY3022855, Eli Lilly), and MCS110 (Novartis). Cannarile et al, *J. Immunotherp. Cancer* 5:53 (2017) which is incorporated by reference in its entirety for all purposes. The payload can be localized to the target cell (e.g., tumor site) by fusing or associating the payload with a Small Leucine Rich Proteoglycans (SLRPs) such as Decorin, Biglycan, or fibromodulaon/Lumican. The Decorin, Biglycan, or Lumican can bind to the collagen near the target cell and this binding will localize the payload at or near the target site. This strategy is particularly useful for keeping cytotoxic payloads localized to the target cells (e.g., a tumor). Decorin and Biglycan can also bind to TGF-beta at or near the target site and reduce suppression of the engineered T-cell, and so these can be used as a payload themselves to reduce TGFb. A Decorin, Biglycan, and/or lumican payload can also be constitutively expressed, or expressed under the control of an RDE with a moderate level of baseline expression (mimicking low level constitutive expression coupled with increased expression upon cell activation). The payload can be one or more of any of the above. The payload can be an imaging agent that allows the target site to be imaged. The payload may be a polypeptide that can be imaged directly, or it can be a polypeptide that interacts with a substrate to make a product that can be imaged, imaging polypeptides include, for example, thymidine kinase (PET), dopamine D2 (D2R) receptor, sodium iodide transporter (NIS), dexoycytidine kinase, somatostatin receptor subtype 2, norepinephrine transporter (NET), cannabinoid receptor, glucose transporter (Glutl), tyrosinase, sodium iodide transporter, dopamine D2 (D2R) receptor, modified haloalkane dehalogenase, tyrosinase, 0-galactosidase, and somatostatin receptor 2. These reporter payloads can be imaged using, for example, optical imaging, ultrasound imaging, computed tomography imaging, optical coherence tomography imaging, radiography imaging, nuclear medical imaging, positron emission tomography imaging, tomography imaging, photo acoustic tomography imaging, x-ray imaging, thermal imaging, fluoroscopy imaging, bioluminescent imaging, and fluorescent imaging. These imaging methods include Positron Emission Tomography (PET) or Single Photon Emission Computed Tomography (SPECT).

Multiple systems are envisioned for use that can kill target cells directly. These include, for example, the introduction of a viral or a bacterial gene into target cells. This approach turns a non-toxic pro-drug to a toxic one. There are systems that have been extensively investigated: the cytosine deaminase gene ("CD") of Escherichia coli, which converts the pro-drug 5-Fluorocytosine ("5-FC") to 5-Fluorouracil ("5-FU"); and the herpes simplex virus thymidine kinase gene ("HSV-tk"), which converts ganciclovir ("GCV") to ganciclovir monophosphate, converted by the cancer cells' enzymes to ganciclovir triphosphate. The HSV-tk/GCV system useful in killing tumor cells directly, involves adenoviral transfer of HSV-tk to tumor cells, with the subsequent administration of ganciclovir. Specifically, recombinant replication-defective adenovirus is employed to transfer the thymidine, HSV-tk, into hepatocellular carcinoma ("HCC") cells to confer sensitivity to ganciclovir. Three useful HCC cell lines include, for example, Hep3B, PLC/PRF/5 and HepG2, which can efficiently infect, in vitro, by a recombinant adenovirus carrying lacZ reporter gene ("Ad-CMV-lacZ"). Expression of HSV-tk in HCC cells infected with a recombinant adenovirus carrying HSV-tk gene ("AdCMVtk") induces sensitivity to ganciclovir in a dose-dependent manner (Qian et al., Induction of sensitivity to ganciclovir in human hepatocellular carcinoma cells by adenovirus-mediated gene transfer of herpes simplex virus thymidine kinase, Hepatology, 22:118-123 (1995)) doi.org/10.1002/hep.1840220119.

When the payload is a gene regulatory RNA, such as, for example, siRNAs, shRNAs, and/or microRNAs (e.g., miR155), the regulatory RNA (e.g., mir155) can be the transgene or can be included in an intron of a transgene encoding a polypeptide. For example, a mir155 cassette as described in Du et al., FEBs J. 273:5421-27 (2006) and Chung et al., Nucl Acids Res. 34:e53 (2006) can be used as the payload or be engineered into an intron of a transgene that is used as the payload. The mir155 cassette (or cassette for other regulatory RNA) can be engineered into a transgene as an intron or the transgene can be the mir155 cassette, optionally with additional nucleotides. The regulatory RNA transgene (or transgene with regulatory RNA as an intron) can be placed under the control of an RDE. RDEs can impact RNA processing and stability in the nucleus. After the transgene encoding the regulatory RNA (e.g., mir155) or encoding a transgene with a regulatory RNA (e.g., mir155) intron is transcribed, the transcript can be processed in the nucleus by the nuclear microprocessor complex or other nuclear components to make the nucleotide stem-loop precursor regulatory RNA (e.g., pre-mir155). The pre-regulatory RNA (e.g., pre-mir155) stem-loop is exported out of the nucleus where it is processed by Dicer to form a short RNA duplex. The short RNA duplex(es) are bound by Argonaute (Ago) to form the core of the multi-subunit complex called the RNA-induced silencing complex (RISC). By operably linking a RDE to the transgene encoding the regulatory RNA (e.g., mir155) or the transgene with the regulatory RNA (e.g., mir155) intron, the expression of regulatory RNA (e.g., mir155) can be regulated by the RDE. Different RDEs can be operably linked to the regulatory RNA (e.g., mir155) transgene or transgene with regulatory RNA (e.g., mir155) intron to provide different timing and kinetics of expression following activation of a eukaryotic cell (e.g., activation of a T-cell by the TCR or a CAR). RDEs can be used that produce expression quickly after activation of the cell (e.g., AU2 or AU101), produce high expression 72-96 hours after activation (e.g., AU5 or AU21), or produce increasing expression through 192 hours after expression (e.g., AU19 or AU22). RDEs can also be selected that will produce continuous expression of regulatory RNA (e.g., mir155) or that will produce expression for a period of time after activation of the cell followed by reduced expression. Multiple regulatory RNA (e.g., mir155) constructs (e.g., with mir155 as the transgene or a transgene with a mir155 intron) with different RDEs can be used to provide continuous expression of regulatory RNA (e.g., mir155) following activation of a cell (e.g., T-cell) by using RDEs that provide different pharmacokinetic profiles of expression which together produce continuous expression (e.g., see Example 11). Alternatively, select RDEs or combinations of RDEs or combinations of regulatory RNA (e.g., mir155) with different RDEs can be used to provide a desired expression profile of the regulatory RNA (e.g., mir155).

Upregulation of mir155 has been associated with activated CD8+ T-cells and the formation of memory T-cells after an immunological challenge. Upregulation of mir155 expression during activation of T-cells (e.g., CAR T-cells activated by target antigens) will potentiate the CAR T-cell response against target cells. Placing mir155 under control of a heterologous RDE (e.g., an RDE that responds to GAPDH) ties upregulation of mir155 to activation of the T-cell so that mir155 is upregulated in activated T-cells (e.g., CD8+, CAR T-cells). This upregulation can increase proliferation of activated T-cells. The upregulation can also decrease T-cell exhaustion and senescence. The upregulation can also potentiate T-cell effector functions resulting in increased target cell killing.

Effector function of T-cells can also be enhanced by downregulating TCF7 and/or Tox expression and/or by upregulating IL-15 expression. TCF7 is a member of the T-cell factor/lymphoid enhancer-binding factor family of high mobility group (HMG) box transcriptional activators. This gene is expressed predominantly in T-cells and plays a critical role in natural killer cell and innate lymphoid cell development. HMG box protein TCF7 can be a regulator in the switch between self-renewal and differentiation. TCF7 can have a dual role in promoting the expression of genes characteristic of self-renewing CD34+ cells while repressing genes activated in partially differentiated CD34− state. TCF7 can regulate a network of transcription factors that switch cells from a naïve, undifferentiated state to a differentiated, effector cell state. When TCF7 is expressed cells adopt a self-renewal state that is more naïve and less differentiated. TCF7 can be downregulated using miRNAs such as, for example, mIR-192, mIR-34a, miR-133a, miR-138-5p, miR-342-5p, miR-491-5p, and/or miR-541-3p. In an example, one of more of these miRNAs can be encoded in one or more introns of a payload that are spliced out when the transcript is bound by hnRNPLL (see above), and when the payload is expressed in an activated cell making hnRNPLL these miRNAs will downregulate TCF7. Alternatively, a transgene encoding TCF7 can be used as an off switch for activated CAR T-cells. If TCF7 is expressed after the effector, CAR T-cell has killed the target cancer cells, this should push the CAR T-cell into a naïve, undifferentiated state (an off state for the CAR T-cell). The transgene encoding TCF7 could be placed under the control of an inducible promoter (e.g., an inducible promoter that is ligand inducible) or it could be placed under control of an RDE that results in expression after eight days or more of cell activation (e.g., see Example 11). Expression of TCF7 can be turned off by removal of ligand (or other inducing factors for the inducible promoter), and/or the RDE control will turn off expression. This can return the CAR T-cell to state where it can be reactivated by binding to target ligand at other cancer cells.

Thymocyte selection-associated high mobility group box (TOX) protein is a member of a small subfamily of proteins (TOX2, TOX3, and TOX4) that share almost identical HMG-box sequences. TOX can be induced by high antigen stimulation of the T cell receptor and TOX can be a central regulator of $T_{EX}$ (exhausted T-cells). Robust TOX expression can result in commitment to development of the $T_{EX}$ cell type. TOX exhaustion may counteract and balance T-cell overstimulation and activation-induced cell death in settings of chronic antigen stimulation. Effector T-cells (e.g., activated CD8+ T-cells) can have low Tox, whereas higher levels of Tox pushes the effector cells to become $T_{EX}$ cells. TEX cells have reduced effector function but are still effective against low level infections or small numbers of cancer cells.

Effector function of T-cells can be enhanced by including a payload encoding an miRNA for Tox (e.g., hsa-mir-26b-5p (MIRT030248) hsa-mir-223-3p (MIRT054680)) under regulation of an RDE. Following activation of the T-cell, the RDE control will result in expression of the miRNA for Tox. This miRNA will lower levels of Tox in the T-cell inhibiting $T_{EX}$ formation by the activated T-cells resulting in more active, effector T-cells against a target. In addition, a payload can be Tox itself, used as on off-switch that pushes the activated T-cells into a TEX phenotype at a desired time. When used as an off-switch, Tox expression can be under control of an inducible promoter that can be induced to express Tox at a desired time (e.g., by adding an appropriate ligand), Tox can be controlled by an RNA control device or a DE (ligand can induce expression), or Tox can be placed under control of an RDE that produces expression at late time intervals after activation of the cell (e.g., see Example 11). Functional state and type of T-cell can tailored by treating T-cells with electromagnetic radiation. Electromagnetic radiation in the UV range can condition T-cells to become Treg cells. For example, a dose of UVA/UVB can induce formation of Tregs. Electromagnetic radiation in the blue light range can activate T-cells.

An exemplary payload is a transgene encoding ApoE (e.g., ApoE2, ApoE3 and/or APoE4) which is secreted from the cell. ApoE can bind to receptors (e.g., LRP8) on Myeloid Derived Suppressor Cells (MDSC) and reduce the survival of MDSCs. MDSCs are a heterogeneous population of suppressive innate immune cells that can expand in certain disease states. In some cancers (e.g., melanoma, lung, breast and ovarian cancers) MDSC levels can substantially rise in the tumor(s) and in the plasma of patients. Such patients with high levels of circulating MDSCs can respond poorly to checkpoint blockade. MDSCs can mediate immunosuppression in these patients and induce angiogenesis. Payload expression of ApoE (e.g., ApoE4) can reduce the number of MDSCs in tumors and circulating in the serum, and result in suppression of tumor progression and metastatic colonization. The reduction in MDSCs in the tumor also enables other immune cells (e.g., CAR T-cells) to more efficiently kill tumor cells. The ApoE payload can also act directly on myeloid malignancies that express the LRP8 receptor. In such examples, the payload delivery of ApoE to a myeloid cancer cell can suppress and/or kill the cancer cell. Thus, ApoE can be a payload for delivery to myeloid malignancies that are LRP8+, including LRP8+AML. Delivery of the ApoE payload by a eukaryotic cell (e.g., primary T-cell) can be combined with another therapeutic agent such as, for example, an anti-cancer agent (e.g., a CAR T-cell, a chemotherapeutic, radiation, a checkpoint inhibitor, or any of the anti-cancer therapeutics described herein). The ApoE effect on MDSCs can potentiate the action of the other anti-cancer agent.

Another exemplary payload is a transgene encoding NO-synthase (e.g., iNOS, nNOS and eNOS). NO synthase can bind to GAPDH and can sequester the GAPDH allowing RDE (which are bound by GAPDH) controlled transgenes (or native genes) to be expressed, or increasing expression from RDE (which are bound by GAPDH, e.g., AU 19 (TMEM-219), AU 20 (TMEM-219snp), AU 21 (CCR7), AU 22 (SEM-A4D), and AU 23 (CDC42-SE2)) controlled transgenes (or native genes) once the cell is activated and glycolysis is induced. Expression of NO synthase can induce RDE (which are bound by GAPDH) controlled expression (through binding to GAPDH) and/or can potentiate RDE (which are bound by GAPDH) controlled expression by decreasing the amount of GAPDH that can bind RDEs and/or increasing the time over which GAPDH cannot bind to RDEs. When NO synthase is used to increase the RDE (which are bound by GAPDH) response to cell activation, a transgene encoding NO synthase can be placed under control of an RDE so that when the cell is activated, expression from the transgene encoding the NO synthase is induced. When NO synthase is used to induce expression from RDE (which are bound by GAPDH) controlled genes, the NO synthase can be placed under inducible control (e.g., inducible promoters, RNA control devices, or destabilizing elements as disclosed in U.S. Pat. No. 9,777,064, which is hereby incorporated by reference in its entirety for all purposes) and induction of NO synthase expression induces expression from the RDE (which are bound by GAPDH) controlled genes.

An exemplary payload is a transgene encoding HSV-Thymidine Kinase (HSV-TK). HSV-TK can be used as an adjuvant, and/or as a super antigen that induces an inflammatory response in the patient. When used in this manner, a cell secretes the HSV-TK payload at the target site inducing an inflammatory response. The transgene encoding the HSV-TK can also be used as a kill switch to eliminate the engineered cells (e.g., CAR T-cells with or without a RDE controlled payload). When used as a kill switch, the HSV-TK can be controlled by a late expressing RDE so the HSV-TK is expressed after the CAR T-cell has acted at the target site, or the transgene expressing the HSV-TK can be controlled by a ligand inducible control means so that the HSV-TK protein is expressed in response to the ligand which is introduced at a desired time. In the kill-switch application, ganciclovir can be provided to the cells and the HSV-TK converts the ganciclovir to GCV-triphosphate which kills the cell by a cytotoxic effect. A transgene expressing HSV-TK can also be included in a viral payload so that when the virus infects target cells the target cells express HSV-TK. Ganciclovir is provided to the target cells which use the HSV-TK to convert the ganciclovir to GCV-triphosphate which is toxic to the target cells.

A eukaryotic cell can bind to a specific antigen via the CAR, DE-CAR, and/or Side-CAR polypeptide causing the CAR, DE-CAR, and/or Side-CAR polypeptide to transmit a signal into the eukaryotic cell, and as a result, the eukaryotic cell can be activated and so express an appropriate RDE-transgene. The activation of the eukaryotic cell expressing the CARS is varied depending on the kind of a eukaryotic cell and the intracellular element of the CARS. The eukaryotic cell can express a RDE transcript that poises the cell for effector function upon stimulation of the eukaryotic cell through a CARS.

A eukaryotic cell expressing the RDE-transgene or RDE transcript, and optionally, a CARS, T-cell receptor, B-cell receptor, innate immunity receptor and/or other receptor or targeting polypeptide can be used as a therapeutic agent to treat a disease. The therapeutic agent can comprise the eukaryotic cell expressing the RDE-transgene or RDE transcript, and optionally, a CARS, T-cell receptor, B-cell receptor, innate immunity receptor and/or other receptor or targeting polypeptide as an active ingredient, and may further comprise a suitable excipient. Examples of the excipient include pharmaceutically acceptable excipients for the composition. The disease against which the eukaryotic cell expressing the RDE-transgene or RDE transcript, and optionally, a CARS, T-cell receptor, B-cell receptor, innate immunity receptor and/or other receptor or targeting polypeptide is administered is not particularly limited as long as the disease shows sensitivity to the eukaryotic cell and/or the product of the RDE-transgene.

Examples of diseases that can be treated include a cancer (blood cancer (leukemia), solid tumor (ovarian cancer) etc.), an inflammatory disease/autoimmune disease (asthma, eczema), hepatitis, and an infectious disease, the cause of which is a virus such as influenza and HIV, a bacterium, or a fungus, for example, tuberculosis, MRSA, VRE, and deep mycosis, other immune mediated diseases such as neurodegenerative diseases like Alzheimer's or Parkinson's, and metabolic diseases like diabetes. A receptor (e.g., a CAR) can target the eukaryotic cell to the diseased cell(s) and when the receptor binds to its target at the diseased cell(s) the receptor can send a signal into the eukaryotic cell leading to expression of the RDE-transgene. The RDE-transgene encodes a polypeptide that is useful in treating or killing the diseased cell(s). A cancer and/or solid tumor can be treated with a eukaryotic cell expressing receptor that binds to a tumor associated (or cancer associated) antigen, such as those described above. When the receptor binds to the tumor associated antigen the receptor sends a signal into the cell that causes the RDE-transgene to be expressed (e.g., the signal effects an RDE binding protein leading to expression of the RDE-transcript). The RDE-transcript can encode a polypeptide that activates the eukaryotic cell so that the eukaryotic cell treats the cancer and/or the RDE-transcript encodes a polypeptide that itself treats the cancer (e.g., a cytotoxic polypeptide).

An autoimmune disease (e.g., pemphigus vulgaris, lupus erythematosus, rheumatoid arthritis, multiple sclerosis, Crohn's disease) can be treated with a eukaryotic cell expressing a RDE-transgene or RDE transcript, and optionally, a CARS, T-cell receptor, B-cell receptor, innate immunity receptor and/or other receptor or targeting polypeptide that binds to the immune proteins associated with the autoimmune disease. The receptor or targeting polypeptide can trigger expression of the RDE-transgene that encodes a polypeptide useful in treating the autoimmune disease (e.g., the polypeptide can regulate the cells causing the autoimmune disease or kill these cells). The eukaryotic cell expressing the RDE-transgene or RDE transcript, and receptor or targeting polypeptide can target cells that make an antibody involved with the autoimmune disease (e.g., the RDE-transgene can encode a polypeptide that kills the antibody producing cells or that inhibits the production of antibody by these cells). The eukaryotic cell expressing the RDE-transgene or RDE transcript, and receptor or targeting polypeptide can target T-lymphocytes involved with the autoimmune disease (e.g., the RDE-transgene can encode a polypeptide that kills the target T-lymphocytes or that regulates the activity of the T-lymphocytes).

The therapeutic agent comprising the eukaryotic cell expressing the CARS, T-cell receptor, B-cell receptor, innate immunity receptor and/or other receptor or targeting polypeptide as an active ingredient can be administered intradermally, intramuscularly, subcutaneously, intraperitoneally, intranasally, intraarterially, intravenously, intratumorally, or into an afferent lymph vessel, by parenteral administration, for example, by injection or infusion, although the administration route is not limited.

The RDE-transgene or RDE transcript, and optionally, CARS, T-cell receptor, B-cell receptor, innate immunity receptor and/or other receptor or targeting polypeptide can be used with a T-lymphocyte that has aggressive anti-tumor properties, such as those described in Pegram et al, CD28z CARs and armored CARs, 2014, Cancer J. 20(2):127-133, which is incorporated by reference in its entirety for all purposes. The RDE transcript can encode a polypeptide that causes aggressive anti-tumor properties in the T-lymphocyte.

A transgene can be controlled by an RDE where the RDE can be modified to inactivate microRNA sites found in the RDE. Using these control elements makes expression of the transgene sensitive to changes in the glycolytic state of the host cell through the interaction of the RDE with glyceraldehyde-3-phosphate dehydrogenase (GAPDH). The glycolytic activity of GAPDH can be increased by increasing the amount and/or activity of triose isomerase. The host cell can be induced to over-express a recombinant triose isomerase, and this over-expression increases the glycolytic activity of GAPDH. A glycolysis inhibitor can be added to decrease expression of the transcript with the RDE. Such glycolysis inhibitors include for example, dimethylfumarate (DMF), rapamycin, 2-deoxyglucose, 3-bromophyruvic acid, iodoacetate, fluoride, oxamate, ploglitazone, dichloroacetic acid, quinones (e.g., chloroquine, hydroxychloroquine, etc.), or other metabolism inhibitors such as, for example, dehydroepiandrosterone. Expression from the RDE controlled transcript can be increased by the addition of GAPDH (or other RDE binding protein) inhibitor that inhibits binding of the RDE by GAPDH (or other RDE binding protein). Such GAPDH inhibitors include, for example, CGP 3466B maleate or Heptelidic acid (both sold by Santa Cruz Biotechnology, Inc.), pentalenolactone, or 3-bromopyruvic acid. Quinones such as, for example, chloroquine and hydroxychloroquine, can de-acidify the endosome impairing antigen processing by APCs, decrease signaling from toll-like receptors, reduces T-cell proliferation, T-cell metabolic activity, T-cell cytokine secretion, interferes with IL-2 production, and interferes with T-cell response to IL-2.

RDEs can be used to reduce CAR expression in immune cells until those immune cells are activated by target or at a desired time. This can result in expression of the CAR at desired times for therapeutic effect while reducing the systemic exposure of a subject to the CAR. The reduced systemic exposure can reduce and/or inhibit the development of an immune response against the CAR as the subject's immune system will see less CAR over time.

Control of receptor (e.g., CAR and/or TCR) expression can be used to modulate the PK-PD axis of an immunotherapy. The amount of receptor expressed on the surface of cell can be modulated with the strength of a promoter, the inducibility of the promoter, the use of bicistronic constructs with different promoter strengths expressing the two cistrons, RDEs (selection of RDE impacts dynamic range and timing of expression), GC3 content of the transcript, RNA control devices, degrons and/or Side-CARs. These control elements used singly or in combination change the amount of receptor on the surface of the cell which changes the input signal (e.g., amount of ligand for the receptor) needed to activate the cell so that it produces an output (e.g., payload delivery or target cell killing). Using this control, the input signal needed for the receptor cells can be optimized for a given target, compartment of the body, reduction of side effects, etc. as desired. RDEs can also be used to change the timing of the output from the cell after activation at the receptor (e.g., CAR and/or TCR).

Some neural degenerative diseases and syndromes are associated with inflammation, as are a number of other non-neural diseases and syndromes. Such inflammation associated diseases can be treated, at least in part, by providing a subject with small molecules (or other molecules) that increase the availability of inhibitory RDE binding proteins within immune cells. Such small molecules include, for example, glycolysis inhibitors (e.g., dimethylfumarate (DMF), rapamycin, 2~deoxyglucose, 3-bromophyruvic acid, iodoacetate, fluoride, oxamate, ploglitazone, dichloroacetic acid), other metabolic inhibitors (e.g., dehydroepiandrosterone), etc. For example, glycolytic inhibitors reduce glycolysis in the cell and can increase the amount of free GAPDH (not involved in glycolysis) for binding to RDEs reducing the expression of these transcripts. A number of inflammatory gene products in immune cells (e.g., gene products that activate the immune system) are regulated by RDEs that can bind GAPDH. Decreasing glycolysis increases the amount of free GAPDH for RDE binding, increases the amount of GAPDH bound to the RDEs of these inflammatory genes and reduces the expression of these inflammatory genes. Inflammatory genes include proinflammatory cytokines such as, for example, IL-1, TNF-α, INF-g, and GM-CSF. These cytokines have 3'-UTRs with RDEs that can bind RDE binding proteins, including GAPDH, to regulate their expression. The increased GAPDH can bind to these RDEs and decrease the expression of these proinflammatory cytokines. Reduced expression of proinflammatory cytokines could reduce activity of the immune system in these subjects reducing inflammation. The reduction in inflammation can have positive therapeutic effects alleviating symptoms and/or treating the underlying disease state in these inflammation related neural diseases, as well as in other inflammation associated diseases and syndromes.

RDEs (e.g., AU elements) can be selected to provide maximal expression at a desired time point and to provide a desired amount of polypeptide at that time point. RDEs can also be selected to provide a desired area under the curve for a polypeptide. As shown in Table 2 of Example 20, different RDEs (e.g., AU elements) reached maximal rates of expression at different times. Also as shown in Table 1, different RDEs provided different amounts of expression with different profiles over time providing different AUC. Using these RDEs in combination with different transgenes allows temporal programming of when the different transgenes reach maximal rates of expression in relation to one another following activation of a cell. In addition, using different RDEs one can program the transgenes to express a desired amount of transgene encoded polypeptide and/or a desired amount of AUC or exposure to the polypeptide encoded by the transgene. Thus, RDEs can be used to provide control that produces desired amounts of different transgene polypeptides at a different (or the same) desired times.

This temporal control can be used to provide desired timing for the production of different transgene polypeptides within a cell. Using this temporal control, a cell can be programmed to express a first transgene that alters the state of the cell so that is prepared to be affected by the polypeptide of a second transgene that is expressed at a later time. For example, the first expressed polypeptide could induce the cell to make and store cytotoxic polypeptides (e.g., granzymes and/or perforins) and the second expressed polypeptide could be involved in the release of the cytotoxic polypeptides. Another example of temporal expression involves it use to program a cell to undergo changes (e.g., differentiation or changing a state of the cell) that requires temporal expression of two or more gene products. RDEs can be used to mimic this temporal expression allowing one to control when the cell changes its state or differentiates (e.g., programmed differentiation of stem cells). In a stem cell example, the temporal and induction control can be used to program a stem cell to differentiate when (and where) it is desired to have the stem cell differentiate into a desired cell type.

The temporal control can also be used to provide desired timing of the production of different transgene polypeptides outside of the cell. Using this temporal control, a cell can be activated and secrete a first transgene polypeptide that conditions and/or alters a target cell so that the target cell is prepared to be acted upon by a polypeptide expressed at later time from a second transgene. For example, the first polypeptide could induce a target cell to express a receptor on the target cell surface (e.g., FasR, Her2, CD20, CTLA-4, PD-L1, etc.) or a polypeptide in the cell. The first transgene could also induce the cell to secrete a factor that induces the target cell to change its state (e.g., the first transgene could induce the cell to secrete CpG which causes the target cell to express OX40 on the target cell surface). The second transgene that reaches maximal rate of expression at a later time can encode a polypeptide that acts on the induced surface receptor (e.g., FasL, Herceptin, Rituximab, Ipilimumab, Nivolumab, anti-OX40 antibody, etc.). The temporal and induction control can also be used to change the state or differentiation of a target cell by providing to the target cell polypeptides in a timed manner where the first polypeptide induces the target cell to alter its state (e.g., differentiation) so that it can be acted upon by the second polypeptide (etc. for additional transgene polypeptides which reach maximal rate of expression at later times).

Autoimmune diseases and other disease states involving an overactive immune system (e.g., SARS-CoV-2 infection) can be treated with a ΔITAM CAR T-cell targeted against autoimmune disease antigen(s). The ΔITAM CAR T-cell can include a payload of IL-4, IL-10 or other immunosuppressive. The ΔITAM CAR T-cell with or without a payload can induce the formation of Tregs that can inhibit the autoimmune disease and/or reduce the toxicity caused by overstimulation or chronic stimulation of the immune system.

Some examples of diseases and payloads that can be treated using RDEs (Gold elements) with different kinetic parameters (e.g., an RDE that gives rapid expression early after activation of the cell followed by a rapid decline in expression or an RDE that delays expression after cell activation for 2-3 days) include the following: DLL3 positive cancers (such as IDH1mut gliomas, melanoma, and SCLC) using an anti-DLL3 CAR and a payload of one or more of anti-4-1BB antibody, anti-CD11b antibody, anti-CTLA4 antibody, anti-IL1b antibody, a BiTE, CCL2, anti- CXCR4 antibody, anti-CXCL12 antibody, HAC, heparinase, hyaluronidase, Hsp60, Hsp70, IL-2, IL-12, IL-15, IL-18, INFγ, miRNA (e.g., mir155), CD40 ligand, ApoE3, ApoE4, TNFα, CCR2, CCR4/CXCL12, CXCR3+CXCL9, CXCL9, ACLY, antagonists of CSF1 receptor, miRNA for Tox (e.g., hsa-mir-26b-5p (MIRT030248) hsa-mir-223-3p (MIRT054680)), miRNA for TCF-7 (e.g., mIR-192, mIR-34a, miR-133a, miR-138-5p, miR-342-5p, miR-491-5p, miR-541-3p), and/or anti-CD28 antibody (including full length and fragments such as single chain antibodies). Optionally, the anti-DLL3 CAR with an RDE controlled payload is combined or administered in succession with another therapy as described above. The combined or sequenced therapy can be an ADC where the antibody binds to a tumor associate antigen, e.g., DLL3. The combination therapy can be provided to a subject prior to, at the same time, or after the administration of the anti-DLL3 CAR with an RDE controlled payload. CD19 positive lymphomas (e.g., NHL) using an anti-CD19 CAR and a payload of IL-12, or one or more of anti-4-1BB antibody, anti-CD11b antibody, anti-CTLA4 antibody, anti-RIlb antibody, a BiTE, CCL2, anti-CXCR4 antibody, anti-CXCL12 antibody, HAC, heparinase, hyaluronidase, Hsp60, Hsp70, IL-2, IL-15, IL-18, INFγ, miRNA (e.g., mir155), CD40 ligand, ApoE3, ApoE4, TNFα, CCR2, CCR4/CXCL12, CXCR3+CXCL9, CXCL9, ACLY, antagonists of CSF1 receptor, miRNA for Tox (e.g., hsa-mir-26b-5p (MIRT030248) hsa-mir-223-3p (MIRT054680)), miRNA for TCF-7 (e.g., mIR-192, mIR-34a, miR-133a, miR-138-5p, miR-342-5p, miR-491-5p, miR-541-3p), and/or anti-CD28 antibody (including full length and fragments such as single chain antibodies). Optionally, the anti-CD19 CAR with an RDE controlled payload is combined or administered in succession with another therapy as described above. The combined or sequenced therapy can be an ADC where the antibody binds to a tumor associate antigen, e.g., CD19. The combination therapy can be provided to a subject prior to, at the same time, or after the administration of the anti-CD19 CAR with an RDE controlled payload. AML with onco-CD43 (sialylation mutant) using an anti-onco-CD43 CAR that recognizes the mutated sialylation and a payload of one or more of anti-CXCL12 antibody, anti-anti-CXCR4 antibody, or IL-12, and/or one or more of anti-4-1BB antibody, anti-CD11b antibody, anti-CTLA4 antibody, anti-IL1b antibody, a BiTE, CCL2, HAC, heparinase, hyaluronidase, Hsp60, Hsp70, IL-2, IL-15, IL-18, INFγ, miRNA (e.g., mir155), CD40 ligand, ApoE3, ApoE4, TNFα, CCR2, CCR4/CXCL12, CXCR3+CXCL9, CXCL9, ACLY, antagonists of CSF1 receptor, miRNA for Tox (e.g., hsa-mir-26b-5p (MIRT030248) hsa-mir-223-3p (MIRT054680)), miRNA for TCF-7 (e.g., mIR-192, mIR-34a, miR-133a, miR-138-5p, miR-342-5p, miR-491-5p, miR-541-3p), and/or anti-CD28 antibody (including full length and fragments such as single chain antibodies). Optionally, the anti-onco-CD43 CAR with an RDE controlled payload is combined or administered in succession with another therapy as described above. The combined or sequenced therapy can be an ADC where the antibody binds to a tumor associated antigen, e.g., onco-CD43. The combination therapy can be provided to a subject prior to, at the same time, or after the administration of the anti-onco-CD43 CAR with an RDE controlled payload. PSCA positive prostate cancer, bladder cancer or pancreatic cancer using an anti-PSCA CAR and a payload of heparinase or IL-12, and/or one or more of anti-4-1BB antibody, anti-CD11b antibody, anti-CTLA4 antibody, anti-IL1b antibody, a BiTE, CCL2, anti-CXCR4 antibody, anti-CXCL12 antibody, HAC, hyaluronidase, Hsp60, Hsp70, IL-2, IL-15, IL-18, INFγ, miRNA (e.g., mir155), CD40 ligand, ApoE3, ApoE4, TNFα, CCR2, CCR4/CXCL12, CXCR3+CXCL9, CXCL9, ACLY, antagonists of CSF1 receptor, miRNA for Tox (e.g., hsa-mir-26b-5p (MIRT030248) hsa-mir-223-3p (MIRT054680)), miRNA for TCF-7 (e.g., mIR-192, mIR-34a, miR-133a, miR-138-5p, miR-342-5p, miR-491-5p, miR-541-3p), and/or anti-CD28 antibody (including full length and fragments such as single chain antibodies). Optionally, the anti-PSCA CAR with an RDE controlled payload is combined or administered in succession with another therapy as described above. The combined or sequenced therapy can be an ADC where the antibody binds to a tumor associated antigen, e.g., PSCA. The combination therapy can be provided to a subject prior to, at the same time, or after the administration of the anti-PSCA CAR with an RDE controlled payload. Triple negative breast cancer with a CAR that recognizes cancer testis antigen, misfolded or mutant EGFR (associated with triple negative breast cancer), and/or folate receptor alpha peptide and a payload of IL-12 and/or one or more of anti-4-1BB antibody, anti-CD11 b antibody, anti-CTLA4 antibody, anti-IL1b antibody, a BiTE, CCL2, anti-CXCR4 antibody, anti-CXCL12 antibody, HAC, heparinase, hyaluronidase, Hsp60, Hsp70, IL-2, IL-15, IL-18, INFγ, miRNA (e.g., mir155), CD40 ligand, ApoE3, ApoE4, TNFα, CCR2, CCR4/CXCL12, CXCR3+CXCL9, CXCL9, ACLY, antagonists of CSF1 receptor, miRNA for Tox (e.g., hsa-mir-26b-5p (MIRT030248) hsa-mir-223-3p (MIRT054680)), miRNA for TCF-7 (e.g., mIR-192, mIR-34a, miR-133a, miR-138-5p, miR-342-5p, miR-491-5p, miR-541-3p), and/or anti-CD28 antibody (including full length and fragments such as single chain antibodies). Optionally, the anti-cancer testis antigen CAR, anti-misfolded or mutant EGFR CAR, or anti-folate receptor alpha CAR with an RDE controlled payload is combined or administered in succession with another therapy as described above. The combined or sequenced therapy can be an ADC where the antibody binds to a tumor associated antigen, e.g., cancer testis antigen, misfolded or mutant EGFR (associated with triple negative breast cancer), and/or folate receptor alpha peptide. The combination therapy can be provided to a subject prior to, at the same time, or after the administration of the anti-cancer testis antigen CAR, anti-misfolded or mutant EGFR CAR, or anti-folate receptor alpha CAR with an RDE controlled payload. SEZ6 positive small cell lung cancer (SCLC), neuroendocrine cancers (e.g., medullary thyroid cancer), large cell lung cancer (LCLC), and malignant pheochromocytoma with a CAR that recognizes SEZ6 and a payload of IL-12 and/or one or more of anti-4-1BB antibody, anti-CD11b antibody, anti-CTLA4 antibody, anti-IL1b antibody, a BiTE, CCL2, anti-CXCR4 antibody, anti-CXCL12 antibody, HAC, heparinase, hyaluronidase, Hsp60, Hsp70, IL-2, IL-15, IL-18, INFγ, miRNA (e.g., mir155), CD40 ligand, ApoE3, ApoE4, TNFα, CCR2, CCR4/CXCL12, CXCR3+CXCL9, CXCL9, ACLY, antagonists of CSF1 receptor, miRNA for Tox (e.g., hsa-mir-26b-5p (MIRT030248) hsa-mir-223-3p (MIRT054680)), miRNA for TCF-7 (e.g., mIR-192, mIR-34a, miR-133a, miR-138-5p, miR-342-5p, miR-491-5p, miR-541-3p), and/or anti-CD28 antibody (including full length and fragments such as single chain antibodies). Optionally, the anti-SEZ6 CAR with an RDE controlled payload is combined or administered in succession with another therapy as described above. The combined or sequenced therapy can be an ADC where the antibody binds to a tumor associated antigen, e.g., SEZ6. The combination therapy can be provided to a subject prior to, at the same time, or after the administration of the anti-SEZ6 CAR with an RDE controlled payload. RNF43 positive colorectal cancer, colon cancer, and endometrial cancers with a CAR that recognizes RNF43 and a payload of IL-12 and/or one or more of anti-4-1BB antibody, anti-CD11b antibody, anti-CTLA4 antibody, anti-IL1b antibody, a BiTE, CCL2, anti-CXCR4 antibody, anti-CXCL12 antibody, HAC, heparinase, hyaluronidase, Hsp60, Hsp70, IL-2, IL-15, IL-18, INFγ, miRNA (e.g., mir155), CD40 ligand, ApoE3, ApoE4, TNFα, CCR2, CCR4/CXCL12, CXCR3+CXCL9, CXCL9, ACLY, antagonists of CSF1 receptor, miRNA for Tox (e.g., hsa-mir-26b-5p (MIRT030248) hsa-mir-223-3p (MIRT054680)), miRNA for TCF-7 (e.g., mIR-192, mIR-34a, miR-133a, miR-138-5p, miR-342-5p, miR-491-5p, miR-541-3p), and/or anti-CD28 antibody (including full length and fragments such as single chain antibodies). Optionally, the anti-RNF43 CAR with an RDE controlled payload is combined or administered in succession with another therapy as described above. The combined or sequenced therapy can be an ADC where the antibody binds to a tumor associated antigen, e.g., RNF43. The combination therapy can be provided to a subject prior to, at the same time, or after the administration of the anti-RNF43 CAR with an RDE controlled payload. TnMUC1 positive breast cancer (e.g., triple negative breast cancer), pancreatic cancer, ovarian cancer, colorectal cancer, non-small cell lung cancer (NSCLC), prostate cancer, colon cancer, multiple myeloma, and/or T-cell acute lymphoblastic leukemia (TALL) with a CAR that recognizes TnMUC1 and a payload of IL-12 and/or one or more of anti-4-1BB antibody, anti-CD11b antibody, anti-CTLA4 antibody, anti-IL1b antibody, a BiTE, CCL2, anti-CXCR4 antibody, anti-CXCL12 antibody, HAC, heparinase, hyaluronidase, Hsp60, Hsp70, IL-2, IL-15, IL-18, INFγ, miRNA (e.g., mir155), CD40 ligand, ApoE3, ApoE4, TNFα, CCR2, CCR4/CXCL12, CXCR3+CXCL9, CXCL9, ACLY, antagonists of CSF1 receptor, miRNA for Tox (e.g., hsa-mir-26b-5p (MIRT030248) hsa-mir-223-3p (MIRT054680)), miRNA for TCF-7 (e.g., mIR-192, mIR-34a, miR-133a, miR-138-5p, miR-342-5p, miR-491-5p, miR-541-3p), and/or anti-CD28 antibody (including full length and fragments such as single chain antibodies). Optionally, the anti-TnMUC1 CAR with an RDE controlled payload is combined or administered in succession with another therapy as described above. The combined or sequenced therapy can be an ADC where the antibody binds to a tumor associated antigen, e.g., TnMUC1. The combination therapy can be provided to a subject prior to, at the same time, or after the administration of the anti-TnMUC1 CAR with an RDE controlled payload. Nectin4 positive urothelial cancer, NSCLC, breast cancer, ovarian cancer, bladder cancer, pancreatic cancer, and other solid tumors with a CAR that recognizes Nectin4 and a payload of IL-12 and/or one or more of anti-4-1BB antibody, anti-CD11b antibody, anti-CTLA4 antibody, anti-RIlb antibody, a BiTE, CCL2, anti-CXCR4 antibody, anti-CXCL12 antibody, HAC, heparinase, hyaluronidase, Hsp60, Hsp70, IL-2, IL-15, IL-18, INFγ, miRNA (e.g., mir155), CD40 ligand, ApoE3, ApoE4, TNFα, CCR2, CCR4/CXCL12, CXCR3+CXCL9, CXCL9, ACLY, antagonists of CSF1 receptor, miRNA for Tox (e.g., hsa-mir-26b-5p (MIRT030248) hsa-mir-223-3p (MIRT054680)), miRNA for TCF-7 (e.g., mIR-192, mIR-34a, miR-133a, miR-138-5p, miR-342-5p, miR-491-5p, miR-541-3p), and/or anti-CD28 antibody (including full length and fragments such as single chain antibodies). Optionally, the anti-Nectin4 CAR with an RDE controlled payload is combined or administered in succession with another therapy as described above. The combined or sequenced therapy can be an ADC where the antibody binds to a tumor associated antigen, e.g., Nectin4. The combination therapy can be provided to a subject prior to, at the same time, or after the administration of the anti-Nectin4 CAR with an RDE controlled payload. EFNA4 positive triple negative breast cancer, ovarian cancer, colorectal cancer, liver cancer, lung cancer, and other solid tumors with a CAR that recognizes EFNA4 and a payload of IL-12 and/or one or more of anti-4-1BB antibody, anti-CD11b antibody, anti-CTLA4 antibody, anti-IL1b antibody, a BiTE, CCL2, anti-CXCR4 antibody, anti-CXCL12 antibody, HAC, heparinase, hyaluronidase, Hsp60, Hsp70, IL-2, IL-15, IL-18, INFγ, miRNA (e.g., mir155), CD40 ligand, ApoE3, ApoE4, TNFα, CCR2, CCR4/CXCL12, CXCR3+CXCL9, CXCL9, ACLY, antagonists of CSF1 receptor, miRNA for Tox (e.g., hsa-mir-26b-5p (MIRT030248) hsa-mir-223-3p (MIRT054680)), miRNA for TCF-7 (e.g., mIR-192, mIR-34a, miR-133a, miR-138-5p, miR-342-5p, miR-491-5p, miR-541-3p), and/or anti-CD28 antibody (including full length and fragments such as single chain antibodies). Optionally, the anti-EFNA4 CAR with an RDE controlled payload is combined or administered in succession with another therapy as described above. The combined or sequenced therapy can be an ADC where the antibody binds to a tumor associated antigen, e.g., EFNA4. The combination therapy can be provided to a subject prior to, at the same time, or after the administration of the anti-EFNA4 CAR with an RDE controlled payload. GPC3 positive hepatocellular carcinoma, lung cancer and other solid tumors with a CAR that recognizes GPC3 and a payload of IL-12 and/or one or more of anti-4-1BB antibody, anti-CD11b antibody, anti-CTLA4 antibody, anti-IL1b antibody, a BiTE, CCL2, anti-CXCR4 antibody, anti-CXCL12 antibody, HAC, heparinase, hyaluronidase, Hsp60, Hsp70, IL-2, IL-15, IL-18, INFγ, miRNA (e.g., mir155), CD40 ligand, ApoE3, ApoE4, TNFα, CCR2, CCR4/CXCL12, CXCR3+CXCL9, CXCL9, ACLY, antagonists of CSF1 receptor, miRNA for Tox (e.g., hsa-mir-26b-5p (MIRT030248) hsa-mir-223-3p (MIRT054680)), miRNA for TCF-7 (e.g., mIR-192, mIR-34a, miR-133a, miR-138-5p, miR-342-5p, miR-491-5p, miR-541-3p), and/or anti-CD28 antibody (including full length and fragments such as single chain antibodies). Optionally, the anti-GPC3 CAR with an RDE controlled payload is combined or administered in succession with another therapy as described above. The combined or sequenced therapy can be an ADC where the antibody binds to a tumor associated antigen, e.g., GPC3. The combination therapy can be provided to a subject prior to, at the same time, or after the administration of the anti-GPC3 CAR with an RDE controlled payload. Complement factor H (CFH) positive breast cancer, lung cancer, nonsmall cell lung cancer (NSCLC), small cell lung cancer (SCLC), and other solid tumors with a CAR that recognizes CFH and a payload of IL-12 and/or one or more of anti-4-1BB antibody, anti-CD11b antibody, anti-CTLA4 antibody, anti-IL1b antibody, a BiTE, CCL2, anti-CXCR4 antibody, anti-CXCL12 antibody, HAC, heparinase, hyaluronidase, Hsp60, Hsp70, IL-2, IL-15, IL-18, INFγ, miRNA (e.g., mir155), CD40 ligand, ApoE3, ApoE4, TNFα, CCR2, CCR4/CXCL12, CXCR3+CXCL9, CXCL9, ACLY, antagonists of CSF1 receptor, miRNA for Tox (e.g., hsa-mir-26b-5p (MIRT030248) hsa-mir-223-3p (MIRT054680)), miRNA for TCF-7 (e.g., mIR-192, mIR-34a, miR-133a, miR-138-5p, miR-342-5p, miR-491-5p, miR-541-3p), anti-CD28 antibody (including full length and fragments such as single chain antibodies) and/or anti-TGFb agents (e.g., anti-TGFb antibody, soluble TGFbR, anti-avB6 integrin antibody, natural TGFb binding proteins, dnTGFBR2, biglycan, decorin). Optionally, the anti-CFH CAR with an RDE controlled payload is combined or administered in succession with another therapy as described above. The combined or sequenced therapy can be an ADC where the antibody binds to a tumor associated antigen, e.g., CFH. The combination therapy can be provided to a subject prior to, at the same time, or after the administration of the anti-CFH CAR with an RDE controlled payload.

In general, any of the above CAR cells with or without an RDE controlled transgene(s) can be used in combination or administered in succession with another molecule (e.g., another therapy). For example, the other molecule can be a polypeptide, lipid, carbohydrate, nucleic acid, small molecule drug, antibody, antibody-drug-conjugate, biological drug, or any combination of the foregoing. The antibody drug conjugate (ADC) includes those described herein. The ADC can bind to the same antigen as the CAR or it can bind to a different antigen. When the ADC and CAR bind to the same antigen, they may bind to the same or different epitopes on the same antigen. The ADC and CAR therapy (with or without a RDE controlled payload) can be provided at the same time, or one can be administered to a subject before the other. For example, the ADC and CAR can target a tumor associate antigen and the ADC can be administered the subject first to reduce the tumor burden, and then the CAR therapy is administered to clear the remaining cancer cells.

Treatment with Gold CARS

The present disclosure relates to a kit having one or more compositions as described herein. Kits can include, for example, nucleic acid(s) encoding a receptor (e.g., a chimeric antigen receptor or a T-cell receptor) and a transgene with an RDE (which produces a transcript encoding the transgene product operably linked to the RDE), and a package insert or other labeling directions for preparation and administration of an immunotherapy to patients. As used herein "package insert" refers to instructions customarily included in commercial packages of therapeutic products, that contain information about the indications, usage, dosage, administration, combination therapy, contraindications and/or warnings concerning the use of such therapeutic products. Exemplary nucleic acids include, for example, GC213 (SEQ ID NO: 5), SK072 (SEQ ID NO: 11), GC251, (SEQ ID NO: 12), PD007 (SEQ ID NO: 13), and/or PD009 (SEQ ID NO: 14).

When used for the treatment of cancer, the response of patients to treatment is defined in several ways: complete response, partial response, stable disease, and disease progression. In a complete response all of the cancer or tumor disappears; there is no evidence of disease. Expression level of tumor marker (if applicable) may fall within the normal range. In a partial response the cancer has shrunk by a percentage but disease remains. Levels of a tumor marker (if applicable) may have fallen (or increased, based on the tumor marker, as an indication of decreased tumor burden) but evidence of disease remains. In stable disease the cancer has neither grown nor shrunk; the amount of disease has not changed. A tumor marker (if applicable) has not changed significantly. In disease progression the cancer has grown; there is more disease now than before treatment. A tumor marker test (if applicable) shows that a tumor marker has risen.

Other measures of the efficacy of cancer treatment include intervals of overall survival (that is time to death from any cause, measured from diagnosis or from initiation of the treatment being evaluated)), cancer-free survival (that is, the length of time after a complete response cancer remains undetectable), and progression-free survival (that is, the length of time after disease stabilization or partial response that resumed tumor growth is not detectable).

There are two standard methods for the evaluation of solid cancer treatment response with regard to tumor size (tumor burden), the WHO and RECIST standards. These methods measure a solid tumor to compare a current tumor with past measurements or to compare changes with future measurements and to make changes in a treatment regimen. In the WHO method, the solid tumor's long and short axes are measured with the product of these two measurements is then calculated; if there are multiple solid tumors, the sum of all the products is calculated. In the RECIST method, only the long axis is measured. If there are multiple solid tumors, the sum of all the long axes measurements is calculated. However, with lymph nodes, the short axis is measured instead of the long axis.

When patients are treated with the methods and compositions described herein, the tumor burden of a treated patient is reduced by about 5%, about 10%, about 15%, about 20%, about 25%, about 30%, about 35%, about 40%, about 45%, about 50%, about 55% about 60%, about 65%, about 70%, about 75%, about 80%, about 90%, about 95%, about 100%, or any range bound by these values. When patients are treated with the methods and compositions described herein, the 1-year survival rate of treated patients is increased by about 5%, about 10%, about 15%, about 20%, about 25%, about 30%, about 35%, about 40%, about 45%, about 50%, about 55% about 60%, about 65%, about 70%, about 75%, about 80%, about 90%, about 95%, about 100%, or any range bound by these values. When patients are treated with the methods and compositions described herein, the 5-year survival rate of treated subjects is increased by about 5%, about 10%, about 15%, about 20%, about 25%, about 30%, about 35%, about 40%, about 45%, about 50%, about 55% about 60%, about 65%, about 70%, about 75%, about 80%, about 90%, about 95%, about 100%, or any range bound by these values. When patients are treated with the methods and compositions described herein, patients have a sustained remission of at least 6 months, at least 7 months, at least 8 months, at least 9 months, at least 10 months, at least 11 months, at least 12 months, at least 14 months, at least 16 months, at least 18 months, at least 20 months, at least 22 months, at least 24 months, at least 27 months, at least 30 months, at least 33 months, at least 36 months, at least 42 months, at least 48 months, at least 54 months, or at least 60 months or more. When patients are treated with the methods and compositions described herein, a complete response is obtained in at least 35%, at least 40% or at least 50% of patients treated and/or partial responses are obtained in at least 50%, at least 60% or at least 70% of patients treated.

The inventions disclosed herein will be better understood from the experimental details which follow. However, one skilled in the art will readily appreciate that the specific methods and results discussed are merely illustrative of the inventions as described more fully in the claims which follow thereafter. Unless otherwise indicated, the disclosure is not limited to specific procedures, materials, or the like, as such may vary. It is also to be understood that the terminology used herein is for the purpose of describing particular embodiments only and is not intended to be limiting.

EXAMPLES

Example 1. Control of T-Cell Effector Activity with an RDE-CAR

A RDE Car is made using the third generation anti-CD19 CAR cassette described in WO 2012/079000, which is hereby incorporated-by-reference in its entirety for all purposes), and the 3'-UTR of the gene encoding IL-2 (NCBI Reference Sequence Number: NM_000586.3), which is hereby incorporated by reference in its entirety for all purposes). A nucleic acid encoding the IL-2 3'-UTR is engineered into the anti-CD19 CAR cassette in an appropriate expression vector. The IL-2, 3'-UTR sequence used was:

```
                                              (SEQ ID NO: 53)
taattaagtgcttcccacttaaaacatatcaggccttctATTTATTTAaat

ATTTAaattttatATTTAttgttgaatgtatggtttgctacctattgtaac

tattattcttaatcttaaaactataaatatggatcttttatgattcttttt

gtaagccctaggggctctaaaatggtttcacttATTTAtcccaaaatATTT

Attattatgttgaatgttaaatatagtatctatgtagattggttagtaaaa

ctATTTAataaatttgataaatataaa
```

The anti-CD19 RDE CAR and anti-CD19 CAR constructs are transfected by routine methods into different populations of T-cells (primary human T-cells), and stable populations of T-cells are selected using appropriate antibiotics (or other selection schemes). T-cell populations with anti-CD19 RDE CARs (CD19−/CD22−/CD3+) and T-cell populations with anti-CD19 CARs (CD19−/CD22−/CD3+) are activated by co-incubation with anti-CD3/CD28 beads and allowed to return to quiescent state after debeading.

Quiescent anti-CD19 RDE CAR T-cells are co-cultured with CD19+/CD22+/CD3-Raji target cells at RDE CAR T-cell:Raji target ratios of 2:1, 5:1, and 10:1. The glycolysis activator glucose is added to the culture medium at concentrations in the range of 1.0 mM to 10 mM (1 mM, 2 mM, 3 mM, 4 mM, 5 mM, 7.5 mM and 10 mM). The RDE-CAR T-cells and the Raji cells are grown together for 24 hours. Cultures are washed, and then stained with anti-CD22 and anti-CD3 reagents, followed by counting of CD22+(Raji target cells) and CD3+ cells (CAR T-cells). These measurements will identify the target cell killing rate (e.g., half-life) and the proliferation rate of the RDE-CAR T-cells at different levels of RDE-CAR expression.

Activated anti-CD19 RDE CAR T-cells are co-cultured with CD19+/CD22+/CD3-Raji target cells at RDE CAR T-cell:Raji target ratios of 2:1, 5:1, and 10:1. The glycolysis activator glucose is added to the culture medium at concentrations in the range of 1.0 mM to 10 mM (1 mM, 2, mM, 3 mM, 4 mM, 5 mM, 7.5 mM and 10 mM). The RDE-CAR T-cells and the Raji cells are grown together for 24 hours. Samples from culture media are taken and tested for IL-2 by ELISA.

As a control activated anti-CD19 CAR T-cells are co-cultured with $CD19^+/CD22^+/CD3-$ Raji target cells at CAR T-cell:Raji target ratios of 2:1, 5:1, and 10:1. The glycolysis activator glucose is added to the culture medium at concentrations in the range of 1.0 mM to 10 mM (1 mM, 2 mM, 3 mM, 4 mM, 5 mM, 7.5 mM and 10 mM). The CAR T-cells and the Raji cells are grown together for 24 hours. Cultures are washed, and then stained with anti-CD22 and anti-CD3 reagents, followed by counting of $CD22^+$ (Raji target cells) and $CD3^+$ cells (CAR T-cells).

As a control, activated anti-CD19 CAR T-cells are co-cultured with $CD19^+/CD22^+/CD3-$ Raji target cells at CAR T-cell:Raji target ratios of 2:1, 5:1, and 10:1. The glycolysis activator glucose is added to the culture medium at concentrations in the range of 1.0 mM to 10 mM (1 mM, 2 mM, 3 mM, 4 mM, 5 mM, 7.5 mM and 10 mM). The CAR T-cells and the Raji cells are grown together for 48 hours. Samples from culture media are taken and tested for TL-2 by ELISA.

Example 2: Removal of MicroRNA Binding Sites from an RDE

The AU-rich element from the 3'-UTR of IL-2 has mir-181 and mir 186 microRNA binding sites. Different combinations of the microRNA sites were removed from the 3'-UTR of IL-2. When the MIR186 micro-RNA sites were removed from the 3'-UTR of IL-2 the dynamic range of expression from constructs with this UTR increased 50 fold. The modified IL-2, 3'-UTR replaces CTT in the sequence with GAA and is shown below (the new GAA is underlined in the sequence):

```
                                    (SEQ ID NO: 54)
taattaagtgcttcccacttaaaacatatcaggccttctATTTATTTAaa

tATTTAaattttatATTTAttgttgaatgtatggtttgctacctattgta

actattattcttaatcttaaaactataaatatggatcttttatgattGAA

tttgtaagccctaggggctctaaaatggtttcacttATTTAtcccaaaat

ATTTAttattatgttgaatgttaaatatagtatctatgtagattggttag

taaaactATTTAataaatttgataaatataaa
```

The AU-rich element from the 3'UTR of IFNg also has micro-RNA binding sites characterized as mir-125. The sequence of the IFNg RDE is:

```
                                    (SEQ ID NO: 55)
tggttgtcctgcctgcaatatttgaattttaaatctaaatctATTTAttaa

tATTTAacattATTTAtatggggaatatatttttagactcatcaatcaaat

aagtATTTAtaatagcaacttttgtgtaatgaaaatgaatatctattaata

tatgtattATTTAtaattcctatatcctgtgactgtctcacttaatccttt

gttttctgactaattaggcaaggctatgtgattacaaggctttatctcagg

ggccaactaggcagccaacctaagcaagatcccatgggttgtgtgtttatt

tcacttgatgatacaatgaacacttataagtgaagtgatactatccagtta

ctgccggtttgaaaatatgcctgcaatctgagccagtgctttaatggcatg

tcagacagaacttgaatgtgtcaggtgaccctgatgaaaacatagcatctc

aggagatttcatgcctggtgcttccaaatattgttgacaactgtgactgta

cccaaatggaaagtaactcatttgttaaaattatcaatatctaatatatat

gaataaagtgtaagttcacaacta
```

Different combinations of the micro-RNA sites were removed from the 3'UTR of IFNg and tested for increased expression. When the mir125 micro-RNA sites were removed from the 3'-UTR of IFN-γ the expression rate from constructs with this UTR is increased.

Expression of GFP in T-cells, transfected with the RDE-GFP plus the microRNA sites, is compared to expression of GFP in T-cells with the RDE-GFP in which the microRNA sites have been removed, following activation with CD3/CD28 beads for 24 hours. The removal of the microRNA sites increased expression of the GFP by a factor of between 2-5 after 24 hours, relative to the cells with microRNA sites.

Example 3: An RDE Construct for Expressing a Second Transgene

Constructs were made using an anti-CD19 CAR cassette as described in WO 2012/079000, which is hereby incorporated-by-reference in its entirety for all purposes), and a GFP-RDE1 (3'-UTR from IFNg) insert. These two inserts/cassettes were placed in the same lenti virus construct. The anti-CD19 CAR cassette and the insert with the GFP-RDE are transcribed in opposite directions, and the control regions for each are located in between the two insert/cassettes. The control region for the GFP-RDE insert was MinP and the RDE was the endogenous 3'-UTR of IFNg. The control region of the anti-CD19 CAR cassette was MND (as described above). $CD4^{+}$ T-cells were transduced with the bicistronic construct.

The transduced T cells were allowed to return to resting state, and then were tested after stimulation as follows. For the 'no stimulation' set, transduced T-cells were incubated for 24 h alone in medium. For the 'Raji co-culture' set and the "CD3/CD28 Beads" set, CD19+ Raji B cells or anti-CD3/anti-CD28 beads were incubated with the transduced T cells for 24 h. At 24 h, the T cells were stained for CD25 and CD69, which are activation markers, and subject to flow cytometry to measure these markers and GFP expression in the T cells.

The transduced T-cells showed an increase in fluorescence when cultured with Raji target cells (activate CAR) of 1.0% to 6.5% (about 6.5 fold), and increase in fluorescence when cultured with CD3/CD28 beads (activate TCR) of 1.0% to 4.4% (about 4.4 fold). The transformed T-cells showed a change in activated cells in the population when cultured with Raji cells of 0.9% to 84.8%, and when cultured with CD3/CD28 beads of 0.9% to 90.8%.

Example 4: A Modified RDE2 Construct for Expressing a Second Transgene

Constructs were made using an anti-CD19 CAR cassette as described in Examples 11 and 12, and a GFP-RDE2.1 (IL-2 RDE) insert. The RDE2.1 was modified to remove the MIR186 microRNA sites, altering nucleotides from the 3'-UTR of IL-2 which was used as RDE2.

These two inserts/cassettes were placed in the same *lenti* virus construct. The anti-CD19 CAR cassette and the insert with the GFP-RDE are transcribed in opposite directions, and the control regions for each are located in between the two insert/cassettes. The control region for the GFP-RDE insert was a MinP. The control region of the anti-CD19 CAR cassette in was MND (as described above). CD4+ T-cells were transduced with the bicistronic construct.

The transduced T cells were allowed to return to resting state, and then were tested after stimulation as follows. For the 'no stimulation' set, transduced T-cells were incubated for 24 h alone in medium. For the 'Raji co-culture' set and the "CD3/CD28 Beads" set, CD19+ Raji B cells or anti-CD3/anti-CD28 beads were incubated with the transduced T cells for 24 h. At 24 h, the T cells were stained for CD25 and CD69, which are activation markers, and subject to flow cytometry to measure these markers and GFP expression in the T cells.

The transduced T-cells showed a change in activated cells in the population when cultured with Raji cells of 3.9% to 12.1%, and when cultured with CD3/CD28 beads of 3.9% to 11.1%.

Example 5: An RDE Construct for Expressing a Luciferase Transgene

Constructs were made using an anti-CD19 CAR cassette as described in WO 2012/079000, which is hereby incorporated-by-reference in its entirety for all purposes), and a Luciferase-RDE1 (3'-UTR of IFNg, Gold1) insert or a Luciferase-3'-UTR (a 3'-UTR that does not confer differential transgene translation in response to metabolic state of the cell, 3'-UTR). The anti-CD19 CAR cassette and the insert with the luciferase-RDE1 are transcribed in opposite directions, and the control regions for each are located in between the two insert/cassettes. The control region for the Luciferase-RDE1 insert and Luciferase-3'-UTR were either a MinP promoter or an NFAT promoter having the sequences of:

```
                                        SEQ ID NO: 56
TAGAGGGTATATAATGGAAGCTCGACTTCCAG
(MinP)

                                        SEQ ID NO: 57
GGAGGAAAAACTGTTTCATACAGAAGGCGTGGAGGAAAAACTGTTTCAT
ACAGAAGGCGTGGAGGAAAAACTGTTTCATACAGAAGGCGTAGATCTAG
ACTCTAGAGGGTATATAATGGAAGCTCGAATTC
(NFAT)
```

The control region of the anti-CD19 CAR cassette was the MND promoter. $CD4^+$ T-cells were transduced with the bicistronic construct.

The transduced T cells were allowed to return to resting state, and then were tested after stimulation as follows. For the 'no stimulation' set, transduced T-cells were incubated for 24 h alone in medium. For the 'Raji co-culture' set and the "CD3/CD28 Beads" set, CD19+ Raji B cells or anti-CD3/anti-CD28 beads were incubated with the transduced T cells for 24 h. At 24 h, the T cells were stained for CD25 and CD69, which are activation markers, and subject to flow cytometry to measure these markers and luciferase expression in the T cells.

Figure 2:
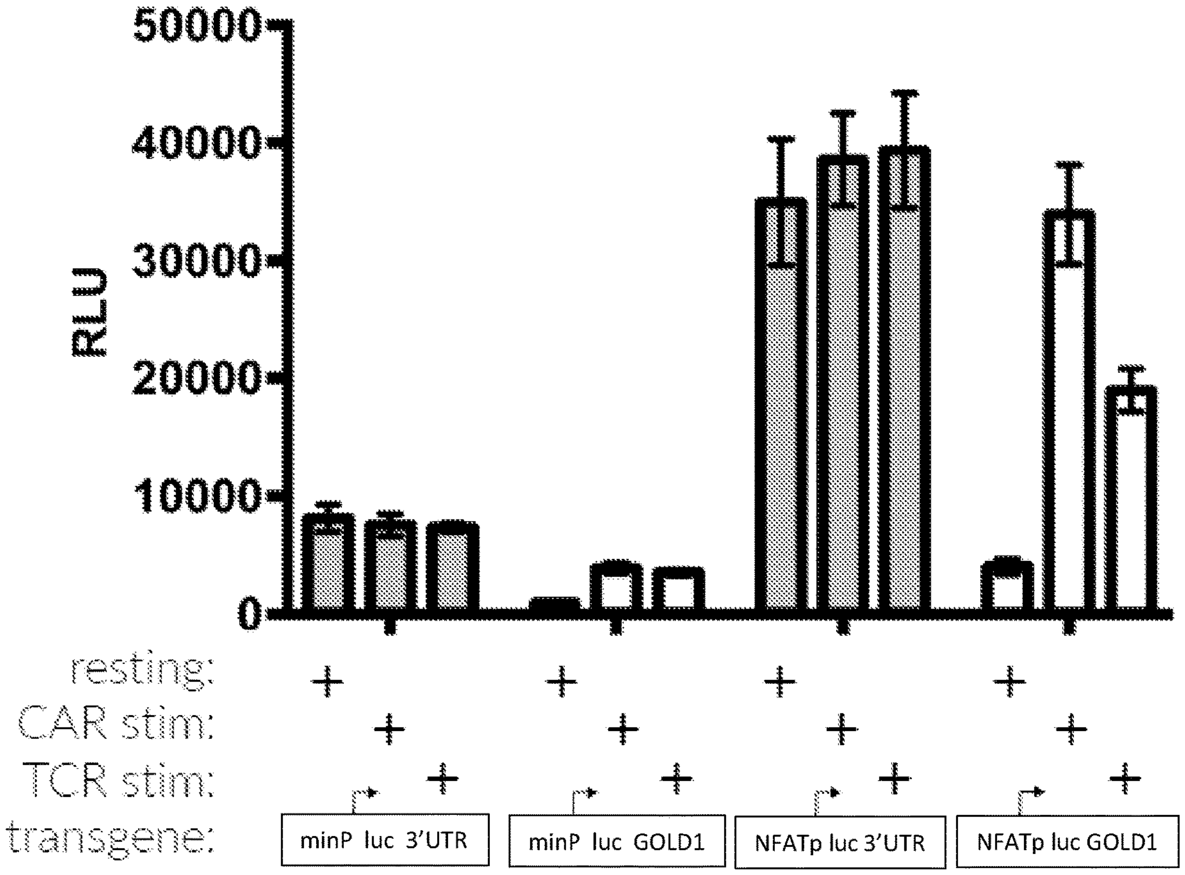
FIG. 2 shows a graph for the bioluminescence from T-cells with luciferase controlled by an RDE following activation of the T-cell by Raji target cells (activate CAR) or by CD3/CD28 beads (activate TCR) as compared to bioluminescence of T-cells at resting.

FIG. 2 shows that the transduced T-cells had an increase in bioluminescence when cultured with Raji target cells (activate CAR) or when cultured with CD3/CD28 beads (activate TCR) as compared to bioluminescence of T-cells at resting. The T-cells with a NFAT promoter and the 3'-UTR of IFNg (Gold1) showed a larger on-off response from CAR stimulation versus TCR stimulation. Under all conditions, T-cells with Gold1 had lower amounts of bioluminescence than T-cells under the same conditions (and same promoter) with Luciferase that was not controlled by the 3'UTR of IFNg (3'-UTR).

Example 6: Comparison of RDEs Controlling Luciferase

Constructs were made using an anti-CD19 CAR cassette as described in WO 2012/079000, which is hereby incorporated-by-reference in its entirety for all purposes), and a Luciferase-RDE1 (3' UTR of IFNg, Gold1) insert, a Luciferase-RDE2 (3'-UTR of IL-2, Gold2) insert, a Luciferase-RDE3 (3'-UTR of IL-2 modified as described above to remove the mir186 sites, Gold3), or a Luciferase-3'-UTR (a 3'-UTR that does not confer differential transgene translation in response to metabolic state of the cell, 3'-UTR). Combinations of these inserts/cassettes shown in FIG. 3 were placed in the similar lenti virus constructs. The anti-CD19 CAR cassette and the insert with the luciferase-RDE are transcribed in opposite directions, and the control regions for each are located in between the two insert/cassettes. The control region for the Luciferase-RDE insert and Luciferase-3'-UTR were either a MinP promoter or an NFAT promoter. The control region of the anti-CD19 CAR cassette was the MND promoter, and CD4+ T-cells were transduced with the bicistronic construct.

The transduced T cells were allowed to return to resting state, and then were tested after stimulation as follows. For the 'no stimulation' set, transduced T-cells were incubated for 24 h alone in medium. For the 'Raji co-culture' set CD19+ Raji B cells were incubated with the transduced T cells for 24 h. At 24 h, the T cells were stained for CD25 and CD69, which are activation markers, and subject to flow cytometry to measure these markers and luciferase expression in the T cells.

Figure 3:
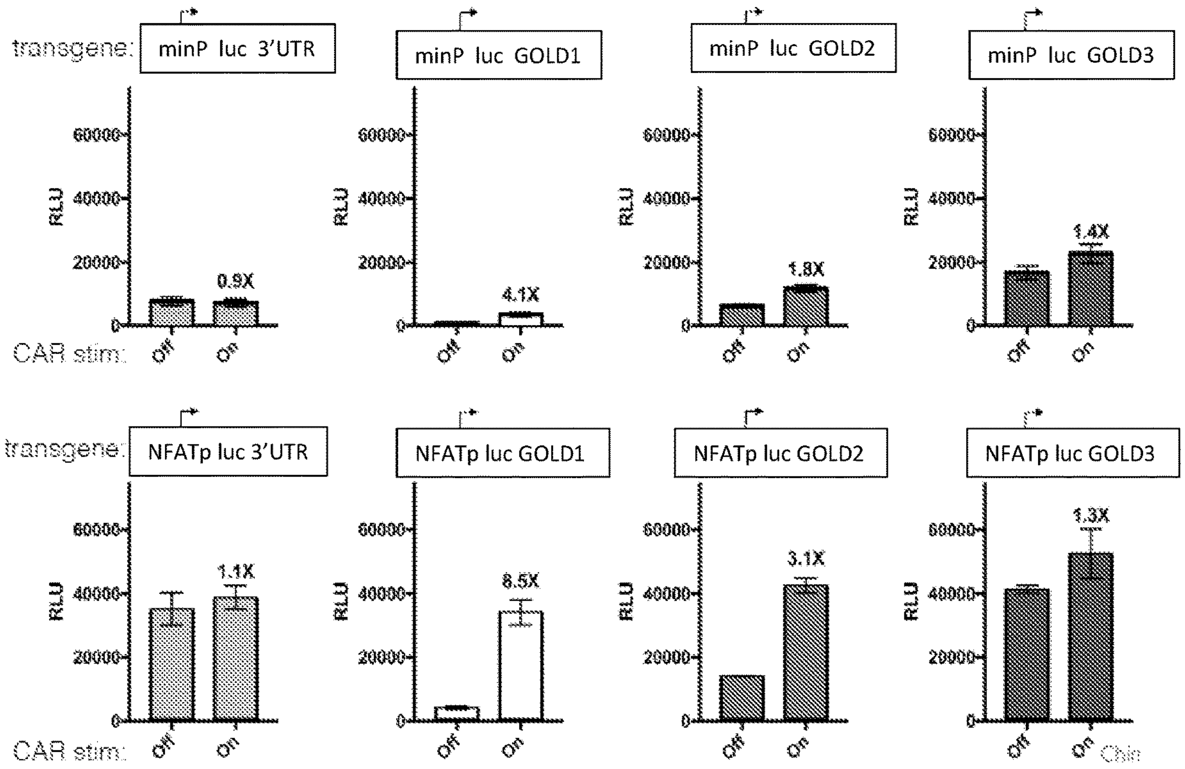
FIG. 3 shows a graph for bioluminescence from T-cells with luciferase controlled by the RDEs Gold1, Gold2, or Gold3 following activation of the T-cell by Raji target cells (activate CAR) as compared to bioluminescence of T-cells at resting.

FIG. 3 shows that the transduced T-cells had an increase in bioluminescence when cultured with Raji target cells (activate CAR) as compared to bioluminescence of T-cells at resting for constructs with RDE1 (Gold1), RDE2 (Gold2), or RDE3 (Gold3). The T-cells with a NFAT promoter and the RDE1 showed a larger on-off response than T-cells with a MinP promoter and the corresponding RDE. Under all conditions, T-cells with an RDE controlling luciferase had lower amounts of bioluminescence than T-cells with luciferase cassettes that were not controlled by an RDE. Combined with the MinP promoter, RDE1 gave a 4.1-fold increase in bioluminescence with CAR stimulation, RDE2 gave a 1.8-fold increase in bioluminescence, and RDE3 gave a 1.4-fold increase. Combined with the NFAT promoter, RDE1 gave a 8.5-fold increase in bioluminescence with CAR stimulation, RDE2 gave a 3.1-fold increase in bioluminescence, and RDE3 gave a 1.3-fold increase. With either promoter, the RDE3 construct gave the highest amount of bioluminescence, the RDE1 construct gave the lowest amount of bioluminescence, and the RDE2 construct gave an amount of bioluminescence between RDE3 and RDE1.

Example 7: An RDE Construct for Expressing IL-12

Constructs were made using an anti-CD19 CAR cassette as described in WO 2012/079000, which is hereby incorporated-by-reference in its entirety for all purposes), and an IL-12-RDE1 (3'-UTR of IFNg) insert or an IL-12 3'-UTR (a 3'-UTR that does not confer differential transgene translation in response to metabolic state of the cell). The anti-CD19 CAR cassette and the insert with the IL-12-RDE1 are transcribed in opposite directions, and the control regions for each are located in between the two insert/cassettes. The control region for the IL-12-RDE1 insert and IL-12 3'-UTR were either a minP promoter or an NFAT promoter. The control region of the anti-CD19 CAR cassette was the MND promoter. CD4+ T-cells were transduced with the bicistronic construct.

The transduced T cells were allowed to return to resting state, and then were tested after stimulation as follows. For the 'no stimulation' set, transduced T-cells were incubated for 24 h alone in medium. For the 'Raji co-culture' set, CD19+ Raji B cells were incubated with the transduced T cells for 24 h. At 24 h, the T cells were stained for CD25 and CD69, which are activation markers, and subject to flow cytometry to measure these markers. IL-12 expression in the T cells was measured by ELISA.

Figure 4:
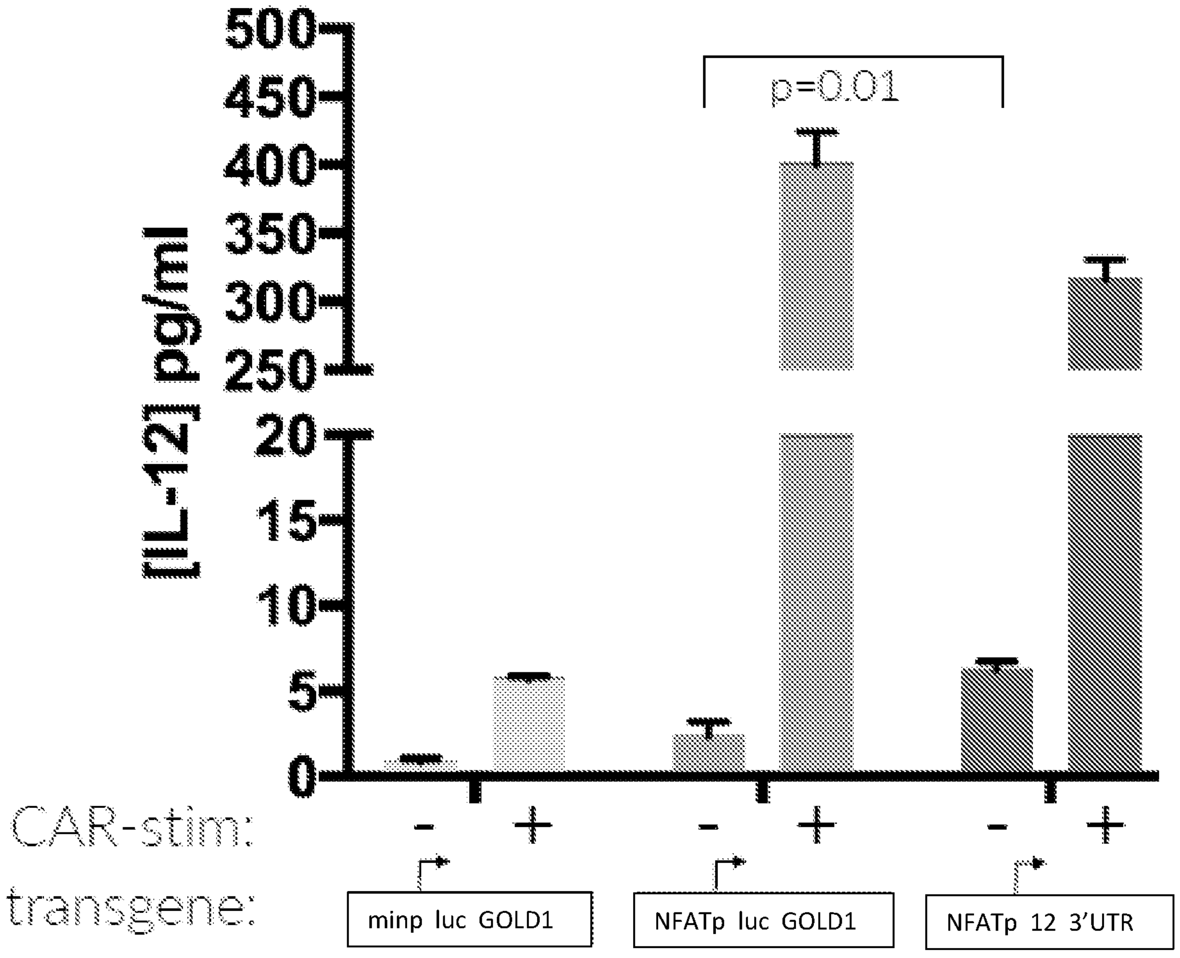
FIG. 4 shows a graph for the IL-12 expression from T-cells with IL-12 expression controlled by an RDE following activation of the T-cell by Raji target cells (activate CAR) as compared to IL-12 expression of T-cells at resting.

FIG. 4 shows that the transduced T-cells had an increase in IL-12 expression when cultured with Raji target cells (activate CAR) as compared to IL-12 expression of T-cells at resting using constructs controlled by the MinP promoter or NFAT promoter. T-cells with the NFAT promoter and RDE1 (Gold1) showed a 168-fold change in IL-12 expression form resting to CAR stimulation. T-cells with the NFAT promoter and a 3'-UTR (not responsive to CAR stimulation, 3'-UTR) showed a 50-fold change in expression, and a minP promoter with RDE1 (Gold1) showed a 6.3 fold change in expression.

Example 8: AU Elements and Steady State Expression

Figure 5:
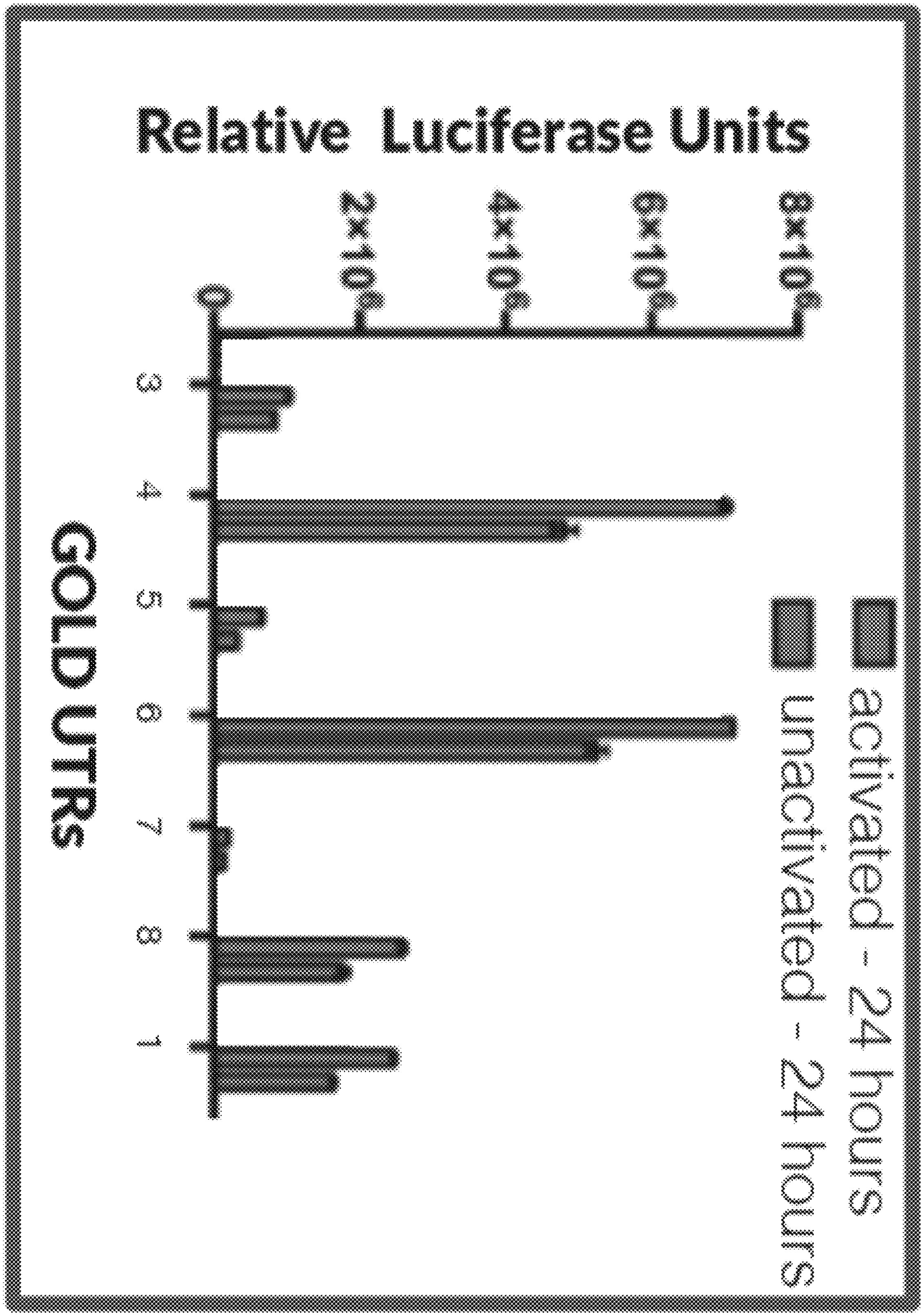
FIG. 5 shows basal luciferase expression and activated luciferase expression for luciferase constructs utilizing different RDEs as control elements in Jurkat cells.

Constructs were made with different RDEs operably linked to a nucleic acid encoding luciferase. The different RDEs used were AU 4 (CTLA4), AU 13 (IL-5), AU 14 (IL-6), AU 15 (IL-9), AU 16 (IL-10), AU 17 (IL-13), and AU 101 (IFNg). These luciferase-AU constructs were transduced into primary T-cells. After the cells returned to the resting stage they were plated and sham induced (basal) or induced with anti-CD3 and anti-CD28 antibody (activated). At 24 hours post activation the amount of luciferase units in each was measured. These amounts are plotted in the bar graph of FIG. 5.

The AU elements in this example had different basal expression levels, different induced expression levels (at 24 hours), and different levels of fold induction. The AU constructs showed different amounts of basal expression, different amounts of induced expression and different amounts of fold induction (or dynamic range).

Example 9: AU Elements and Expression Parameters

Constructs were made with different RDEs operably linked to a nucleic acid encoding luciferase. The different RDEs used were AU 2 (CSF2), AU 3 (CD247), AU 5 (EDN1), AU 7 (SLC2A1), AU 10 (Myc), AU 19 (TMEM-219), AU 20 (TMEM-219snp), AU 21 (CCR7), AU 22 (SEM-A4D), AU 23 (CDC42-SE2), and AU 101 (IFNg). These luciferase-AU constructs were transduced into primary T-cells. After the cells returned to the resting stage they were plated and either not treated (basal) or activated with anti-CD3 and anti-CD28 antibody (activated). At 24 hours post activation the amount of luciferase units in each was measured. These amounts are plotted in the bar graph of FIG. 6. Alternatively, after the cells returned to resting stage they were plated into 96-well plates in quadruplicate for measuring at each time point: 1 day, 3 days, 6 days and 8 days. The cells were either not treated or activated with anti-CD3 and anti-CD28 antibody, and luciferase activity was measured at 1 day, 3 days, 6 days and 8 days. These results are plotted in the bar graph of FIG. 7, and shown in Table 1 below. FIG. 8 shows selected data plotted in a bar graph. The numbers in parentheses in Table 1 below are the Luciferase Units on Days 3, 6, and 8 divided by the Luciferase Units of Day 1.

TABLE 1

| | Luciferase Units | | | |
|---|---|---|---|---|
| AU Construct | Day 1 | Day 3 | Day 6 | Day 8 |
| AU 2 (CSF2) | 60051 | 306035 (5) | 578305 (10) | 591953 (10) |
| AU 101 (IFNg) | 85816 | 473395 (6) | 724129 (8) | 817447 (10) |
| AU 5 (EDN1) | 69391 | 613921 (9) | 838040 (12) | 1023000 (15) |
| AU 3 (CD247) | 44939 | 595753 (13) | 961839 (21) | 1116000 (25) |
| AU 20 (TMEM-219snp) | 1135000 | 10750000 (9) | 21020000 (19) | 25480000 (22) |
| AU 10 (Myc) | 1233000 | 16020000 (13) | 26780000 (22) | 27800000 (23) |
| AU 7 (SLC2A1) | 4914 | 80906 (16) | 132974 (27) | 136537 (28) |
| AU 21 (CCR7) | 27128 | 465140 (17) | 604016 (22) | 692715 (26) |
| AU 23 (CDC42-SE2) | 71105 | 1215000 (17) | 2012000 (28) | 2110000 (30) |
| AU 22 (SEM-A4D) | 226815 | 2829000 (12) | 6106000 (27) | 7396000 (33) |
| AU 19 (TMEM-219) | 833146 | 11260000 (14) | 22560000 (27) | 27500000 (33) |

Figure 6:
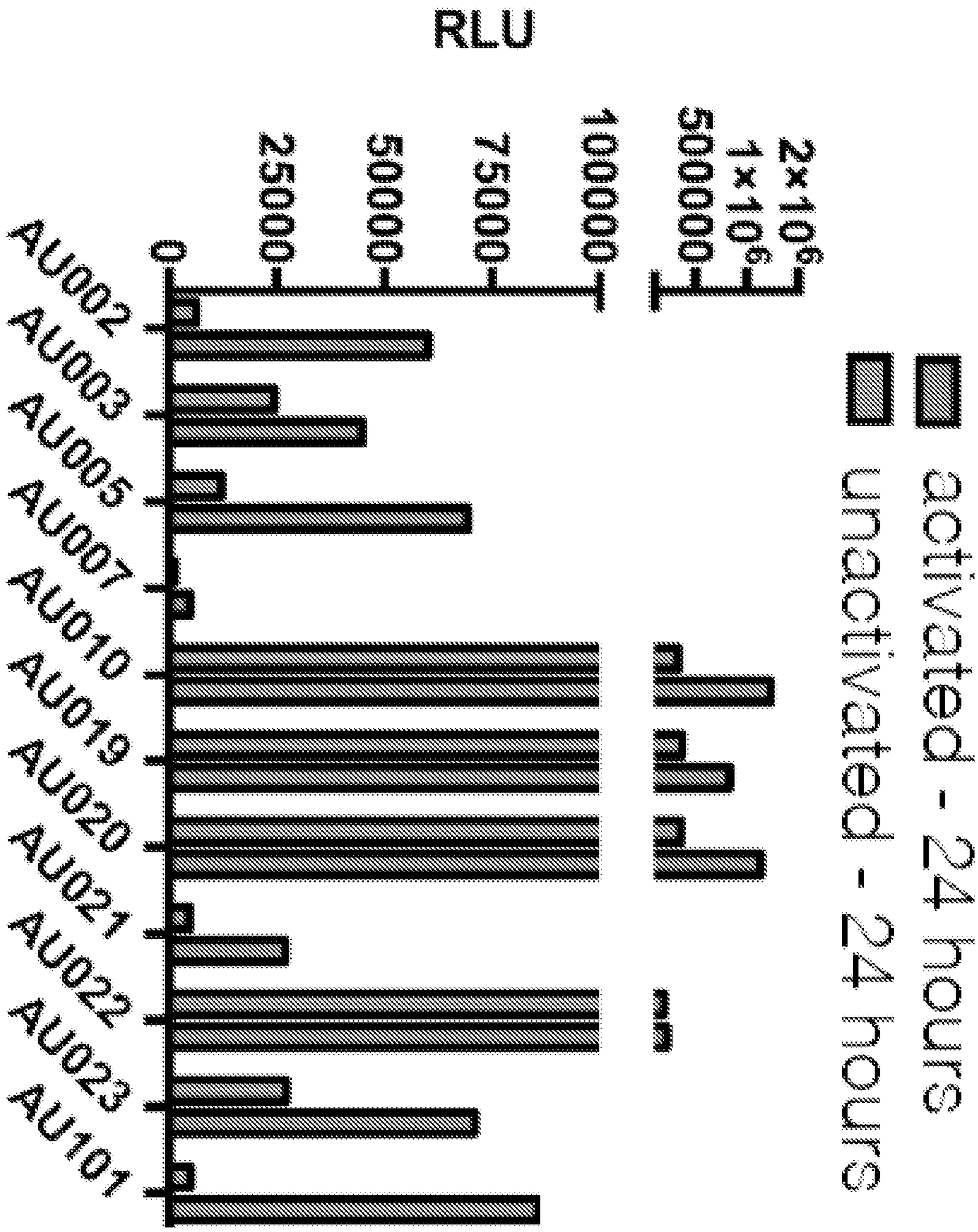
FIG. 6 shows basal luciferase expression and activated luciferase expression for luciferase constructs utilizing different RDEs as control elements in primary T-cells.
Figure 7:
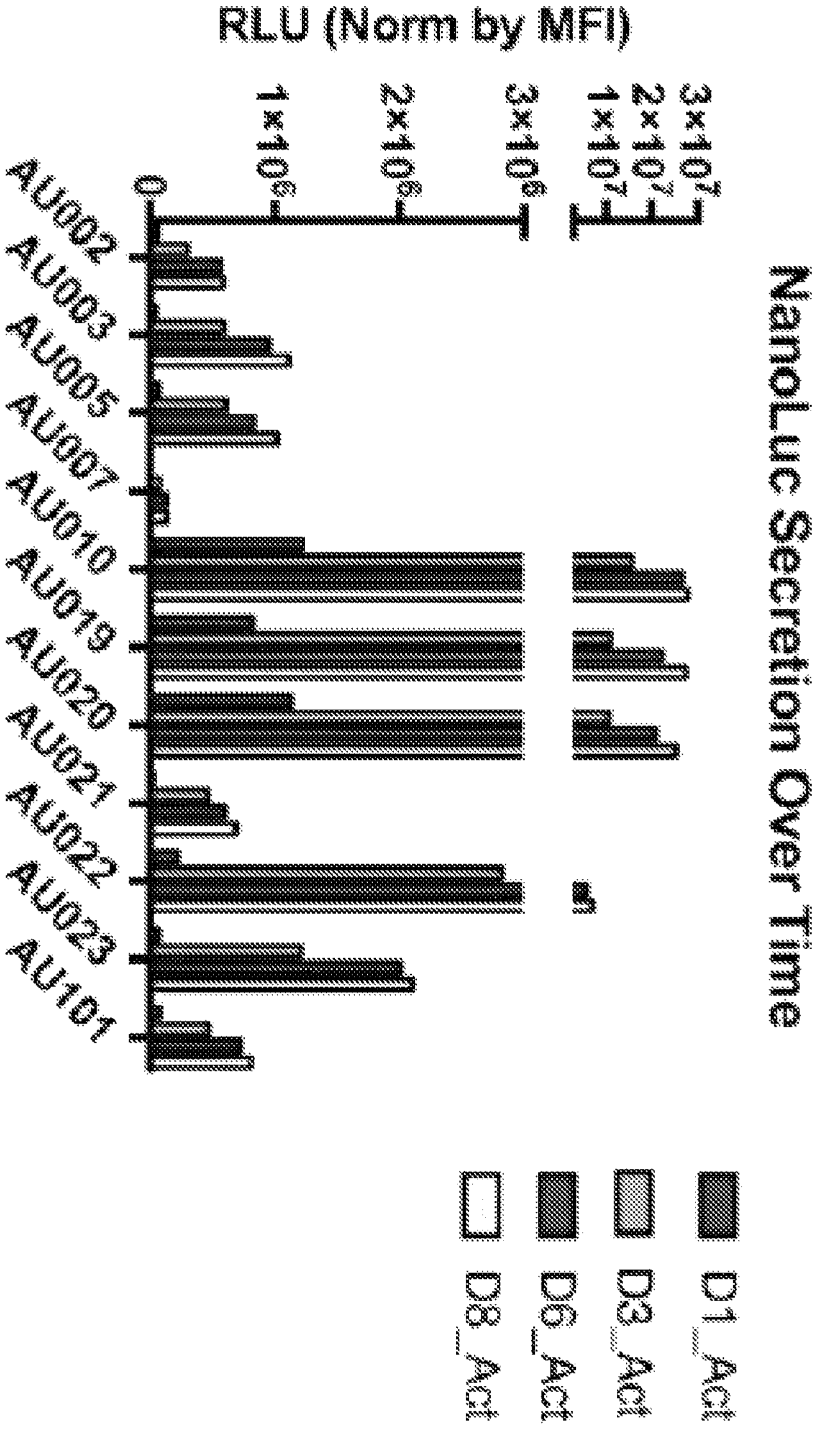
FIG. 7 shows activated luciferase/basal luciferase expression after 1, 3, 6, and 8 days for luciferase constructs utilizing different RDEs as control elements.
Figure 8:
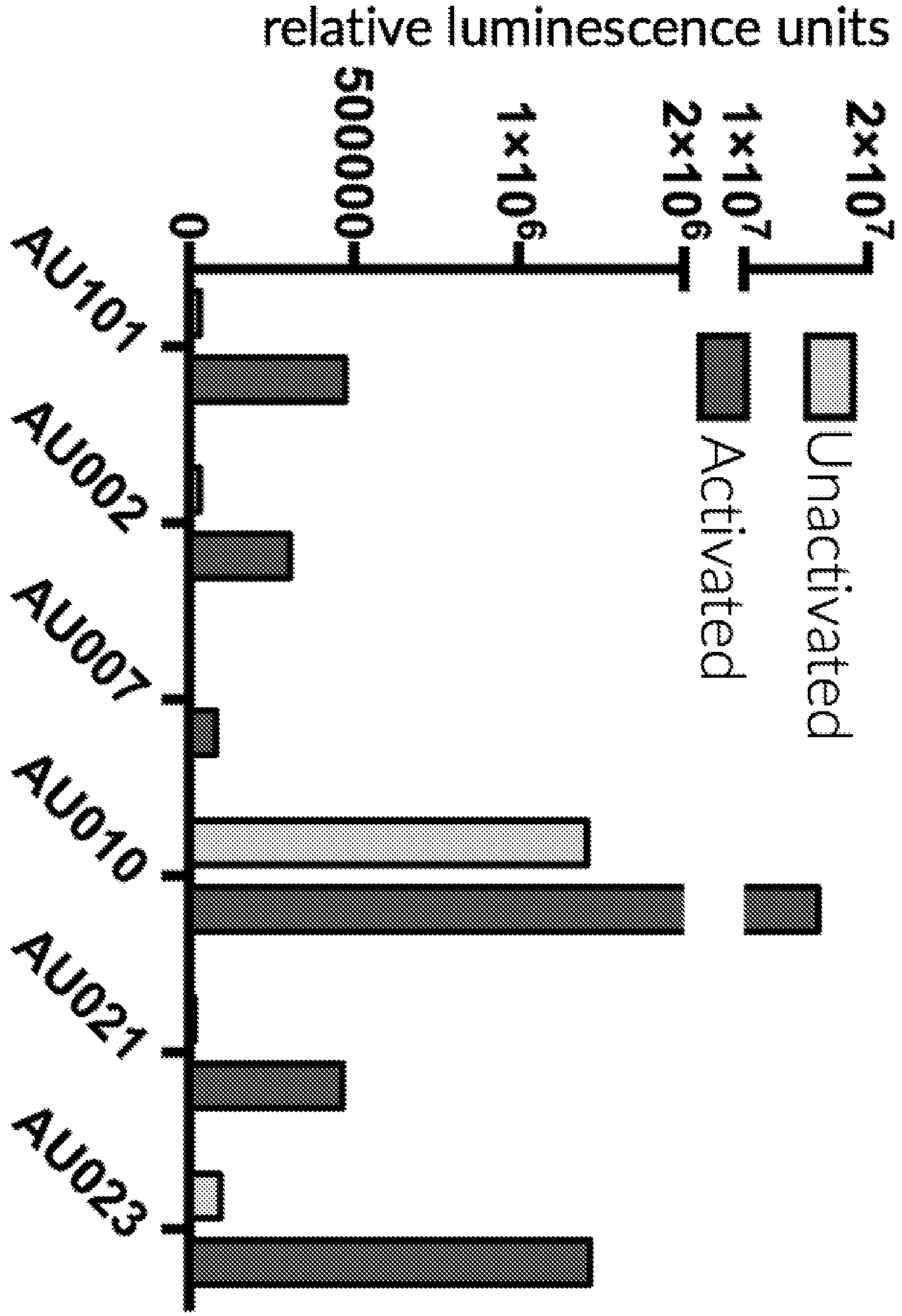
FIG. 8 shows basal luciferase expression and activated luciferase expression for luciferase constructs utilizing different RDEs as control elements.

The AU elements in FIG. 6, FIG. 7 and Table 1 had different basal expression levels, different induced expression levels (at 24 hours), and different levels of fold induction. The basal expression levels differed over an about 2000 fold range for these AU elements (AU 7 to AU 20), and the induced expression levels differed over an about 5500 fold range (AU 7 to AU 10). Basal expression for the constructs ranged from 1390 for AU 7 (SLC2A1) to 2,927,000 for AU 20 (TMEM-219snp). Activated expression ranged from 4914 for AU 7 (day 1) to 27,800,0000 for AU 10 (day 8). FIG. 8 and Table 1 show that some AU elements had lower levels of output, for example, AU 101 (IFNg), AU 2 (CSF2), AU 5 (EDN1), AU 7 (SLC2A1), AU 21 (CCR7), and AU 23 (CDC42-SE2). Some AU elements had intermediate amounts of output: AU 19 (TMEM-219) and AU 22 (SEM-A4D). And some AU element had high output: AU 20 (TMEM-219snp) and AU 10 (Myc).

Figure 9:
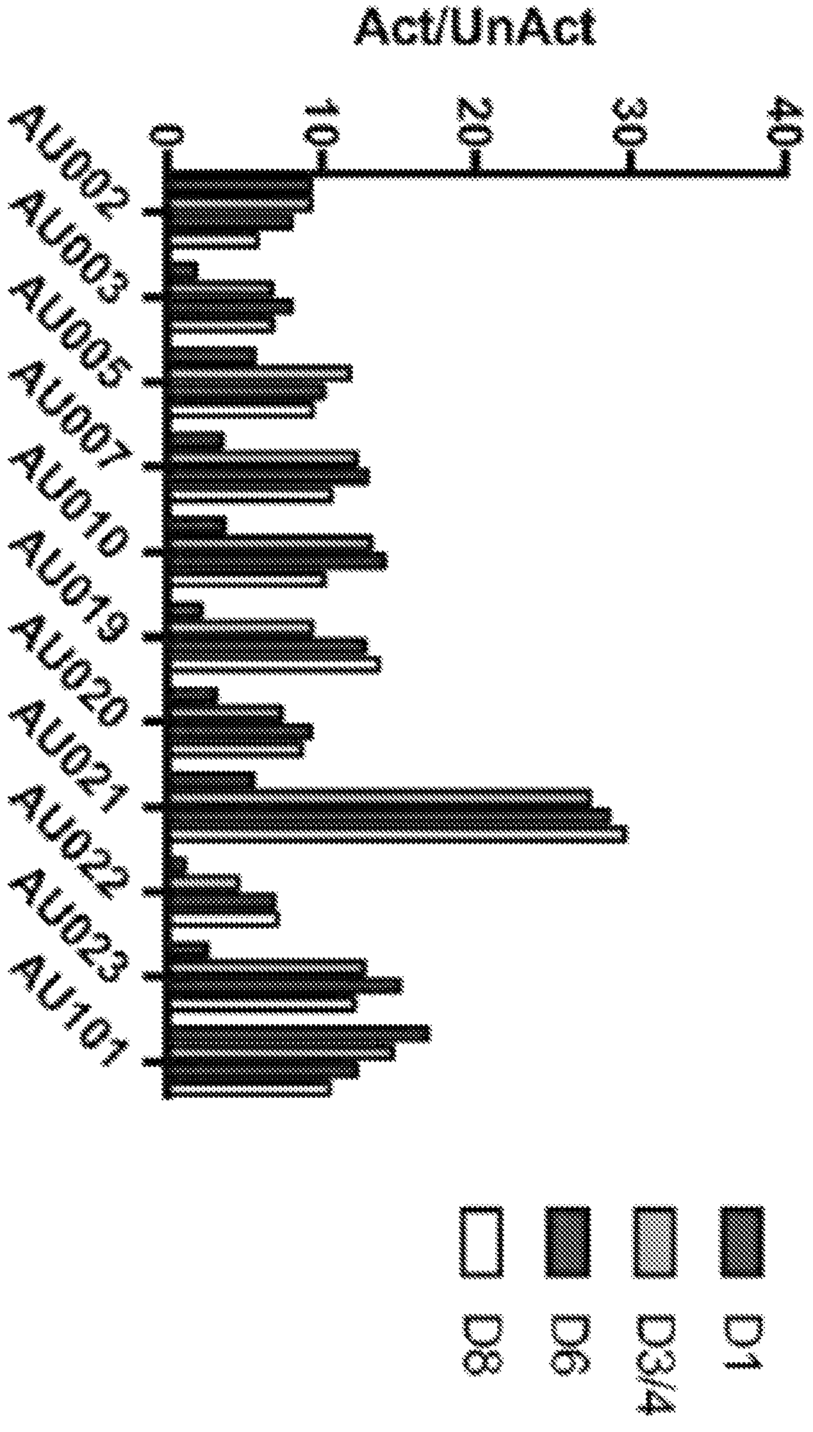
FIG. 9 shows the dynamic range (activated luciferase/basal luciferase) measured 1, 3/4, 6, and 8 days after activation for luciferase constructs utilizing different RDEs as control elements.
Figure 10:
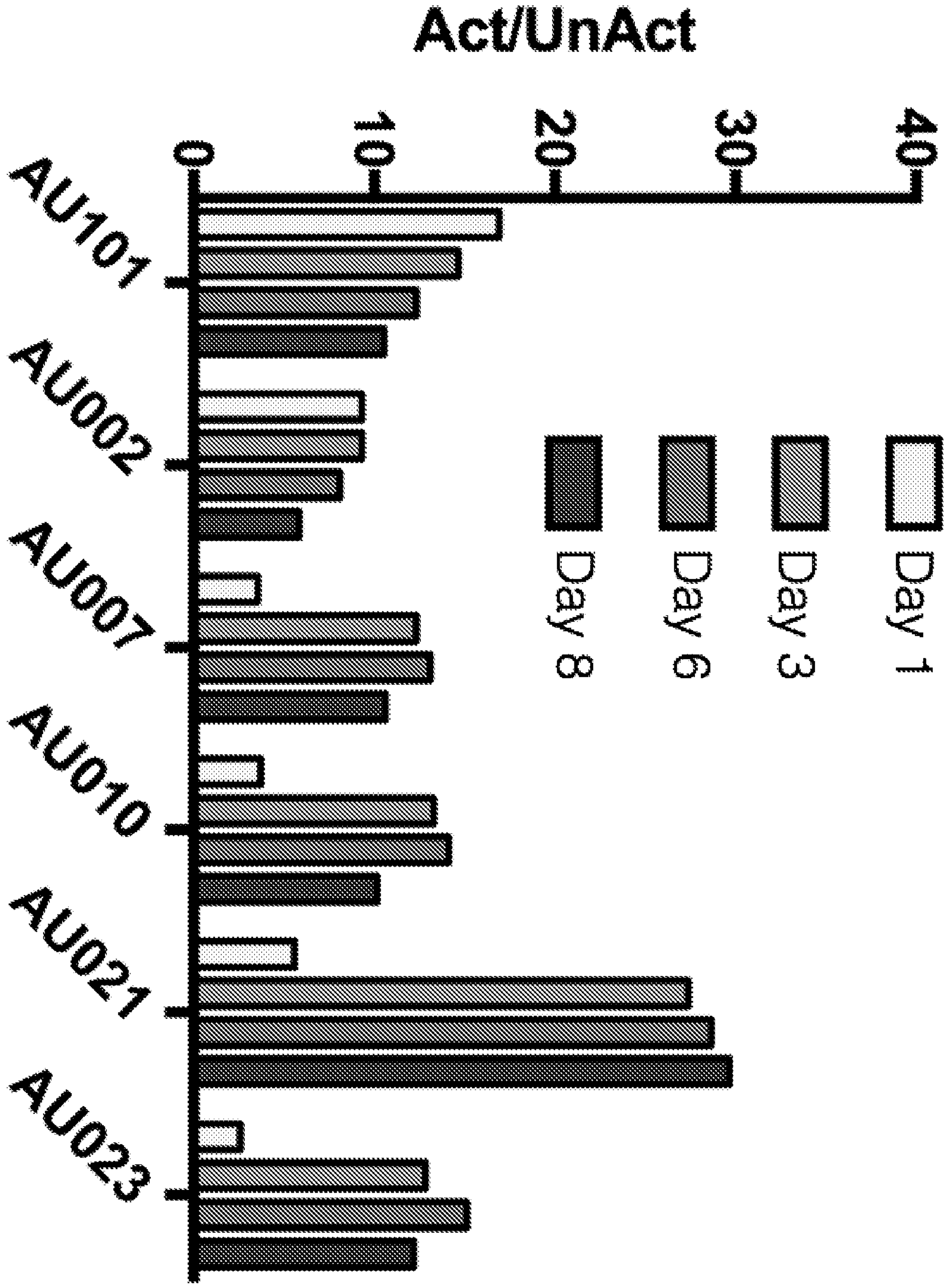
FIG. 10 shows the dynamic range (activated luciferase/basal luciferase) measured 1, 3/4, 6, and 8 days after activation for luciferase constructs utilizing different RDEs as control elements.

The Luciferase data was also analyzed for dynamic range (fold induction or luciferase activated/luciferase basal) of each luciferase-AU construct. The dynamic range (fold induction) for each AU construct at Days 1, 3/4 (activated expression was measured on Day 3 and basal expression was measured on Day 4), 6 and 8. This data is shown below in Table 2, and plotted in bar graphs in FIG. 9 and FIG. 10.

TABLE 2

| | Fold Induction | | | |
|---|---|---|---|---|
| AU Construct | Day 1 | Day 3/4* | Day 6 | Day 8 |
| AU 2 | 9.3 | 9.3 | 8.1 | 5.8 |
| AU 101 | 16.9 | 14.6 | 12.3 | 10.5 |
| AU 5 | 5.7 | 11.9 | 10.1 | 9.4 |
| AU 21 | 5.6 | 27.3 | 28.6 | 29.6 |
| AU 3 | 1.8 | 6.7 | 8.1 | 6.8 |
| AU 20 | 3.1 | 7.3 | 9.3 | 8.7 |
| AU 10 | 3.7 | 13.2 | 14.1 | 10.2 |

TABLE 2-continued

| | Fold Induction | | | |
|---|---|---|---|---|
| AU Construct | Day 1 | Day 3/4* | Day 6 | Day 8 |
| AU 7 | 3.5 | 12.3 | 13.1 | 10.6 |
| AU 23 | 2.6 | 12.8 | 15.1 | 12.2 |
| AU 19 | 2.3 | 9.3 | 12.9 | 13.8 |
| AU 22 | 1.2 | 4.6 | 6.9 | 7.1 |

*Induction was measured on Day 3 and basal was measured on Day 4.

At Day 1 dynamic range (fold induction=activated/basal) ranged from about 1 (AU 22) to about 17 (AU 101). At Day 3/4, dynamic range varied from about 4.5 (AU 22) to about 27 (AU21). At Day 6, dynamic range varies from about 7 (AU 22) to about 29 (AU 21). On Day 8, dynamic range varied from about 7 (AU22) to about 30 (AU 21). The AU constructs showed a number of related patterns. AU 2 and AU 101 showed a rapid increase in dynamic range on Day 1, and then the dynamic range decreased on days 6 and 8. AU 5 and AU 21 show increasing dynamic range from day 0 to day 3/4, and then the dynamic range is maintained through days 6 and 8. AU 3, AU 20, AU 10, AU 7 and AU 23 showed rising dynamic range from day 0 to day 6, and then the dynamic range decreased on day 8. AU 19, and AU 22, showed rising dynamic ranges from day 0 to day 8.

AU 21 and AU 23 showed accelerating dynamic range and these AU constructs also had low basal expression (day 1=4865 and 27363, respectively). AU 2 and AU 101 showed decreasing dynamic range from 24 hours to 72 hours and these AU elements also had low basal expression. AU 5 and AU 20 also showed decreasing dynamic range from day 1 to day 3/4 (though more expression than AU 2 and AU 101) and AU 5 had low basal expression whereas AU 20 had high basal expression. AU 10, AU 19 and AU 22 showed consistent dynamic range from day 1 to day 3/4 and had high basal levels of expression. AU 3 and AU 7 also had consistent dynamic range from day 1 to day 3/4 and had low basal expression levels.

The above data shows that different AU elements have different temporal effects on expression from days 1-8. Some AU elements show accelerating dynamic range over different portions of the time range. The AU elements show different amounts of total expression ($C_{max}$) and different times to maximum expression ($T_{m}$ax). The AU elements also show different maximum dynamic ranges and time to reach these maximums. These differing kinetics of expression can be used to provide customized basal, $C_{max}$, $T_{max}$, dynamic range, and time to max dynamic range for a desired transgene. These differing kinetics can also be used to provide temporally distinct expression for two transgenes in a cell after activation of the cell.

Example 10: AU Element Control with Glucose and Galactose

Figure 11:
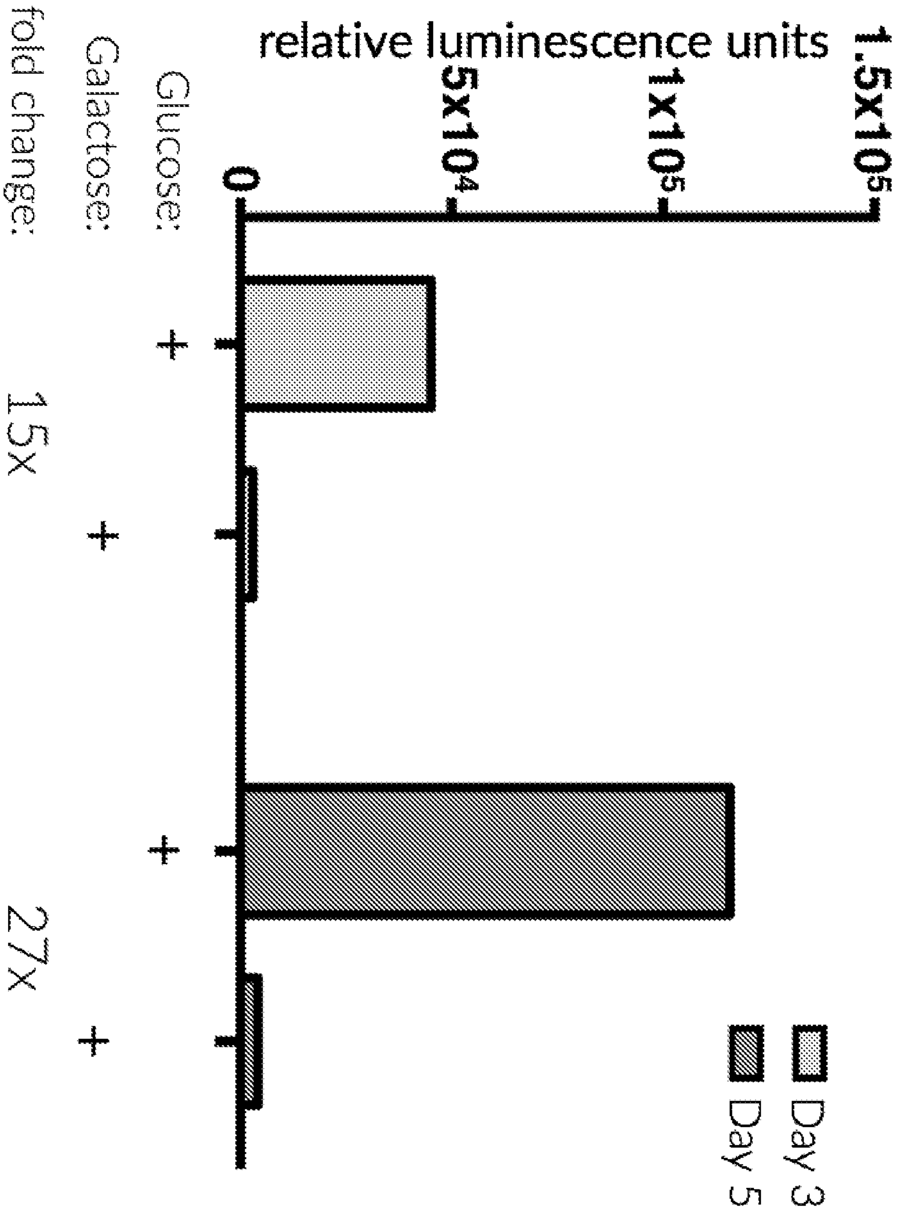
FIG. 11 shows the impact on luciferase expression for luciferase constructs utilizing an RDE as a control element in the presence of glucose and galactose.

Constructs were made with different RDEs operably linked to a nucleic acid encoding luciferase. The RDE was an AU element responsive to glycolytic state of the cell. The AU element—luciferase constructs were transduced into T-cells. After the cells reached the resting state, they were split into wells and fed media including either glucose or galactose. Luciferase activity was measured on days 3 and 5. These results are shown in the bar graph of FIG. 11. The results show that glucose increased expression of luciferase compared to galactose and the amount of expression increased from days 3 to 5. On day 3 the glucose treated cells had 15× more expression of luciferase than the galactose treated cells and on day 5 this had grown to 27× more expression.

Example 11: Payload Delivery Using Gold in a Mouse Lymphoma Model

Constructs were made using an anti-CD19 CAR cassette as described in WO 2012/079000, which is hereby incorporated-by-reference in its entirety for all purposes, and a Luciferase-AU (3' UTR of IL-6) insert. These constructs were placed in a bicistronic *lenti* virus construct. The anti-CD19 CAR cassette and the insert with the luciferase-RDE are transcribed in opposite directions on the bicistronic vector, and the control regions for each are located in between the two insert/cassettes. The control region for the Luciferase-RDE insert was a MinP promoter. The control region of the anti-CD19 CAR cassette was the MND promoter. $CD4^+$ T-cells were transduced with the bicistronic construct.

A second construct was made using the anti-CD19 CAR cassette described above and a Luciferase insert (without the RDE element so that expression was constitutive). Both constructs were separately transduced into different groups of T-cells.

The transduced T cells were allowed to return to resting state, and then were tested after stimulation as follows. For the 'no stimulation' set, transduced T-cells were incubated for 24 h alone in medium. For the 'Raji co-culture' set CD19+ Raji B cells were incubated with the transduced T cells for 24 h. At 24 h, the T cells were stained for CD25 and CD69, which are activation markers, and subject to flow cytometry to measure these markers and luciferase expression in the T cells. These in vitro results showed that the anti-CD19 CAR T-cells made luciferase after activation of the T-cells through the CAR.

These anti-CD19 CAR T-cells with the luciferase-RDE were also tested in a mouse model for lymphoma. CD19+ Raji cells were implanted in the flanks of NSG mice. After tumor formation, the anti-CD19 CAR T-cells were injected into the mice and the mice were scanned for luminescence. Imaging of the mice showed luminescence at the tumor sites from anti-CD19 CAR T-cells that have been activated by the CD19 positive tumor. The amount of luminescence increased over time as more T-cells were activated. In contrast, the anti-CD19 CAR T-cells with constitutive expression of luciferase should luminescence throughout the mice as well as at the site of the tumors in the flanks of the mice.

Example 12: miRNA as a Payload

A payload transgene encoding IL-12 is engineered to have an artificial intron encoding a mir155 cassette as disclosed in Du et al., FEBs Journal 273:5421-5427 (2006) or Chung et al., Nucl Acids Res 34:e53 (2006). The mir155 cassette is engineered to include an AU element such as, for example, AU101 (IFNg) or AU14 (IL-6), operably linked to it, and the transgene is also engineered with an AU element such as AU101 or AU14. This transgene with the mir155 intron is engineered into primary T-cells. An anti-CD19 CAR as described in Example 14 is also engineered into the primary T-cells.

The anti-CD19 CAR T cells with the IL-12 payload are allowed to return to resting state, and then are tested after stimulation as follows. For the 'no stimulation' set, transduced T-cells are incubated for 24 h alone in medium. For the 'Raji co-culture' set CD19+ Raji B cells are incubated with the transduced T cells for 24 h. At 24 h, the T cells are stained for CD25 and CD69, which are activation markers, and subject to flow cytometry to measure these markers. The cells are also tested for expression of the payload IL-12.

These anti-CD19 CAR T-cells with the IL-12 payload are also tested in a mouse model for lymphoma. CD19+ Raji cells are implanted in the flanks of NSG mice. After tumor formation, the anti-CD19 CAR T-cells with the IL-12 payload are injected into the mice. At every third day starting at day 4 after administration, tumor killing in the mice is measured using calipers.

Example 13: IL-12 Payload Delivery

A construct with an anti-CD19 CAR as described in Example 14 was made. A construct with the NFAT promoter operably linked to a nucleic acid encoding IL-12 followed by AU101 (the RDE from INFg) was also made. The IL-12 transcript made from the construct operably links the coding sequence for IL-12 to the AU101 RDE. A second IL-12 construct was made that provided constitutive expression of IL-12. A third construct placed Luciferase under control of an AU14 (IL-6).

The constructs were transduced into primary T-cells which were then allowed to return to a resting state. This produced anti-CD19 CAR T-cells with payloads of IL-12 (RDE controlled or constitutive) or luciferase.

The primary T-cells with the anti-CD19 CAR and IL-12 payload (RDE controlled or constitutive) or luciferase payload were administered to mice bearing CD19+ tumors in their flanks. Killing of tumor cells was monitored over 42 days. The mice which received T-cells with the anti-CD19 CAR and luciferase payload showed a moderate amount of tumor cell killing (about 3 logs). The mice receiving the IL-12 payloads had a large amount of tumor cell killing (6-7 logs). A comparison of IL-12 serum levels in the mice receiving the constitutive or AU101 controlled IL-12 had 10-fold differences in the systemic IL-12 levels with the AU101 controlled payload having 10 times lower amounts of IL-12 than the constitutive IL-12 payload.

The RDE control of IL-12 expression lowered systemic IL-12 levels in the mice but gave localized concentrations of IL-12 that improved tumor cell killing. After the activated CAR T-cells kill the tumor cells these CAR T-cells can migrate from the tumor site to lymph nodes and/or the spleen where they can educate other T-cells and form memory T-cells.

Example 14: Coordinated Delivery of CXCL9 and an Anti-PD1 Therapy to DLL3+ Cancer Cells An anti-DLL3 CAR is made as described in Example 20. This CAR construct is engineered into T-cells also as described in Example 20.

Two payload cassettes are made for delivery by the anti-DLL3 CAR T-cell. First, a construct is made that encodes CXCL9 as a secreted payload operably linked to an RDE with an early expression profile (early maximal expression after activation of the cell) such as AU2 (CSF-2, maximal fold induction on day 1), AU101 (IFNg, maximal fold induction on day 1), or AU5 (EDN1, maximal fold induction on day 3/4). Second, a construct is made that encodes an anti-PD1 antibody (e.g., Pembrolizumab (Keytruda®)) as a secreted payload operably linked to an RDE with a late expression profile (late maximal expression after activation of the cell) such as AU22 (SEM-A4D, maximal fold induction on day 8) or AU19 (TMEM-219, maximal fold induction on day 8). The two payloads can be placed into a bicistronic construct, placed on the same construct, or the payloads can be expressed from separate constructs. The payload construct(s) are engineered into the anti-DLL3 CAR T-cell as described above in Example 20.

When this engineered CAR T-cell is administered to NSG mouse model as described in Example 20. The CAR T-cells are activated by DLL3 at the tumor target, and the RDE constructs with the CXCL9 express this payload first, and then at a later time the anti-PD1 antibody payload is expressed. The AU2, AU5 or AU101 RDE of the CXCL9 construct has an early maximal expression of about 1 day after activation of the cell by DLL3 at a cancer target. The CXCL9 can be secreted early after activation of the T-cell by DLL3 and the CXCL9 can potentiate the T-cell responses to tumors treated with anti-PD1 antibodies. After CXCL9 secretion, anti-PD1 is maximally secreted at a later time (about 8 days) and the effect of this antibody can be increased by the pretreatment with CXCL9.

The early expression of CXCL9 potentiates the activity and cancer killing from the anti-PD1 antibody.

Example 15: Combination Therapy

CAR constructs are made using an anti-DLL3 antibody domain such as described in US20170137533 (which is incorporated by reference in its entirety for all purposes) as SC16.15 or SC16.25. This anti-DLL3 antibody domain is made into a single chain antibody (scFv), and the anti-DLL3 scFv is combined with the transmembrane and intracellular portions of a CAR (such as those described in WO 2012/079000, which is hereby incorporated-by-reference in its entirety for all purposes) to make an anti-DLL3 CAR.

Payload constructs are made by engineering a transgene with an RDE so that when the transgene is transcribed the transcript for the transgene operably links the transgene to the RDE. The payload transgene can encode an anti-4-1BB antibody, an anti-CD11b antibody, an anti-CTLA4 antibody, an anti-IL1b antibody, a BiTE, a CCL2, an anti-CXCR4 antibody, an anti-CXCL12 antibody, a HAC, a heparinase, a hyaluronidase, a Hsp60, a Hsp70, an IL-2, an IL-12, an IL-15, an IL-18, an INFγ, a miRNA (e.g., mir155), a CD40 ligand, an ApoE3, an ApoE4, an antagonists of CSF1 receptor, a TNFα, and/or an anti-CD28 antibody. The RDE can be AU101 (INFg) or AU14 (IL-6).

The constructs are transduced into primary T-cells which are then allowed to return to a resting state. This produced anti-DLL3 CAR T-cells with one or more of the payloads: anti-CXCL12 antibody, anti-CXCR4 antibody, IL-12, anti-4-1BB antibody, anti-CD11b antibody, anti-CTLA4 antibody, anti-IL1b antibody, a BiTE, CCL2, HAC, heparinase, hyaluronidase, Hsp60, Hsp70, IL-2, IL-15, IL-18, INFγ, miRNA (e.g., mir155), CD40 ligand, ApoE3, ApoE4, TNFα, CCR2, CCR4/CXCL12, CXCR3+CXCL9, CXCL9, ACLY, antagonists of CSF1 receptor, miRNA for Tox (e.g., hsa-mir-26b-5p (MIRT030248) hsa-mir-223-3p (MIRT054680)), miRNA for TCF-7 (e.g., mIR-192, mIR-34a, miR-133a, miR-138-5p, miR-342-5p, miR-491-5p, miR-541-3p), and/or anti-CD28 antibody (including full length and fragments such as single chain antibodies).

An antibody drug conjugate (ADC) is made between an anti-DLL3 antibody such as described in US20170137533 (which is incorporated by reference in its entirety for all purposes) as SC16.15 or SC16.25. This anti-DLL3 antibody domain is converted to an appropriate format (e.g., a Fab, F(ab')2 or full-length IgG) and conjugated to one or more drugs (e.g., etoposide, irinotecan, cisplatin and/or carboplatin).

An NSG mouse model from Jackson Laboratories is used to establish cancer xenografts of human melanoma, human small cell lung cancer (SCLC), and human IDH1mut glioma. After the cancer xenograft is established in the mice, the mice are treated with the primary T-cells with the anti-DLL3 CAR and one of the payloads, anti-DLL3 ADC, or primary T-cells with the anti-DLL3 CAR and one of the payloads and the anti-DLL3 ADC. Cancer xenograft killing is then compared between the ADC, different payloads of the DLL3-CAR T-cells, and the different payloads of the DLL3 CAR T-cells with the anti-DLL3 ADC.

Example 16: Notch Inhibitors Enhance T-cell Activation

A anti-DLL3 CAR is made as described above. This anti-DLL3 CAR is placed into a primary T-cell as described above. The anti-DLL3 CAR T-cells can also include a payload under the control of an RDE.

The anti-DLL3 CAR T-cells are mixed with SHP77 cells (cancer cell line expression DLL3) at different ratios (e.g., CAR T-cell to SHP77 of 1:1, 1:3, 1:10) in the presence of absence of dibenzazepine (a gamma secretase inhibitor) at concentrations of 1 nM, 10 nM, 100 nM and 1 uM.

The anti-DLL3 CAR T-cell are also administered to a NSG mouse model as described in Example 20. These administrations are also done with or without administration of dibenzazepine.

Example 17: Anti-TNMUC1 CAR and Payload Delivery

Constructs GC215 (no CAR vector with secreted nano-luciferase and LNGFR engineered to 83% GC3), GC216 (no CAR vector with secreted nano-luciferase and LNGFR engineered to 53% GC3), SK062 (SEQ ID NO: 9, has 83% GC3 in LNGFR) and SK072 (SEQ ID NO: 11, has 53% GC3 in LNGFR) anti-TnMUC1 CARs, SK148 (SEQ ID NO: 10, has 83% GC3 in LNGFR) and GC213 (SEQ ID NO: 5, has 53% GC3 in LNGFR) anti-TnMUC1 CARs with an IL-12 payload under the control of RDE, were compared in a mouse tumor model. These constructs were transduced into donor T-cells and the transfected T-cells were administered to mice at either a one million or three million dose of cells. Prior to administration of T-cells, mice were inoculated with HS766T cells (a metastatic, pancreatic carcinoma cell line) to grow tumors that are TnMUC1 positive. The HS766T cells were also engineered with luciferase as a reporter for the tumor cells.

Figure 12:
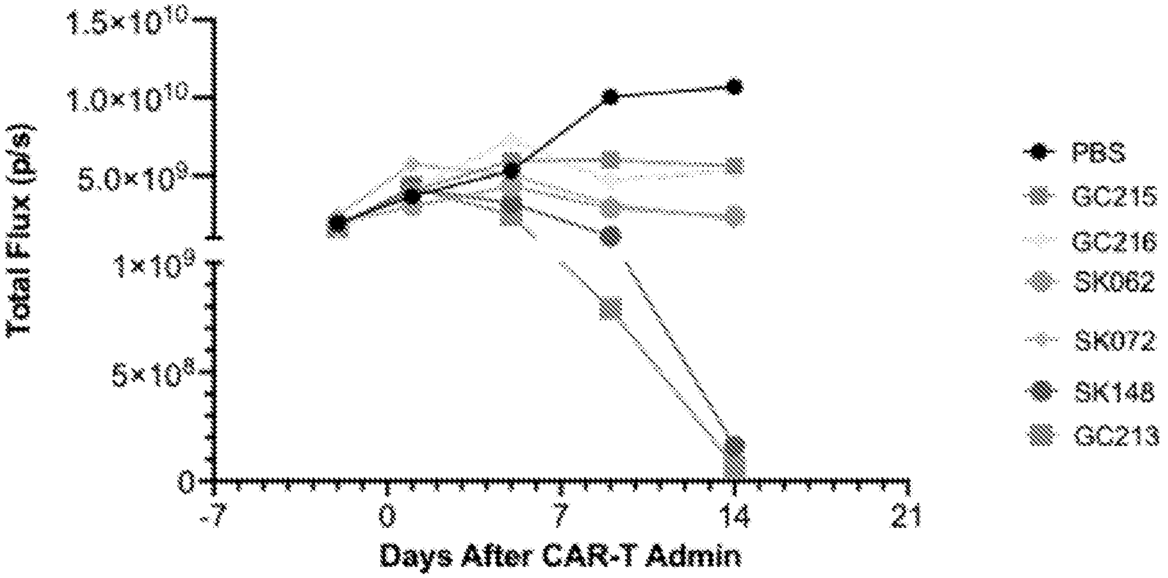
FIG. 12 compares the efficacy of SK072, GC213, GC216 and PBS against a metastatic pancreatic carcinoma (HS766T) in a mouse model.

Results for this study are shown in FIG. 12. GC213 (anti-TNMUC1 CAR+IL-12, 53% GC3 in LNGFR) and SK148 (anti-TNMUC1 CAR+IL-12, 83% GC3 in LNGFR) produced the greatest amount of tumor killing at day 14. Scans of the mice that received three million T-cells with GC213 show that eight of ten mice are tumor free at Day 67 of the study.

Example 18: Cytokine Secretion from Anti-TNMUC1 CAR T-cells

Constructs GC215 (no CAR vector with secreted nano-luciferase and LNGFR engineered to 83% GC3), GC216 (no CAR vector with secreted nano-luciferase and LNGFR engineered to 53% GC3), SK062 (SEQ ID NO: 9, has 83% GC3 in LNGFR) and SK072 (SEQ ID NO: 11, has 53% GC3 in LNGFR) anti-TnMUC1 CARs, SK148 (SEQ ID NO: 10, has 83% GC3 in LNGFR) and GC213 (SEQ ID NO: 5, has 53% GC3 in LNGFR) anti-TnMUC1 CARs with an IL-12 payload under the control of RDE, were compared in an in vitro model for cytokine secretion. These constructs were transduced into donor T-cells and the transfected T-cells were mixed with one of PL45 (pancreatic adenocarcinoma), HS766T (metastatic pancreatic carcinoma), or MCF7 (breast adenocarcinoma). These cell lines were also modified with GC084 which added luciferase to the cell lines.

Figure 13:
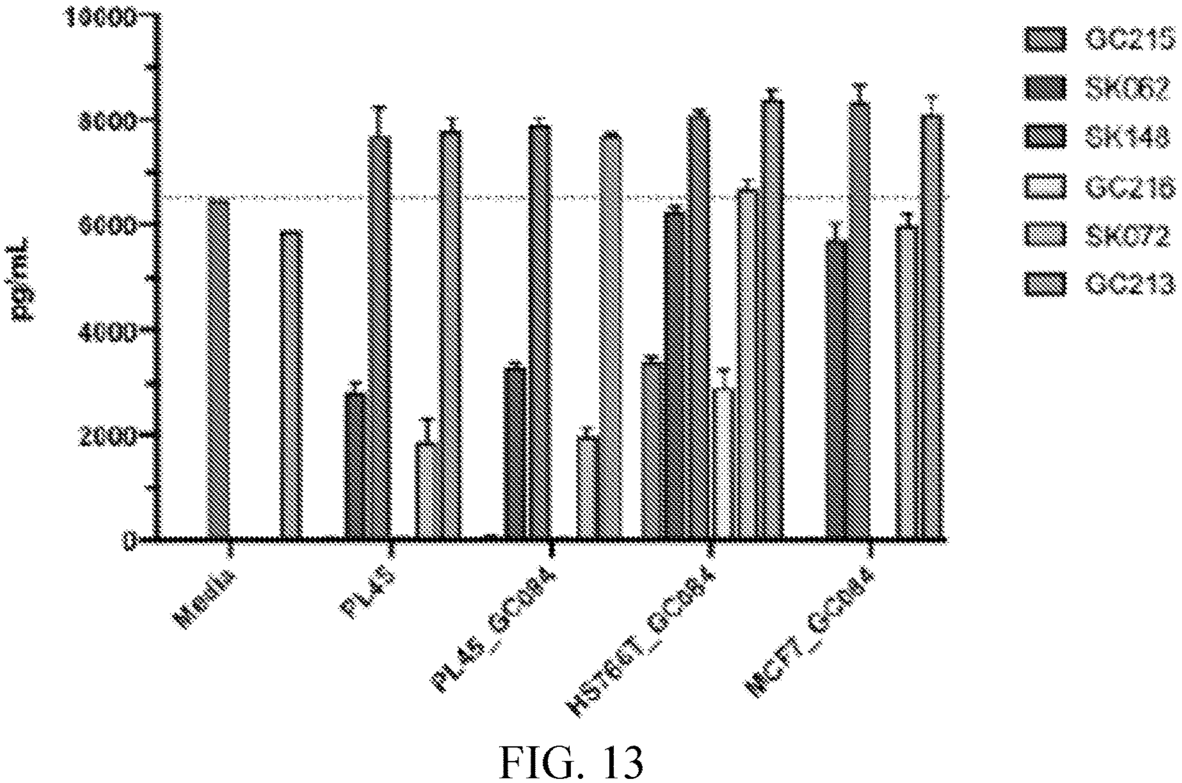
FIG. 13 shows levels of IFNg in vitro.
Figure 14:
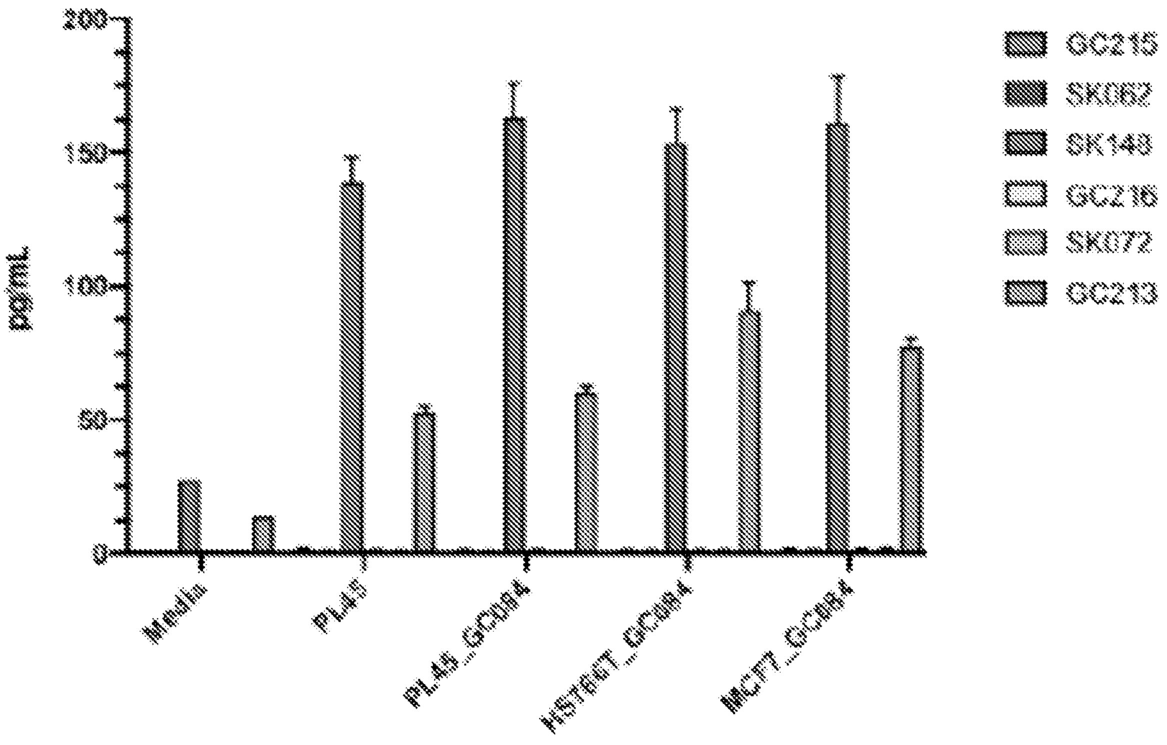
FIG. 14 shows levels of IL-12 in vitro.

Results for this study are shown in FIG. 13 and FIG. 14. FIG. 13 shows the levels of IFNg secreted from the transduced T-cells after interaction with target cancer cells that have the TnMUC1 target. FIG. 13 shows that IFNg secretion increases upon co-culture with tumors. FIG. 14 secretion of IL-12 is observed only in SK148 and GC213 the constructs with IL-12 payload. More IL-12 secreted with SK148, the anti-TnMuc1 CAR construct with 83% GC3 LNGFR compared to GC213, the anti-TnMuc1 CAR construct with 53% GC3 LNGFR. IL-12 secretion increases upon co-culture with all of the tumor cell lines.

Example 19: Cytoxicity of Anti-TNMUC1 CAR T-cells Against Different Cancer Cells Constructs GC215 (no CAR vector with secreted nano-luciferase and LNGFR engineered to 83% GC3), GC216 (no CAR vector with secreted nano-luciferase and LNGFR engineered to 53% GC3), SK062 (SEQ ID NO: 9, has 83% GC3 in LNGFR) and SK072 (SEQ ID NO: 11, has 53% GC3 in LNGFR) anti-TnMUC1 CARs, SK148 (SEQ ID NO: 10, has 83% GC3 in LNGFR) and GC213 (SEQ ID NO: 5, has 53% GC3 in LNGFR) anti-TnMUC1 CARs with an IL-12 payload under the control of RDE, were compared in an in vitro model for cytotoxicity against tumor cell lines. These constructs were transduced into donor T-cells and the transfected T-cells were mixed with one of PL45 (pancreatic adenocarcinoma), HS766T (metastatic pancreatic carcinoma), or MCF7 (breast adenocarcinoma) at different effector to target cell ratios (1:1, 3:1, and 9:1). These cell lines were also modified with GC084 which added luciferase to the cell lines.

Figure 15:
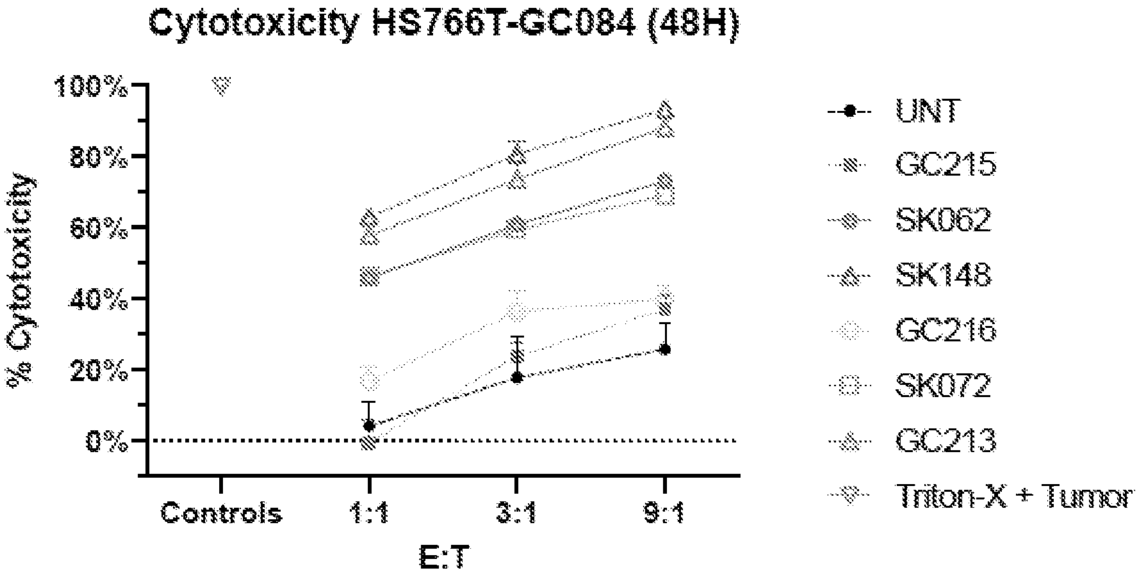
FIG. 15 shows in vitro cytotoxicity.
Figure 16:
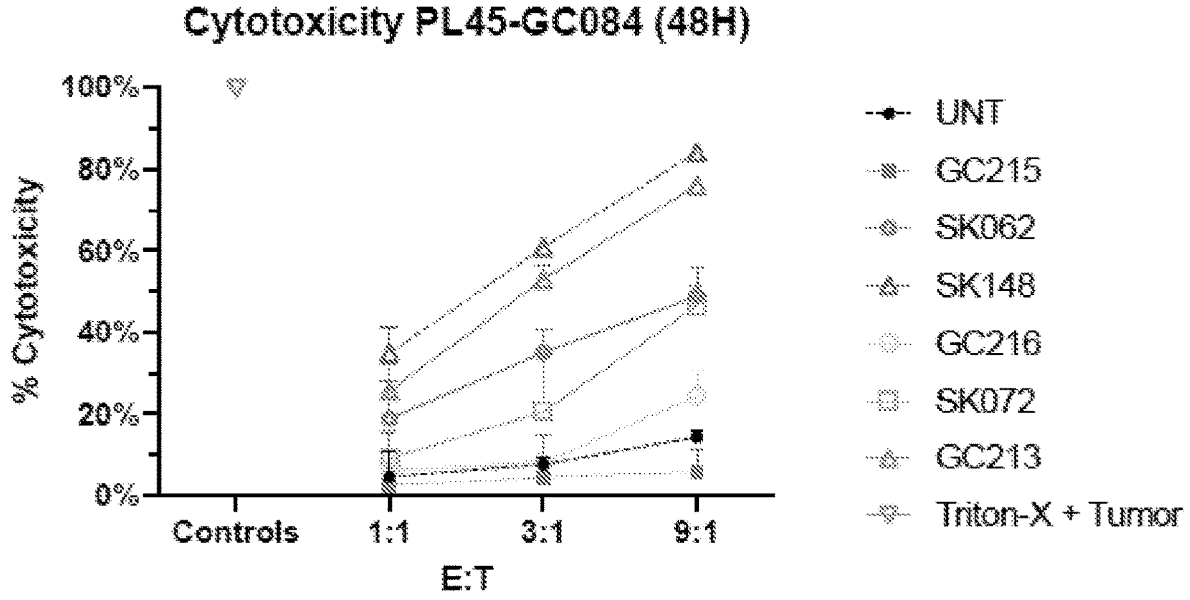
FIG. 16 shows in vitro cytotoxicity.
Figure 17:
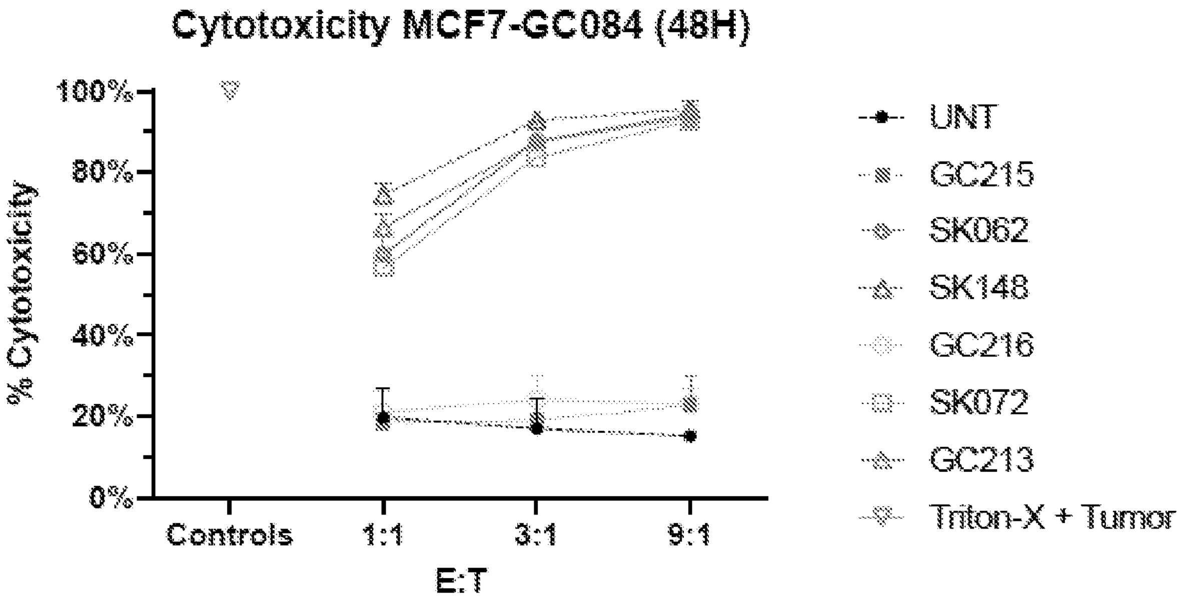
FIG. 17 shows in vitro cytotoxicity.

Results for this study are show in FIG. 15, FIG. 16, and FIG. 17. The T-cells transduced with anti-TNMuc1 CARs have higher cytotoxicity against each of the tumor cell lines than the constructs without an anti-TnMuc1 CAR. The constructs with anti-TnMuc1 CARs and an IL-12 payload produced more cytotoxicity against HS766T and PL45 tumor cells than the constructs without the IL-12 payload.

Example 20: Efficacy of Anti-TNMUC1 CAR T-cells Against Pancreatic Cancer Using T-Cells from Different Donors Constructs GC216 (no CAR vector with secreted nano-luciferase and LNGFR engineered to 53% GC3), SK072 (SEQ ID NO: 11, has 53% GC3 in LNGFR) anti-TnMUC1 CARs, and GC213 (SEQ ID NO: 5, has 53% GC3 in LNGFR) anti-TnMUC1 CARs with an IL-12 payload under the control of RDE, were compared using T-cells from three different donors (180, 580 and 598).

These constructs were transduced into the three different donor T-cells and the transfected T-cells were administered to mice. Prior to administration of T-cells, mice were inoculated with HS766T cells (a metastatic, pancreatic carcinoma cell line) to grow tumors that are TnMUC1 positive. The HS766T cells were also engineered with luciferase as a reporter for the tumor cells.

Figure 18:
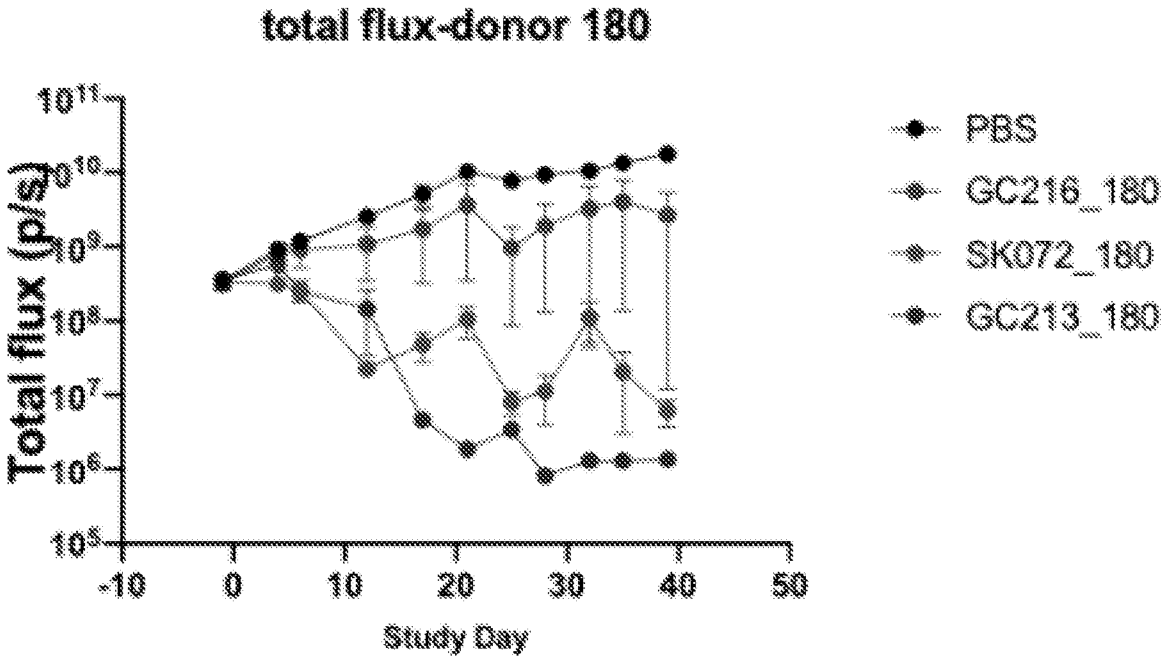
FIG. 18 shows the efficacy of SK072, GC213, GC216 and PBS in T-cells from donor 180 against a metastatic pancreatic carcinoma (HS766T) in a mouse model.
Figure 19:
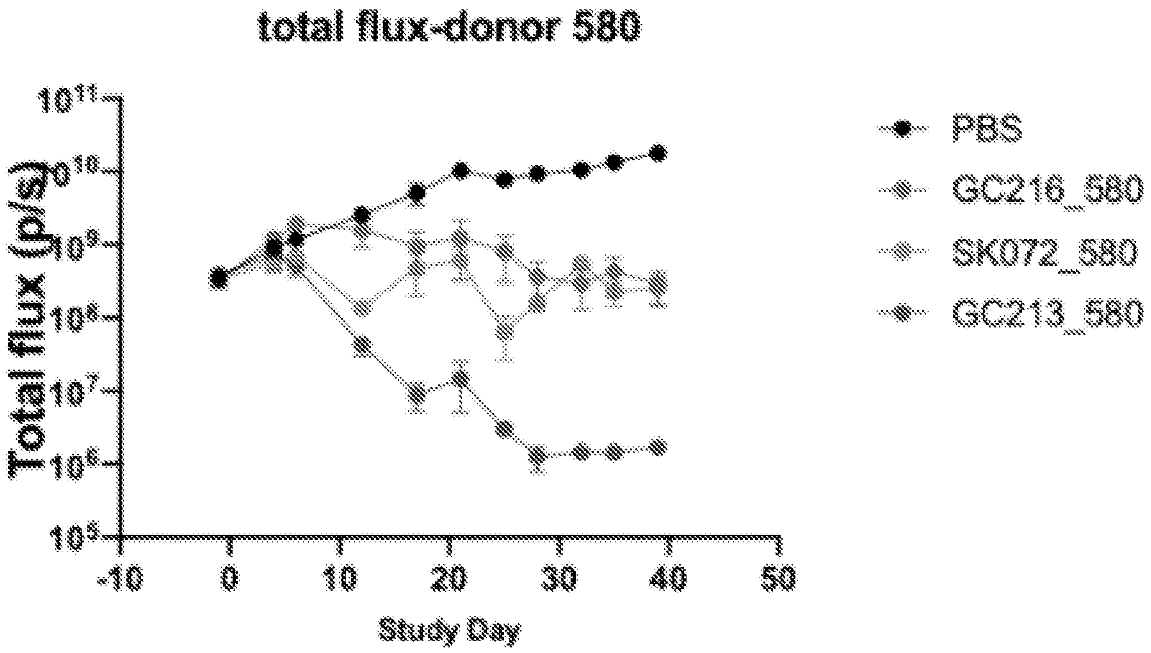
FIG. 19 shows the efficacy of SK072, GC213, GC216 and PBS in T-cells from donor 580 against a metastatic pancreatic carcinoma (HS766T) in a mouse model.
Figure 20:
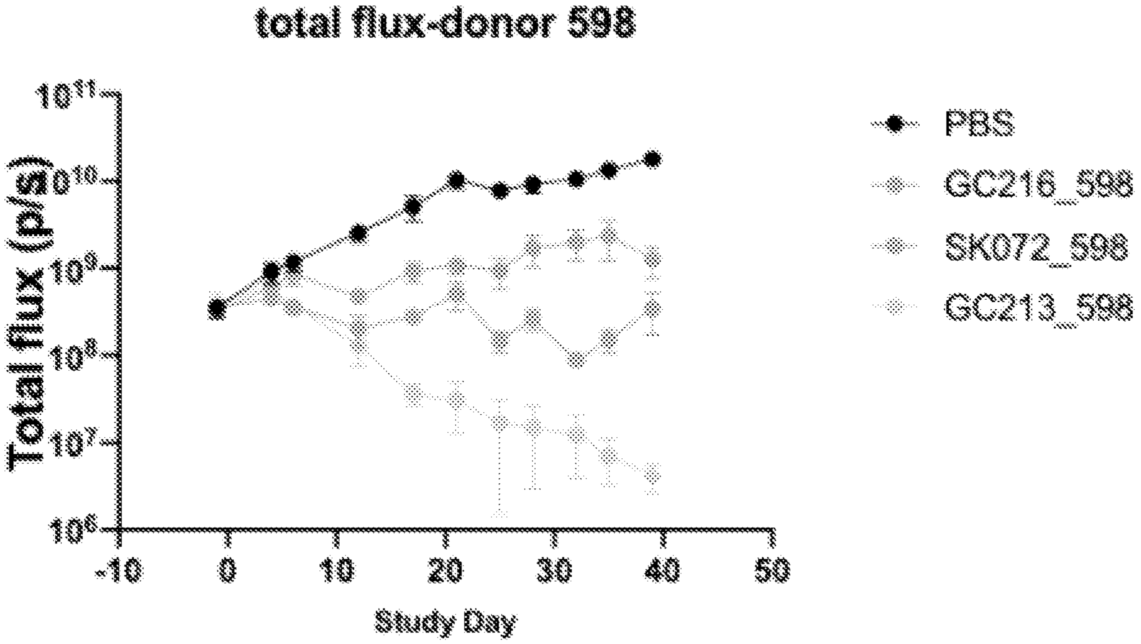
FIG. 20 shows the efficacy of SK072, GC213, GC216 and PBS in T-cells from donor 598 against a metastatic pancreatic carcinoma (HS766T) in a mouse model.

Results for this study are shown in FIGS. 18, 19 and 20. GC213 (anti-TNMUC1 CAR+IL-12, 53% GC3 in LNGFR) produced the greatest amount of tumor killing in the T-cells from all three of the donors.

Example 21: Anti-TNMUC1 CAR and Payload Delivery

Constructs GC216 (no CAR vector with secreted nano-luciferase and LNGFR engineered to 53% GC3), SK072 (SEQ ID NO: 11, has 53% GC3 in LNGFR) anti-TnMUC1 CARs, SK201 smol2 promoter with an anti-TnMUC1 CAR and a secreted N-luciferase payload under IFNg Gold control, SK209 NFAT/MND promoter with an anti-TnMUC1 CAR and a membrane bound IL-12 payload under IFNg Gold control, GC213 (SEQ ID NO: 5, has 53% GC3 in LNGFR) anti-TnMUC1 CARs with an IL-12 payload under the control of RDE, and GC251 (SEQ ID NO: 12), were compared in a mouse tumor model. These constructs were transduced into donor T-cells and the transfected T-cells were administered to mice at either a one million or three million dose of cells. Prior to administration of T-cells, mice were inoculated with HS766T cells (a metastatic, pancreatic carcinoma cell line) to grow tumors that are TnMUC1 positive. The HS766T cells were also engineered with luciferase as a reporter for the tumor cells.

Figure 21:
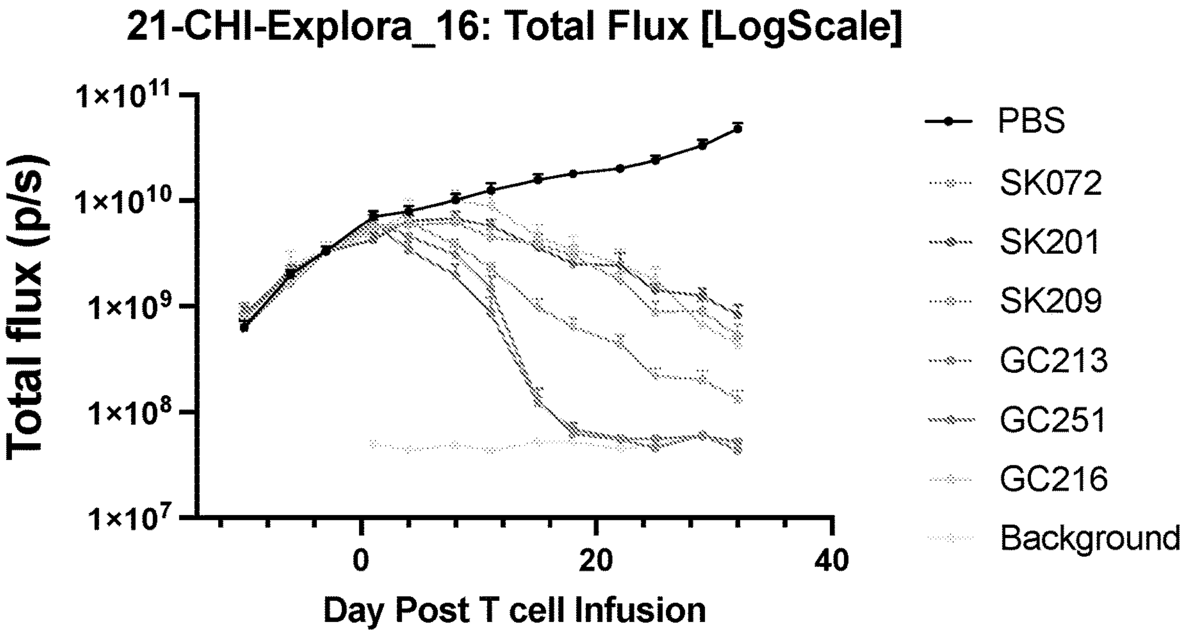
FIG. 21 shows the efficacy of SK072, SK201, SK209, GC213, GC251, and GC216 against a pancreatic cancer model in mice.

Results for this study are shown in FIG. 21. GC213 (anti-TNMUC1 CAR+IL-12, 53% GC3 in LNGFR) and GC251 (anti-TNMUC1 CAR+IL-12, 83% GC3 in LNGFR) produced the greatest amount of tumor killing at day 14. Scans of the mice that received three million T-cells with GC213 show that eight of ten mice are tumor free at Day 67 of the study.

Example 22: Rapamycin Reverses Expression of a Payload Under Gold Control after Cell Activation A bicistronic vector with an anti-DLL3-CAR and nano-luceiferase under the control of an IFNg Gold element is made using the methods and materials described above. This bicistronic vector is transduced into primary T-cells, and transduced T-cells are obtained. When the transduced T-cells are mixed with SHP-77 cells that display the DLL3 antigen, the primary T-cells are activated and nano-luciferase is expressed.

The ability of rapamycin to inhibit the expression of nano-luciferase following activation of the primary T-cells was tested. Primary T-cells transduced with the bicistronic vector encoding the anti-DLL3 CAR and nano-luciferase were mixed with SHP-77 cells and then three treatment regimens were used. No rapamycin (NoRx), rapamycin added concurrently with the SHP-77 cells (Concurrent Rx), or rapamycin added 24 hours after SHP-77 cells was added (Delay Rx). New media was mixed with the cells every 24 hours. If the cells had received rapamycin in the media in the earlier time period, rapamycin was included with the media at subsequent media changes.

Figure 22:
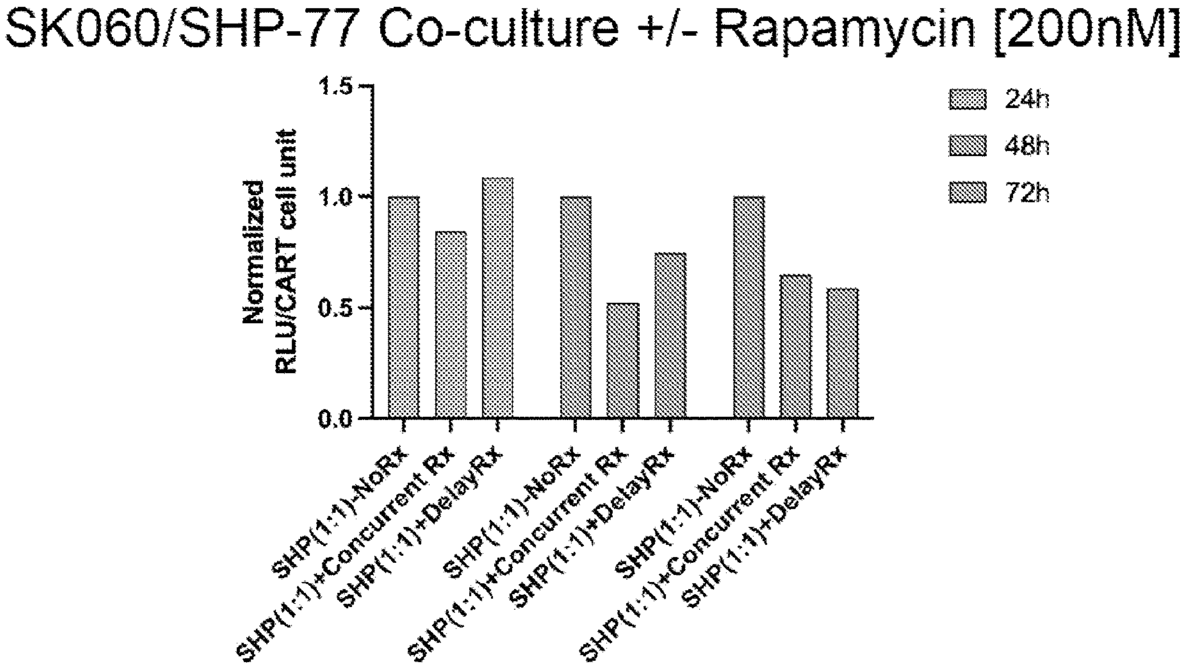
FIG. 22 shows the inhibitory effect of rapamycin on expression of a payload under Gold control following activation of the cell.

The results are shown in FIG. 22. FIG. 22 normalizes the nano-luciferase activity to that of the NoRx sample. Levels of nano-luciferase were measured at 24 hours, 48 hours and 72 hours post mixing with SHP-77 cells. The data shows that both the Concurrent Rx and the Delay Rx reduced expression of nano-luciferase showing the rapamycin can reverse the Gold controlled expression of the nano-luciferase payload.

Example 23: IL-12 Biodistribution for Anti-TNMUC1 CAR with an IL-12 Payload

GC251 (SEQ ID NO: 12, anti-TNMUC1 CAR+IL-12, 83% GC3 in LNGFR) was transduced into donor T-cells and the transfected T-cells were administered to mice in a two million dose of cells. Prior to administration of Gold CAR T-cells, mice were inoculated with PC3 cells (a bone metastasis of a grade IV prostatic adenocarcinoma) to grow tumors that are TnMUC1 positive. The PC3 cells were also engineered with luciferase as a reporter for the tumor cells.

Figure 23:
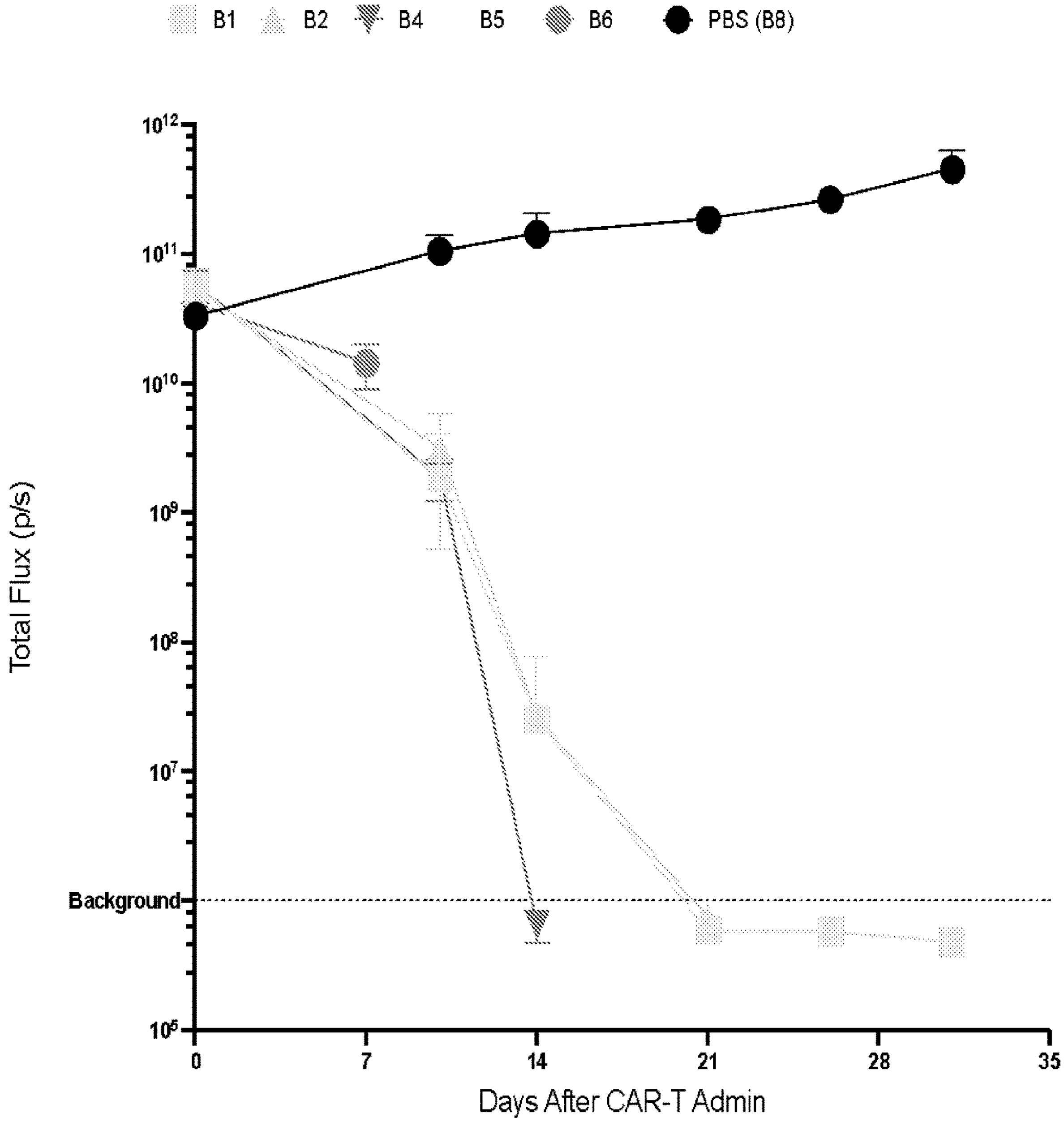
FIG. 23 shows regression of prostate cancer in a mouse treated with anti-TnMUC1 Gold CAR T-cells.

Mice were sacrificed at days 2 (B6), 7 (B5), 10 (B4), 14 (B3), 21 (B2), and 35 (B1) after administration of the Gold CAR T-cells. Tumors, blood and spleen were collected from the mice, and the samples were tested for IL-12, IL-1b, IL-6, IL-8, IL-12p70, and TNFα. At this dose, the Gold CAR T-cells (GC251) completely regressed the PC3 tumors by 14-21 days (see FIG. 23).

Figure 24:
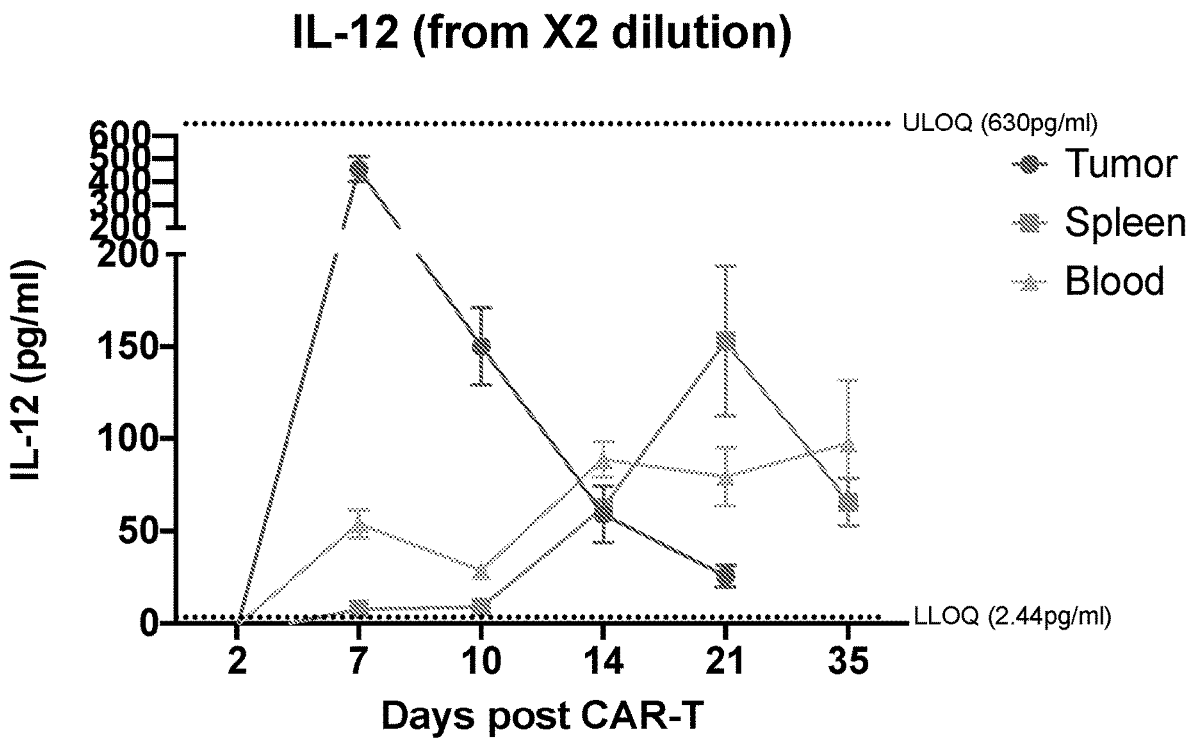
FIG. 24 shows IL-12 levels in a tumor, in the blood and in the spleen of mice treated with TnMUC1 Gold CAR T-cells.

In the tumor samples, IL-12 rose to a max at day 7 and then dropped as the tumor was clear (FIG. 24). The IL-12 levels in the tumor were much higher in the tumor than in the blood or spleen. IL-1b, IL-6, IL-8 and IL-12p70 also had higher levels in tumor until days 10-14 when the tumor was cleared, and had lower levels in blood and spleen. These results show that Gold control of IL-12 delivered IL-12 to the tumors in these mice until the tumors were cleared. These results also show that the IL-12 payload induced an inflammatory response at the tumor until the tumors were cleared.

All publications, patents and patent applications discussed and cited herein are incorporated herein by reference in their entireties. It is understood that the disclosed invention is not limited to the particular methodology, protocols and materials described as these can vary. It is also understood that the terminology used herein is for the purposes of describing particular embodiments only and is not intended to limit the scope of the present invention which will be limited only by the appended claims.

Those skilled in the art will recognize, or be able to ascertain using no more than routine experimentation, many equivalents to the specific embodiments of the invention described herein. Such equivalents are intended to be encompassed by the following claims.

What is claimed is:

1. A method for treating a pancreatic cancer, a prostate cancer, or a triple negative, breast cancer, comprising the steps of:

a) obtaining a primary T-cell comprising a heterologous nucleic acid encoding:

i) an anti-TnMUC1 chimeric antigen receptor, and ii) an IL-12 payload, wherein said heterologous nucleic acid is selected from the group consisting of SEQ ID NO:5, SEQ ID NO:12, SEQ ID NO:13 and SEQ ID NO:14; and b) administering the primary T-cell to a subject diagnosed with the pancreatic cancer, the prostate cancer, or the triple negative, breast cancer, thereby treating the pancreatic cancer, the prostate cancer, or the triple negative, breast cancer.

2. The method of claim 1, wherein the primary T-cell comprises SEQ ID NO: 5.

3. The method of claim 1, wherein the primary T-cell comprises SEQ ID NO: 12.

4. The method of claim 1, wherein the primary T-cell comprises SEQ ID NO: 13.

5. The method of claim 1, wherein the primary T-cell comprises SEQ ID NO: 14.

6. The method of claim 4, wherein the method is for treating a pancreatic cancer, and the TnMUC1 is associated with a pancreatic cancer cell.

7. The method of claim 4, wherein the method is for treating a prostate cancer, and the TnMUC1 is associated with a prostate cancer cell.

8. The method of claim 4, wherein the method is for treating a triple negative breast cancer, and the TnMUC1 is associated with a triple negative, breast cancer cell.

9. The method of claim 5, wherein the method is for treating a pancreatic cancer, and the TnMUC1 is associated with a pancreatic cancer cell.

10. The method of claim 5, wherein the method is for treating a prostate cancer, and the TnMUC1 is associated with a prostate cancer cell.

11. The method of claim 5, wherein the method is for treating a triple negative breast cancer, and the TnMUC1 is associated with a triple negative, breast cancer cell.

12. The method of claim 3, wherein the method is for treating a pancreatic cancer, and the TnMUC1 is associated with a pancreatic cancer cell.

13. The method of claim 3, wherein the method is for treating a prostate cancer, and the TnMUC1 is associated with a prostate cancer cell.

14. The method of claim 3, wherein the method is for treating a triple negative breast cancer, and the TnMUC1 is associated with a triple negative, breast cancer cell.

15. The method of claim 2, wherein the method is for treating a pancreatic cancer, and the TnMUC1 is associated with a pancreatic cancer cell.

16. The method of claim 2, wherein the method is for treating a prostate cancer, and the TnMUC1 is associated with a prostate cancer cell.

17. The method of claim 2, wherein the method is for treating a triple negative breast cancer, and the TnMUC1 is associated with a triple negative, breast cancer cell.

* * * * *